US011512324B2

(12) United States Patent
Bowen et al.

(10) Patent No.: US 11,512,324 B2
(45) Date of Patent: Nov. 29, 2022

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Todd A. Ciche, San Diego, CA (US); Stanislaw Flasinski, Ballwin, MO (US); Arlene R. Howe, Clarkson Valley, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 0 days.

(21) Appl. No.: 16/580,583

(22) Filed: Sep. 24, 2019

(65) Prior Publication Data

US 2020/0095603 A1 Mar. 26, 2020

Related U.S. Application Data

(60) Provisional application No. 62/736,236, filed on Sep. 25, 2018.

(51) Int. Cl.

| | |
|---|---|
| ***C12N 15/82*** | (2006.01) |
| ***C07K 14/325*** | (2006.01) |
| ***A01N 63/50*** | (2020.01) |
| ***G01N 33/569*** | (2006.01) |
| ***G01N 33/00*** | (2006.01) |
| ***A01N 63/10*** | (2020.01) |

(52) U.S. Cl.

CPC ......... *C12N 15/8286* (2013.01); *A01N 63/10* (2020.01); *A01N 63/50* (2020.01); *C07K 14/325* (2013.01); *G01N 33/0098* (2013.01); *G01N 33/56961* (2013.01)

(58) Field of Classification Search

None

See application file for complete search history.

(56) References Cited

U.S. PATENT DOCUMENTS

| | | | |
|---|---|---|---|
| 6,174,860 | B1 | 1/2001 | Kramer et al. |
| 2012/0278954 | A1 | 11/2012 | Bowen et al. |
| 2018/0208940 | A1 | 7/2018 | Bowen et al. |
| 2018/0346925 | A1 | 12/2018 | Bowen et al. |

FOREIGN PATENT DOCUMENTS

| | | |
|---|---|---|
| WO | WO 99/54472 | * 10/1999 |

OTHER PUBLICATIONS

Guo et al, 2004, Proc. Natl. Acad. Sci. USA 101: 9205-9210.*
Stilwell et al, 2018, mSphere 3:1-16 (e00530-17).*
CABI, https://www.cabi.org/isc/datasheet/51706, accessed Mar. 22, 2021.*
Yang et al (2017, J. Invert. Pathol. 148:43-50).*
Blackburn et al., Remarkable Susceptibility of the Diamondback Moth (*Plutella xylostella*) to Ingestion of Pir Toxins from Photorhabdus Luminescens, Entomologia Experimentalis et Applicata, 2006, 31-37, 121-1.
Li et al., Photorhabdus Luminescens PirAB-Fusion Protein Exhibits Both Cytotoxicity and Insecticidal Activity, FEMS Microbiology Letters, 2014, 23-31, 356-1.
Waterfield et al. The Photorhabdus Pir Toxins are Similar to a Developmentally Regulated Insect Protein But Show No Juvenile Hormone Esterase Activity, FEMS Microbiology Letters, 2005, 47-52, 245-1.
Wu and Yi, Haemocoel Injection of PirA1B1 to Galleria Mellonella Larvae Leads to Disruption of the Haemocyte Immune Functions, Scientific Reports 6, Article No. 34996, 2016, 34996, 6.
Yang et al., PirAB Protein from Xenorhabdus Nematophila HB310 Exhibits a Binary Toxin with Insecticidal Activity and Cytotoxicity in Galleria Mellonella, Journal of Invertebrate Pathology, 2017, 43-50, 148.
Zhang et al., XaxAB-Like Binary Toxin From Photorhabdus Luminescens Exhibits Both Insecticidal Activity and Cytotoxicity, FEMS Microbiology Letters, 2014, 48-56, 350-1.
Invitation to Pay Additional Fees regarding PCT Application No. PCT/US2019/52782, dated Nov. 27, 2019, 3 pages.
International Search Report and Written Opinion regarding PCT Application No. PCT/US2019/52782, dated Jan. 31, 2020.

* cited by examiner

*Primary Examiner* — Anne Kubelik
(74) *Attorney, Agent, or Firm* — Dentons US LLP; Timothy Ball

(57) ABSTRACT

A pesticidal protein class of PirA, PirB, and PirAB fusion proteins exhibiting toxic activity against Coleopteran, Lepidopteran, and Hemipteran pest species is disclosed. DNA constructs are provided which contain a recombinant nucleic acid sequence encoding the PirA, PirB, and PirAB fusion proteins. Transgenic plants, plant cells, seed, and plant parts resistant to Coleopteran, Lepidopteran, and Hemipteran infestation are provided which contain recombinant nucleic acid sequences encoding the PirA, PirB, and PirAB fusion proteins. Methods for detecting the presence of the recombinant nucleic acid sequences or the proteins of the present invention in a biological sample, and methods of controlling Coleopteran, Lepidopteran, and Hemipteran species pests using the PirA, PirB, and PirAB fusion proteins are also provided.

41 Claims, No Drawings

Specification includes a Sequence Listing.

SEQUENCE LISTING

```
<160> NUMBER OF SEQ ID NOS: 160

<210> SEQ ID NO 1
<211> LENGTH: 408
<212> TYPE: DNA
<213> ORGANISM: Xenorhabdus nematophila
<220> FEATURE:
<221> NAME/KEY: misc_feature
<222> LOCATION: (1)..(408)
<223> OTHER INFORMATION: A nucleic acid sequence obtained from
      Xenorhabdus nematophila strain ISB000002 encoding a TIC4771 PirA
      pesticidal protein sequence.

<400> SEQUENCE: 1

atgattacaa taaatataag tggtggtagt ataaaaatta gtaacaacat aggatcagaa      60

actgatatca aaaatacacc tttttcagaa cctctttcaa ttagtaatta taaggatatg     120

acaatagagc cacattcgtc tatccaagca acaagaactg atacaccaat tattcctgaa     180

acacgaccaa attattatgt agctaattcc ggccctgccg catcagtgag agctgttttt     240

tattggtctc attcttttac atcagaatgg ttcgaacatt catctatcat tgtaaaagca     300

ggagaagatg gaatattgaa ctcacctagc aattctgtat attacagtaa ggttgtcatt     360

tacaacgata cggataaacg ggcctttgtc acaggttatg acaaataa                  408


<210> SEQ ID NO 2
<211> LENGTH: 135
<212> TYPE: PRT
<213> ORGANISM: Xenorhabdus nematophila
<220> FEATURE:
<221> NAME/KEY: MISC_FEATURE
<222> LOCATION: (1)..(135)
<223> OTHER INFORMATION: The amino acid sequence of the TIC4771 PirA
      protein.

<400> SEQUENCE: 2

Met Ile Thr Ile Asn Ile Ser Gly Gly Ser Ile Lys Ile Ser Asn Asn
1               5                   10                  15
```

-continued

```
Ile Gly Ser Glu Thr Asp Ile Lys Asn Thr Pro Phe Ser Glu Pro Leu
            20                  25                  30

Ser Ile Ser Asn Tyr Lys Asp Met Thr Ile Glu Pro His Ser Ser Ile
        35                  40                  45

Gln Ala Thr Arg Thr Asp Thr Pro Ile Ile Pro Glu Thr Arg Pro Asn
    50                  55                  60

Tyr Tyr Val Ala Asn Ser Gly Pro Ala Ala Ser Val Arg Ala Val Phe
65                  70                  75                  80

Tyr Trp Ser His Ser Phe Thr Ser Glu Trp Phe Glu His Ser Ser Ile
                85                  90                  95

Ile Val Lys Ala Gly Glu Asp Gly Ile Leu Asn Ser Pro Ser Asn Ser
            100                 105                 110

Val Tyr Tyr Ser Lys Val Val Ile Tyr Asn Asp Thr Asp Lys Arg Ala
        115                 120                 125

Phe Val Thr Gly Tyr Asp Lys
    130                 135
```

<210> SEQ ID NO 3
<211> LENGTH: 1287
<212> TYPE: DNA
<213> ORGANISM: Xenorhabdus nematophila
<220> FEATURE:
<221> NAME/KEY: misc_feature
<222> LOCATION: (1)..(1287)
<223> OTHER INFORMATION: A nucleic acid sequence obtained from Xenorhabdus nematophila strain ISB000002 encoding a TIC4772 PirB pesticidal protein sequence.

<400> SEQUENCE: 3

```
atgaataacg aacttatgaa cacaaatgaa tcacaacctt cagagacatt atctttaatt     60

aatgaatcta tattaacagc accttatgcc gtttctaccc ctaattatga atgggatatg    120

tcatcaataa taaaagatgc cattattgga ggtataggat ttattcccgg gccgggttca    180

gcaatatcgt ttttgctagg gctattttgg ccgcaacaaa cagacaatac ctgggagcaa    240

attctccaaa aagtagaaca gatgatagag gaagcgaatt taaaaactat tcaaggaata    300

ctgaacggag atatacaaga aataaaagga aagatggaac atgtggaata tatgctagaa    360

acctcaccag gcactcaaga aagccatgac gcatatatgt tcttagcgag atatctggta    420

agtatagatg aaaaattcaa atctttttgat aataaaacaa attatcaaat tcttccaatg    480

tacaccaata cgcttatgtt acaggcacct tactggaaaa tgggtataga gaagaaaaat    540

gatattttgc taacagatat agaagttaat gaattaaaac agcttatcga aaatctatat    600

gccaaggcca atagctatat tcatgaagtg tatacccgtg aatacgataa tgcggtaaat    660

acctcaacag caacaacgat taccaataat ttattgtctg taagagggta ttgtttatta    720

catggattag agtgccttga agtccttgat catatacaaa ataataatct tgatcagagc    780

ttctatccga aaactatcag ttattctact gtatttgatc gctcaacaaa caaaacaaga    840

ctccaggctc ttaccgaaga cgagcaaatg gaagaaccac tcaaaccctc ttttattaat    900

ggggaatata ataaaataaa atcactgatt ggatatgtac agagaattgg aaacgcccct    960

agagttggag gtataaaaat tacatttact aatggatcat ctcatactct gggtacagtg   1020

acctcagaat caaactcaat tgaactaaat gatagtgtta taaccagtgt ggaagtatgg   1080

ggaaatggtg ctgttgatga ggcattcttt acattaagtg acggtcgtca atttaggctt   1140

ggtcaacgct atgccagtaa ctacagaaaa tatgctgttg atggccacta tatttcagga   1200

ttgtacttag ccagtgatga gccttcactt gctggtcaag ccgcaggtat tgcagtttca   1260
```

```
tatcatatat tggttgataa gaaataa                                         1287


<210> SEQ ID NO 4
<211> LENGTH: 428
<212> TYPE: PRT
<213> ORGANISM: Xenorhabdus nematophila
<220> FEATURE:
<221> NAME/KEY: MISC_FEATURE
<222> LOCATION: (1)..(482)
<223> OTHER INFORMATION: The amino acid sequence of the TIC4772 PirB
      protein.

<400> SEQUENCE: 4

Met Asn Asn Glu Leu Met Asn Thr Asn Glu Ser Gln Pro Ser Glu Thr
1               5                   10                  15

Leu Ser Leu Ile Asn Glu Ser Ile Leu Thr Ala Pro Tyr Ala Val Ser
            20                  25                  30

Thr Pro Asn Tyr Glu Trp Asp Met Ser Ser Ile Ile Lys Asp Ala Ile
        35                  40                  45

Ile Gly Gly Ile Gly Phe Ile Pro Gly Pro Gly Ser Ala Ile Ser Phe
    50                  55                  60

Leu Leu Gly Leu Phe Trp Pro Gln Gln Thr Asp Asn Thr Trp Glu Gln
65                  70                  75                  80

Ile Leu Gln Lys Val Glu Gln Met Ile Glu Glu Ala Asn Leu Lys Thr
                85                  90                  95

Ile Gln Gly Ile Leu Asn Gly Asp Ile Gln Glu Ile Lys Gly Lys Met
            100                 105                 110

Glu His Val Glu Tyr Met Leu Glu Thr Ser Pro Gly Thr Gln Glu Ser
        115                 120                 125

His Asp Ala Tyr Met Phe Leu Ala Arg Tyr Leu Val Ser Ile Asp Glu
    130                 135                 140

Lys Phe Lys Ser Phe Asp Asn Lys Thr Asn Tyr Gln Ile Leu Pro Met
145                 150                 155                 160

Tyr Thr Asn Thr Leu Met Leu Gln Ala Pro Tyr Trp Lys Met Gly Ile
                165                 170                 175

Glu Lys Lys Asn Asp Ile Leu Leu Thr Asp Ile Glu Val Asn Glu Leu
            180                 185                 190

Lys Gln Leu Ile Glu Asn Leu Tyr Ala Lys Ala Asn Ser Tyr Ile His
        195                 200                 205

Glu Val Tyr Thr Arg Glu Tyr Asp Asn Ala Val Asn Thr Ser Thr Ala
    210                 215                 220

Thr Thr Ile Thr Asn Asn Leu Leu Ser Val Arg Gly Tyr Cys Leu Leu
225                 230                 235                 240

His Gly Leu Glu Cys Leu Glu Val Leu Asp His Ile Gln Asn Asn Asn
                245                 250                 255

Leu Asp Gln Ser Phe Tyr Pro Lys Thr Ile Ser Tyr Ser Thr Val Phe
            260                 265                 270

Asp Arg Ser Thr Asn Lys Thr Arg Leu Gln Ala Leu Thr Glu Asp Glu
        275                 280                 285

Gln Met Glu Glu Pro Leu Lys Pro Ser Phe Ile Asn Gly Glu Tyr Asn
    290                 295                 300

Lys Ile Lys Ser Leu Ile Gly Tyr Val Gln Arg Ile Gly Asn Ala Pro
305                 310                 315                 320

Arg Val Gly Gly Ile Lys Ile Thr Phe Thr Asn Gly Ser Ser His Thr
                325                 330                 335
```

-continued

```
Leu Gly Thr Val Thr Ser Glu Ser Asn Ser Ile Glu Leu Asn Asp Ser
            340                 345                 350

Val Ile Thr Ser Val Glu Val Trp Gly Asn Gly Ala Val Asp Glu Ala
        355                 360                 365

Phe Phe Thr Leu Ser Asp Gly Arg Gln Phe Arg Leu Gly Gln Arg Tyr
    370                 375                 380

Ala Ser Asn Tyr Arg Lys Tyr Ala Val Asp Gly His Tyr Ile Ser Gly
385                 390                 395                 400

Leu Tyr Leu Ala Ser Asp Glu Pro Ser Leu Ala Gly Gln Ala Ala Gly
                405                 410                 415

Ile Ala Val Ser Tyr His Ile Leu Val Asp Lys Lys
            420                 425


<210> SEQ ID NO 5
<211> LENGTH: 1692
<212> TYPE: DNA
<213> ORGANISM: Artificial
<220> FEATURE:
<223> OTHER INFORMATION: A nucleic acid sequence encoding a PirAB fusion
      protein, TIC6880 comprised of the TIC4771 and TIC4772 coding
      sequences in operable linkage and in frame.

<400> SEQUENCE: 5

atgattacaa taaatataag tggtggtagt ataaaaatta gtaacaacat aggatcagaa     60

actgatatca gaaatacacc tttttcagaa cctctttcaa ttagtaatta taaggatatg    120

acaatagagc cacattcgtc tatccaagca acaagaactg atacaccaat tattcctgaa    180

acacgaccaa attattatgt agctaattcc ggccctgccg catcagtgag agctgttttt    240

tattggtctc attcttttac atcagaatgg ttcgaacatt catctatcat tgtaaaagca    300

ggagaagatg gaatattgaa ctcacctagc aattctgtat attacagtaa ggttgtcatt    360

tacaacgata cggataaacg ggcctttgtc acaggttatg acaaaatgaa taacgaactt    420

atgaacacaa atgaatcaca accttcagag acattatctt taattaatga atctatatta    480

acagcacctt atgccgtttc taccccctaat tatgaatggg atatgtcatc aataataaaa    540

gatgccatta ttggaggtat aggatttatt cccgggccgg gttcagcaat atcgtttttg    600

ctagggctat tttggccgca acaaacagac aatacctggg agcaaattct ccaaaaagta    660

gaacagatga tagaggaagc gaatttaaaa actattcaag gaatactgaa cggagatata    720

caagaaataa aaggaaagat ggaacatgtg gaatatatgc tagaaacctc accaggcact    780

caagaaagcc atgacgcata tatgttctta gcgagatatc tggtaagtat agatgaaaaa    840

ttcaaatctt ttgataataa aacaaattat caaattcttc caatgtacac caatacgctt    900

atgttacagg caccttactg gaaaatgggt atagagaaga aaaatgatat tttgctaaca    960

gatatagaag ttaatgaatt aaaacagctt atcgaaagtc tatatgccaa ggccaatagc   1020

tatattcatg aagtgtatac ccgtgaatac gataatgcgg taaatacctc aacagcaaca   1080

acgattacca ataatttatt gtctgtaaga gggtattgtt tattacatgg attagagtgc   1140

cttgaagtcc ttgatcatat acaaaataat aatcttgatc agagcttcta tccgaaaact   1200

atcagttatt ctactgtatt tgatcgctca acaaacaaaa caagactcca ggctcttacc   1260

gaagacgagc aaatggaaga accactcaaa ccctctttta ttaatgggga atataataaa   1320

ataaaatcac tgattggata tgtacagaga attggaaacg cccctagagt tggaggtata   1380

aaaattacat ttactaatgg atcatctcat actctgggta cagtgacctc agaatcaaac   1440

tcaattgaac taaatgatag tgttataacc agtgtggaag tatggggaaa tggtgctgtt   1500
```

gatgaggcat tctttacatt aagtgacggt cgtcaattta ggcttggtca acgctatgcc 1560
agtaactaca gaaaatatgc tgttgatggc cactatattt caggattgta cttagccagt 1620
gatgagcctt cacttgctgg tcaagccgca ggtattgcag tttcatatca tatattggtt 1680
gataagaaat aa 1692

<210> SEQ ID NO 6
<211> LENGTH: 563
<212> TYPE: PRT
<213> ORGANISM: Artificial
<220> FEATURE:
<223> OTHER INFORMATION: The amino acid sequence of the TIC6880 PirAB fusion protein

<400> SEQUENCE: 6

Met Ile Thr Ile Asn Ile Ser Gly Gly Ser Ile Lys Ile Ser Asn Asn
1 5 10 15

Ile Gly Ser Glu Thr Asp Ile Arg Asn Thr Pro Phe Ser Glu Pro Leu
20 25 30

Ser Ile Ser Asn Tyr Lys Asp Met Thr Ile Glu Pro His Ser Ser Ile
35 40 45

Gln Ala Thr Arg Thr Asp Thr Pro Ile Ile Pro Glu Thr Arg Pro Asn
50 55 60

Tyr Tyr Val Ala Asn Ser Gly Pro Ala Ala Ser Val Arg Ala Val Phe
65 70 75 80

Tyr Trp Ser His Ser Phe Thr Ser Glu Trp Phe Glu His Ser Ser Ile
85 90 95

Ile Val Lys Ala Gly Glu Asp Gly Ile Leu Asn Ser Pro Ser Asn Ser
100 105 110

Val Tyr Tyr Ser Lys Val Val Ile Tyr Asn Asp Thr Asp Lys Arg Ala
115 120 125

Phe Val Thr Gly Tyr Asp Lys Met Asn Asn Glu Leu Met Asn Thr Asn
130 135 140

Glu Ser Gln Pro Ser Glu Thr Leu Ser Leu Ile Asn Glu Ser Ile Leu
145 150 155 160

Thr Ala Pro Tyr Ala Val Ser Thr Pro Asn Tyr Glu Trp Asp Met Ser
165 170 175

Ser Ile Ile Lys Asp Ala Ile Ile Gly Gly Ile Gly Phe Ile Pro Gly
180 185 190

Pro Gly Ser Ala Ile Ser Phe Leu Leu Gly Leu Phe Trp Pro Gln Gln
195 200 205

Thr Asp Asn Thr Trp Glu Gln Ile Leu Gln Lys Val Glu Gln Met Ile
210 215 220

Glu Glu Ala Asn Leu Lys Thr Ile Gln Gly Ile Leu Asn Gly Asp Ile
225 230 235 240

Gln Glu Ile Lys Gly Lys Met Glu His Val Glu Tyr Met Leu Glu Thr
245 250 255

Ser Pro Gly Thr Gln Glu Ser His Asp Ala Tyr Met Phe Leu Ala Arg
260 265 270

Tyr Leu Val Ser Ile Asp Glu Lys Phe Lys Ser Phe Asp Asn Lys Thr
275 280 285

Asn Tyr Gln Ile Leu Pro Met Tyr Thr Asn Thr Leu Met Leu Gln Ala
290 295 300

Pro Tyr Trp Lys Met Gly Ile Glu Lys Lys Asn Asp Ile Leu Leu Thr
305 310 315 320

```
Asp Ile Glu Val Asn Glu Leu Lys Gln Leu Ile Glu Ser Leu Tyr Ala
                325                 330                 335

Lys Ala Asn Ser Tyr Ile His Glu Val Tyr Thr Arg Glu Tyr Asp Asn
            340                 345                 350

Ala Val Asn Thr Ser Thr Ala Thr Thr Ile Thr Asn Asn Leu Leu Ser
        355                 360                 365

Val Arg Gly Tyr Cys Leu Leu His Gly Leu Glu Cys Leu Glu Val Leu
    370                 375                 380

Asp His Ile Gln Asn Asn Asn Leu Asp Gln Ser Phe Tyr Pro Lys Thr
385                 390                 395                 400

Ile Ser Tyr Ser Thr Val Phe Asp Arg Ser Thr Asn Lys Thr Arg Leu
                405                 410                 415

Gln Ala Leu Thr Glu Asp Glu Gln Met Glu Glu Pro Leu Lys Pro Ser
            420                 425                 430

Phe Ile Asn Gly Glu Tyr Asn Lys Ile Lys Ser Leu Ile Gly Tyr Val
        435                 440                 445

Gln Arg Ile Gly Asn Ala Pro Arg Val Gly Gly Ile Lys Ile Thr Phe
    450                 455                 460

Thr Asn Gly Ser Ser His Thr Leu Gly Thr Val Thr Ser Glu Ser Asn
465                 470                 475                 480

Ser Ile Glu Leu Asn Asp Ser Val Ile Thr Ser Val Glu Val Trp Gly
                485                 490                 495

Asn Gly Ala Val Asp Glu Ala Phe Phe Thr Leu Ser Asp Gly Arg Gln
            500                 505                 510

Phe Arg Leu Gly Gln Arg Tyr Ala Ser Asn Tyr Arg Lys Tyr Ala Val
        515                 520                 525

Asp Gly His Tyr Ile Ser Gly Leu Tyr Leu Ala Ser Asp Glu Pro Ser
    530                 535                 540

Leu Ala Gly Gln Ala Ala Gly Ile Ala Val Ser Tyr His Ile Leu Val
545                 550                 555                 560

Asp Lys Lys
```

<210> SEQ ID NO 7
<211> LENGTH: 426
<212> TYPE: DNA
<213> ORGANISM: Xenorhabdus ehlersii
<220> FEATURE:
<221> NAME/KEY: misc_feature
<222> LOCATION: (1)..(426)
<223> OTHER INFORMATION: A nucleic acid sequence obtained from Xenorhabdus ehlersii strain 85823 encoding a TIC7575 PirA pesticidal protein sequence.

<400> SEQUENCE: 7

```
atgaatacaa tcaatataaa tataagtggc agtaccgtta cagtcataag caataacgat      60

tccaatccag aaccattaac ttataataca aacacaccag catcagaccc tcttacagcc     120

agtccttata gggatatgac aatagagcca cactcttcta ttgaagcaac aagaaccgat     180

acaccgatta ttcccgaaac tcgtcccaat tactatgtag ccaattctgg ccccgcatca     240

tcagttaggg ctgtttttta ttggtctcat tctttcacat cagaatggtt cgaatattcc     300

tctatcatag tgaaagccgg gaaagacgga atattacaat caccgaataa cgctttatat     360

tacagtaaag ttgtcattta taacgatacc gataaacgtg cctttgttac cggatataat     420

aagtaa                                                               426
```

<210> SEQ ID NO 8
<211> LENGTH: 141
<212> TYPE: PRT
<213> ORGANISM: Xenorhabdus ehlersii
<220> FEATURE:
<221> NAME/KEY: MISC_FEATURE
<222> LOCATION: (1)..(141)
<223> OTHER INFORMATION: The amino acid sequence of the TIC7575 PirA
      protein.

<400> SEQUENCE: 8

```
Met Asn Thr Ile Asn Ile Asn Ile Ser Gly Ser Thr Val Thr Val Ile
1               5                   10                  15

Ser Asn Asn Asp Ser Asn Pro Glu Pro Leu Thr Tyr Asn Thr Asn Thr
            20                  25                  30

Pro Ala Ser Asp Pro Leu Thr Ala Ser Pro Tyr Arg Asp Met Thr Ile
        35                  40                  45

Glu Pro His Ser Ser Ile Glu Ala Thr Arg Thr Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Glu Trp
                85                  90                  95

Phe Glu Tyr Ser Ser Ile Ile Val Lys Ala Gly Lys Asp Gly Ile Leu
            100                 105                 110

Gln Ser Pro Asn Asn Ala Leu Tyr Tyr Ser Lys Val Val Ile Tyr Asn
        115                 120                 125

Asp Thr Asp Lys Arg Ala Phe Val Thr Gly Tyr Asn Lys
    130                 135                 140
```

<210> SEQ ID NO 9
<211> LENGTH: 1278
<212> TYPE: DNA
<213> ORGANISM: Xenorhabdus ehlersii
<220> FEATURE:
<221> NAME/KEY: misc_feature
<222> LOCATION: (1)..(1278)
<223> OTHER INFORMATION: A nucleic acid sequence obtained from
      Xenorhabdus ehlersii strain 85823 encoding a TIC7576 PirB
      pesticidal protein sequence.

<400> SEQUENCE: 9

```
atgaatatct caccgattaa tgtatctgaa aatgaaacat tacctgaact cactgatgtt      60

atgcttattg tgccttatac aacatctacc cctgattatg aatgggatat gtcatcaatt     120

ataaaggatg cgattattgg cggcgtaggg tttattccag gagcaggctc tgcaatgtcc     180

ttcctattgg gactattttg gcctcaacag aaagataata catgggaaca gatcctccaa     240

aaagtagaac agatgataga gaatgccgtt ctgcaaacta ttaaaggaat acttaatgga     300

gatatacaag aaatcaaggg gaaaatggaa catgtgcaat acatgctgga aacctcgcct     360

ggcagtcagg aaagtcatga cgcatatatg ttcctggcta gatacctggt gagtatagat     420

gaaaaattca agtcttttga taataaaaca aactaccaga tcctgccgat gtacactaac     480

acggttatgt tacaaatccc ttattggaaa atgggaatag agaagaaaaa tgatattggg     540

ctgacagata ttgaagtcaa tgagttaaaa cagcttatcg ataaattggt cgacaaggcc     600

aagagttaca tccatacgat gtatacgaat gaatataatg atgccataaa tacatcaaca     660

gcatcgagtg tcactaataa tttactctct gtaagaggat attgtttatt acacggttta     720

gagtgtattg agttaattga acatctacaa aacaatagcc tcgaaagtgg tttttatcct     780
```

```
aaaactatca gttattcaac tgtatttgat cgtcagacta acaaaatgag aattcaggct    840

cttacagaag acgatcaaat gcaggaaccc tttaagccat ctttaatcaa cggcaaatac    900

aataaaatac aatccttgct tggatatgta caaagaattg gaaatgcacc tagagtgggg    960

ggtattaaaa tcacctttgc caacggttca tcctatacac ttggcacagt aacatcagaa   1020

acgagttcaa ttgaactcaa tgatagtgtt atcgaaagat tggaagtatg gggcaatggc   1080

gctgttgatg aggcattatt tacgttaagt gatgggcgtc aactcagagt cggtgagcgc   1140

tacgcgacaa aatatagaaa atatgctgtt gatggacact atattgcagg actgtactta   1200

gctagcgatg aaccttcact tgctggtcaa gccgcaggta ttgccgtttc ataccatatg   1260

ttggatgata aaaaataa                                                 1278


<210> SEQ ID NO 10
<211> LENGTH: 425
<212> TYPE: PRT
<213> ORGANISM: Xenorhabdus ehlersii
<220> FEATURE:
<221> NAME/KEY: MISC_FEATURE
<222> LOCATION: (1)..(425)
<223> OTHER INFORMATION: The amino acid sequence of the TIC7576 PirB
      protein.

<400> SEQUENCE: 10

Met Asn Ile Ser Pro Ile Asn Val Ser Glu Asn Glu Thr Leu Pro Glu
1               5                   10                  15

Leu Thr Asp Val Met Leu Ile Val Pro Tyr Thr Thr Ser Thr Pro Asp
            20                  25                  30

Tyr Glu Trp Asp Met Ser Ser Ile Ile Lys Asp Ala Ile Ile Gly Gly
        35                  40                  45

Val Gly Phe Ile Pro Gly Ala Gly Ser Ala Met Ser Phe Leu Leu Gly
    50                  55                  60

Leu Phe Trp Pro Gln Gln Lys Asp Asn Thr Trp Glu Gln Ile Leu Gln
65                  70                  75                  80

Lys Val Glu Gln Met Ile Glu Asn Ala Val Leu Gln Thr Ile Lys Gly
                85                  90                  95

Ile Leu Asn Gly Asp Ile Gln Glu Ile Lys Gly Lys Met Glu His Val
            100                 105                 110

Gln Tyr Met Leu Glu Thr Ser Pro Gly Ser Gln Glu Ser His Asp Ala
        115                 120                 125

Tyr Met Phe Leu Ala Arg Tyr Leu Val Ser Ile Asp Glu Lys Phe Lys
    130                 135                 140

Ser Phe Asp Asn Lys Thr Asn Tyr Gln Ile Leu Pro Met Tyr Thr Asn
145                 150                 155                 160

Thr Val Met Leu Gln Ile Pro Tyr Trp Lys Met Gly Ile Glu Lys Lys
                165                 170                 175

Asn Asp Ile Gly Leu Thr Asp Ile Glu Val Asn Glu Leu Lys Gln Leu
            180                 185                 190

Ile Asp Lys Leu Val Asp Lys Ala Lys Ser Tyr Ile His Thr Met Tyr
        195                 200                 205

Thr Asn Glu Tyr Asn Asp Ala Ile Asn Thr Ser Thr Ala Ser Ser Val
    210                 215                 220

Thr Asn Asn Leu Leu Ser Val Arg Gly Tyr Cys Leu Leu His Gly Leu
225                 230                 235                 240

Glu Cys Ile Glu Leu Ile Glu His Leu Gln Asn Asn Ser Leu Glu Ser
                245                 250                 255
```

-continued

```
Gly Phe Tyr Pro Lys Thr Ile Ser Tyr Ser Thr Val Phe Asp Arg Gln
            260                 265                 270

Thr Asn Lys Met Arg Ile Gln Ala Leu Thr Glu Asp Asp Gln Met Gln
        275                 280                 285

Glu Pro Phe Lys Pro Ser Leu Ile Asn Gly Lys Tyr Asn Lys Ile Gln
    290                 295                 300

Ser Leu Leu Gly Tyr Val Gln Arg Ile Gly Asn Ala Pro Arg Val Gly
305                 310                 315                 320

Gly Ile Lys Ile Thr Phe Ala Asn Gly Ser Ser Tyr Thr Leu Gly Thr
                325                 330                 335

Val Thr Ser Glu Thr Ser Ser Ile Glu Leu Asn Asp Ser Val Ile Glu
            340                 345                 350

Arg Leu Glu Val Trp Gly Asn Gly Ala Val Asp Glu Ala Leu Phe Thr
        355                 360                 365

Leu Ser Asp Gly Arg Gln Leu Arg Val Gly Glu Arg Tyr Ala Thr Lys
    370                 375                 380

Tyr Arg Lys Tyr Ala Val Asp Gly His Tyr Ile Ala Gly Leu Tyr Leu
385                 390                 395                 400

Ala Ser Asp Glu Pro Ser Leu Ala Gly Gln Ala Ala Gly Ile Ala Val
                405                 410                 415

Ser Tyr His Met Leu Asp Asp Lys Lys
            420                 425
```

<210> SEQ ID NO 11
<211> LENGTH: 1701
<212> TYPE: DNA
<213> ORGANISM: Artificial
<220> FEATURE:
<223> OTHER INFORMATION: A nucleic acid sequence encoding a PirAB fusion protein, TIC9316 comprised of the TIC7575 and TIC7576 coding sequences in operable linkage and in frame.

<400> SEQUENCE: 11

```
atgaatacaa tcaatataaa tataagtggc agtaccgtta cagtcataag caataacgat     60

tccaatccag aaccattaac ttataataca aacacaccag catcagaccc tcttacagcc    120

agtccttata gggatatgac aatagagcca cactcttcta ttgaagcaac aagaaccgat    180

acaccgatta ttcccgaaac tcgtcccaat tactatgtag ccaattctgg ccccgcatca    240

tcagttaggg ctgtttttta ttggtctcat tctttcacat cagaatggtt cgaatattcc    300

tctatcatag tgaaagccgg gaaagacgga atattacaat caccgaataa cgctttatat    360

tacagtaaag ttgtcattta taacgatacc gataaacgtg cctttgttac cggatataat    420

aagatgaata tctcaccgat taatgtatct gaaaatgaaa cattacctga actcactgat    480

gttatgctta ttgtgcctta tacaacatct acccctgatt atgaatggga tatgtcatca    540

attataaagg atgcgattat tggcggcgta gggtttattc caggagcagg ctctgcaatg    600

tccttcctat tgggactatt ttggcctcaa cagaaagata atacatggga acagatcctc    660

caaaaagtag aacagatgat agagaatgcc gttctgcaaa ctattaaagg aatacttaat    720

ggagatatac aagaaatcaa ggggaaaatg gaacatgtgc aatacatgct ggaaacctcg    780

cctggcagtc aggaaagtca tgacgcatat atgttcctgg ctagatacct ggtgagtata    840

gatgaaaaat tcaagtcttt tgataataaa acaaactacc agatcctgcc gatgtacact    900

aacacggtta tgttacaaat cccttattgg aaaatgggaa tagagaagaa aaatgatatt    960

gggctgacag atattgaagt caatgagtta aaacagctta tcgataaatt ggtcgacaag   1020
```

-continued

```
gccaagagtt acatccatac gatgtatacg aatgaatata atgatgccat aaatacatca   1080

acagcatcga gtgtcactaa taatttactc tctgtaagag gatattgttt attacacggt   1140

ttagagtgta ttgagttaat tgaacatcta caaaacaata gcctcgaaag tggtttttat   1200

cctaaaacta tcagttattc aactgtattt gatcgtcaga ctaacaaaat gagaattcag   1260

gctcttacag aagacgatca aatgcaggaa ccctttaagc catctttaat caacggcaaa   1320

tacaataaaa tacaatcctt gcttggatat gtacaaagaa ttggaaatgc acctagagtg   1380

gggggtatta aaatcacctt tgccaacggt tcatcctata cacttggcac agtaacatca   1440

gaaacgagtt caattgaact caatgatagt gttatcgaaa gattggaagt atggggcaat   1500

ggcgctgttg atgaggcatt atttacgtta agtgatgggc gtcaactcag agtcggtgag   1560

cgctacgcga caaaatatag aaaatatgct gttgatggac actatattgc aggactgtac   1620

ttagctagcg atgaaccttc acttgctggt caagccgcag gtattgccgt ttcataccat   1680

atgttggatg ataaaaaata a                                               1701
```

<210> SEQ ID NO 12
<211> LENGTH: 566
<212> TYPE: PRT
<213> ORGANISM: Artificial
<220> FEATURE:
<223> OTHER INFORMATION: The amino acid sequence of the TIC9316 PirAB
      fusion protein.

<400> SEQUENCE: 12

```
Met Asn Thr Ile Asn Ile Asn Ile Ser Gly Ser Thr Val Thr Val Ile
1               5                   10                  15

Ser Asn Asn Asp Ser Asn Pro Glu Pro Leu Thr Tyr Asn Thr Asn Thr
            20                  25                  30

Pro Ala Ser Asp Pro Leu Thr Ala Ser Pro Tyr Arg Asp Met Thr Ile
        35                  40                  45

Glu Pro His Ser Ser Ile Glu Ala Thr Arg Thr Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Glu Trp
                85                  90                  95

Phe Glu Tyr Ser Ser Ile Ile Val Lys Ala Gly Lys Asp Gly Ile Leu
            100                 105                 110

Gln Ser Pro Asn Asn Ala Leu Tyr Tyr Ser Lys Val Val Ile Tyr Asn
        115                 120                 125

Asp Thr Asp Lys Arg Ala Phe Val Thr Gly Tyr Asn Lys Met Asn Ile
    130                 135                 140

Ser Pro Ile Asn Val Ser Glu Asn Glu Thr Leu Pro Glu Leu Thr Asp
145                 150                 155                 160

Val Met Leu Ile Val Pro Tyr Thr Thr Ser Thr Pro Asp Tyr Glu Trp
                165                 170                 175

Asp Met Ser Ser Ile Ile Lys Asp Ala Ile Ile Gly Gly Val Gly Phe
            180                 185                 190

Ile Pro Gly Ala Gly Ser Ala Met Ser Phe Leu Leu Gly Leu Phe Trp
        195                 200                 205

Pro Gln Gln Lys Asp Asn Thr Trp Glu Gln Ile Leu Gln Lys Val Glu
    210                 215                 220

Gln Met Ile Glu Asn Ala Val Leu Gln Thr Ile Lys Gly Ile Leu Asn
225                 230                 235                 240
```

```
Gly Asp Ile Gln Glu Ile Lys Gly Lys Met Glu His Val Gln Tyr Met
                245                 250                 255

Leu Glu Thr Ser Pro Gly Ser Gln Glu Ser His Asp Ala Tyr Met Phe
            260                 265                 270

Leu Ala Arg Tyr Leu Val Ser Ile Asp Glu Lys Phe Lys Ser Phe Asp
        275                 280                 285

Asn Lys Thr Asn Tyr Gln Ile Leu Pro Met Tyr Thr Asn Thr Val Met
    290                 295                 300

Leu Gln Ile Pro Tyr Trp Lys Met Gly Ile Glu Lys Lys Asn Asp Ile
305                 310                 315                 320

Gly Leu Thr Asp Ile Glu Val Asn Glu Leu Lys Gln Leu Ile Asp Lys
                325                 330                 335

Leu Val Asp Lys Ala Lys Ser Tyr Ile His Thr Met Tyr Thr Asn Glu
            340                 345                 350

Tyr Asn Asp Ala Ile Asn Thr Ser Thr Ala Ser Ser Val Thr Asn Asn
        355                 360                 365

Leu Leu Ser Val Arg Gly Tyr Cys Leu Leu His Gly Leu Glu Cys Ile
    370                 375                 380

Glu Leu Ile Glu His Leu Gln Asn Asn Ser Leu Glu Ser Gly Phe Tyr
385                 390                 395                 400

Pro Lys Thr Ile Ser Tyr Ser Thr Val Phe Asp Arg Gln Thr Asn Lys
                405                 410                 415

Met Arg Ile Gln Ala Leu Thr Glu Asp Asp Gln Met Gln Glu Pro Phe
            420                 425                 430

Lys Pro Ser Leu Ile Asn Gly Lys Tyr Asn Lys Ile Gln Ser Leu Leu
        435                 440                 445

Gly Tyr Val Gln Arg Ile Gly Asn Ala Pro Arg Val Gly Gly Ile Lys
    450                 455                 460

Ile Thr Phe Ala Asn Gly Ser Ser Tyr Thr Leu Gly Thr Val Thr Ser
465                 470                 475                 480

Glu Thr Ser Ser Ile Glu Leu Asn Asp Ser Val Ile Glu Arg Leu Glu
                485                 490                 495

Val Trp Gly Asn Gly Ala Val Asp Glu Ala Leu Phe Thr Leu Ser Asp
            500                 505                 510

Gly Arg Gln Leu Arg Val Gly Glu Arg Tyr Ala Thr Lys Tyr Arg Lys
        515                 520                 525

Tyr Ala Val Asp Gly His Tyr Ile Ala Gly Leu Tyr Leu Ala Ser Asp
    530                 535                 540

Glu Pro Ser Leu Ala Gly Gln Ala Ala Gly Ile Ala Val Ser Tyr His
545                 550                 555                 560

Met Leu Asp Asp Lys Lys
                565
```

<210> SEQ ID NO 13
<211> LENGTH: 426
<212> TYPE: DNA
<213> ORGANISM: Xenorhabdus cabanillasii
<220> FEATURE:
<221> NAME/KEY: misc_feature
<222> LOCATION: (1)..(426)
<223> OTHER INFORMATION: A nucleic acid sequence obtained from Xenorhabdus cabanillasii strain 85908 encoding a TIC7660 PirA pesticidal protein sequence.

<400> SEQUENCE: 13

```
atgatcacaa taaatataaa tgtaaacggc aatgatgtta caggtacaaa taataatgaa      60
```

```
cctactccag tatcgacaac ttacggtcca aatacaccag catcagaacc ccctgtagtc    120

agtaattata gtgatataac aatagaaccg cattcttctg tgcaggcaac aagaattgat    180

acgcctgtta ttcctgaagc acgccccgat tactatgtag ccaactccgg ccctgcacca    240

tcagttaggg ctgtttttta ttggtctcat tctttcacat cagaatggtt cgaatcttcc    300

tctatcacag tgaaagcagg agaggacgga atattaaaag cacctggtaa ctctttatat    360

tacagcaaag tcgtcattta taatgatacg gataaacgag cctttgttac tggatataat    420

aaataa                                                               426
```

<210> SEQ ID NO 14
<211> LENGTH: 141
<212> TYPE: PRT
<213> ORGANISM: Xenorhabdus cabanillasii
<220> FEATURE:
<221> NAME/KEY: MISC_FEATURE
<222> LOCATION: (1)..(141)
<223> OTHER INFORMATION: The amino acid sequence of the TIC7660 PirA protein.

<400> SEQUENCE: 14

```
Met Ile Thr Ile Asn Ile Asn Val Asn Gly Asn Asp Val Thr Gly Thr
1               5                   10                  15

Asn Asn Asn Glu Pro Thr Pro Val Ser Thr Thr Tyr Gly Pro Asn Thr
            20                  25                  30

Pro Ala Ser Glu Pro Pro Val Val Ser Asn Tyr Ser Asp Ile Thr Ile
        35                  40                  45

Glu Pro His Ser Ser Val Gln Ala Thr Arg Ile Asp Thr Pro Val Ile
    50                  55                  60

Pro Glu Ala Arg Pro Asp Tyr Tyr Val Ala Asn Ser Gly Pro Ala Pro
65                  70                  75                  80

Ser Val Arg Ala Val Phe Tyr Trp Ser His Ser Phe Thr Ser Glu Trp
                85                  90                  95

Phe Glu Ser Ser Ser Ile Thr Val Lys Ala Gly Glu Asp Gly Ile Leu
            100                 105                 110

Lys Ala Pro Gly Asn Ser Leu Tyr Tyr Ser Lys Val Val Ile Tyr Asn
        115                 120                 125

Asp Thr Asp Lys Arg Ala Phe Val Thr Gly Tyr Asn Lys
    130                 135                 140
```

<210> SEQ ID NO 15
<211> LENGTH: 1278
<212> TYPE: DNA
<213> ORGANISM: Xenorhabdus cabanillasii
<220> FEATURE:
<221> NAME/KEY: misc_feature
<222> LOCATION: (1)..(1278)
<223> OTHER INFORMATION: A nucleic acid sequence obtained from Xenorhabdus cabanillasii strain 85908 encoding a TIC7661 PirB pesticidal protein sequence.

<400> SEQUENCE: 15

```
atgaatacta cacctattac tgtatctaca aatgaaacat cgcctttaat gactgacgta     60

atgcccatgg atctttatgc aatatccaca cctgattatg aatgggacat gtcgtcaatc    120

ataaaggatg ctgttattgg tggcatagga tttattccag gtccgggccc ggcaatatcc    180

ttcctgttag ggctattttg gcctcagcag aaagacaata cttgggagca aattctccag    240

aaagtagagc agatgataga gaatgctgtt ctacaaacta ttaaaggaat acttaatgga    300
```

-continued

```
gaagttcaag agatcaaagg gaaaatggaa catgtagaat ccatgctgaa aaactcgcct    360

ggcagtcagg aaagtcatga tgcatatatg ttcctggcga gatatctggt tagtatagat    420

gaaaaattca aatcttttga caatagaaca aattaccagc ttctcccaat gtatactaac    480

actattatgt tacagatccc ttattggaaa atgggaatag agaagaaaaa agatattggg    540

ctgacagata ttgaagttaa tgaattaaaa gaacttatcg ataaattggt tgataaggcc    600

aaaaactata ttcatacgat gtatactaat gaacataata atgctgtaaa cacatcaaca    660

gcagagagtg tcactaataa tttattatct gtaagaggat attgtttatt acacggttta    720

gaatgtattg agttaatcga gcatatacag aataatagcc ttgagagtgg tttctatcct    780

aaaattatca gttattcgac tgcgtttgat cgtcctacta acaaaatgag aattcaggct    840

cttacagaag atgatgcaat gcaggagcct ttcaaaccat ctttaatcaa tgggaaatat    900

aataaaatcc aatccttgac tggatatgta caaagaattg ggaatgcacc tagagttggt    960

ggtatcagaa tcacatttac caacggctca tcttatacac ttggtacagt gacctcagaa   1020

acgcattcaa ttaagctaaa cgatagtgtt atcgaaagct tggaagtatg gggaatggt    1080

gctgttgatg aggcgttatt taagttaagt gatgggcgtt tattgcgtat tggtgagcgc   1140

tacgcgaaaa aatacagaaa atatgctgtt gataatcact atattgcggg gatttactta   1200

gccagcgatg agccttcact tgctggtcaa gccgcaggta ttgccgtttc atatcatatg   1260

atggctgaca aaaaataa                                                 1278
```

<210> SEQ ID NO 16
<211> LENGTH: 425
<212> TYPE: PRT
<213> ORGANISM: Xenorhabdus cabanillasii
<220> FEATURE:
<221> NAME/KEY: MISC_FEATURE
<222> LOCATION: (1)..(425)
<223> OTHER INFORMATION: The amino acid sequence of the TIC7661 PirB protein.

<400> SEQUENCE: 16

```
Met Asn Thr Thr Pro Ile Thr Val Ser Thr Asn Glu Thr Ser Pro Leu
1               5                   10                  15

Met Thr Asp Val Met Pro Met Asp Leu Tyr Ala Ile Ser Thr Pro Asp
            20                  25                  30

Tyr Glu Trp Asp Met Ser Ser Ile Ile Lys Asp Ala Val Ile Gly Gly
        35                  40                  45

Ile Gly Phe Ile Pro Gly Pro Gly Pro Ala Ile Ser Phe Leu Leu Gly
    50                  55                  60

Leu Phe Trp Pro Gln Gln Lys Asp Asn Thr Trp Glu Gln Ile Leu Gln
65                  70                  75                  80

Lys Val Glu Gln Met Ile Glu Asn Ala Val Leu Gln Thr Ile Lys Gly
                85                  90                  95

Ile Leu Asn Gly Glu Val Gln Glu Ile Lys Gly Lys Met Glu His Val
            100                 105                 110

Glu Ser Met Leu Lys Asn Ser Pro Gly Ser Gln Glu Ser His Asp Ala
        115                 120                 125

Tyr Met Phe Leu Ala Arg Tyr Leu Val Ser Ile Asp Glu Lys Phe Lys
    130                 135                 140

Ser Phe Asp Asn Arg Thr Asn Tyr Gln Leu Leu Pro Met Tyr Thr Asn
145                 150                 155                 160

Thr Ile Met Leu Gln Ile Pro Tyr Trp Lys Met Gly Ile Glu Lys Lys
                165                 170                 175
```

```
Lys Asp Ile Gly Leu Thr Asp Ile Glu Val Asn Glu Leu Lys Glu Leu
            180                 185                 190

Ile Asp Lys Leu Val Asp Lys Ala Lys Asn Tyr Ile His Thr Met Tyr
        195                 200                 205

Thr Asn Glu His Asn Asn Ala Val Asn Thr Ser Thr Ala Glu Ser Val
    210                 215                 220

Thr Asn Asn Leu Leu Ser Val Arg Gly Tyr Cys Leu Leu His Gly Leu
225                 230                 235                 240

Glu Cys Ile Glu Leu Ile Glu His Ile Gln Asn Asn Ser Leu Glu Ser
                245                 250                 255

Gly Phe Tyr Pro Lys Ile Ile Ser Tyr Ser Thr Ala Phe Asp Arg Pro
            260                 265                 270

Thr Asn Lys Met Arg Ile Gln Ala Leu Thr Glu Asp Asp Ala Met Gln
        275                 280                 285

Glu Pro Phe Lys Pro Ser Leu Ile Asn Gly Lys Tyr Asn Lys Ile Gln
    290                 295                 300

Ser Leu Thr Gly Tyr Val Gln Arg Ile Gly Asn Ala Pro Arg Val Gly
305                 310                 315                 320

Gly Ile Arg Ile Thr Phe Thr Asn Gly Ser Ser Tyr Thr Leu Gly Thr
                325                 330                 335

Val Thr Ser Glu Thr His Ser Ile Lys Leu Asn Asp Ser Val Ile Glu
            340                 345                 350

Ser Leu Glu Val Trp Gly Asn Gly Ala Val Asp Glu Ala Leu Phe Lys
        355                 360                 365

Leu Ser Asp Gly Arg Leu Leu Arg Ile Gly Glu Arg Tyr Ala Lys Lys
    370                 375                 380

Tyr Arg Lys Tyr Ala Val Asp Asn His Tyr Ile Ala Gly Ile Tyr Leu
385                 390                 395                 400

Ala Ser Asp Glu Pro Ser Leu Ala Gly Gln Ala Ala Gly Ile Ala Val
                405                 410                 415

Ser Tyr His Met Met Ala Asp Lys Lys
            420                 425
```

<210> SEQ ID NO 17
<211> LENGTH: 1701
<212> TYPE: DNA
<213> ORGANISM: Artificial
<220> FEATURE:
<223> OTHER INFORMATION: A nucleic acid sequence encoding a PirAB fusion protein, TIC9317 comprised of the TIC7660 and TIC7661 coding sequences in operable linkage and in frame.

<400> SEQUENCE: 17

```
atgatcacaa taaatataaa tgtaaacggc aatgatgtta caggtacaaa taataatgaa      60

cctactccag tatcgacaac ttacggtcca aatacaccag catcagaacc ccctgtagtc     120

agtaattata gtgatataac aatagaaccg cattcttctg tgcaggcaac aagaattgat     180

acgcctgtta ttcctgaagc acgccccgat tactatgtag ccaactccgg ccctgcacca     240

tcagttaggg ctgtttttta ttggtctcat tctttcacat cagaatggtt cgaatcttcc     300

tctatcacag tgaaagcagg agaggacgga atattaaaag cacctggtaa ctctttatat     360

tacagcaaag tcgtcattta taatgatacg gataaacgag cctttgttac tggatataat     420

aaaatgaata ctacacctat tactgtatct acaaatgaaa catcgccttt aatgactgac     480

gtaatgccca tggatcttta tgcaatatcc acacctgatt atgaatggga catgtcgtca     540
```

```
atcataaagg atgctgttat tggtggcata ggatttattc caggtccggg cccggcaata    600

tccttcctgt tagggctatt ttggcctcag cagaaagaca atacttggga gcaaattctc    660

cagaaagtag agcagatgat agagaatgct gttctacaaa ctattaaagg aatacttaat    720

ggagaagttc aagagatcaa agggaaaatg gaacatgtag aatccatgct gaaaaactcg    780

cctggcagtc aggaaagtca tgatgcatat atgttcctgg cgagatatct ggttagtata    840

gatgaaaaat tcaaatcttt tgacaataga acaaattacc agcttctccc aatgtatact    900

aacactatta tgttacagat cccttattgg aaaatgggaa tagagaagaa aaaagatatt    960

gggctgacag atattgaagt taatgaatta aaagaactta tcgataaatt ggttgataag   1020

gccaaaaact atattcatac gatgtatact aatgaacata ataatgctgt aaacacatca   1080

acagcagaga gtgtcactaa taatttatta tctgtaagag gatattgttt attacacggt   1140

ttagaatgta ttgagttaat cgagcatata cagaataata gccttgagag tggtttctat   1200

cctaaaatta tcagttattc gactgcgttt gatcgtccta ctaacaaaat gagaattcag   1260

gctcttacag aagatgatgc aatgcaggag cctttcaaac catctttaat caatgggaaa   1320

tataataaaa tccaatcctt gactggatat gtacaaagaa ttgggaatgc acctagagtt   1380

ggtggtatca gaatcacatt taccaacggc tcatcttata cacttggtac agtgacctca   1440

gaaacgcatt caattaagct aaacgatagt gttatcgaaa gcttggaagt atgggggaat   1500

ggtgctgttg atgaggcgtt atttaagtta agtgatgggc gtttattgcg tattggtgag   1560

cgctacgcga aaaaatacag aaaatatgct gttgataatc actatattgc ggggatttac   1620

ttagccagcg atgagccttc acttgctggt caagccgcag gtattgccgt ttcatatcat   1680

atgatggctg acaaaaaata a                                             1701
```

<210> SEQ ID NO 18
<211> LENGTH: 566
<212> TYPE: PRT
<213> ORGANISM: Artificial
<220> FEATURE:
<223> OTHER INFORMATION: The amino acid sequence of the TIC9317 PirAB fusion protein.

<400> SEQUENCE: 18

```
Met Ile Thr Ile Asn Ile Asn Val Asn Gly Asn Asp Val Thr Gly Thr
1               5                   10                  15

Asn Asn Asn Glu Pro Thr Pro Val Ser Thr Thr Tyr Gly Pro Asn Thr
            20                  25                  30

Pro Ala Ser Glu Pro Pro Val Val Ser Asn Tyr Ser Asp Ile Thr Ile
        35                  40                  45

Glu Pro His Ser Ser Val Gln Ala Thr Arg Ile Asp Thr Pro Val Ile
    50                  55                  60

Pro Glu Ala Arg Pro Asp Tyr Tyr Val Ala Asn Ser Gly Pro Ala Pro
65                  70                  75                  80

Ser Val Arg Ala Val Phe Tyr Trp Ser His Ser Phe Thr Ser Glu Trp
                85                  90                  95

Phe Glu Ser Ser Ser Ile Thr Val Lys Ala Gly Glu Asp Gly Ile Leu
            100                 105                 110

Lys Ala Pro Gly Asn Ser Leu Tyr Tyr Ser Lys Val Val Ile Tyr Asn
        115                 120                 125

Asp Thr Asp Lys Arg Ala Phe Val Thr Gly Tyr Asn Lys Met Asn Thr
    130                 135                 140

Thr Pro Ile Thr Val Ser Thr Asn Glu Thr Ser Pro Leu Met Thr Asp
```

```
145                 150                 155                 160

Val Met Pro Met Asp Leu Tyr Ala Ile Ser Thr Pro Asp Tyr Glu Trp
                165                 170                 175

Asp Met Ser Ser Ile Ile Lys Asp Ala Val Ile Gly Gly Ile Gly Phe
            180                 185                 190

Ile Pro Gly Pro Gly Pro Ala Ile Ser Phe Leu Leu Gly Leu Phe Trp
        195                 200                 205

Pro Gln Gln Lys Asp Asn Thr Trp Glu Gln Ile Leu Gln Lys Val Glu
    210                 215                 220

Gln Met Ile Glu Asn Ala Val Leu Gln Thr Ile Lys Gly Ile Leu Asn
225                 230                 235                 240

Gly Glu Val Gln Glu Ile Lys Gly Lys Met Glu His Val Glu Ser Met
                245                 250                 255

Leu Lys Asn Ser Pro Gly Ser Gln Glu Ser His Asp Ala Tyr Met Phe
            260                 265                 270

Leu Ala Arg Tyr Leu Val Ser Ile Asp Glu Lys Phe Lys Ser Phe Asp
        275                 280                 285

Asn Arg Thr Asn Tyr Gln Leu Leu Pro Met Tyr Thr Asn Thr Ile Met
    290                 295                 300

Leu Gln Ile Pro Tyr Trp Lys Met Gly Ile Glu Lys Lys Lys Asp Ile
305                 310                 315                 320

Gly Leu Thr Asp Ile Glu Val Asn Glu Leu Lys Glu Leu Ile Asp Lys
                325                 330                 335

Leu Val Asp Lys Ala Lys Asn Tyr Ile His Thr Met Tyr Thr Asn Glu
            340                 345                 350

His Asn Asn Ala Val Asn Thr Ser Thr Ala Glu Ser Val Thr Asn Asn
        355                 360                 365

Leu Leu Ser Val Arg Gly Tyr Cys Leu Leu His Gly Leu Glu Cys Ile
    370                 375                 380

Glu Leu Ile Glu His Ile Gln Asn Asn Ser Leu Glu Ser Gly Phe Tyr
385                 390                 395                 400

Pro Lys Ile Ile Ser Tyr Ser Thr Ala Phe Asp Arg Pro Thr Asn Lys
                405                 410                 415

Met Arg Ile Gln Ala Leu Thr Glu Asp Asp Ala Met Gln Glu Pro Phe
            420                 425                 430

Lys Pro Ser Leu Ile Asn Gly Lys Tyr Asn Lys Ile Gln Ser Leu Thr
        435                 440                 445

Gly Tyr Val Gln Arg Ile Gly Asn Ala Pro Arg Val Gly Gly Ile Arg
    450                 455                 460

Ile Thr Phe Thr Asn Gly Ser Ser Tyr Thr Leu Gly Thr Val Thr Ser
465                 470                 475                 480

Glu Thr His Ser Ile Lys Leu Asn Asp Ser Val Ile Glu Ser Leu Glu
                485                 490                 495

Val Trp Gly Asn Gly Ala Val Asp Glu Ala Leu Phe Lys Leu Ser Asp
            500                 505                 510

Gly Arg Leu Leu Arg Ile Gly Glu Arg Tyr Ala Lys Lys Tyr Arg Lys
        515                 520                 525

Tyr Ala Val Asp Asn His Tyr Ile Ala Gly Ile Tyr Leu Ala Ser Asp
    530                 535                 540

Glu Pro Ser Leu Ala Gly Gln Ala Ala Gly Ile Ala Val Ser Tyr His
545                 550                 555                 560

Met Met Ala Asp Lys Lys
                565
```

<210> SEQ ID NO 19
<211> LENGTH: 420
<212> TYPE: DNA
<213> ORGANISM: Xenorhabdus ehlersii
<220> FEATURE:
<221> NAME/KEY: misc_feature
<222> LOCATION: (1)..(420)
<223> OTHER INFORMATION: A nucleic acid sequence obtained from Xenorhabdus ehlersii strain 85887 encoding a TIC7662 PirA pesticidal protein sequence.

<400> SEQUENCE: 19

```
atgagtacaa tcaatatcaa tataagtagc agtaccgtta ccgtcatcac gaataacgga      60

gaaacgccag tcccactcac ttacaataca aatacacctg aatcagaacc tcttaccgtc     120

aatccttata gggatatgac aatagagcca cgctcttcta ttgaagcaac aaggattgat     180

acaccgatta ttcccgaaac acgccctaat tattatgtag ccaattcagg cccggcttca     240

tcagttaggg ccgtttttta ttggtcccat tctttcacat cacaatggtt cgaatattcc     300

tctatcatcg tcaaagccgg ggaagatggc atattagaat caccaagcaa ttctttatat     360

tacagcaaag tcgtcattta taatgatacc gataaacgcg cctttgtgac gggatataat     420
```

<210> SEQ ID NO 20
<211> LENGTH: 141
<212> TYPE: PRT
<213> ORGANISM: Xenorhabdus ehlersii
<220> FEATURE:
<221> NAME/KEY: MISC_FEATURE
<222> LOCATION: (1)..(141)
<223> OTHER INFORMATION: The amino acid sequence of the TIC7662 PirA protein.

<400> SEQUENCE: 20

```
Met Ser Thr Ile Asn Ile Asn Ile Ser Ser Ser Thr Val Thr Val Ile
1               5                   10                  15

Thr Asn Asn Gly Glu Thr Pro Val Pro Leu Thr Tyr Asn Thr Asn Thr
            20                  25                  30

Pro Glu Ser Glu Pro Leu Thr Val Asn Pro Tyr Arg Asp Met Thr Ile
        35                  40                  45

Glu Pro Arg Ser Ser Ile Glu Ala Thr Arg Ile Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Gln Trp
                85                  90                  95

Phe Glu Tyr Ser Ser Ile Ile Val Lys Ala Gly Glu Asp Gly Ile Leu
            100                 105                 110

Glu Ser Pro Ser Asn Ser Leu Tyr Tyr Ser Lys Val Val Ile Tyr Asn
        115                 120                 125

Asp Thr Asp Lys Arg Ala Phe Val Thr Gly Tyr Asn Lys
    130                 135                 140
```

<210> SEQ ID NO 21
<211> LENGTH: 1278
<212> TYPE: DNA
<213> ORGANISM: Xenorhabdus ehlersii
<220> FEATURE:
<221> NAME/KEY: misc_feature
<222> LOCATION: (1)..(1278)
<223> OTHER INFORMATION: A nucleic acid sequence obtained from Xenorhabdus ehlersii strain 85887 encoding a TIC7663 PirB -continued pesticidal protein sequence.

<400> SEQUENCE: 21
atgaatacca ctctgattaa tgtatctgaa aaagaaacat tgcctgtaca aactgatatc 60
atgcttatcg cgccttattc agtatcgacc cccgattatg aatgggatat gtcctcactc 120
atcaaggatg ccattattgg tggcgtaggg tttattcccg tcgtaggttc cgcaatgtcc 180
ttcctgctag gattattttg gccccaacag aaagataata cttgggagca aattctccaa 240
aaagtcgagc agatgatcga gaatgcccag ctaaatacga ttaaaggaat acttaatggc 300
gatatacaag agatcaaagg aaaaatggag catgtacaat acatgttgga aacctcgccg 360
ggcagtcaag aaagtcatga tgcctatatg ttcctggcca gatatctggt gagtatcgat 420
gagaaattta agtcttttga taataaaaca aactatcaaa ttttgccgat gtatacgaac 480
acggttatgt tgcagatccc ttattggaaa atggggatcg agaagaaaaa tgatattggg 540
ctgaccgata ttgaagtcaa tgagttaaaa cagcttatcg acacattggt tgacagagcc 600
aggaactata ttcatacgat gtatgaaaga gaatatgata atgccatcaa cacctcaacc 660
gcggcgagcg tcactaataa tttattgtcc gtcagaggat attgcctgtt acacggttta 720
gagtgtattg aaaccattga acatctgcaa aataatagcc ttaatagtgg tttctatcct 780
aaaaccatta gttattcaac ggtatttgat cgtcccacga acaaaacgag aattcaggct 840
ctgaccgaag atgaccaaat gcaagagcct ttcaagccag ctttaattgg cggtaagtac 900 aataaaaataa aatcattgct tggctatgta cgaagaattg ggaatgcccc cagagtgggg 960
ggaattaagg tcacctttac caacggatca tcttatacac ttggcacagt cacatcagaa 1020
acggactcaa ttgagctaaa tgagagtgtt atcgaaagat tagaagtatg gggcaatggt 1080
gctgttgatg aggcattatt tacgttaagc gatgggcgcc aactcaggat cggcgagcgc 1140
tacgcgaaaa aatacagaaa atatgctgtt gatggacact atatttcagg gctgtactta 1200
gccagcgatg aaccttccct tgctggtcag gccgcaggta ttgccgtttc ataccatatg 1260
cttgctgata aaaaataa 1278

<210> SEQ ID NO 22
<211> LENGTH: 425
<212> TYPE: PRT
<213> ORGANISM: Xenorhabdus ehlersii
<220> FEATURE:
<221> NAME/KEY: MISC_FEATURE
<222> LOCATION: (1)..(425)
<223> OTHER INFORMATION: The amino acid sequence of the TIC7663 PirB protein.

<400> SEQUENCE: 22

Met Asn Thr Thr Leu Ile Asn Val Ser Glu Lys Glu Thr Leu Pro Val
1 5 10 15

Gln Thr Asp Ile Met Leu Ile Ala Pro Tyr Ser Val Ser Thr Pro Asp
20 25 30

Tyr Glu Trp Asp Met Ser Ser Leu Ile Lys Asp Ala Ile Ile Gly Gly
35 40 45

Val Gly Phe Ile Pro Val Val Gly Ser Ala Met Ser Phe Leu Leu Gly
50 55 60

Leu Phe Trp Pro Gln Gln Lys Asp Asn Thr Trp Glu Gln Ile Leu Gln
65 70 75 80

Lys Val Glu Gln Met Ile Glu Asn Ala Gln Leu Asn Thr Ile Lys Gly
85 90 95

-continued

```
Ile Leu Asn Gly Asp Ile Gln Glu Ile Lys Gly Lys Met Glu His Val
            100                 105                 110

Gln Tyr Met Leu Glu Thr Ser Pro Gly Ser Gln Glu Ser His Asp Ala
        115                 120                 125

Tyr Met Phe Leu Ala Arg Tyr Leu Val Ser Ile Asp Glu Lys Phe Lys
    130                 135                 140

Ser Phe Asp Asn Lys Thr Asn Tyr Gln Ile Leu Pro Met Tyr Thr Asn
145                 150                 155                 160

Thr Val Met Leu Gln Ile Pro Tyr Trp Lys Met Gly Ile Glu Lys Lys
                165                 170                 175

Asn Asp Ile Gly Leu Thr Asp Ile Glu Val Asn Glu Leu Lys Gln Leu
            180                 185                 190

Ile Asp Thr Leu Val Asp Arg Ala Arg Asn Tyr Ile His Thr Met Tyr
        195                 200                 205

Glu Arg Glu Tyr Asp Asn Ala Ile Asn Thr Ser Thr Ala Ala Ser Val
    210                 215                 220

Thr Asn Asn Leu Leu Ser Val Arg Gly Tyr Cys Leu Leu His Gly Leu
225                 230                 235                 240

Glu Cys Ile Glu Thr Ile Glu His Leu Gln Asn Asn Ser Leu Asn Ser
                245                 250                 255

Gly Phe Tyr Pro Lys Thr Ile Ser Tyr Ser Thr Val Phe Asp Arg Pro
            260                 265                 270

Thr Asn Lys Thr Arg Ile Gln Ala Leu Thr Glu Asp Asp Gln Met Gln
        275                 280                 285

Glu Pro Phe Lys Pro Ala Leu Ile Gly Gly Lys Tyr Asn Lys Ile Lys
    290                 295                 300

Ser Leu Leu Gly Tyr Val Arg Arg Ile Gly Asn Ala Pro Arg Val Gly
305                 310                 315                 320

Gly Ile Lys Val Thr Phe Thr Asn Gly Ser Ser Tyr Thr Leu Gly Thr
                325                 330                 335

Val Thr Ser Glu Thr Asp Ser Ile Glu Leu Asn Glu Ser Val Ile Glu
            340                 345                 350

Arg Leu Glu Val Trp Gly Asn Gly Ala Val Asp Glu Ala Leu Phe Thr
        355                 360                 365

Leu Ser Asp Gly Arg Gln Leu Arg Ile Gly Glu Arg Tyr Ala Lys Lys
    370                 375                 380

Tyr Arg Lys Tyr Ala Val Asp Gly His Tyr Ile Ser Gly Leu Tyr Leu
385                 390                 395                 400

Ala Ser Asp Glu Pro Ser Leu Ala Gly Gln Ala Ala Gly Ile Ala Val
                405                 410                 415

Ser Tyr His Met Leu Ala Asp Lys Lys
            420                 425
```

<210> SEQ ID NO 23
<211> LENGTH: 1701
<212> TYPE: DNA
<213> ORGANISM: Artificial
<220> FEATURE:
<223> OTHER INFORMATION: A nucleic acid sequence encoding a PirAB fusion protein, TIC9318 comprised of the TIC7662 and TIC7663 coding sequences in operable linkage and in frame.

<400> SEQUENCE: 23

```
atgagtacaa tcaatatcaa tataagtagc agtaccgtta ccgtcatcac gaataacgga      60

gaaacgccag tcccactcac ttacaataca aatacacctg aatcagaacc tcttaccgtc     120
```

-continued

```
aatccttata gggatatgac aatagagcca cgctcttcta ttgaagcaac aaggattgat    180

acaccgatta ttcccgaaac acgccctaat tattatgtag ccaattcagg cccggcttca    240

tcagttaggg ccgtttttta ttggtcccat tctttcacat cacaatggtt cgaatattcc    300

tctatcatcg tcaaagccgg ggaagatggc atattagaat caccaagcaa ttctttatat    360

tacagcaaag tcgtcattta taatgatacc gataaacgcg cctttgtgac gggatataat    420

aagatgaata ccactctgat taatgtatct gaaaaagaaa cattgcctgt acaaactgat    480

atcatgctta tcgcgcctta ttcagtatcg acccccgatt atgaatggga tatgtcctca    540

ctcatcaagg atgccattat tggtggcgta gggtttattc ccgtcgtagg ttccgcaatg    600

tccttcctgc taggattatt ttggccccaa cagaaagata atacttggga gcaaattctc    660

caaaaagtcg agcagatgat cgagaatgcc cagctaaata cgattaaagg aatacttaat    720

ggcgatatac aagagatcaa aggaaaaatg gagcatgtac aatacatgtt ggaaacctcg    780

ccgggcagtc aagaaagtca tgatgcctat atgttcctgg ccagatatct ggtgagtatc    840

gatgagaaat ttaagtcttt tgataataaa acaaactatc aaattttgcc gatgtatacg    900

aacacggtta tgttgcagat ccccttattgg aaaatgggga tcgagaagaa aaatgatatt    960

gggctgaccg atattgaagt caatgagtta aaacagctta tcgacacatt ggttgacaga   1020

gccaggaact atattcatac gatgtatgaa agagaatatg ataatgccat caacacctca   1080

accgcggcga gcgtcactaa taatttattg tccgtcagag gatattgcct gttacacggt   1140

ttagagtgta ttgaaaccat tgaacatctg caaaataata gccttaatag tggtttctat   1200

cctaaaacca ttagttattc aacggtattt gatcgtccca cgaacaaaac gagaattcag   1260

gctctgaccg aagatgacca aatgcaagag cctttcaagc cagctttaat tggcggtaag   1320

tacaataaaa taaaatcatt gcttggctat gtacgaagaa ttgggaatgc ccccagagtg   1380

gggggaatta aggtcacctt taccaacgga tcatcttata cacttggcac agtcacatca   1440

gaaacggact caattgagct aaatgagagt gttatcgaaa gattagaagt atggggcaat   1500

ggtgctgttg atgaggcatt atttacgtta agcgatgggc gccaactcag gatcggcgag   1560

cgctacgcga aaaaatacag aaaatatgct gttgatggac actatatttc agggctgtac   1620

ttagccagcg atgaaccttc ccttgctggt caggccgcag gtattgccgt ttcataccat   1680

atgcttgctg ataaaaaata a                                              1701
```

```
<210> SEQ ID NO 24
<211> LENGTH: 566
<212> TYPE: PRT
<213> ORGANISM: Artificial
<220> FEATURE:
<223> OTHER INFORMATION: The amino acid sequence of the TIC9318 PirAB
      fusion protein.

<400> SEQUENCE: 24

Met Ser Thr Ile Asn Ile Asn Ile Ser Ser Ser Thr Val Thr Val Ile
1               5                   10                  15

Thr Asn Asn Gly Glu Thr Pro Val Pro Leu Thr Tyr Asn Thr Asn Thr
            20                  25                  30

Pro Glu Ser Glu Pro Leu Thr Val Asn Pro Tyr Arg Asp Met Thr Ile
        35                  40                  45

Glu Pro Arg Ser Ser Ile Glu Ala Thr Arg Ile Asp Thr Pro Ile Ile
    50                  55                  60

Pro Glu Thr Arg Pro Asn Tyr Tyr Val Ala Asn Ser Gly Pro Ala Ser
65                  70                  75                  80
```

-continued

```
Ser Val Arg Ala Val Phe Tyr Trp Ser His Ser Phe Thr Ser Gln Trp
                85                  90                  95

Phe Glu Tyr Ser Ser Ile Ile Val Lys Ala Gly Glu Asp Gly Ile Leu
            100                 105                 110

Glu Ser Pro Ser Asn Ser Leu Tyr Tyr Ser Lys Val Val Ile Tyr Asn
        115                 120                 125

Asp Thr Asp Lys Arg Ala Phe Val Thr Gly Tyr Asn Lys Met Asn Thr
    130                 135                 140

Thr Leu Ile Asn Val Ser Glu Lys Glu Thr Leu Pro Val Gln Thr Asp
145                 150                 155                 160

Ile Met Leu Ile Ala Pro Tyr Ser Val Ser Thr Pro Asp Tyr Glu Trp
                165                 170                 175

Asp Met Ser Ser Leu Ile Lys Asp Ala Ile Ile Gly Gly Val Gly Phe
            180                 185                 190

Ile Pro Val Val Gly Ser Ala Met Ser Phe Leu Leu Gly Leu Phe Trp
        195                 200                 205

Pro Gln Gln Lys Asp Asn Thr Trp Glu Gln Ile Leu Gln Lys Val Glu
    210                 215                 220

Gln Met Ile Glu Asn Ala Gln Leu Asn Thr Ile Lys Gly Ile Leu Asn
225                 230                 235                 240

Gly Asp Ile Gln Glu Ile Lys Gly Lys Met Glu His Val Gln Tyr Met
                245                 250                 255

Leu Glu Thr Ser Pro Gly Ser Gln Glu Ser His Asp Ala Tyr Met Phe
            260                 265                 270

Leu Ala Arg Tyr Leu Val Ser Ile Asp Glu Lys Phe Lys Ser Phe Asp
        275                 280                 285

Asn Lys Thr Asn Tyr Gln Ile Leu Pro Met Tyr Thr Asn Thr Val Met
    290                 295                 300

Leu Gln Ile Pro Tyr Trp Lys Met Gly Ile Glu Lys Lys Asn Asp Ile
305                 310                 315                 320

Gly Leu Thr Asp Ile Glu Val Asn Glu Leu Lys Gln Leu Ile Asp Thr
                325                 330                 335

Leu Val Asp Arg Ala Arg Asn Tyr Ile His Thr Met Tyr Glu Arg Glu
            340                 345                 350

Tyr Asp Asn Ala Ile Asn Thr Ser Thr Ala Ala Ser Val Thr Asn Asn
        355                 360                 365

Leu Leu Ser Val Arg Gly Tyr Cys Leu Leu His Gly Leu Glu Cys Ile
    370                 375                 380

Glu Thr Ile Glu His Leu Gln Asn Asn Ser Leu Asn Ser Gly Phe Tyr
385                 390                 395                 400

Pro Lys Thr Ile Ser Tyr Ser Thr Val Phe Asp Arg Pro Thr Asn Lys
                405                 410                 415

Thr Arg Ile Gln Ala Leu Thr Glu Asp Asp Gln Met Gln Glu Pro Phe
            420                 425                 430

Lys Pro Ala Leu Ile Gly Gly Lys Tyr Asn Lys Ile Lys Ser Leu Leu
        435                 440                 445

Gly Tyr Val Arg Arg Ile Gly Asn Ala Pro Arg Val Gly Gly Ile Lys
    450                 455                 460

Val Thr Phe Thr Asn Gly Ser Ser Tyr Thr Leu Gly Thr Val Thr Ser
465                 470                 475                 480

Glu Thr Asp Ser Ile Glu Leu Asn Glu Ser Val Ile Glu Arg Leu Glu
                485                 490                 495
```

```
Val Trp Gly Asn Gly Ala Val Asp Glu Ala Leu Phe Thr Leu Ser Asp
            500                 505                 510

Gly Arg Gln Leu Arg Ile Gly Glu Arg Tyr Ala Lys Lys Tyr Arg Lys
        515                 520                 525

Tyr Ala Val Asp Gly His Tyr Ile Ser Gly Leu Tyr Leu Ala Ser Asp
    530                 535                 540

Glu Pro Ser Leu Ala Gly Gln Ala Ala Gly Ile Ala Val Ser Tyr His
545                 550                 555                 560

Met Leu Ala Asp Lys Lys
                565
```

<210> SEQ ID NO 25
<211> LENGTH: 408
<212> TYPE: DNA
<213> ORGANISM: Xenorhabdus poinarii
<220> FEATURE:
<221> NAME/KEY: misc_feature
<222> LOCATION: (1)..(408)
<223> OTHER INFORMATION: A nucleic acid sequence obtained from Xenorhabdus poinarii strain 86198 encoding a TIC7664 PirA pesticidal protein sequence.

<400> SEQUENCE: 25

```
atgatcacaa tcaatatcag tggtggtaat gtaacaatta ataacaatat cagttcagta      60

acggatatcc aaaaacccct tgatgcagaa cccctctcag tcacgaatta taaggatctg     120

acaatagagc cgcactcatc tattcaagca accagaacgg acaccccat tattcctgaa     180

acacgcccta attattatgt tgctaactca ggccctgctt catccgttaa agcggtgttt     240

tattggtcgc attcgtttac atcggaatgg ttcgagtatt catctatcat agtaaaagca     300

ggagaggatg gaatattaaa atcaccgagt aatgccgtat attacagtaa agtagtaatt     360

tataatgata cagataagcg ggcttttgtg actggatata acatgtaa                   408
```

<210> SEQ ID NO 26
<211> LENGTH: 135
<212> TYPE: PRT
<213> ORGANISM: Xenorhabdus poinarii
<220> FEATURE:
<221> NAME/KEY: MISC_FEATURE
<222> LOCATION: (1)..(135)
<223> OTHER INFORMATION: The amino acid sequence of the TIC7664 PirA protein.

<400> SEQUENCE: 26

```
Met Ile Thr Ile Asn Ile Ser Gly Gly Asn Val Thr Ile Asn Asn Asn
1               5                   10                  15

Ile Ser Ser Val Thr Asp Ile Gln Lys Pro Leu Asp Ala Glu Pro Leu
            20                  25                  30

Ser Val Thr Asn Tyr Lys Asp Leu Thr Ile Glu Pro His Ser Ser Ile
        35                  40                  45

Gln Ala Thr Arg Thr Asp Thr Pro Ile Ile Pro Glu Thr Arg Pro Asn
    50                  55                  60

Tyr Tyr Val Ala Asn Ser Gly Pro Ala Ser Ser Val Lys Ala Val Phe
65                  70                  75                  80

Tyr Trp Ser His Ser Phe Thr Ser Glu Trp Phe Glu Tyr Ser Ser Ile
                85                  90                  95

Ile Val Lys Ala Gly Glu Asp Gly Ile Leu Lys Ser Pro Ser Asn Ala
            100                 105                 110

Val Tyr Tyr Ser Lys Val Val Ile Tyr Asn Asp Thr Asp Lys Arg Ala
        115                 120                 125
```

```
Phe Val Thr Gly Tyr Asn Met
    130                 135


<210> SEQ ID NO 27
<211> LENGTH: 1245
<212> TYPE: DNA
<213> ORGANISM: Xenorhabdus poinarii
<220> FEATURE:
<221> NAME/KEY: misc_feature
<222> LOCATION: (1)..(1245)
<223> OTHER INFORMATION: A nucleic acid sequence obtained from
      Xenorhabdus poinarii strain 86198 encoding a TIC7665 PirB
      pesticidal protein sequence.

<400> SEQUENCE: 27

atgaataata gtccaatgaa tgatcagtta tcaatagcac cttattcaat ttcgacaccc     60

aattatgaat gggatatgtc atcaatcata aaagatgcca ttatcggtgg cataggattt    120

attcccggac caggctctgc aatctctttt ttattagggc tgttctggcc tcaacagaca    180

gacaatacct gggatcaaat cctccaaaaa atcgaacaga tgatagaaga agcgaattta    240

aaaaccatta aaggtatatt aaatggagat atacaagaaa ttaaaggaaa aatggaccat    300

gtgcaatata tgctagagaa ttctcctggc agccaggaaa gccatgatgc ttatatgttt    360

ttagcaaggt ttttggtcag tattgatgaa aaattcaaat ctttcgatga tagaacaaat    420

tatcaaattc ttcccatgta tacgaacacc attatgttac aagcgcctta ttggaaaatg    480

ggcctcgaaa agaaagagga tatcggttta agcgatattg aagttagcga attaaaagaa    540

cttatcgata aattatatac taaatcatat gattatatcc ataacacgta taatcgtgaa    600

tatgataatg caatcaatac gtcaaccgca gagagtatca ccaataattt attgtctgtc    660

agaggatatt gtttattaca tggttgtgaa tgtcttgaag ttattgcgca tatacaaaac    720

aatagccttg ataaaggctt ctaccctaaa acgatcagct attcgagtgt tttcgatcgt    780

cctacaaaca aaatgaggat tcaggcgctt acagaagatg accaaatgca agaaccgttc    840

aaaccttctt tcgtcaatgg tcaatataat aaaataaaat cattggaggg ttatgtcaca    900

aggatcggca atgccccccg agtcggtgga attaaaatca catttgaaaa caacgcatct    960

tatactcttg gtactgtgac ttcagaaaca acctttattg aactcaatga gagtgttata   1020

accagcatag aagtgtgggg aaatggggcc gttgatgagg cattctttac attgagtgac   1080

ggtcgccaaa tgcggcttgg tcaacgctat gccagtcgct acagaaaata tgctgtcgat   1140

ggtcattata tctcaggatt gtacttagcc agtgatgaac catcccttgc tggtcaagcc   1200

gccggtattg ccgtttcata tcatatgatt gttgataaac aataa                   1245


<210> SEQ ID NO 28
<211> LENGTH: 414
<212> TYPE: PRT
<213> ORGANISM: Xenorhabdus poinarii
<220> FEATURE:
<221> NAME/KEY: MISC_FEATURE
<222> LOCATION: (1)..(414)
<223> OTHER INFORMATION: The amino acid sequence of the TIC7665 PirB
      protein.

<400> SEQUENCE: 28

Met Asn Asn Ser Pro Met Asn Asp Gln Leu Ser Ile Ala Pro Tyr Ser
1               5                   10                  15

Ile Ser Thr Pro Asn Tyr Glu Trp Asp Met Ser Ser Ile Ile Lys Asp
            20                  25                  30
```

```
Ala Ile Ile Gly Gly Ile Gly Phe Ile Pro Gly Pro Gly Ser Ala Ile
        35                  40                  45

Ser Phe Leu Leu Gly Leu Phe Trp Pro Gln Gln Thr Asp Asn Thr Trp
    50                  55                  60

Asp Gln Ile Leu Gln Lys Ile Glu Gln Met Ile Glu Glu Ala Asn Leu
65                  70                  75                  80

Lys Thr Ile Lys Gly Ile Leu Asn Gly Asp Ile Gln Glu Ile Lys Gly
                85                  90                  95

Lys Met Asp His Val Gln Tyr Met Leu Glu Asn Ser Pro Gly Ser Gln
            100                 105                 110

Glu Ser His Asp Ala Tyr Met Phe Leu Ala Arg Phe Leu Val Ser Ile
        115                 120                 125

Asp Glu Lys Phe Lys Ser Phe Asp Asp Arg Thr Asn Tyr Gln Ile Leu
    130                 135                 140

Pro Met Tyr Thr Asn Thr Ile Met Leu Gln Ala Pro Tyr Trp Lys Met
145                 150                 155                 160

Gly Leu Glu Lys Lys Glu Asp Ile Gly Leu Ser Asp Ile Glu Val Ser
                165                 170                 175

Glu Leu Lys Glu Leu Ile Asp Lys Leu Tyr Thr Lys Ser Tyr Asp Tyr
            180                 185                 190

Ile His Asn Thr Tyr Asn Arg Glu Tyr Asp Asn Ala Ile Asn Thr Ser
        195                 200                 205

Thr Ala Glu Ser Ile Thr Asn Asn Leu Leu Ser Val Arg Gly Tyr Cys
    210                 215                 220

Leu Leu His Gly Cys Glu Cys Leu Glu Val Ile Ala His Ile Gln Asn
225                 230                 235                 240

Asn Ser Leu Asp Lys Gly Phe Tyr Pro Lys Thr Ile Ser Tyr Ser Ser
                245                 250                 255

Val Phe Asp Arg Pro Thr Asn Lys Met Arg Ile Gln Ala Leu Thr Glu
            260                 265                 270

Asp Asp Gln Met Gln Glu Pro Phe Lys Pro Ser Phe Val Asn Gly Gln
        275                 280                 285

Tyr Asn Lys Ile Lys Ser Leu Glu Gly Tyr Val Thr Arg Ile Gly Asn
    290                 295                 300

Ala Pro Arg Val Gly Gly Ile Lys Ile Thr Phe Glu Asn Asn Ala Ser
305                 310                 315                 320

Tyr Thr Leu Gly Thr Val Thr Ser Glu Thr Thr Phe Ile Glu Leu Asn
                325                 330                 335

Glu Ser Val Ile Thr Ser Ile Glu Val Trp Gly Asn Gly Ala Val Asp
            340                 345                 350

Glu Ala Phe Phe Thr Leu Ser Asp Gly Arg Gln Met Arg Leu Gly Gln
        355                 360                 365

Arg Tyr Ala Ser Arg Tyr Arg Lys Tyr Ala Val Asp Gly His Tyr Ile
    370                 375                 380

Ser Gly Leu Tyr Leu Ala Ser Asp Glu Pro Ser Leu Ala Gly Gln Ala
385                 390                 395                 400

Ala Gly Ile Ala Val Ser Tyr His Met Ile Val Asp Lys Gln
                405                 410
```

<210> SEQ ID NO 29
<211> LENGTH: 1650
<212> TYPE: DNA
<213> ORGANISM: Artificial
<220> FEATURE:
<223> OTHER INFORMATION: A nucleic acid sequence encoding a PirAB fusion protein, TIC9319 comprised of the TIC7664 and TIC7665 coding sequences in operable linkage and in frame.

<400> SEQUENCE: 29

```
atgatcacaa tcaatatcag tggtggtaat gtaacaatta ataacaatat cagttcagta     60
acggatatcc aaaaacccct tgatgcagaa cccctctcag tcacgaatta taaggatctg    120
acaatagagc cgcactcatc tattcaagca accagaacgg acaccccccat tattcctgaa    180
acacgcccta attattatgt tgctaactca ggccctgctt catccgttaa agcggtgttt    240
tattggtcgc attcgtttac atcggaatgg ttcgagtatt catctatcat agtaaaagca    300
ggagaggatg gaatattaaa atcaccgagt aatgccgtat attacagtaa agtagtaatt    360
tataatgata cagataagcg ggcttttgtg actggatata acatgatgaa taatagtcca    420
atgaatgatc agttatcaat agcaccttat tcaatttcga cacccaatta tgaatgggat    480
atgtcatcaa tcataaaaga tgccattatc ggtggcatag gatttattcc cggaccaggc    540
tctgcaatct ctttttttatt agggctgttc tggcctcaac agacagacaa tacctgggat    600
caaatcctcc aaaaaatcga acagatgata gaagaagcga atttaaaaac cattaaaggt    660
atattaaatg gagatataca agaaattaaa ggaaaaatgg accatgtgca atatatgcta    720
gagaattctc ctggcagcca ggaaagccat gatgcttata tgtttttagc aaggtttttg    780
gtcagtattg atgaaaaatt caaatctttc gatgatagaa caaattatca aattcttccc    840
atgtatacga acaccattat gttacaagcg ccttattgga aaatgggcct cgaaaagaaa    900
gaggatatcg gtttaagcga tattgaagtt agcgaattaa aagaacttat cgataaatta    960
tatactaaat catatgatta tatccataac acgtataatc gtgaatatga taatgcaatc   1020
aatacgtcaa ccgcagagag tatcaccaat aatttattgt ctgtcagagg atattgttta   1080
ttacatggtt gtgaatgtct tgaagttatt gcgcatatac aaaacaatag ccttgataaa   1140
ggcttctacc ctaaaacgat cagctattcg agtgttttcg atcgtcctac aaacaaaatg   1200
aggattcagg cgcttacaga agatgaccaa atgcaagaac cgttcaaacc ttctttcgtc   1260
aatggtcaat ataataaaat aaaatcattg gagggttatg tcacaaggat cggcaatgcc   1320
ccccgagtcg gtggaattaa aatcacattt gaaaacaacg catcttatac tcttggtact   1380
gtgacttcag aaacaacctt tattgaactc aatgagagtg ttataaccag catagaagtg   1440
tggggaaatg gggccgttga tgaggcattc tttacattga gtgacggtcg ccaaatgcgg   1500
cttggtcaac gctatgccag tcgctacaga aaatatgctg tcgatggtca ttatatctca   1560
ggattgtact tagccagtga tgaaccatcc cttgctggtc aagccgccgg tattgccgtt   1620
tcatatcata tgattgttga taaacaataa                                    1650
```

<210> SEQ ID NO 30
<211> LENGTH: 549
<212> TYPE: PRT
<213> ORGANISM: Artificial
<220> FEATURE:
<223> OTHER INFORMATION: The amino acid sequence of the TIC9319 PirAB fusion protein.

<400> SEQUENCE: 30

```
Met Ile Thr Ile Asn Ile Ser Gly Gly Asn Val Thr Ile Asn Asn Asn
1               5                   10                  15

Ile Ser Ser Val Thr Asp Ile Gln Lys Pro Leu Asp Ala Glu Pro Leu
            20                  25                  30

Ser Val Thr Asn Tyr Lys Asp Leu Thr Ile Glu Pro His Ser Ser Ile
```

-continued

```
        35                  40                  45

Gln Ala Thr Arg Thr Asp Thr Pro Ile Ile Pro Glu Thr Arg Pro Asn
    50                  55                  60

Tyr Tyr Val Ala Asn Ser Gly Pro Ala Ser Ser Val Lys Ala Val Phe
65                  70                  75                  80

Tyr Trp Ser His Ser Phe Thr Ser Glu Trp Phe Glu Tyr Ser Ser Ile
                85                  90                  95

Ile Val Lys Ala Gly Glu Asp Gly Ile Leu Lys Ser Pro Ser Asn Ala
            100                 105                 110

Val Tyr Tyr Ser Lys Val Val Ile Tyr Asn Asp Thr Asp Lys Arg Ala
        115                 120                 125

Phe Val Thr Gly Tyr Asn Met Met Asn Asn Ser Pro Met Asn Asp Gln
    130                 135                 140

Leu Ser Ile Ala Pro Tyr Ser Ile Ser Thr Pro Asn Tyr Glu Trp Asp
145                 150                 155                 160

Met Ser Ser Ile Ile Lys Asp Ala Ile Ile Gly Gly Ile Gly Phe Ile
                165                 170                 175

Pro Gly Pro Gly Ser Ala Ile Ser Phe Leu Leu Gly Leu Phe Trp Pro
            180                 185                 190

Gln Gln Thr Asp Asn Thr Trp Asp Gln Ile Leu Gln Lys Ile Glu Gln
        195                 200                 205

Met Ile Glu Glu Ala Asn Leu Lys Thr Ile Lys Gly Ile Leu Asn Gly
    210                 215                 220

Asp Ile Gln Glu Ile Lys Gly Lys Met Asp His Val Gln Tyr Met Leu
225                 230                 235                 240

Glu Asn Ser Pro Gly Ser Gln Glu Ser His Asp Ala Tyr Met Phe Leu
                245                 250                 255

Ala Arg Phe Leu Val Ser Ile Asp Glu Lys Phe Lys Ser Phe Asp Asp
            260                 265                 270

Arg Thr Asn Tyr Gln Ile Leu Pro Met Tyr Thr Asn Thr Ile Met Leu
        275                 280                 285

Gln Ala Pro Tyr Trp Lys Met Gly Leu Glu Lys Lys Glu Asp Ile Gly
    290                 295                 300

Leu Ser Asp Ile Glu Val Ser Glu Leu Lys Glu Leu Ile Asp Lys Leu
305                 310                 315                 320

Tyr Thr Lys Ser Tyr Asp Tyr Ile His Asn Thr Tyr Asn Arg Glu Tyr
                325                 330                 335

Asp Asn Ala Ile Asn Thr Ser Thr Ala Glu Ser Ile Thr Asn Asn Leu
            340                 345                 350

Leu Ser Val Arg Gly Tyr Cys Leu Leu His Gly Cys Glu Cys Leu Glu
        355                 360                 365

Val Ile Ala His Ile Gln Asn Asn Ser Leu Asp Lys Gly Phe Tyr Pro
    370                 375                 380

Lys Thr Ile Ser Tyr Ser Ser Val Phe Asp Arg Pro Thr Asn Lys Met
385                 390                 395                 400

Arg Ile Gln Ala Leu Thr Glu Asp Asp Gln Met Gln Glu Pro Phe Lys
                405                 410                 415

Pro Ser Phe Val Asn Gly Gln Tyr Asn Lys Ile Lys Ser Leu Glu Gly
            420                 425                 430

Tyr Val Thr Arg Ile Gly Asn Ala Pro Arg Val Gly Gly Ile Lys Ile
        435                 440                 445

Thr Phe Glu Asn Asn Ala Ser Tyr Thr Leu Gly Thr Val Thr Ser Glu
    450                 455                 460
```

```
Thr Thr Phe Ile Glu Leu Asn Glu Ser Val Ile Thr Ser Ile Glu Val
465                 470                 475                 480

Trp Gly Asn Gly Ala Val Asp Glu Ala Phe Phe Thr Leu Ser Asp Gly
                485                 490                 495

Arg Gln Met Arg Leu Gly Gln Arg Tyr Ala Ser Arg Tyr Arg Lys Tyr
            500                 505                 510

Ala Val Asp Gly His Tyr Ile Ser Gly Leu Tyr Leu Ala Ser Asp Glu
        515                 520                 525

Pro Ser Leu Ala Gly Gln Ala Ala Gly Ile Ala Val Ser Tyr His Met
    530                 535                 540

Ile Val Asp Lys Gln
545
```

<210> SEQ ID NO 31
<211> LENGTH: 402
<212> TYPE: DNA
<213> ORGANISM: Photorhabdus luminescens
<220> FEATURE:
<221> NAME/KEY: misc_feature
<222> LOCATION: (1)..(402)
<223> OTHER INFORMATION: A nucleic acid sequence obtained from Photorhabdus luminescens strain 86197 encoding a TIC7666 PirA pesticidal protein sequence.

<400> SEQUENCE: 31

```
atgtctagaa taaccattgt tgttgattca gatgatcaga aagcagaatt ttattctaat      60

tctcctgttc cagtatataa agatttaaat gcagttggtc ctttgagtga tgtgactata     120

tcacctcatg ccagtgtgga agtgtttaga atagatacac cagtaattcc agaatccaga     180

agctctctga gagttgtaaa tacagggcta tcaaatagtg ttacggctaa attttactgg     240

tctcatagtt ttacctctga atggtttgag tctggttcta tagatgtagg attaggagaa     300

gagaaggtgt taaacgtgcc tagcaactct ttttattata gtaaatttgt tatctataat     360

aacacggaca aagttgctta tgtgacggca aatttggttt aa                        402
```

<210> SEQ ID NO 32
<211> LENGTH: 133
<212> TYPE: PRT
<213> ORGANISM: Photorhabdus luminescens
<220> FEATURE:
<221> NAME/KEY: MISC_FEATURE
<222> LOCATION: (1)..(133)
<223> OTHER INFORMATION: The amino acid sequence of the TIC7666 PirA protein.

<400> SEQUENCE: 32

```
Met Ser Arg Ile Thr Ile Val Val Asp Ser Asp Asp Gln Lys Ala Glu
1               5                   10                  15

Phe Tyr Ser Asn Ser Pro Val Pro Val Tyr Lys Asp Leu Asn Ala Val
            20                  25                  30

Gly Pro Leu Ser Asp Val Thr Ile Ser Pro His Ala Ser Val Glu Val
        35                  40                  45

Phe Arg Ile Asp Thr Pro Val Ile Pro Glu Ser Arg Ser Ser Leu Arg
    50                  55                  60

Val Val Asn Thr Gly Leu Ser Asn Ser Val Thr Ala Lys Phe Tyr Trp
65                  70                  75                  80

Ser His Ser Phe Thr Ser Glu Trp Phe Glu Ser Gly Ser Ile Asp Val
                85                  90                  95

Gly Leu Gly Glu Glu Lys Val Leu Asn Val Pro Ser Asn Ser Phe Tyr
```

```
            100                 105                 110

Tyr Ser Lys Phe Val Ile Tyr Asn Asn Thr Asp Lys Val Ala Tyr Val
        115                 120                 125

Thr Ala Asn Leu Val
    130


<210> SEQ ID NO 33
<211> LENGTH: 1260
<212> TYPE: DNA
<213> ORGANISM: Photorhabdus luminescens
<220> FEATURE:
<221> NAME/KEY: misc_feature
<222> LOCATION: (1)..(1260)
<223> OTHER INFORMATION: A nucleic acid sequence obtained from
      Photorhabdus luminescens strain 86197 encoding a TIC7667
      pesticidal PirB protein sequence.

<400> SEQUENCE: 33

atgcatacag aaaatgtttt agacataaga accattgtgg ctaatgaata tgctgtaaaa      60

acgagtgcat tagagtggga tgttactgat attgtaaaaa atgcaatcat agggggaata     120

tcctttatcc cttcggttgg tcccgctata tcttttttag tcggtttatt ctggcctcaa     180

tcgaaagaaa atatatggga agggattgtc aaacaaattg aaaggatgat agaggagtct     240

gcgttaaaga cgattaaagg tatccttgct ggtgatattg catatataca agaacgaatg     300

gcaaccgttg ctgatcttct tgataagcat ccaggatcag aagaagcgag gagtgctttt     360

aataacctgg cagaaaatat agatggctat cacaaaaagt ttagtaattt ttcggatgat     420

gttaattatc agatattacc catgttttct actacggtta tgatgcagat aacatattgg     480

gttgctggtt tagagagaaa agatgaaatt gggcttagta atattgatgt tgaaaaagtc     540

cgaggattaa ttaaaaagac ggtagaacag gctaatagtt atattaacaa tatatatgat     600

agagagctta atgatgctct taataactcg acggctgaca ctgttgcaaa taatgttatg     660

tctgttcatg gtcactgtcg tttacatggg attgaatata tcagtatttg ggataaatta     720

agtgaagctg agtcggtaaa taataaaatc tatgttgatg ttttaagtta ttctactttc     780

tttgaccgtc aaacagcaaa agccagaatt caggcattga ctccagagaa agatatgact     840

ccacctctca aaccggctct taatggagga aaaagaagaa agatagattc gttaacggga     900

catattgtgc gtattggagg ggctgcgagg gtaggagggc tgacagttgt atttgatgat     960

ggtaatcgcc atcaattagg tacaatatct ggtgagacgt catctatttc tctgaatggt    1020

agtcgaatta ccagtttgga agtatgggga aatggtgctg ttgatcaagc ggtctttact    1080

ttaaatgatg gtcgttcatt gtcattgggc tcgcctggaa catctcgata taggaagttt    1140

tatgttggtg aaagccacta tattgcaggg atatatttgt ccagtgatta caacccatta    1200

gctggtcagg cagcaaatat tgctgtatct tatcagttga taaatgatga tgaaaaataa    1260


<210> SEQ ID NO 34
<211> LENGTH: 419
<212> TYPE: PRT
<213> ORGANISM: Photorhabdus luminescens
<220> FEATURE:
<221> NAME/KEY: MISC_FEATURE
<222> LOCATION: (1)..(419)
<223> OTHER INFORMATION: The amino acid sequence of the TIC7667 PirB
      protein.

<400> SEQUENCE: 34

Met His Thr Glu Asn Val Leu Asp Ile Arg Thr Ile Val Ala Asn Glu
1               5                   10                  15
```

-continued

```
Tyr Ala Val Lys Thr Ser Ala Leu Glu Trp Asp Val Thr Asp Ile Val
            20                  25                  30

Lys Asn Ala Ile Ile Gly Gly Ile Ser Phe Ile Pro Ser Val Gly Pro
        35                  40                  45

Ala Ile Ser Phe Leu Val Gly Leu Phe Trp Pro Gln Ser Lys Glu Asn
    50                  55                  60

Ile Trp Glu Gly Ile Val Lys Gln Ile Glu Arg Met Ile Glu Glu Ser
65                  70                  75                  80

Ala Leu Lys Thr Ile Lys Gly Ile Leu Ala Gly Asp Ile Ala Tyr Ile
                85                  90                  95

Gln Glu Arg Met Ala Thr Val Ala Asp Leu Leu Asp Lys His Pro Gly
            100                 105                 110

Ser Glu Glu Ala Arg Ser Ala Phe Asn Asn Leu Ala Glu Asn Ile Asp
        115                 120                 125

Gly Tyr His Lys Lys Phe Ser Asn Phe Ser Asp Asp Val Asn Tyr Gln
    130                 135                 140

Ile Leu Pro Met Phe Ser Thr Thr Val Met Met Gln Ile Thr Tyr Trp
145                 150                 155                 160

Val Ala Gly Leu Glu Arg Lys Asp Glu Ile Gly Leu Ser Asn Ile Asp
                165                 170                 175

Val Glu Lys Val Arg Gly Leu Ile Lys Lys Thr Val Glu Gln Ala Asn
            180                 185                 190

Ser Tyr Ile Asn Asn Ile Tyr Asp Arg Glu Leu Asn Asp Ala Leu Asn
        195                 200                 205

Asn Ser Thr Ala Asp Thr Val Ala Asn Asn Val Met Ser Val His Gly
    210                 215                 220

His Cys Arg Leu His Gly Ile Glu Tyr Ile Ser Ile Trp Asp Lys Leu
225                 230                 235                 240

Ser Glu Ala Glu Ser Val Asn Asn Lys Ile Tyr Val Asp Val Leu Ser
                245                 250                 255

Tyr Ser Thr Phe Phe Asp Arg Gln Thr Ala Lys Ala Arg Ile Gln Ala
            260                 265                 270

Leu Thr Pro Glu Lys Asp Met Thr Pro Pro Leu Lys Pro Ala Leu Asn
        275                 280                 285

Gly Gly Lys Arg Arg Lys Ile Asp Ser Leu Thr Gly His Ile Val Arg
    290                 295                 300

Ile Gly Gly Ala Ala Arg Val Gly Gly Leu Thr Val Val Phe Asp Asp
305                 310                 315                 320

Gly Asn Arg His Gln Leu Gly Thr Ile Ser Gly Glu Thr Ser Ser Ile
                325                 330                 335

Ser Leu Asn Gly Ser Arg Ile Thr Ser Leu Glu Val Trp Gly Asn Gly
            340                 345                 350

Ala Val Asp Gln Ala Val Phe Thr Leu Asn Asp Gly Arg Ser Leu Ser
        355                 360                 365

Leu Gly Ser Pro Gly Thr Ser Arg Tyr Arg Lys Phe Tyr Val Gly Glu
    370                 375                 380

Ser His Tyr Ile Ala Gly Ile Tyr Leu Ser Ser Asp Tyr Asn Pro Leu
385                 390                 395                 400

Ala Gly Gln Ala Ala Asn Ile Ala Val Ser Tyr Gln Leu Ile Asn Asp
                405                 410                 415

Asp Glu Lys
```

<210> SEQ ID NO 35
<211> LENGTH: 1659
<212> TYPE: DNA
<213> ORGANISM: Artificial
<220> FEATURE:
<223> OTHER INFORMATION: A nucleic acid sequence encoding a PirAB fusion protein, TIC9322 comprised of the TIC7666 and TIC7667 coding sequences in operable linkage and in frame.

<400> SEQUENCE: 35
atgtctagaa taaccattgt tgttgattca gatgatcaga aagcagaatt ttattctaat 60
tctcctgttc cagtatataa agatttaaat gcagttggtc ctttgagtga tgtgactata 120
tcacctcatg ccagtgtgga agtgtttaga atagatacac cagtaattcc agaatccaga 180
agctctctga gagttgtaaa tacagggcta tcaaatagtg ttacggctaa attttactgg 240
tctcatagtt ttacctctga atggtttgag tctggttcta tagatgtagg attaggagaa 300
gagaaggtgt taaacgtgcc tagcaactct ttttattata gtaaatttgt tatctataat 360
aacacggaca aagttgctta tgtgacggca aatttggtta tgcatacaga aaatgtttta 420
gacataagaa ccattgtggc taatgaatat gctgtaaaaa cgagtgcatt agagtgggat 480
gttactgata ttgtaaaaaa tgcaatcata gggggaatat cctttatccc ttcggttggt 540
cccgctatat ctttttttagt cggtttattc tggcctcaat cgaaagaaaa tatatgggaa 600
gggattgtca aacaaattga aaggatgata gaggagtctg cgttaaagac gattaaaggt 660
atccttgctg gtgatattgc atatatacaa gaacgaatgg caaccgttgc tgatcttctt 720
gataagcatc caggatcaga agaagcgagg agtgctttta ataacctggc agaaaatata 780
gatggctatc acaaaaagtt tagtaatttt tcggatgatg ttaattatca gatattaccc 840
atgttttcta ctacggttat gatgcagata acatattggg ttgctggttt agagagaaaa 900
gatgaaattg ggcttagtaa tattgatgtt gaaaaagtcc gaggattaat taaaaagacg 960
gtagaacagg ctaatagtta tattaacaat atatatgata gagagcttaa tgatgctctt 1020
aataactcga cggctgacac tgttgcaaat aatgttatgt ctgttcatgg tcactgtcgt 1080
ttacatggga ttgaatatat cagtatttgg gataaattaa gtgaagctga gtcggtaaat 1140
aataaaatct atgttgatgt tttaagttat tctactttct ttgaccgtca aacagcaaaa 1200
gccagaattc aggcattgac tccagagaaa gatatgactc cacctctcaa accggctctt 1260
aatggaggaa aaagaagaaa gatagattcg ttaacgggac atattgtgcg tattggaggg 1320
gctgcgaggg taggagggct gacagttgta tttgatgatg gtaatcgcca tcaattaggt 1380
acaatatctg gtgagacgtc atctatttct ctgaatggta gtcgaattac cagtttggaa 1440
gtatggggaa atggtgctgt tgatcaagcg gtctttactt taaatgatgg tcgttcattg 1500
tcattgggct cgcctggaac atctcgatat aggaagtttt atgttggtga aagccactat 1560
attgcaggga tatatttgtc cagtgattac aacccattag ctggtcaggc agcaaatatt 1620
gctgtatctt atcagttgat aaatgatgat gaaaaataa 1659

<210> SEQ ID NO 36
<211> LENGTH: 552
<212> TYPE: PRT
<213> ORGANISM: Artificial
<220> FEATURE:
<223> OTHER INFORMATION: The amino acid sequence of the TIC9322 PirAB fusion protein.

<400> SEQUENCE: 36

Met Ser Arg Ile Thr Ile Val Val Asp Ser Asp Asp Gln Lys Ala Glu

-continued

```
1               5                   10                  15

Phe Tyr Ser Asn Ser Pro Val Pro Val Tyr Lys Asp Leu Asn Ala Val
            20                  25                  30

Gly Pro Leu Ser Asp Val Thr Ile Ser Pro His Ala Ser Val Glu Val
        35                  40                  45

Phe Arg Ile Asp Thr Pro Val Ile Pro Glu Ser Arg Ser Ser Leu Arg
    50                  55                  60

Val Val Asn Thr Gly Leu Ser Asn Ser Val Thr Ala Lys Phe Tyr Trp
65                  70                  75                  80

Ser His Ser Phe Thr Ser Glu Trp Phe Glu Ser Gly Ser Ile Asp Val
                85                  90                  95

Gly Leu Gly Glu Glu Lys Val Leu Asn Val Pro Ser Asn Ser Phe Tyr
            100                 105                 110

Tyr Ser Lys Phe Val Ile Tyr Asn Asn Thr Asp Lys Val Ala Tyr Val
        115                 120                 125

Thr Ala Asn Leu Val Met His Thr Glu Asn Val Leu Asp Ile Arg Thr
    130                 135                 140

Ile Val Ala Asn Glu Tyr Ala Val Lys Thr Ser Ala Leu Glu Trp Asp
145                 150                 155                 160

Val Thr Asp Ile Val Lys Asn Ala Ile Ile Gly Gly Ile Ser Phe Ile
                165                 170                 175

Pro Ser Val Gly Pro Ala Ile Ser Phe Leu Val Gly Leu Phe Trp Pro
            180                 185                 190

Gln Ser Lys Glu Asn Ile Trp Glu Gly Ile Val Lys Gln Ile Glu Arg
        195                 200                 205

Met Ile Glu Glu Ser Ala Leu Lys Thr Ile Lys Gly Ile Leu Ala Gly
    210                 215                 220

Asp Ile Ala Tyr Ile Gln Glu Arg Met Ala Thr Val Ala Asp Leu Leu
225                 230                 235                 240

Asp Lys His Pro Gly Ser Glu Glu Ala Arg Ser Ala Phe Asn Asn Leu
                245                 250                 255

Ala Glu Asn Ile Asp Gly Tyr His Lys Lys Phe Ser Asn Phe Ser Asp
            260                 265                 270

Asp Val Asn Tyr Gln Ile Leu Pro Met Phe Ser Thr Thr Val Met Met
        275                 280                 285

Gln Ile Thr Tyr Trp Val Ala Gly Leu Glu Arg Lys Asp Glu Ile Gly
    290                 295                 300

Leu Ser Asn Ile Asp Val Glu Lys Val Arg Gly Leu Ile Lys Lys Thr
305                 310                 315                 320

Val Glu Gln Ala Asn Ser Tyr Ile Asn Asn Ile Tyr Asp Arg Glu Leu
                325                 330                 335

Asn Asp Ala Leu Asn Asn Ser Thr Ala Asp Thr Val Ala Asn Asn Val
            340                 345                 350

Met Ser Val His Gly His Cys Arg Leu His Gly Ile Glu Tyr Ile Ser
        355                 360                 365

Ile Trp Asp Lys Leu Ser Glu Ala Glu Ser Val Asn Asn Lys Ile Tyr
    370                 375                 380

Val Asp Val Leu Ser Tyr Ser Thr Phe Phe Asp Arg Gln Thr Ala Lys
385                 390                 395                 400

Ala Arg Ile Gln Ala Leu Thr Pro Glu Lys Asp Met Thr Pro Pro Leu
                405                 410                 415

Lys Pro Ala Leu Asn Gly Gly Lys Arg Arg Lys Ile Asp Ser Leu Thr
            420                 425                 430
```

```
Gly His Ile Val Arg Ile Gly Gly Ala Ala Arg Val Gly Gly Leu Thr
        435                 440                 445

Val Val Phe Asp Asp Gly Asn Arg His Gln Leu Gly Thr Ile Ser Gly
    450                 455                 460

Glu Thr Ser Ser Ile Ser Leu Asn Gly Ser Arg Ile Thr Ser Leu Glu
465                 470                 475                 480

Val Trp Gly Asn Gly Ala Val Asp Gln Ala Val Phe Thr Leu Asn Asp
                485                 490                 495

Gly Arg Ser Leu Ser Leu Gly Ser Pro Gly Thr Ser Arg Tyr Arg Lys
            500                 505                 510

Phe Tyr Val Gly Glu Ser His Tyr Ile Ala Gly Ile Tyr Leu Ser Ser
        515                 520                 525

Asp Tyr Asn Pro Leu Ala Gly Gln Ala Ala Asn Ile Ala Val Ser Tyr
    530                 535                 540

Gln Leu Ile Asn Asp Asp Glu Lys
545                 550


<210> SEQ ID NO 37
<211> LENGTH: 402
<212> TYPE: DNA
<213> ORGANISM: Photorhabdus luminescens
<220> FEATURE:
<221> NAME/KEY: misc_feature
<222> LOCATION: (1)..(402)
<223> OTHER INFORMATION: A nucleic acid sequence obtained from
      Photorhabdus luminescens strain 86194 encoding a TIC7668 PirA
      pesticidal protein sequence.

<400> SEQUENCE: 37

atgtctagaa taactattgt tgttgattca gatgaacaga aagcagaagt ttactctaat      60

tcccctgttc cagtacataa agacttaaat gcagttggtc ctttgagtga tgtgactata     120

tcacctcatg ctagtgtgga agtatttaga atagatacac caataattcc agaatccaga     180

agatctctga gagttgtaaa taccgggcta gcaaatagtg tcacggctaa attttactgg     240

tctcatagtt ttacctctga atggtttgag tctggttcta tagatgtagg attaggagaa     300

gagaaggtgt taaacgtgcc taataactct ttttattata gtaaatttgt tatctataat     360

aatacggata aagttgctta tgtgacggca aatttggttt aa                        402


<210> SEQ ID NO 38
<211> LENGTH: 133
<212> TYPE: PRT
<213> ORGANISM: Photorhabdus luminescens
<220> FEATURE:
<221> NAME/KEY: MISC_FEATURE
<222> LOCATION: (1)..(133)
<223> OTHER INFORMATION: The amino acid sequence of the TIC7668 PirA
      protein.

<400> SEQUENCE: 38

Met Ser Arg Ile Thr Ile Val Val Asp Ser Asp Glu Gln Lys Ala Glu
1               5                   10                  15

Val Tyr Ser Asn Ser Pro Val Pro Val His Lys Asp Leu Asn Ala Val
            20                  25                  30

Gly Pro Leu Ser Asp Val Thr Ile Ser Pro His Ala Ser Val Glu Val
        35                  40                  45

Phe Arg Ile Asp Thr Pro Ile Ile Pro Glu Ser Arg Arg Ser Leu Arg
    50                  55                  60

Val Val Asn Thr Gly Leu Ala Asn Ser Val Thr Ala Lys Phe Tyr Trp
```

-continued 65 70 75 80

Ser His Ser Phe Thr Ser Glu Trp Phe Glu Ser Gly Ser Ile Asp Val
85 90 95

Gly Leu Gly Glu Glu Lys Val Leu Asn Val Pro Asn Asn Ser Phe Tyr
100 105 110

Tyr Ser Lys Phe Val Ile Tyr Asn Asn Thr Asp Lys Val Ala Tyr Val
115 120 125

Thr Ala Asn Leu Val
130

<210> SEQ ID NO 39
<211> LENGTH: 1260
<212> TYPE: DNA
<213> ORGANISM: Photorhabdus luminescens
<220> FEATURE:
<221> NAME/KEY: misc_feature
<222> LOCATION: (1)..(1260)
<223> OTHER INFORMATION: A nucleic acid sequence obtained from Photorhabdus luminescens strain 86194 encoding a TIC7669 PirB pesticidal protein sequence.

<400> SEQUENCE: 39
atgcatacag aaaatgtttt agacataaga accattgtgg ctaatgaata tgccgtaaaa 60
acgagtgcag tagagtggga tgttactgat attgtaaaaa atgcaatcat cgggggaata 120
tcttttatac cttcagttgg ccctgctata tcttttttag tcggtttatt ctggcctcaa 180
tcaaaagaaa atatatggga agggattgtc aaacaaattg aaaggatgat agaggagtct 240
gcattaaaga cgattaaagg tatccttgct ggtgatattg catatataca agaacgaatg 300
gcaaccgttg ctgatcttct tgataagcat ccgggatctg aagaagcgag gagtgctttt 360
aataacctgg cagaaaatat agatggttat cacaaaaaat ttaataattt ttccgatgat 420
gttaactatc agatattacc catgttttct actacggtta tgatgcagat aacatattgg 480
gtcgctggtt tagagagaag aaatgaaatc gggcttagtg atattgatat tgaaaaagtc 540
cgagggttaa tcaaaaagac ggtagaacag gcgaatagtt atattaataa tatatatgat 600
agagagctta atgatgctct taataactcg acggctgaca ctgttgcaaa taatgtgatg 660
tctgttcatg gtcactgtcg tttacatggg attgaatata tcagtatttg ggataaatta 720
agtgaagcag agtcagtaaa taatagaatc tatgttgatg ttttaagtta ttctactttc 780
tttgaccgtc aaacagcaaa agccagaatt caggcattga ctccagagaa agatatggct 840
ccacctctca aaccggctct taatgacggg aaaagaagaa agatcgattc gttaacggga 900
catattgtgc gtattggagg ggctccgaga gtcggagggc tgacagttgt atttgatgat 960
ggtagtagcc atcgattagg tacaatatct ggtgagacgg catctatttc tctgaatggc 1020
agtcgaatta ccagtttgga agtatggggc aatggtgctg ttgatcaagc ggtctttact 1080
ttgagtgatg gtcgttcatt atcatttggc gcacctggaa catctcgata taggaaattt 1140
tatgttggcg aaagtcacta tattgcaggg gtatatttgt ccagtgacta cagcccatta 1200
gcaggtcagg cagcaaatat cgctgtatct tatcagttga taaatgatga tgaaaaataa 1260

<210> SEQ ID NO 40
<211> LENGTH: 419
<212> TYPE: PRT
<213> ORGANISM: Photorhabdus luminescens
<220> FEATURE:
<221> NAME/KEY: MISC_FEATURE
<222> LOCATION: (1)..(419)
<223> OTHER INFORMATION: The amino acid sequence of the TIC7669 PirB protein.

<400> SEQUENCE: 40

Met His Thr Glu Asn Val Leu Asp Ile Arg Thr Ile Val Ala Asn Glu
1 5 10 15

Tyr Ala Val Lys Thr Ser Ala Val Glu Trp Asp Val Thr Asp Ile Val
20 25 30

Lys Asn Ala Ile Ile Gly Gly Ile Ser Phe Ile Pro Ser Val Gly Pro
35 40 45

Ala Ile Ser Phe Leu Val Gly Leu Phe Trp Pro Gln Ser Lys Glu Asn
50 55 60

Ile Trp Glu Gly Ile Val Lys Gln Ile Glu Arg Met Ile Glu Glu Ser
65 70 75 80

Ala Leu Lys Thr Ile Lys Gly Ile Leu Ala Gly Asp Ile Ala Tyr Ile
85 90 95

Gln Glu Arg Met Ala Thr Val Ala Asp Leu Leu Asp Lys His Pro Gly
100 105 110

Ser Glu Glu Ala Arg Ser Ala Phe Asn Asn Leu Ala Glu Asn Ile Asp
115 120 125

Gly Tyr His Lys Lys Phe Asn Asn Phe Ser Asp Asp Val Asn Tyr Gln
130 135 140

Ile Leu Pro Met Phe Ser Thr Thr Val Met Met Gln Ile Thr Tyr Trp
145 150 155 160

Val Ala Gly Leu Glu Arg Arg Asn Glu Ile Gly Leu Ser Asp Ile Asp
165 170 175

Ile Glu Lys Val Arg Gly Leu Ile Lys Lys Thr Val Glu Gln Ala Asn
180 185 190

Ser Tyr Ile Asn Asn Ile Tyr Asp Arg Glu Leu Asn Asp Ala Leu Asn
195 200 205

Asn Ser Thr Ala Asp Thr Val Ala Asn Asn Val Met Ser Val His Gly
210 215 220

His Cys Arg Leu His Gly Ile Glu Tyr Ile Ser Ile Trp Asp Lys Leu
225 230 235 240

Ser Glu Ala Glu Ser Val Asn Asn Arg Ile Tyr Val Asp Val Leu Ser
245 250 255

Tyr Ser Thr Phe Phe Asp Arg Gln Thr Ala Lys Ala Arg Ile Gln Ala
260 265 270

Leu Thr Pro Glu Lys Asp Met Ala Pro Pro Leu Lys Pro Ala Leu Asn
275 280 285

Asp Gly Lys Arg Arg Lys Ile Asp Ser Leu Thr Gly His Ile Val Arg
290 295 300

Ile Gly Gly Ala Pro Arg Val Gly Gly Leu Thr Val Val Phe Asp Asp
305 310 315 320

Gly Ser Ser His Arg Leu Gly Thr Ile Ser Gly Glu Thr Ala Ser Ile
325 330 335

Ser Leu Asn Gly Ser Arg Ile Thr Ser Leu Glu Val Trp Gly Asn Gly
340 345 350

Ala Val Asp Gln Ala Val Phe Thr Leu Ser Asp Gly Arg Ser Leu Ser
355 360 365

Phe Gly Ala Pro Gly Thr Ser Arg Tyr Arg Lys Phe Tyr Val Gly Glu
370 375 380

Ser His Tyr Ile Ala Gly Val Tyr Leu Ser Ser Asp Tyr Ser Pro Leu
385 390 395 400

```
Ala Gly Gln Ala Ala Asn Ile Ala Val Ser Tyr Gln Leu Ile Asn Asp
                405                 410                 415

Asp Glu Lys
```

<210> SEQ ID NO 41
<211> LENGTH: 1659
<212> TYPE: DNA
<213> ORGANISM: Artificial
<220> FEATURE:
<223> OTHER INFORMATION: A nucleic acid sequence encoding a PirAB fusion protein, TIC9320 comprised of the TIC7668 and TIC7669 coding sequences in operable linkage and in frame.

<400> SEQUENCE: 41

```
atgtctagaa taactattgt tgttgattca gatgaacaga aagcagaagt ttactctaat     60

tcccctgttc cagtacataa agacttaaat gcagttggtc ctttgagtga tgtgactata    120

tcacctcatg ctagtgtgga agtatttaga atagatacac caataattcc agaatccaga    180

agatctctga gagttgtaaa taccgggcta gcaaatagtg tcacggctaa attttactgg    240

tctcatagtt ttacctctga atggtttgag tctggttcta tagatgtagg attaggagaa    300

gagaaggtgt taaacgtgcc taataactct ttttattata gtaaatttgt tatctataat    360

aatacggata aagttgctta tgtgacggca aatttggtta tgcatacaga aaatgtttta    420

gacataagaa ccattgtggc taatgaatat gccgtaaaaa cgagtgcagt agagtgggat    480

gttactgata ttgtaaaaaa tgcaatcatc gggggaatat cttttatacc ttcagttggc    540

cctgctatat ctttttttagt cggtttattc tggcctcaat caaaagaaaa tatatgggaa    600

gggattgtca aacaaattga aaggatgata gaggagtctg cattaaagac gattaaaggt    660

atccttgctg gtgatattgc atatatacaa gaacgaatgg caaccgttgc tgatcttctt    720

gataagcatc cgggatctga agaagcgagg agtgctttta ataacctggc agaaaatata    780

gatggttatc acaaaaaatt taataatttt tccgatgatg ttaactatca gatattaccc    840

atgttttcta ctacggttat gatgcagata acatattggg tcgctggttt agagagaaga    900

aatgaaatcg ggcttagtga tattgatatt gaaaaagtcc gagggttaat caaaaagacg    960

gtagaacagg cgaatagtta tattaataat atatatgata gagagcttaa tgatgctctt   1020

aataactcga cggctgacac tgttgcaaat aatgtgatgt ctgttcatgg tcactgtcgt   1080

ttacatggga ttgaatatat cagtatttgg gataaattaa gtgaagcaga gtcagtaaat   1140

aatagaatct atgttgatgt tttaagttat tctactttct ttgaccgtca aacagcaaaa   1200

gccagaattc aggcattgac tccagagaaa gatatggctc cacctctcaa accggctctt   1260

aatgacggga aaagaagaaa gatcgattcg ttaacgggac atattgtgcg tattggaggg   1320

gctccgagag tcggagggct gacagttgta tttgatgatg gtagtagcca tcgattaggt   1380

acaatatctg gtgagacggc atctatttct ctgaatggca gtcgaattac cagtttggaa   1440

gtatggggca atggtgctgt tgatcaagcg gtctttactt tgagtgatgg tcgttcatta   1500

tcatttggcg cacctggaac atctcgatat aggaaatttt atgttggcga aagtcactat   1560

attgcagggg tatatttgtc cagtgactac agcccattag caggtcaggc agcaaatatc   1620

gctgtatctt atcagttgat aaatgatgat gaaaaataa                          1659
```

<210> SEQ ID NO 42
<211> LENGTH: 552
<212> TYPE: PRT
<213> ORGANISM: Artificial
<220> FEATURE:

<223> OTHER INFORMATION: The amino acid sequence of the TIC9320 PirAB fusion protein

<400> SEQUENCE: 42

```
Met Ser Arg Ile Thr Ile Val Val Asp Ser Asp Glu Gln Lys Ala Glu
1               5                   10                  15

Val Tyr Ser Asn Ser Pro Val Pro Val His Lys Asp Leu Asn Ala Val
            20                  25                  30

Gly Pro Leu Ser Asp Val Thr Ile Ser Pro His Ala Ser Val Glu Val
        35                  40                  45

Phe Arg Ile Asp Thr Pro Ile Ile Pro Glu Ser Arg Arg Ser Leu Arg
    50                  55                  60

Val Val Asn Thr Gly Leu Ala Asn Ser Val Thr Ala Lys Phe Tyr Trp
65                  70                  75                  80

Ser His Ser Phe Thr Ser Glu Trp Phe Glu Ser Gly Ser Ile Asp Val
                85                  90                  95

Gly Leu Gly Glu Glu Lys Val Leu Asn Val Pro Asn Asn Ser Phe Tyr
            100                 105                 110

Tyr Ser Lys Phe Val Ile Tyr Asn Asn Thr Asp Lys Val Ala Tyr Val
        115                 120                 125

Thr Ala Asn Leu Val Met His Thr Glu Asn Val Leu Asp Ile Arg Thr
    130                 135                 140

Ile Val Ala Asn Glu Tyr Ala Val Lys Thr Ser Ala Val Glu Trp Asp
145                 150                 155                 160

Val Thr Asp Ile Val Lys Asn Ala Ile Ile Gly Gly Ile Ser Phe Ile
                165                 170                 175

Pro Ser Val Gly Pro Ala Ile Ser Phe Leu Val Gly Leu Phe Trp Pro
            180                 185                 190

Gln Ser Lys Glu Asn Ile Trp Glu Gly Ile Val Lys Gln Ile Glu Arg
        195                 200                 205

Met Ile Glu Glu Ser Ala Leu Lys Thr Ile Lys Gly Ile Leu Ala Gly
    210                 215                 220

Asp Ile Ala Tyr Ile Gln Glu Arg Met Ala Thr Val Ala Asp Leu Leu
225                 230                 235                 240

Asp Lys His Pro Gly Ser Glu Glu Ala Arg Ser Ala Phe Asn Asn Leu
                245                 250                 255

Ala Glu Asn Ile Asp Gly Tyr His Lys Lys Phe Asn Asn Phe Ser Asp
            260                 265                 270

Asp Val Asn Tyr Gln Ile Leu Pro Met Phe Ser Thr Thr Val Met Met
        275                 280                 285

Gln Ile Thr Tyr Trp Val Ala Gly Leu Glu Arg Arg Asn Glu Ile Gly
    290                 295                 300

Leu Ser Asp Ile Asp Ile Glu Lys Val Arg Gly Leu Ile Lys Lys Thr
305                 310                 315                 320

Val Glu Gln Ala Asn Ser Tyr Ile Asn Asn Ile Tyr Asp Arg Glu Leu
                325                 330                 335

Asn Asp Ala Leu Asn Asn Ser Thr Ala Asp Thr Val Ala Asn Asn Val
            340                 345                 350

Met Ser Val His Gly His Cys Arg Leu His Gly Ile Glu Tyr Ile Ser
        355                 360                 365

Ile Trp Asp Lys Leu Ser Glu Ala Glu Ser Val Asn Asn Arg Ile Tyr
    370                 375                 380

Val Asp Val Leu Ser Tyr Ser Thr Phe Phe Asp Arg Gln Thr Ala Lys
385                 390                 395                 400
```

```
Ala Arg Ile Gln Ala Leu Thr Pro Glu Lys Asp Met Ala Pro Pro Leu
                405                 410                 415

Lys Pro Ala Leu Asn Asp Gly Lys Arg Arg Lys Ile Asp Ser Leu Thr
            420                 425                 430

Gly His Ile Val Arg Ile Gly Gly Ala Pro Arg Val Gly Gly Leu Thr
        435                 440                 445

Val Val Phe Asp Asp Gly Ser Ser His Arg Leu Gly Thr Ile Ser Gly
    450                 455                 460

Glu Thr Ala Ser Ile Ser Leu Asn Gly Ser Arg Ile Thr Ser Leu Glu
465                 470                 475                 480

Val Trp Gly Asn Gly Ala Val Asp Gln Ala Val Phe Thr Leu Ser Asp
                485                 490                 495

Gly Arg Ser Leu Ser Phe Gly Ala Pro Gly Thr Ser Arg Tyr Arg Lys
            500                 505                 510

Phe Tyr Val Gly Glu Ser His Tyr Ile Ala Gly Val Tyr Leu Ser Ser
        515                 520                 525

Asp Tyr Ser Pro Leu Ala Gly Gln Ala Ala Asn Ile Ala Val Ser Tyr
    530                 535                 540

Gln Leu Ile Asn Asp Asp Glu Lys
545                 550


<210> SEQ ID NO 43
<211> LENGTH: 420
<212> TYPE: DNA
<213> ORGANISM: Unknown
<220> FEATURE:
<223> OTHER INFORMATION: A nucleic acid sequence obtained from an
      unknown bacterial strain comprised within a microbiome encoding a
      TIC7939 pesticidal PirA protein sequence.

<400> SEQUENCE: 43

atgacgtgtg agattctgca tatgacaagc aaaggcgatg aaatgcagtc gattgcagcg      60

acggatgctc aaacgttaca ggaggcgcct aaagatgaag tgaattttaa gcagacaaaa     120

ggggatatga tggtccctgg ggggcagtct gcacagggag cgcgctacga tactccgatt     180

attcctgaac ttcatccgtc ttactatgta tcaaattcag gacctgcagc tacggtgaaa     240

gctgtcttct actggtccca ctcatttacc tcgaagtggt ttgaatataa ttcagttacg     300

gttctcaggg ggactactga gcggcttagt gcgccaagca actcacttta ttacagcaag     360

gtcgttgtct ttaataatga gaaagagcct gcttatgtta ctgtaacgac cattcggtaa     420


<210> SEQ ID NO 44
<211> LENGTH: 139
<212> TYPE: PRT
<213> ORGANISM: Unknown
<220> FEATURE:
<223> OTHER INFORMATION: The amino acid sequence of the TIC7939 PirA
      protein.

<400> SEQUENCE: 44

Met Thr Cys Glu Ile Leu His Met Thr Ser Lys Gly Asp Glu Met Gln
1               5                   10                  15

Ser Ile Ala Ala Thr Asp Ala Gln Thr Leu Gln Glu Ala Pro Lys Asp
            20                  25                  30

Glu Val Asn Phe Lys Gln Thr Lys Gly Asp Met Met Val Pro Gly Gly
        35                  40                  45

Gln Ser Ala Gln Gly Ala Arg Tyr Asp Thr Pro Ile Ile Pro Glu Leu
    50                  55                  60
```

```
His Pro Ser Tyr Tyr Val Ser Asn Ser Gly Pro Ala Ala Thr Val Lys
65                  70                  75                  80

Ala Val Phe Tyr Trp Ser His Ser Phe Thr Ser Lys Trp Phe Glu Tyr
                85                  90                  95

Asn Ser Val Thr Val Leu Arg Gly Thr Thr Glu Arg Leu Ser Ala Pro
            100                 105                 110

Ser Asn Ser Leu Tyr Tyr Ser Lys Val Val Val Phe Asn Asn Glu Lys
        115                 120                 125

Glu Pro Ala Tyr Val Thr Val Thr Thr Ile Arg
    130                 135


<210> SEQ ID NO 45
<211> LENGTH: 1260
<212> TYPE: DNA
<213> ORGANISM: Unknown
<220> FEATURE:
<223> OTHER INFORMATION: A nucleic acid sequence obtained from an
      unknown bacterial strain comprised within a microbiome encoding a
      TIC7940 PirB pesticidal protein sequence.

<400> SEQUENCE: 45

atgaccacga accccattgt tcatagagag tttgattatg cggaccttta cggcgacgat      60

agtcgatcca gcccacaaaa caatgattgg gactatttag ttgtagcaaa gattcttgtt     120

gttcaggggc ttaagcatat tcctgtcgtg ggcggggctc tttcgagtct aactaacgct     180

ctctggccga aaaaaaaaga taatgtctgg acgcaagctc ttggagagat tgagcagtat     240

attgatagtc agaatctgaa ggtgattcag ggcatactca atggtgagat acttgagatc     300

caagggaaga tggagcacgt tacagcgctt cttgagaagc atcctaatac caaggaatct     360

tacaatgcgt ataaggattt agctcagtat cttgatagta agcagagaaa gtttggagca     420

tttgatgctg agcagaacta tcatttgatt cctatgtatg catctatgat tttgctgcag     480

gcgacgtatt ggcgaaccgg aattgacagg cgaaatgaaa tcggcctgac tgatatcgat     540

gttgagtctc taaagaggct tattgctgat cttgttttcg aatcgaggga atatatcggt     600

cgcgtctacg atgaggcggt cgaaagggtg tatgctgaag ctaatcccag agatgtgaca     660

aattatatgt actctgttag ggttatagc ttgctgcacg gtgttgagac tgttgaaata      720

atcgatcgcg ttagaagatt gggcgttgat agcggcttca atgttggtgt ggtaagttat     780

tctacggtgg ttgggacagt tacaaaccgc gtaagaactc aagctctcac tccagatgat     840

gaaatgaaag agccattaag gccggagttc gttgacgatg aagttaatca gatcgcgtct     900

ataactgggt atattggtcc tcttattgat agtaagccca cgattggcgg cttgttcgtg     960

gtctttgaaa acggcaactg ctacaaaatg gggcggagt caggcacgtc ttattctata     1020

gaccttcgtg gaagtactat ctcaaccgtt gaagtttggt atcagggatt actagaaggg    1080

gttcggttta cattgagtga tgatagagat ctgctgattg gccagcggca atccgagagg    1140

tccaaatata gacgatttga agtggaaggg cattacgttt caggagtgta tttggatcgt    1200

gatgaaacga cctatcgcgg gcgagctgcc aatatttcag tgtcttacca tatcgcgtag    1260


<210> SEQ ID NO 46
<211> LENGTH: 419
<212> TYPE: PRT
<213> ORGANISM: Unknown
<220> FEATURE:
<223> OTHER INFORMATION: The amino acid sequence of the TIC7940 PirB
      protein.
```

<400> SEQUENCE: 46

```
Met Thr Thr Asn Pro Ile Val His Arg Glu Phe Asp Tyr Ala Asp Leu
1               5                   10                  15

Tyr Gly Asp Asp Ser Arg Ser Ser Pro Gln Asn Asn Asp Trp Asp Tyr
            20                  25                  30

Leu Val Val Ala Lys Ile Leu Val Val Gln Gly Leu Lys His Ile Pro
        35                  40                  45

Val Val Gly Gly Ala Leu Ser Ser Leu Thr Asn Ala Leu Trp Pro Lys
    50                  55                  60

Lys Lys Asp Asn Val Trp Thr Gln Ala Leu Gly Glu Ile Glu Gln Tyr
65                  70                  75                  80

Ile Asp Ser Gln Asn Leu Lys Val Ile Gln Gly Ile Leu Asn Gly Glu
                85                  90                  95

Ile Leu Glu Ile Gln Gly Lys Met Glu His Val Thr Ala Leu Leu Glu
            100                 105                 110

Lys His Pro Asn Thr Lys Glu Ser Tyr Asn Ala Tyr Lys Asp Leu Ala
        115                 120                 125

Gln Tyr Leu Asp Ser Lys Gln Arg Lys Phe Gly Ala Phe Asp Ala Glu
    130                 135                 140

Gln Asn Tyr His Leu Ile Pro Met Tyr Ala Ser Met Ile Leu Leu Gln
145                 150                 155                 160

Ala Thr Tyr Trp Arg Thr Gly Ile Asp Arg Arg Asn Glu Ile Gly Leu
                165                 170                 175

Thr Asp Ile Asp Val Glu Ser Leu Lys Arg Leu Ile Ala Asp Leu Val
            180                 185                 190

Phe Glu Ser Arg Glu Tyr Ile Gly Arg Val Tyr Asp Glu Ala Val Glu
        195                 200                 205

Arg Val Tyr Ala Glu Ala Asn Pro Arg Asp Val Thr Asn Tyr Met Tyr
    210                 215                 220

Ser Val Arg Gly Tyr Ser Leu Leu His Gly Val Glu Thr Val Glu Ile
225                 230                 235                 240

Ile Asp Arg Val Arg Arg Leu Gly Val Asp Ser Gly Phe Asn Val Gly
                245                 250                 255

Val Val Ser Tyr Ser Thr Val Val Gly Thr Val Thr Asn Arg Val Arg
            260                 265                 270

Thr Gln Ala Leu Thr Pro Asp Asp Glu Met Lys Glu Pro Leu Arg Pro
        275                 280                 285

Glu Phe Val Asp Asp Glu Val Asn Gln Ile Ala Ser Ile Thr Gly Tyr
    290                 295                 300

Ile Gly Pro Leu Ile Asp Ser Lys Pro Thr Ile Gly Gly Leu Phe Val
305                 310                 315                 320

Val Phe Glu Asn Gly Asn Cys Tyr Lys Met Gly Ala Glu Ser Gly Thr
                325                 330                 335

Ser Tyr Ser Ile Asp Leu Arg Gly Ser Thr Ile Ser Thr Val Glu Val
            340                 345                 350

Trp Tyr Gln Gly Leu Leu Glu Gly Val Arg Phe Thr Leu Ser Asp Asp
        355                 360                 365

Arg Asp Leu Leu Ile Gly Gln Arg Gln Ser Glu Arg Ser Lys Tyr Arg
    370                 375                 380

Arg Phe Glu Val Glu Gly His Tyr Val Ser Gly Val Tyr Leu Asp Arg
385                 390                 395                 400

Asp Glu Thr Thr Tyr Arg Gly Arg Ala Ala Asn Ile Ser Val Ser Tyr
                405                 410                 415
```

His Ile Ala

<210> SEQ ID NO 47
<211> LENGTH: 1677
<212> TYPE: DNA
<213> ORGANISM: Artificial
<220> FEATURE:
<223> OTHER INFORMATION: A nucleic acid sequence encoding a PirAB fusion protein, TIC9321 comprised of the TIC7939 and TIC7940 coding sequences in operable linkage and in frame.

<400> SEQUENCE: 47
atgacgtgtg agattctgca tatgacaagc aaaggcgatg aaatgcagtc gattgcagcg 60
acggatgctc aaacgttaca ggaggcgcct aaagatgaag tgaattttaa gcagacaaaa 120
ggggatatga tggtccctgg ggggcagtct gcacagggag cgcgctacga tactccgatt 180
attcctgaac ttcatccgtc ttactatgta tcaaattcag gacctgcagc tacggtgaaa 240
gctgtcttct actggtccca ctcatttacc tcgaagtggt ttgaatataa ttcagttacg 300
gttctcaggg ggactactga gcggcttagt gcgccaagca actcacttta ttacagcaag 360
gtcgttgtct ttaataatga gaaagagcct gcttatgtta ctgtaacgac cattcggatg 420
accacgaacc ccattgttca tagagagttt gattatgcgg acctttacgg cgacgatagt 480
cgatccagcc cacaaaacaa tgattgggac tatttagttg tagcaaagat tcttgttgtt 540
caggggctta agcatattcc tgtcgtgggc ggggctcttt cgagtctaac taacgctctc 600
tggccgaaaa aaaaagataa tgtctggacg caagctcttg gagagattga gcagtatatt 660
gatagtcaga atctgaaggt gattcagggc atactcaatg gtgagatact tgagatccaa 720
gggaagatgg agcacgttac agcgcttctt gagaagcatc ctaataccaa ggaatcttac 780
aatgcgtata aggatttagc tcagtatctt gatagtaagc agagaaagtt tggagcattt 840
gatgctgagc agaactatca tttgattcct atgtatgcat ctatgatttt gctgcaggcg 900
acgtattggc gaaccggaat tgacaggcga aatgaaatcg gcctgactga tatcgatgtt 960
gagtctctaa agaggcttat tgctgatctt gttttcgaat cgagggaata tatcggtcgc 1020
gtctacgatg aggcggtcga aagggtgtat gctgaagcta atcccagaga tgtgacaaat 1080
tatatgtact ctgttagggg ttatagcttg ctgcacggtg ttgagactgt tgaaataatc 1140
gatcgcgtta gaagattggg cgttgatagc ggcttcaatg ttggtgtggt aagttattct 1200
acggtggttg ggacagttac aaaccgcgta agaactcaag ctctcactcc agatgatgaa 1260
atgaaagagc cattaaggcc ggagttcgtt gacgatgaag ttaatcagat cgcgtctata 1320
actgggtata ttggtcctct tattgatagt aagcccacga ttggcggctt gttcgtggtc 1380
tttgaaaacg gcaactgcta caaaatgggg gcggagtcag gcacgtctta ttctatagac 1440
cttcgtggaa gtactatctc aaccgttgaa gtttggtatc agggattact agaaggggtt 1500
cggtttacat tgagtgatga tagagatctg ctgattggcc agcggcaatc cgagaggtcc 1560
aaatatagac gatttgaagt ggaagggcat tacgtttcag gagtgtattt ggatcgtgat 1620
gaaacgacct atcgcgggcg agctgccaat atttcagtgt cttaccatat cgcgtag 1677

<210> SEQ ID NO 48
<211> LENGTH: 558
<212> TYPE: PRT
<213> ORGANISM: Artificial
<220> FEATURE:
<223> OTHER INFORMATION: The amino acid sequence of the TIC9321 PirAB fusion protein.

<400> SEQUENCE: 48

Met Thr Cys Glu Ile Leu His Met Thr Ser Lys Gly Asp Glu Met Gln
1               5                   10                  15

Ser Ile Ala Ala Thr Asp Ala Gln Thr Leu Gln Glu Ala Pro Lys Asp
            20                  25                  30

Glu Val Asn Phe Lys Gln Thr Lys Gly Asp Met Met Val Pro Gly Gly
        35                  40                  45

Gln Ser Ala Gln Gly Ala Arg Tyr Asp Thr Pro Ile Ile Pro Glu Leu
    50                  55                  60

His Pro Ser Tyr Tyr Val Ser Asn Ser Gly Pro Ala Ala Thr Val Lys
65                  70                  75                  80

Ala Val Phe Tyr Trp Ser His Ser Phe Thr Ser Lys Trp Phe Glu Tyr
                85                  90                  95

Asn Ser Val Thr Val Leu Arg Gly Thr Thr Glu Arg Leu Ser Ala Pro
            100                 105                 110

Ser Asn Ser Leu Tyr Tyr Ser Lys Val Val Val Phe Asn Asn Glu Lys
        115                 120                 125

Glu Pro Ala Tyr Val Thr Val Thr Thr Ile Arg Met Thr Thr Asn Pro
    130                 135                 140

Ile Val His Arg Glu Phe Asp Tyr Ala Asp Leu Tyr Gly Asp Asp Ser
145                 150                 155                 160

Arg Ser Ser Pro Gln Asn Asn Asp Trp Asp Tyr Leu Val Val Ala Lys
                165                 170                 175

Ile Leu Val Val Gln Gly Leu Lys His Ile Pro Val Val Gly Gly Ala
            180                 185                 190

Leu Ser Ser Leu Thr Asn Ala Leu Trp Pro Lys Lys Lys Asp Asn Val
        195                 200                 205

Trp Thr Gln Ala Leu Gly Glu Ile Glu Gln Tyr Ile Asp Ser Gln Asn
    210                 215                 220

Leu Lys Val Ile Gln Gly Ile Leu Asn Gly Glu Ile Leu Glu Ile Gln
225                 230                 235                 240

Gly Lys Met Glu His Val Thr Ala Leu Leu Glu Lys His Pro Asn Thr
                245                 250                 255

Lys Glu Ser Tyr Asn Ala Tyr Lys Asp Leu Ala Gln Tyr Leu Asp Ser
            260                 265                 270

Lys Gln Arg Lys Phe Gly Ala Phe Asp Ala Glu Gln Asn Tyr His Leu
        275                 280                 285

Ile Pro Met Tyr Ala Ser Met Ile Leu Leu Gln Ala Thr Tyr Trp Arg
    290                 295                 300

Thr Gly Ile Asp Arg Arg Asn Glu Ile Gly Leu Thr Asp Ile Asp Val
305                 310                 315                 320

Glu Ser Leu Lys Arg Leu Ile Ala Asp Leu Val Phe Glu Ser Arg Glu
                325                 330                 335

Tyr Ile Gly Arg Val Tyr Asp Glu Ala Val Glu Arg Val Tyr Ala Glu
            340                 345                 350

Ala Asn Pro Arg Asp Val Thr Asn Tyr Met Tyr Ser Val Arg Gly Tyr
        355                 360                 365

Ser Leu Leu His Gly Val Glu Thr Val Glu Ile Ile Asp Arg Val Arg
    370                 375                 380

Arg Leu Gly Val Asp Ser Gly Phe Asn Val Gly Val Val Ser Tyr Ser
385                 390                 395                 400

Thr Val Val Gly Thr Val Thr Asn Arg Val Arg Thr Gln Ala Leu Thr

```
                405                 410                 415

Pro Asp Asp Glu Met Lys Glu Pro Leu Arg Pro Glu Phe Val Asp Asp
            420                 425                 430

Glu Val Asn Gln Ile Ala Ser Ile Thr Gly Tyr Ile Gly Pro Leu Ile
        435                 440                 445

Asp Ser Lys Pro Thr Ile Gly Gly Leu Phe Val Val Phe Glu Asn Gly
    450                 455                 460

Asn Cys Tyr Lys Met Gly Ala Glu Ser Gly Thr Ser Tyr Ser Ile Asp
465                 470                 475                 480

Leu Arg Gly Ser Thr Ile Ser Thr Val Glu Val Trp Tyr Gln Gly Leu
                485                 490                 495

Leu Glu Gly Val Arg Phe Thr Leu Ser Asp Asp Arg Asp Leu Leu Ile
            500                 505                 510

Gly Gln Arg Gln Ser Glu Arg Ser Lys Tyr Arg Arg Phe Glu Val Glu
        515                 520                 525

Gly His Tyr Val Ser Gly Val Tyr Leu Asp Arg Asp Glu Thr Thr Tyr
    530                 535                 540

Arg Gly Arg Ala Ala Asn Ile Ser Val Ser Tyr His Ile Ala
545                 550                 555


<210> SEQ ID NO 49
<211> LENGTH: 1695
<212> TYPE: DNA
<213> ORGANISM: Artificial
<220> FEATURE:
<223> OTHER INFORMATION: A synthetic coding sequence used for expression
      in plant cells encoding a TIC6880PL PirAB fusion protein with an
      additional alanine codon inserted after the initiating methionine
      codon.

<400> SEQUENCE: 49

atggctatca cgataaacat ctcgggcggg agcatcaaga tttccaacaa cattggctcc      60

gagacggaca tccgcaacac gcccttctcc gagccgctct ccatctccaa ctacaaagac     120

atgacgatag agcctcattc ctccatccag gccacgcgga ccgacacacc catcatccct     180

gagacccggc cgaactacta cgtggccaac tctggcccgg cggcctccgt gcgcgccgtc     240

ttctactggt cgcacagttt cacatcggag tggtttgagc actcctccat cattgtcaaa     300

gctggcgagg acggcatcct taactcgccc tccaacagcg tgtactacag caaggtggtc     360

atctacaatg acacggacaa gcgcgccttc gtcacgggct acgacaagat gaacaacgaa     420

ctcatgaaca ccaacgagtc gcagccttcc gagactctga gcctgattaa cgagtccatc     480

ctcaccgcgc cctacgcggt ctccacgccg aactacgagt gggacatgtc gtcgattatt     540

aaggacgcca taatcggcgg tattggcttc atccctggcc ctgggagcgc catctccttc     600

ctccttggtt tgttctggcc gcagcaaacc gacaacacct gggagcagat actccagaag     660

gtcgagcaaa tgattgagga agccaacctc aagaccatcc agggcatcct gaacggcgac     720

atccaggaga tcaagggcaa gatggagcac gtagagtaca tgctggagac ctcgccaggc     780

actcaggaga gtcacgacgc ctacatgttc ctggcgcgct acttagtttc catcgacgag     840

aagttcaaga gcttcgacaa caagacgaac taccagatcc tgcccatgta caccaacacc     900

ctgatgctcc aggctcccta ctggaagatg ggcatcgaga agaagaacga catcctactt     960

actgacattg aggtgaacga actcaagcag ctcatcgaga gcctgtacgc gaaggccaac    1020

agctacatcc acgaagtgta cacccgagag tacgacaacg cggtgaacac cagtaccgcg    1080

accaccatca ccaacaacct cctgagcgtg cgaggctact gcctcttgca cgggctcgaa    1140
```

```
tgcctggagg tgctcgacca catccagaac aacaacctgg accagtcgtt ctacccgaag   1200

accatctcct actccaccgt ctttgaccgg tccaccaaca agactcggct gcaagcgctg   1260

accgaggacg agcagatgga ggaacctctg aaaccatcct tcatcaacgg cgagtacaac   1320

aagatcaaga gcctgatcgg gtacgtgcag cggattggca acgcgccgcg agtgggcggc   1380

atcaagataa ccttcacgaa cgggtccagc cacaccttgg gcaccgtcac gagcgagtcc   1440

aactccatcg agctgaacga ctccgtcatc acctccgtcg aggtgtgggg caatggtgcg   1500

gtggacgagg cgttcttcac tctctcggac ggtcgccagt tccgcctggg ccagcgttac   1560

gcctccaact accgcaagta cgcggtggac gggcactaca tctccggcct gtacctggcc   1620

tcggacgagc catccctggc cgggcaagcg gctggcattg ccgtcagcta ccacatcctg   1680

gtggacaaga agtga                                                    1695
```

```
<210> SEQ ID NO 50
<211> LENGTH: 564
<212> TYPE: PRT
<213> ORGANISM: Artificial
<220> FEATURE:
<223> OTHER INFORMATION: The amino acid sequence of the TIC6880PL PirAB
      fusion protein.

<400> SEQUENCE: 50

Met Ala Ile Thr Ile Asn Ile Ser Gly Gly Ser Ile Lys Ile Ser Asn
1               5                   10                  15

Asn Ile Gly Ser Glu Thr Asp Ile Arg Asn Thr Pro Phe Ser Glu Pro
            20                  25                  30

Leu Ser Ile Ser Asn Tyr Lys Asp Met Thr Ile Glu Pro His Ser Ser
        35                  40                  45

Ile Gln Ala Thr Arg Thr Asp Thr Pro Ile Ile Pro Glu Thr Arg Pro
    50                  55                  60

Asn Tyr Tyr Val Ala Asn Ser Gly Pro Ala Ala Ser Val Arg Ala Val
65                  70                  75                  80

Phe Tyr Trp Ser His Ser Phe Thr Ser Glu Trp Phe Glu His Ser Ser
                85                  90                  95

Ile Ile Val Lys Ala Gly Glu Asp Gly Ile Leu Asn Ser Pro Ser Asn
            100                 105                 110

Ser Val Tyr Tyr Ser Lys Val Val Ile Tyr Asn Asp Thr Asp Lys Arg
        115                 120                 125

Ala Phe Val Thr Gly Tyr Asp Lys Met Asn Asn Glu Leu Met Asn Thr
    130                 135                 140

Asn Glu Ser Gln Pro Ser Glu Thr Leu Ser Leu Ile Asn Glu Ser Ile
145                 150                 155                 160

Leu Thr Ala Pro Tyr Ala Val Ser Thr Pro Asn Tyr Glu Trp Asp Met
                165                 170                 175

Ser Ser Ile Ile Lys Asp Ala Ile Ile Gly Gly Ile Gly Phe Ile Pro
            180                 185                 190

Gly Pro Gly Ser Ala Ile Ser Phe Leu Leu Gly Leu Phe Trp Pro Gln
        195                 200                 205

Gln Thr Asp Asn Thr Trp Glu Gln Ile Leu Gln Lys Val Glu Gln Met
    210                 215                 220

Ile Glu Glu Ala Asn Leu Lys Thr Ile Gln Gly Ile Leu Asn Gly Asp
225                 230                 235                 240

Ile Gln Glu Ile Lys Gly Lys Met Glu His Val Glu Tyr Met Leu Glu
                245                 250                 255
```

```
Thr Ser Pro Gly Thr Gln Glu Ser His Asp Ala Tyr Met Phe Leu Ala
            260                 265                 270

Arg Tyr Leu Val Ser Ile Asp Glu Lys Phe Lys Ser Phe Asp Asn Lys
        275                 280                 285

Thr Asn Tyr Gln Ile Leu Pro Met Tyr Thr Asn Thr Leu Met Leu Gln
    290                 295                 300

Ala Pro Tyr Trp Lys Met Gly Ile Glu Lys Lys Asn Asp Ile Leu Leu
305                 310                 315                 320

Thr Asp Ile Glu Val Asn Glu Leu Lys Gln Leu Ile Glu Ser Leu Tyr
                325                 330                 335

Ala Lys Ala Asn Ser Tyr Ile His Glu Val Tyr Thr Arg Glu Tyr Asp
            340                 345                 350

Asn Ala Val Asn Thr Ser Thr Ala Thr Thr Ile Thr Asn Asn Leu Leu
        355                 360                 365

Ser Val Arg Gly Tyr Cys Leu Leu His Gly Leu Glu Cys Leu Glu Val
    370                 375                 380

Leu Asp His Ile Gln Asn Asn Asn Leu Asp Gln Ser Phe Tyr Pro Lys
385                 390                 395                 400

Thr Ile Ser Tyr Ser Thr Val Phe Asp Arg Ser Thr Asn Lys Thr Arg
                405                 410                 415

Leu Gln Ala Leu Thr Glu Asp Glu Gln Met Glu Glu Pro Leu Lys Pro
            420                 425                 430

Ser Phe Ile Asn Gly Glu Tyr Asn Lys Ile Lys Ser Leu Ile Gly Tyr
        435                 440                 445

Val Gln Arg Ile Gly Asn Ala Pro Arg Val Gly Gly Ile Lys Ile Thr
    450                 455                 460

Phe Thr Asn Gly Ser Ser His Thr Leu Gly Thr Val Thr Ser Glu Ser
465                 470                 475                 480

Asn Ser Ile Glu Leu Asn Asp Ser Val Ile Thr Ser Val Glu Val Trp
                485                 490                 495

Gly Asn Gly Ala Val Asp Glu Ala Phe Phe Thr Leu Ser Asp Gly Arg
            500                 505                 510

Gln Phe Arg Leu Gly Gln Arg Tyr Ala Ser Asn Tyr Arg Lys Tyr Ala
        515                 520                 525

Val Asp Gly His Tyr Ile Ser Gly Leu Tyr Leu Ala Ser Asp Glu Pro
    530                 535                 540

Ser Leu Ala Gly Gln Ala Ala Gly Ile Ala Val Ser Tyr His Ile Leu
545                 550                 555                 560

Val Asp Lys Lys
```

<210> SEQ ID NO 51
<211> LENGTH: 1701
<212> TYPE: DNA
<213> ORGANISM: Artificial
<220> FEATURE:
<223> OTHER INFORMATION: A synthetic coding sequence used for expression in plant cells encoding a TIC9316 PirAB fusion protein.

<400> SEQUENCE: 51

```
atgaacacca tcaacatcaa catctccggc tcgaccgtga cggtgatctc gaacaacgac      60

tccaacccgg agccgctcac ctacaacacg aacacaccag cgagcgatcc tctgacggcc     120

agcccgtacc gggacatgac catcgagccg cacagctcca ttgaggcgac gcgcacagac     180

acgcccatca tcccggagac ccggccgaac tactacgtcg ccaactccgg cccggcctcc     240
```

-continued

```
tcagtccgcg ctgtgttcta ctggtcgcac agcttcacgt cagaatggtt cgagtacagc    300

tctatcatag tcaaggcggg caaggacggc atcctccagt cgcccaacaa cgccctgtac    360

tacagcaagg tcgtgatcta caacgacacc gacaagcgcg ccttcgtcac cggctacaac    420

aagatgaaca tcagcccgat caacgtctcg gagaacgaga cgctcccgga gctgaccgac    480

gtgatgctga tcgtcccata cacgaccagc acgccggatt acgagtggga catgtcgtcg    540

atcattaagg atgcgatcat cggaggcgtt ggcttcatcc ctggcgcggg ctcggccatg    600

agcttcctgc tcggcctgtt ctggccgcag cagaaggata acacttggga gcagatactt    660

cagaaggtgg aacagatgat cgagaacgcg gtcctccaaa cgatcaaggg catcctcaac    720

ggcgacatcc aggagattaa gggaaagatg gagcacgttc agtacatgct cgaaaccagc    780

cctgggagcc aggagagcca cgacgcctac atgttcttgg cacgttacct cgtctcgatt    840

gacgagaagt tcaagtcctt cgacaacaag acaaactacc agatcttgcc aatgtacacc    900

aatacggtta tgttacagat tccgtactgg aagatgggca tcgagaagaa gaatgacatc    960

ggcttgaccg acatcgaggt caatgagctt aagcaactta tcgacaagct ggtggacaag   1020

gccaagtcct acatccacac aatgtacacc aacgagtaca acgacgcgat caacaccagc   1080

accgcctcaa gcgtcacaaa caacctcctg tccgtgcgcg gttactgcct tctgcacggc   1140

ctggagtgca tcgaacttat tgagcatctc cagaacaaca gcctggagtc cggcttctac   1200

ccgaagacga tcagctactc cacggtcttc gaccggcaga ccaacaagat gcggatacaa   1260

gcgctcactg aggacgacca gatgcaagaa cccttcaagc cctcgctcat caacgggaag   1320

tacaacaaga tccagagcct cctcggctac gtccagcgca tcggcaacgc gccgcgcgtc   1380

ggcgggatca agatcacgtt cgccaacggg tctagttaca cgctgggcac cgtgaccagc   1440

gagacctcca gtattgagct taacgactcg gtgatcgagc ggctggaggt gtggggcaac   1500

ggcgcggtgg acgaggcgct gttcaccctc tcggacgggc ggcagctccg ggtcggcgag   1560

cggtacgcga ccaagtaccg taagtacgcc gtggacggcc actacatcgc cggtctgtac   1620

ctcgccagtg acgagcccag cctagcgggc caggcggctg gcatcgccgt gtcgtaccac   1680

atgctcgacg acaagaagtg a                                             1701
```

<210> SEQ ID NO 52
<211> LENGTH: 1701
<212> TYPE: DNA
<213> ORGANISM: Artificial
<220> FEATURE:
<223> OTHER INFORMATION: A synthetic coding sequence used for expression in plant cells encoding a TIC9317 PirAB fusion protein.

<400> SEQUENCE: 52

```
atgattacga tcaacatcaa cgtgaacggc aacgacgtga cgggcaccaa caacaatgag     60

cccactccag tcagcacgac gtacggcccg aacactccgg cctcggagcc accggtcgtc    120

tcgaactact ccgacatcac cattgagccg cacagctcgg tccaggccac gcggatcgac    180

acgccggtga tcccggaggc ccggccggac tactacgtgg cgaactcggg ccctgcgccg    240

tccgtgcggg ccgtgttcta ctggtcgcac tcgttcacct ccgagtggtt cgagtcgtcc    300

agcatcaccg tgaaggcggg cgaggacgga atcctcaagg ctccagggaa cagcctgtac    360

tacagcaagg tcgtcatcta caacgacaca gacaagcggg ccttcgttac cgggtacaac    420

aagatgaaca ccactccgat tactgtaagc actaacgaaa catcgcctct catgacggac    480

gtgatgccga tggacctgta cgccatctcg acgccagact acgagtggga catgagttcc    540
```

```
atcatcaagg acgccgtaat tggcggcatc gggttcatcc ctgggcccgg cccggccatc    600

tccttcctgc tgggcctgtt ctggccgcag cagaaggaca acacatggga gcagatactc    660

cagaaggtcg agcaaatgat tgagaatgcc gtgttgcaga cgatcaaggg aatcctaaac    720

ggcgaagtac aggagatcaa gggcaagatg gagcacgtcg agtctatgct caagaactcg    780

ccaggctctc aggagtcaca cgacgcctac atgttcctgg ctcgttacct cgtttcaatt    840

gacgagaagt tcaagagctt cgacaaccgc accaactacc aactgttgcc gatgtacacc    900

aatacgatta tgctccagat accttattgg aagatgggca tcgagaagaa gaaggacatt    960

ggcctgaccg acattgaagt caacgagctt aaggagctga tcgacaagct ggtggacaag   1020

gccaagaact acatccacac aatgtacacg aacgagcaca acaacgccgt gaacaccagc   1080

actgccgagt ccgtcacgaa caatctcctc agcgtgcgcg gctactgcct gttacacggg   1140

ctggagtgca ttgagctaat cgagcacatc cagaacaact ccctggagag cgggttctac   1200

ccgaagatca tcagctacag caccgctttc gaccgcccga caaacaagat gcgtatccaa   1260

gcgctcacgg aggacgacgc gatgcaagag ccgtttaaac cgtcgctcat taacggcaag   1320

tacaacaaga tccagagcct cacgggctac gtgcagcgga tcggcaacgc gccgcgcgtc   1380

ggcggcatcc gcatcacgtt caccaacggg tcgtcctaca cgctcgggac ggtgacctcc   1440

gagacgcaca gcatcaagct gaacgactcc gtgatcgagt cgttagaggt ctggggaaac   1500

ggtgccgtgg acgaggccct gttcaagctg tccgacgggc ggctcctccg catcggcgag   1560

cggtacgcca agaagtaccg caagtacgcg gtggacaacc actacatcgc gggcatctac   1620

ctagcgagcg acgagccgtc cctggcgggt caagccgccg ggatcgccgt gagctatcac   1680

atgatggcgg acaagaaatg a                                              1701
```

<210> SEQ ID NO 53
<211> LENGTH: 1701
<212> TYPE: DNA
<213> ORGANISM: Artificial
<220> FEATURE:
<223> OTHER INFORMATION: A synthetic coding sequence used for expression in plant cells encoding a TIC9318 PirAB fusion protein.

<400> SEQUENCE: 53

```
atgtccacca tcaacatcaa catctcctcc agcacggtca ctgtgattac aaacaatggc     60

gagacgcccg tcccgctcac ctacaacacc aacacgccgg agtcggagcc gctgacggtc    120

aacccgtacc gcgacatgac catcgagccg cgctcctcca ttgaggcgac ccgcatcgac    180

acgccgatca tcccggagac gagaccgaac tactatgtgg cgaactccgg cccggccagc    240

agcgtccggg cggtattcta ctggtcgcac agcttcacct cgcaatggtt cgagtattcg    300

tcgatcatcg tgaaggcggg tgaggacggc atactggagt cgccgtcgaa cagcctctac    360

tacagcaagg tggtgatcta caacgacacg gacaagaggg cattcgtcac gggctacaac    420

aagatgaaca ccaccctcat caacgtaagt gagaaggaga cgctgccggt gcagaccgac    480

atcatgctga tcgcgccgta ctccgtgtcc acgccggact acgagtggga catgtcatcg    540

ctcatcaagg acgcgatcat cggcggcgtc ggattcatcc ctgtcgtcgg ctcggccatg    600

tccttcctcc tcggcctgtt ctggccgcag cagaaggaca acacttggga acaaatactg    660

cagaaggtcg agcagatgat cgagaacgcg cagctcaaca cgattaaggg cattctgaac    720

ggcgacatcc aggagattaa gggcaagatg gagcacgtgc agtacatgct tgagacaagt    780

ccagggagtc aggagtcaca cgacgcctac atgttcttag cccgctacct agtgagcatc    840
```

```
gacgagaagt tcaagtcgtt cgacaacaag acaaactacc aaatcttgcc aatgtacacg    900

aataccgtca tgctacagat cccatactgg aagatgggaa ttgagaagaa gaacgacatt    960

ggcttgacgg acatcgaagt caacgagctt aaacagctta tcgacactct ggtggaccgc   1020

gcgcgcaact acatccacac catgtacgag cgagagtacg acaacgccat caacacctca   1080

accgctgcct cggtgaccaa caacctgctc tccgtgcgcg ggtactgcct cctgcacggg   1140

ctggagtgca tcgagactat cgagcacctt cagaacaaca gcctcaacag tgggttctac   1200

ccgaagacca tcagctacag cactgtcttc gaccggccca cgaacaagac ccgcatccag   1260

gctctgacgg aagacgacca aatgcaagag ccgttcaagc ccgcgctgat cggcggcaag   1320

tacaacaaga tcaagtccct gttgggctac gtgcgaagga tcggcaacgc tccacgggtc   1380

ggcggcatca aggtgacgtt caccaatggg tcgagctaca cgctcgggac ggtcacgtcg   1440

gaaaccgact ccatcgaact gaacgagtcg gtcatcgagc ggctggaggt gtggggcaac   1500

ggagccgtgg acgaggccct ctttaccctg agcgatggcc gccagctccg catcggcgag   1560

cggtacgcca agaaataccg gaagtacgcg gtggatgggc actacatcag cggcctctac   1620

ctcgcgtcgg acgagccctc cctcgccggt caagcagccg ggatcgcggt gtcctaccac   1680

atgctcgcag acaagaagtg a                                             1701
```

```
<210> SEQ ID NO 54
<211> LENGTH: 1650
<212> TYPE: DNA
<213> ORGANISM: Artificial
<220> FEATURE:
<223> OTHER INFORMATION: A synthetic coding sequence used for expression
      in plant cells encoding a TIC9319 PirAB fusion protein.

<400> SEQUENCE: 54
```

```
atgattacca tcaacatctc cggcgggaac gtgaccatca acaacaacat ctccagcgta     60

accgacatcc agaagccgct ggacgccgag ccgctgtccg tgacgaacta caaggacttg    120

acgatagagc cgcactcctc gatccaggcg acccgcacgg acacgccgat catcccggag    180

acccgcccga actactacgt ggccaactcg ggtccggctt ccagcgtgaa ggccgtgttc    240

tactggagcc actccttcac gtcggagtgg ttcgagtaca gctccatcat tgtgaaggcc    300

ggtgaggacg gcatcctcaa gagcccgtcc aacgccgtgt actactcgaa ggtcgtcatc    360

tacaacgaca cggacaagcg ggccttcgtg acgggctaca acatgatgaa caatagcccg    420

atgaacgacc agctctccat cgcgccgtac tccatctcca cgcccaacta cgagtgggac    480

atgagcagta tcatcaagga cgccatcatc ggcggcatcg gcttcatacc gggccctggc    540

agcgccatct ccttcctgct gggcctgttc tggccgcagc aaacggataa cacttgggac    600

caaatacttc agaagatcga gcaaatgatt gaggaagcta accttaagac catcaaggga    660

atactgaacg gcgacatcca ggagatcaag ggcaagatgg accacgtgca gtacatgctg    720

gagaactctc ccggaagcca ggaatcccac gacgcctaca tgttcctggc ccgtttcctc    780

gtgtccatcg acgagaagtt caagagcttc gacgaccgga ccaactacca aatcttgcca    840

atgtacacca acactatcat gttgcaagct ccttactgga agatgggcct ggagaagaag    900

gaagacattg gcctgtcgga cattgaggtt tcggaattga aggagctaat tgacaagctc    960

tacaccaaga gctacgacta catccacaac acctacaacc gcgagtacga caacgcgatc   1020

aacacatcca ccgccgagtc aatcaccaac aatctgctca gcgtgcgcgg ctactgcctc   1080

ctccacggct gtgaatgtct cgaagtcatc gcccacatcc agaacaacag cctcgacaag   1140
```

-continued

```
ggcttctacc cgaagaccat cagctactca agcgtgttcg accgccctac gaacaagatg   1200
cgaatccagg cgctgaccga agacgaccag atgcaagaac ccttcaagcc ctcgttcgta   1260
aacggccagt acaacaagat caagagcctg gagggctacg tgacccggat cggcaacgcg   1320
ccgcgcgtcg gcgggatcaa gatcacgttc gagaacaacg ccagctacac gctgggcacc   1380
gtcacctcgg agaccacgtt catcgagctg aacgagtcgg tcatcaccag cattgaggtc   1440
tggggcaacg gcgcggtgga cgaggcgttc ttcacgctga gcgacgggag gcagatgagg   1500
ctcgggcagc ggtacgcgag ccgctaccgc aagtacgcgg tggacgggca ctacatctcg   1560
ggcctgtacc tcgccagcga cgagcctagc ctcgcgggcc aggcagccgg gatcgccgtg   1620
agctaccaca tgatcgtgga caagcagtga                                    1650
```

<210> SEQ ID NO 55
<211> LENGTH: 1659
<212> TYPE: DNA
<213> ORGANISM: Artificial
<220> FEATURE:
<223> OTHER INFORMATION: A synthetic coding sequence used for expression in plant cells encoding a TIC9320 PirAB fusion protein.

<400> SEQUENCE: 55

```
atgagccgaa tcacaattgt cgtggattcg gacgaacaga aggccgaggt gtacagcaat     60
tctccggtcc cggtccacaa ggacttaaat gccgtgggcc cgctttccga cgtcaccatc    120
tcgccgcacg cctcagtcga ggtcttccgc atcgacacgc cgatcatccc ggagtcccgg    180
cgctcgctga gggtggtgaa cacgggcctg gccaacagcg tgacggccaa gttctactgg    240
agccactcct tcacgagcga gtggttcgag tcgggctcaa tcgacgtggg cctgggcgag    300
gagaaggtgc taaatgtccc gaacaactca ttctactact cgaagttcgt gatctacaac    360
aacaccgaca aggtggcgta cgttaccgcc aacctcgtaa tgcacacgga gaacgtgctc    420
gacattcgta ccattgtggc aaacgagtac gccgtcaaga cgtcggcggt cgagtgggac    480
gtcaccgaca ttgttaagaa cgcgatcatc ggcggcatct cattcatccc tagcgtgggc    540
ccggccatca gcttcctggt gggcctattc tggccacaga gcaaggagaa catctgggag    600
ggcatcgtca agcagataga gcgcatgatc gaggagtccg ccctcaagac gattaagggc    660
atcctggcgg gcgacatcgc ctacatacag gagcggatgg ccacggtggc cgacctcctg    720
gataaacacc ctgggagtga ggaggcccga tctgccttta acaacctcgc cgagaacatt    780
gacggctacc acaagaaatt caacaacttc tcagatgatg tcaattacca gatcctgcca    840
atgttcagca ctaccgtgat gatgcagatc acatactggg tcgctgggct tgagcgccgc    900
aacgaaatcg gattgtccga catcgacatc gagaaggttc gcgggcttat taagaagacc    960
gtggaacaag ctaactccta catcaataac atctacgacc gggagcttaa cgatgccctg   1020
aacaattcca ccgctgatac cgttgccaac aacgttatgt ctgtgcacgg gcactgccgc   1080
ctccacggca ttgagtacat ctccatctgg gacaagctga gtgaggccga gtcggtcaac   1140
aaccgcatct atgtggacgt actgtcctac tcaaccttct tcgaccgcca gacggcgaag   1200
gcccgcatac aagctctgac accggagaag gacatggctc cgccgctgaa acccgcgctg   1260
aacgacggga agcgccggaa gatcgacagc ctaacgggcc acatcgtccg aatcggcggc   1320
gcaccacgag tcggcggcct gacggtggtg ttcgacgacg gcagttcgca tcgtctcggc   1380
acgataagtg gcgaaaccgc ttcaatcagc ctcaacgggt cgcggatcac gtcgctggag   1440
gtgtggggaa atggtgccgt ggaccaggcg gtcttcacgc tctcggacgg gcggtccctc   1500
```

```
agcttcggag cgcctggcac ctcgcgctac cgtaagttct acgtcggcga gtcgcattac   1560

atcgcgggcg tttatctgtc gtccgactac tcacctctgg cgggtcaagc tgcgaacatc   1620

gcggtgtcct accaactcat caacgacgac gagaagtga                          1659
```

<210> SEQ ID NO 56
<211> LENGTH: 1659
<212> TYPE: DNA
<213> ORGANISM: Artificial
<220> FEATURE:
<223> OTHER INFORMATION: A synthetic coding sequence used for expression in plant cells encoding a TIC9322 PirAB fusion protein.

<400> SEQUENCE: 56

```
atgtcccgca tcacaatcgt agtggactcg gacgaccaga aggccgagtt ctacagcaac     60

tcgccggtgc ctgtgtacaa ggacttgaac gccgtgggtc cgctcagcga cgtcacaatc    120

tctcctcacg catctgtgga ggtcttccgg atcgacacgc cggtgatccc ggagtctcgg    180

tcgtctctgc gcgtcgtcaa caccggcctc tccaattcgg tgacggctaa gttctactgg    240

agccactcgt tcacatcgga gtggttcgag tccggctcca tcgacgtggg cctcggcgag    300

gagaaggtgc ttaatgtgcc gtccaactcc ttctactatt ccaagttcgt gatctacaac    360

aacaccgaca aggtggccta cgtcaccgcg aacctcgtga tgcacaccga gaacgtccta    420

gacatcagga ccatcgtggc gaacgagtac gcggtgaaga cctccgccct ggaatgggac    480

gtgaccgaca ttgtcaagaa tgcgatcatc ggcgggatct cgttcatccc gagcgtggga    540

ccggctatct cctttctcgt gggattgttc tggccgcaat cgaaggagaa catctgggag    600

ggaatcgtga agcagatcga gcggatgatc gaggaatctg ctctcaagac gatcaagggc    660

atcctcgcgg gagacatcgc ctacatccag gagcggatgg ccacggtggc cgacctcctg    720

gacaagcacc ctggatcgga ggaggcccga agcgcgttca acaacctcgc cgagaacatc    780

gacggctacc acaagaaatt ctcaaacttt agtgatgatg tcaactacca gatacttccg    840

atgttcagca ccaccgtgat gatgcagatt acatactggg tggcgggcct agagcgaaag    900

gacgagatcg gcctctcgaa catcgacgtg gagaaggtgc gtgggcttat taagaagacc    960

gtagaacaag caaactctta catcaacaac atctacgaca gagagttaaa cgacgcattg   1020

aacaactcta ccgcagatac tgtggcaaac aacgtcatga gcgtgcacgg gcactgccgc   1080

ctgcacggga ttgagtacat cagtatttgg gataagctga gtgaggccga aagcgtgaac   1140

aacaaaatct acgttgacgt gctgagctac tctacattct ttgaccgcca gacggcgaag   1200

gccaggatac aggcgttgac gccggagaag gacatgacgc cgccgctcaa gccagccctg   1260

aacggcggca agcggcgcaa gatcgactcc ctcaccggcc acatcgtccg tatcggcggt   1320

gccgcgcggg tcggcggcct gaccgtggtg ttcgacgacg ggaacaggca ccagcttgga   1380

acgatcagcg gcgagactag ctcaatctcc cttaatggct cccgcatcac ctcgctggag   1440

gtgtggggaa acggcgcggt ggatcaggcc gtgttcacgc tgaacgacgg tcgttcgctc   1500

agcctgggct cgcccggcac ctctcgctac cgcaagttct acgtgggcga gtcgcactac   1560

atcgcgggca tctacctcag cagtgactac aacccgctcg ctgggcaagc tgcgaacatc   1620

gccgtctcct accagctcat caacgacgac gagaagtag                          1659
```

<210> SEQ ID NO 57
<211> LENGTH: 345
<212> TYPE: DNA
<213> ORGANISM: Shewanella violacea
<220> FEATURE:

<221> NAME/KEY: misc_feature
<222> LOCATION: (1)..(345)
<223> OTHER INFORMATION: A nucleic acid sequence obtained from Shewanella violacea strain DSS12 encoding a TIC10357 pesticidal PirA protein sequence.

<400> SEQUENCE: 57
atgagtgatt tagaagtaaa aataggtgtt aatcctgctg atgttcgtta tacagctaat 60
tttaaagttg caccaaacga cggatatgtg atgtatgaaa aaaatacgcc aatcattcca 120
gaaattggtg tgaatattac ggttataaat acaggtcgtg aagaaatgga agttcactat 180
gaatgggctc caccatttgg tggatggcaa tgtgcatcta caacaataat cccacctgat 240
ggtaagcctg tttatattgc tcatccgtca aatgcttttt attatcagcg aatcattgct 300
tataacaaaa aagaatcaac agcgttcggg aattgcgaat actaa 345

<210> SEQ ID NO 58
<211> LENGTH: 114
<212> TYPE: PRT
<213> ORGANISM: Shewanella violacea
<220> FEATURE:
<221> NAME/KEY: MISC_FEATURE
<222> LOCATION: (1)..(114)
<223> OTHER INFORMATION: The amino acid sequence of the TIC10357 PirA protein.

<400> SEQUENCE: 58

Met Ser Asp Leu Glu Val Lys Ile Gly Val Asn Pro Ala Asp Val Arg
1               5                   10                  15

Tyr Thr Ala Asn Phe Lys Val Ala Pro Asn Asp Gly Tyr Val Met Tyr
            20                  25                  30

Glu Lys Asn Thr Pro Ile Ile Pro Glu Ile Gly Val Asn Ile Thr Val
        35                  40                  45

Ile Asn Thr Gly Arg Glu Glu Met Glu Val His Tyr Glu Trp Ala Pro
    50                  55                  60

Pro Phe Gly Gly Trp Gln Cys Ala Ser Thr Thr Ile Ile Pro Pro Asp
65                  70                  75                  80

Gly Lys Pro Val Tyr Ile Ala His Pro Ser Asn Ala Phe Tyr Tyr Gln
                85                  90                  95

Arg Ile Ile Ala Tyr Asn Lys Lys Glu Ser Thr Ala Phe Gly Asn Cys
            100                 105                 110

Glu Tyr

<210> SEQ ID NO 59
<211> LENGTH: 1284
<212> TYPE: DNA
<213> ORGANISM: Shewanella violacea
<220> FEATURE:
<221> NAME/KEY: misc_feature
<222> LOCATION: (1)..(1284)
<223> OTHER INFORMATION: A nucleic acid sequence obtained from Shewanella violacea strain DSS12 encoding a TIC10366 pesticidal PirB protein sequence.

<400> SEQUENCE: 59
atgaataatg aatatatcgt aacaatggaa aagaaaaaca acatagaatt aaaaagtagt 60
ggtcgttata cattagatga tttttaccat gatcatgctt atgcatttaa agtcgctttg 120
actattggac ttaaaaaaat accttatgtt ggaagtattt tatctacact tgttaaaata 180
ttatggccta ctggagcatc aggtgaatct ttacaaaact tatgggaaat ggaaagaaat 240
gaaattcaat caatgattga tgaagctaca cttcatacta taaacgatat attaaacgga 300

```
attgtaaatt cactcggtga taaaatagcc gatattaata gaactataga aaattacggg    360

tttgcagctg caaaagatga ttatataaac ttaatttcaa attatataat tggattggaa    420

gaacagttta aatttgaaag tgaaggctct gaatttatag cttatgcaac aatgccactg    480

ttatctatta ctgttggttt gcaattatca tatttggcat ttggtttaga taataaagct    540

aactttggac ttgatagtgc tgatatagat aaatgtagta gaaacataga tgaaatttat    600

aaagatgtta aaaaatatat agaaaaatat gctaagtggt ctgattctga ctcttacagt    660

aatgctaata gtgaaaacat atataatgaa gttatgggat ctcgtgcttt ttgtgcttta    720

aatggatttg aacacattga aatctggtct gaaatacaat cacgtaaatc acttgatttt    780

tcaattataa gtacatctgt atcttattct gttgaggtcg gtgttttaac gcctaacatg    840

acaaggatgg caacagctgt tgaagttggc ccgcctttgt tacctgttat ggttgatgga    900

catagaaaca agatagttaa aattgagggt tgggatagtg tagaaattaa tagttatcgt    960

cgtgtcggtt gccttaaaat cacttatgaa aatggtgatg tttacgatat gggtgttaaa   1020

acatctaatc ctgttagcat ttcacttgat ggtgaatttg tagataccgt aaaagtcgtt   1080

caaggtgata catatgcaat taattacatc aaattcacat taactgatgg acgcacaatg   1140

tcagttggtg aacaaagcgg tgatacacaa ctattaggtt ttgataatca tactattgct   1200

gcaatttttg ttgatgaagg ttcttcagat aaaatttcat gtgttagcgt ttcatgcatt   1260

cctaagcagt acgaagaaga atag                                          1284
```

```
<210> SEQ ID NO 60
<211> LENGTH: 427
<212> TYPE: PRT
<213> ORGANISM: Shewanella violacea
<220> FEATURE:
<221> NAME/KEY: MISC_FEATURE
<222> LOCATION: (1)..(427)
<223> OTHER INFORMATION: The amino acid sequence of the TIC10366 PirB
      protein.

<400> SEQUENCE: 60

Met Asn Asn Glu Tyr Ile Val Thr Met Glu Lys Lys Asn Asn Ile Glu
1               5                   10                  15

Leu Lys Ser Ser Gly Arg Tyr Thr Leu Asp Asp Phe Tyr His Asp His
            20                  25                  30

Ala Tyr Ala Phe Lys Val Ala Leu Thr Ile Gly Leu Lys Lys Ile Pro
        35                  40                  45

Tyr Val Gly Ser Ile Leu Ser Thr Leu Val Lys Ile Leu Trp Pro Thr
    50                  55                  60

Gly Ala Ser Gly Glu Ser Leu Gln Asn Leu Trp Glu Met Glu Arg Asn
65                  70                  75                  80

Glu Ile Gln Ser Met Ile Asp Glu Ala Thr Leu His Thr Ile Asn Asp
                85                  90                  95

Ile Leu Asn Gly Ile Val Asn Ser Leu Gly Asp Lys Ile Ala Asp Ile
            100                 105                 110

Asn Arg Thr Ile Glu Asn Tyr Gly Phe Ala Ala Ala Lys Asp Asp Tyr
        115                 120                 125

Ile Asn Leu Ile Ser Asn Tyr Ile Ile Gly Leu Glu Glu Gln Phe Lys
    130                 135                 140

Phe Glu Ser Glu Gly Ser Glu Phe Ile Ala Tyr Ala Thr Met Pro Leu
145                 150                 155                 160

Leu Ser Ile Thr Val Gly Leu Gln Leu Ser Tyr Leu Ala Phe Gly Leu
```

-continued

```
                165                 170                 175

Asp Asn Lys Ala Asn Phe Gly Leu Asp Ser Ala Asp Ile Asp Lys Cys
            180                 185                 190

Ser Arg Asn Ile Asp Glu Ile Tyr Lys Asp Val Lys Lys Tyr Ile Glu
        195                 200                 205

Lys Tyr Ala Lys Trp Ser Asp Ser Asp Ser Tyr Ser Asn Ala Asn Ser
    210                 215                 220

Glu Asn Ile Tyr Asn Glu Val Met Gly Ser Arg Ala Phe Cys Ala Leu
225                 230                 235                 240

Asn Gly Phe Glu His Ile Glu Ile Trp Ser Glu Ile Gln Ser Arg Lys
                245                 250                 255

Ser Leu Asp Phe Ser Ile Ile Ser Thr Ser Val Ser Tyr Ser Val Glu
            260                 265                 270

Val Gly Val Leu Thr Pro Asn Met Thr Arg Met Ala Thr Ala Val Glu
        275                 280                 285

Val Gly Pro Pro Leu Leu Pro Val Met Val Asp Gly His Arg Asn Lys
    290                 295                 300

Ile Val Lys Ile Glu Gly Trp Asp Ser Val Glu Ile Asn Ser Tyr Arg
305                 310                 315                 320

Arg Val Gly Cys Leu Lys Ile Thr Tyr Glu Asn Gly Asp Val Tyr Asp
                325                 330                 335

Met Gly Val Lys Thr Ser Asn Pro Val Ser Ile Ser Leu Asp Gly Glu
            340                 345                 350

Phe Val Asp Thr Val Lys Val Val Gln Gly Asp Thr Tyr Ala Ile Asn
        355                 360                 365

Tyr Ile Lys Phe Thr Leu Thr Asp Gly Arg Thr Met Ser Val Gly Glu
    370                 375                 380

Gln Ser Gly Asp Thr Gln Leu Leu Gly Phe Asp Asn His Thr Ile Ala
385                 390                 395                 400

Ala Ile Phe Val Asp Glu Gly Ser Ser Asp Lys Ile Ser Cys Val Ser
                405                 410                 415

Val Ser Cys Ile Pro Lys Gln Tyr Glu Glu Glu
            420                 425
```

<210> SEQ ID NO 61
<211> LENGTH: 1626
<212> TYPE: DNA
<213> ORGANISM: Artificial
<220> FEATURE:
<223> OTHER INFORMATION: A nucleic acid sequence encoding a PirAB fusion protein, TIC10375 comprised of the TIC10357 and TIC10366 coding sequences in operable linkage and in frame.

<400> SEQUENCE: 61

```
atgagtgatt tagaagtaaa aataggtgtt aatcctgctg atgttcgtta tacagctaat     60

tttaaagttg caccaaacga cggatatgtg atgtatgaaa aaaatacgcc aatcattcca    120

gaaattggtg tgaatattac ggttataaat acaggtcgtg aagaaatgga agttcactat    180

gaatgggctc caccatttgg tggatggcaa tgtgcatcta caacaataat cccacctgat    240

ggtaagcctg tttatattgc tcatccgtca aatgcttttt attatcagcg aatcattgct    300

tataacaaaa aagaatcaac agcgttcggg aattgcgaat acatgaataa tgaatatatc    360

gtaacaatgg aaaagaaaaa caacatagaa ttaaaaagta gtggtcgtta tacattagat    420

gatttttacc atgatcatgc ttatgcattt aaagtcgctt tgactattgg acttaaaaaa    480

ataccttatg ttggaagtat tttatctaca cttgttaaaa tattatggcc tactggagca    540
```

```
tcaggtgaat ctttacaaaa cttatgggaa atggaaagaa atgaaattca atcaatgatt    600

gatgaagcta cacttcatac tataaacgat atattaaacg gaattgtaaa ttcactcggt    660

gataaaatag ccgatattaa tagaactata gaaaattacg ggtttgcagc tgcaaaagat    720

gattatataa acttaatttc aaattatata attggattgg aagaacagtt taaatttgaa    780

agtgaaggct ctgaatttat agcttatgca acaatgccac tgttatctat tactgttggt    840

ttgcaattat catatttggc atttggttta gataataaag ctaactttgg acttgatagt    900

gctgatatag ataaatgtag tagaaacata gatgaaattt ataaagatgt taaaaaatat    960

atagaaaaat atgctaagtg gtctgattct gactcttaca gtaatgctaa tagtgaaaac   1020

atatataatg aagttatggg atctcgtgct ttttgtgctt taaatggatt tgaacacatt   1080

gaaatctggt ctgaaataca atcacgtaaa tcacttgatt tttcaattat aagtacatct   1140

gtatcttatt ctgttgaggt cggtgtttta acgcctaaca tgacaaggat ggcaacagct   1200

gttgaagttg gcccgccttt gttacctgtt atggttgatg gacatagaaa caagatagtt   1260

aaaattgagg gttgggatag tgtagaaatt aatagttatc gtcgtgtcgg ttgccttaaa   1320

atcacttatg aaaatggtga tgtttacgat atgggtgtta aaacatctaa tcctgttagc   1380

atttcacttg atggtgaatt tgtagatacc gtaaaagtcg ttcaaggtga tacatatgca   1440

attaattaca tcaaattcac attaactgat ggacgcacaa tgtcagttgg tgaacaaagc   1500

ggtgatacac aactattagg ttttgataat catactattg ctgcaatttt tgttgatgaa   1560

ggttcttcag ataaaatttc atgtgttagc gtttcatgca ttcctaagca gtacgaagaa   1620

gaatag                                                              1626
```

<210> SEQ ID NO 62
<211> LENGTH: 541
<212> TYPE: PRT
<213> ORGANISM: Artificial
<220> FEATURE:
<223> OTHER INFORMATION: The amino acid sequence of the TIC10375 PirAB fusion protein.

<400> SEQUENCE: 62

```
Met Ser Asp Leu Glu Val Lys Ile Gly Val Asn Pro Ala Asp Val Arg
1               5                   10                  15

Tyr Thr Ala Asn Phe Lys Val Ala Pro Asn Asp Gly Tyr Val Met Tyr
            20                  25                  30

Glu Lys Asn Thr Pro Ile Ile Pro Glu Ile Gly Val Asn Ile Thr Val
        35                  40                  45

Ile Asn Thr Gly Arg Glu Glu Met Glu Val His Tyr Glu Trp Ala Pro
    50                  55                  60

Pro Phe Gly Gly Trp Gln Cys Ala Ser Thr Thr Ile Ile Pro Pro Asp
65                  70                  75                  80

Gly Lys Pro Val Tyr Ile Ala His Pro Ser Asn Ala Phe Tyr Tyr Gln
                85                  90                  95

Arg Ile Ile Ala Tyr Asn Lys Lys Glu Ser Thr Ala Phe Gly Asn Cys
            100                 105                 110

Glu Tyr Met Asn Asn Glu Tyr Ile Val Thr Met Glu Lys Lys Asn Asn
        115                 120                 125

Ile Glu Leu Lys Ser Ser Gly Arg Tyr Thr Leu Asp Asp Phe Tyr His
    130                 135                 140

Asp His Ala Tyr Ala Phe Lys Val Ala Leu Thr Ile Gly Leu Lys Lys
145                 150                 155                 160
```

```
Ile Pro Tyr Val Gly Ser Ile Leu Ser Thr Leu Val Lys Ile Leu Trp
                165                 170                 175

Pro Thr Gly Ala Ser Gly Glu Ser Leu Gln Asn Leu Trp Glu Met Glu
            180                 185                 190

Arg Asn Glu Ile Gln Ser Met Ile Asp Glu Ala Thr Leu His Thr Ile
        195                 200                 205

Asn Asp Ile Leu Asn Gly Ile Val Asn Ser Leu Gly Asp Lys Ile Ala
    210                 215                 220

Asp Ile Asn Arg Thr Ile Glu Asn Tyr Gly Phe Ala Ala Ala Lys Asp
225                 230                 235                 240

Asp Tyr Ile Asn Leu Ile Ser Asn Tyr Ile Ile Gly Leu Glu Glu Gln
                245                 250                 255

Phe Lys Phe Glu Ser Glu Gly Ser Glu Phe Ile Ala Tyr Ala Thr Met
            260                 265                 270

Pro Leu Leu Ser Ile Thr Val Gly Leu Gln Leu Ser Tyr Leu Ala Phe
        275                 280                 285

Gly Leu Asp Asn Lys Ala Asn Phe Gly Leu Asp Ser Ala Asp Ile Asp
    290                 295                 300

Lys Cys Ser Arg Asn Ile Asp Glu Ile Tyr Lys Asp Val Lys Lys Tyr
305                 310                 315                 320

Ile Glu Lys Tyr Ala Lys Trp Ser Asp Ser Asp Ser Tyr Ser Asn Ala
                325                 330                 335

Asn Ser Glu Asn Ile Tyr Asn Glu Val Met Gly Ser Arg Ala Phe Cys
            340                 345                 350

Ala Leu Asn Gly Phe Glu His Ile Glu Ile Trp Ser Glu Ile Gln Ser
        355                 360                 365

Arg Lys Ser Leu Asp Phe Ser Ile Ile Ser Thr Ser Val Ser Tyr Ser
    370                 375                 380

Val Glu Val Gly Val Leu Thr Pro Asn Met Thr Arg Met Ala Thr Ala
385                 390                 395                 400

Val Glu Val Gly Pro Pro Leu Leu Pro Val Met Val Asp Gly His Arg
                405                 410                 415

Asn Lys Ile Val Lys Ile Glu Gly Trp Asp Ser Val Glu Ile Asn Ser
            420                 425                 430

Tyr Arg Arg Val Gly Cys Leu Lys Ile Thr Tyr Glu Asn Gly Asp Val
        435                 440                 445

Tyr Asp Met Gly Val Lys Thr Ser Asn Pro Val Ser Ile Ser Leu Asp
    450                 455                 460

Gly Glu Phe Val Asp Thr Val Lys Val Val Gln Gly Asp Thr Tyr Ala
465                 470                 475                 480

Ile Asn Tyr Ile Lys Phe Thr Leu Thr Asp Gly Arg Thr Met Ser Val
                485                 490                 495

Gly Glu Gln Ser Gly Asp Thr Gln Leu Leu Gly Phe Asp Asn His Thr
            500                 505                 510

Ile Ala Ala Ile Phe Val Asp Glu Gly Ser Ser Asp Lys Ile Ser Cys
        515                 520                 525

Val Ser Val Ser Cys Ile Pro Lys Gln Tyr Glu Glu Glu
    530                 535                 540
```

<210> SEQ ID NO 63
<211> LENGTH: 435
<212> TYPE: DNA
<213> ORGANISM: Photorhabdus luminescens
<220> FEATURE:

<221> NAME/KEY: misc_feature
<222> LOCATION: (1)..(435)
<223> OTHER INFORMATION: A nucleic acid sequence obtained from
      Photorhabdus luminescens strain laumondii TTO1 encoding a TIC10358
      pesticidal PirA protein sequence.

<400> SEQUENCE: 63
atgccagtca atcagattgg cttacataat gaaaaggtga aaaatatgag aaaaataaca     60
gttgataatg atgtggtagg acatgatact gaaatcaact cggttgtttc atcaactgcg    120
gagaaaattc gccaacagtt tggagtaaag gtcgacccta attcaagtca ggaaaagttc    180
tacattgcaa caccgattat tcctgaatcc cgaaagaata tcgttgtaac caatgaaggt    240
ctcgccgatg ttatcacggc gaaatattac tggtcacatt cttttacgtc agaatatttt    300
gaggataact cagttgatgt caaggttgga gagagcaaag tgttggttgc cccttcaaac    360
ccgttgtatt acagcaaagt agtcattttc aacaacacta aatccgtggc atttgtaaca    420
gtaagagaaa aataa                                                     435

<210> SEQ ID NO 64
<211> LENGTH: 144
<212> TYPE: PRT
<213> ORGANISM: Photorhabdus luminescens
<220> FEATURE:
<221> NAME/KEY: MISC_FEATURE
<222> LOCATION: (1)..(144)
<223> OTHER INFORMATION: The amino acid sequence of the TIC10358 PirA
      protein.

<400> SEQUENCE: 64

Met Pro Val Asn Gln Ile Gly Leu His Asn Glu Lys Val Lys Asn Met
1               5                   10                  15

Arg Lys Ile Thr Val Asp Asn Asp Val Val Gly His Asp Thr Glu Ile
            20                  25                  30

Asn Ser Val Val Ser Ser Thr Ala Glu Lys Ile Arg Gln Gln Phe Gly
        35                  40                  45

Val Lys Val Asp Pro Asn Ser Ser Gln Glu Lys Phe Tyr Ile Ala Thr
    50                  55                  60

Pro Ile Ile Pro Glu Ser Arg Lys Asn Ile Val Val Thr Asn Glu Gly
65                  70                  75                  80

Leu Ala Asp Val Ile Thr Ala Lys Tyr Tyr Trp Ser His Ser Phe Thr
                85                  90                  95

Ser Glu Tyr Phe Glu Asp Asn Ser Val Asp Val Lys Val Gly Glu Ser
            100                 105                 110

Lys Val Leu Val Ala Pro Ser Asn Pro Leu Tyr Tyr Ser Lys Val Val
        115                 120                 125

Ile Phe Asn Asn Thr Lys Ser Val Ala Phe Val Thr Val Arg Glu Lys
    130                 135                 140

<210> SEQ ID NO 65
<211> LENGTH: 1254
<212> TYPE: DNA
<213> ORGANISM: Photorhabdus luminescens
<220> FEATURE:
<221> NAME/KEY: misc_feature
<222> LOCATION: (1)..(1254)
<223> OTHER INFORMATION: A nucleic acid sequence obtained from
      Photorhabdus luminescens strain laumondii TTO1 encoding a TIC10367
      pesticidal PirB protein sequence.

<400> SEQUENCE: 65
atgagcgata ttgttaagta taacgatgta agtgcaccga tcccttatgc tgtttattca     60

-continued

```
aatgccgtat atgcatttga gtgggattca tctgctattc taaagcaagc cgtcgtcaag    120

ggattgtcgt atgtaccaca tgtagggaaa tatctttctt acattgttgg ttttttttgg    180

aaagataaag agaaagacat ttggcaggag gttgtaggaa aagttcaaca actggttgaa    240

gatagtatat taaaagcagt taaaggtata ctctcaggta acatcaatga attaaaagaa    300

aaaatgaatg aggtaatccg ttctctggag aagaatttag gtacccaaga agcaagggat    360

gactacatgc atcttgccag gagtatggtt ggaaaagaag ctagcttgat ttttcatgaa    420

aataagacaa attttcacat attgccgatg tattccacac ttgccctgat gcagattatg    480

tattggactg ttggcattga gcgtcgcaag gaaatcggat tgagtgatat tgaagtcgag    540

aatctaaggt catatatcaa aaagttagtt agtgatgcag agcatcacgt gaatagagtt    600

tataagttag aacttgatag tgtagtgtca gactctgatg ttaatcgcgt ggctgataat    660

atcatgtatg tccatggata ttgtcaaata catggtctgg aatatatgga catcattaaa    720

aatatccaat ccagaggtaa taatattact gggttttatc cgagaactat cagctactct    780

acattctttg gttcgccaac aagtgatgcg cgtattttgg cattaaggcc agagaaggat    840

atgccagaac cgttcaaacc caaattttta aatgaacggt ttaataaaat tgcatcggtc    900

aaagggtaca tagtacgaat tggtggcgct aaacgtgttg gggggctgga gataacattt    960

gagaatggca gcaagtatca acagggccaa gcaacgaatg agcatgaaat cgtcaatctc   1020

aaaggtaatt tgattaagac gttggaagta tgggggaatg gggccattga tgaagcaaaa   1080

tttacattaa cgaatggaga tgtgttgaca ataggtcaac gtaattcctc taattaccgt   1140

aagttctctc ttgatggtca ttatatttgc ggggtgttca tcgcaaatga tcgttctgga   1200

ctggctggtc aagcagctaa tattgccgtt tcttatcacc aattagttga gtaa         1254
```

<210> SEQ ID NO 66
<211> LENGTH: 417
<212> TYPE: PRT
<213> ORGANISM: Photorhabdus luminescens
<220> FEATURE:
<221> NAME/KEY: MISC_FEATURE
<222> LOCATION: (1)..(417)
<223> OTHER INFORMATION: The amino acid sequence of the TIC10367 PirB
      protein.

<400> SEQUENCE: 66

```
Met Ser Asp Ile Val Lys Tyr Asn Asp Val Ser Ala Pro Ile Pro Tyr
1               5                   10                  15

Ala Val Tyr Ser Asn Ala Val Tyr Ala Phe Glu Trp Asp Ser Ser Ala
            20                  25                  30

Ile Leu Lys Gln Ala Val Val Lys Gly Leu Ser Tyr Val Pro His Val
        35                  40                  45

Gly Lys Tyr Leu Ser Tyr Ile Val Gly Phe Phe Trp Lys Asp Lys Glu
    50                  55                  60

Lys Asp Ile Trp Gln Glu Val Val Gly Lys Val Gln Gln Leu Val Glu
65                  70                  75                  80

Asp Ser Ile Leu Lys Ala Val Lys Gly Ile Leu Ser Gly Asn Ile Asn
                85                  90                  95

Glu Leu Lys Glu Lys Met Asn Glu Val Ile Arg Ser Leu Glu Lys Asn
            100                 105                 110

Leu Gly Thr Gln Glu Ala Arg Asp Asp Tyr Met His Leu Ala Arg Ser
        115                 120                 125

Met Val Gly Lys Glu Ala Ser Leu Ile Phe His Glu Asn Lys Thr Asn
```

```
    130                 135                 140

Phe His Ile Leu Pro Met Tyr Ser Thr Leu Ala Leu Met Gln Ile Met
145                 150                 155                 160

Tyr Trp Thr Val Gly Ile Glu Arg Arg Lys Glu Ile Gly Leu Ser Asp
                165                 170                 175

Ile Glu Val Glu Asn Leu Arg Ser Tyr Ile Lys Lys Leu Val Ser Asp
            180                 185                 190

Ala Glu His His Val Asn Arg Val Tyr Lys Leu Glu Leu Asp Ser Val
        195                 200                 205

Val Ser Asp Ser Asp Val Asn Arg Val Ala Asp Asn Ile Met Tyr Val
    210                 215                 220

His Gly Tyr Cys Gln Ile His Gly Leu Glu Tyr Met Asp Ile Ile Lys
225                 230                 235                 240

Asn Ile Gln Ser Arg Gly Asn Asn Ile Thr Gly Phe Tyr Pro Arg Thr
                245                 250                 255

Ile Ser Tyr Ser Thr Phe Phe Gly Ser Pro Thr Ser Asp Ala Arg Ile
            260                 265                 270

Leu Ala Leu Arg Pro Glu Lys Asp Met Pro Glu Pro Phe Lys Pro Lys
        275                 280                 285

Phe Leu Asn Glu Arg Phe Asn Lys Ile Ala Ser Val Lys Gly Tyr Ile
    290                 295                 300

Val Arg Ile Gly Gly Ala Lys Arg Val Gly Gly Leu Glu Ile Thr Phe
305                 310                 315                 320

Glu Asn Gly Ser Lys Tyr Gln Gln Gly Gln Ala Thr Asn Glu His Glu
                325                 330                 335

Ile Val Asn Leu Lys Gly Asn Leu Ile Lys Thr Leu Glu Val Trp Gly
            340                 345                 350

Asn Gly Ala Ile Asp Glu Ala Lys Phe Thr Leu Thr Asn Gly Asp Val
        355                 360                 365

Leu Thr Ile Gly Gln Arg Asn Ser Ser Asn Tyr Arg Lys Phe Ser Leu
    370                 375                 380

Asp Gly His Tyr Ile Cys Gly Val Phe Ile Ala Asn Asp Arg Ser Gly
385                 390                 395                 400

Leu Ala Gly Gln Ala Ala Asn Ile Ala Val Ser Tyr His Gln Leu Val
                405                 410                 415

Glu


<210> SEQ ID NO 67
<211> LENGTH: 1686
<212> TYPE: DNA
<213> ORGANISM: Artificial
<220> FEATURE:
<223> OTHER INFORMATION: A nucleic acid sequence encoding a PirAB fusion
      protein, TIC10376 comprised of the TIC10358 and TIC10367 coding
      sequences in operable linkage and in frame.

<400> SEQUENCE: 67

atgccagtca atcagattgg cttacataat gaaaaggtga aaaatatgag aaaaataaca     60

gttgataatg atgtggtagg acatgatact gaaatcaact cggttgtttc atcaactgcg    120

gagaaaattc gccaacagtt tggagtaaag gtcgacccta attcaagtca ggaaaagttc    180

tacattgcaa caccgattat tcctgaatcc cgaaagaata tcgttgtaac caatgaaggt    240

ctcgccgatg ttatcacggc gaaatattac tggtcacatt cttttacgtc agaatatttt    300

gaggataact cagttgatgt caaggttgga gagagcaaag tgttggttgc cccttcaaac    360
```

```
ccgttgtatt acagcaaagt agtcattttc aacaacacta aatccgtggc atttgtaaca    420

gtaagagaaa aaatgagcga tattgttaag tataacgatg taagtgcacc gatcccttat    480

gctgtttatt caaatgccgt atatgcattt gagtgggatt catctgctat tctaaagcaa    540

gccgtcgtca agggattgtc gtatgtacca catgtaggga aatatctttc ttacattgtt    600

ggtttttttt ggaaagataa agagaaagac atttggcagg aggttgtagg aaaagttcaa    660

caactggttg aagatagtat attaaaagca gttaaaggta tactctcagg taacatcaat    720

gaattaaaag aaaaaatgaa tgaggtaatc cgttctctgg agaagaattt aggtacccaa    780

gaagcaaggg atgactacat gcatcttgcc aggagtatgg ttggaaaaga agctagcttg    840

atttttcatg aaaataagac aaattttcac atattgccga tgtattccac acttgccctg    900

atgcagatta tgtattggac tgttggcatt gagcgtcgca aggaaatcgg attgagtgat    960

attgaagtcg agaatctaag gtcatatatc aaaaagttag ttagtgatgc agagcatcac   1020

gtgaatagag tttataagtt agaacttgat agtgtagtgt cagactctga tgttaatcgc   1080

gtggctgata atatcatgta tgtccatgga tattgtcaaa tacatggtct ggaatatatg   1140

gacatcatta aaaatatcca atccagaggt aataatatta ctgggtttta tccgagaact   1200

atcagctact ctacattctt tggttcgcca acaagtgatg cgcgtatttt ggcattaagg   1260

ccagagaagg atatgccaga accgttcaaa cccaaatttt taaatgaacg gtttaataaa   1320

attgcatcgg tcaaagggta catagtacga attggtggcg ctaaacgtgt tggggggctg   1380

gagataacat ttgagaatgg cagcaagtat caacagggcc aagcaacgaa tgagcatgaa   1440

atcgtcaatc tcaaaggtaa tttgattaag acgttggaag tatgggggaa tggggccatt   1500

gatgaagcaa aatttacatt aacgaatgga gatgtgttga caataggtca acgtaattcc   1560

tctaattacc gtaagttctc tcttgatggt cattatattt gcggggtgtt catcgcaaat   1620

gatcgttctg gactggctgg tcaagcagct aatattgccg tttcttatca ccaattagtt   1680

gagtaa                                                              1686
```

<210> SEQ ID NO 68
<211> LENGTH: 561
<212> TYPE: PRT
<213> ORGANISM: Artificial
<220> FEATURE:
<223> OTHER INFORMATION: The amino acid sequence of the TIC10376 PirAB fusion protein.

<400> SEQUENCE: 68

```
Met Pro Val Asn Gln Ile Gly Leu His Asn Glu Lys Val Lys Asn Met
1               5                   10                  15

Arg Lys Ile Thr Val Asp Asn Asp Val Val Gly His Asp Thr Glu Ile
            20                  25                  30

Asn Ser Val Val Ser Ser Thr Ala Glu Lys Ile Arg Gln Gln Phe Gly
        35                  40                  45

Val Lys Val Asp Pro Asn Ser Ser Gln Glu Lys Phe Tyr Ile Ala Thr
    50                  55                  60

Pro Ile Ile Pro Glu Ser Arg Lys Asn Ile Val Val Thr Asn Glu Gly
65                  70                  75                  80

Leu Ala Asp Val Ile Thr Ala Lys Tyr Tyr Trp Ser His Ser Phe Thr
                85                  90                  95

Ser Glu Tyr Phe Glu Asp Asn Ser Val Asp Val Lys Val Gly Glu Ser
            100                 105                 110

Lys Val Leu Val Ala Pro Ser Asn Pro Leu Tyr Tyr Ser Lys Val Val
```

115 120 125

Ile Phe Asn Asn Thr Lys Ser Val Ala Phe Val Thr Val Arg Glu Lys
130 135 140

Met Ser Asp Ile Val Lys Tyr Asn Asp Val Ser Ala Pro Ile Pro Tyr
145 150 155 160

Ala Val Tyr Ser Asn Ala Val Tyr Ala Phe Glu Trp Asp Ser Ser Ala
165 170 175

Ile Leu Lys Gln Ala Val Val Lys Gly Leu Ser Tyr Val Pro His Val
180 185 190

Gly Lys Tyr Leu Ser Tyr Ile Val Gly Phe Phe Trp Lys Asp Lys Glu
195 200 205

Lys Asp Ile Trp Gln Glu Val Val Gly Lys Val Gln Gln Leu Val Glu
210 215 220

Asp Ser Ile Leu Lys Ala Val Lys Gly Ile Leu Ser Gly Asn Ile Asn
225 230 235 240

Glu Leu Lys Glu Lys Met Asn Glu Val Ile Arg Ser Leu Glu Lys Asn
245 250 255

Leu Gly Thr Gln Glu Ala Arg Asp Asp Tyr Met His Leu Ala Arg Ser
260 265 270

Met Val Gly Lys Glu Ala Ser Leu Ile Phe His Glu Asn Lys Thr Asn
275 280 285

Phe His Ile Leu Pro Met Tyr Ser Thr Leu Ala Leu Met Gln Ile Met
290 295 300

Tyr Trp Thr Val Gly Ile Glu Arg Arg Lys Glu Ile Gly Leu Ser Asp
305 310 315 320

Ile Glu Val Glu Asn Leu Arg Ser Tyr Ile Lys Lys Leu Val Ser Asp
325 330 335

Ala Glu His His Val Asn Arg Val Tyr Lys Leu Glu Leu Asp Ser Val
340 345 350

Val Ser Asp Ser Asp Val Asn Arg Val Ala Asp Asn Ile Met Tyr Val
355 360 365

His Gly Tyr Cys Gln Ile His Gly Leu Glu Tyr Met Asp Ile Ile Lys
370 375 380

Asn Ile Gln Ser Arg Gly Asn Asn Ile Thr Gly Phe Tyr Pro Arg Thr
385 390 395 400

Ile Ser Tyr Ser Thr Phe Phe Gly Ser Pro Thr Ser Asp Ala Arg Ile
405 410 415

Leu Ala Leu Arg Pro Glu Lys Asp Met Pro Glu Pro Phe Lys Pro Lys
420 425 430

Phe Leu Asn Glu Arg Phe Asn Lys Ile Ala Ser Val Lys Gly Tyr Ile
435 440 445

Val Arg Ile Gly Gly Ala Lys Arg Val Gly Gly Leu Glu Ile Thr Phe
450 455 460

Glu Asn Gly Ser Lys Tyr Gln Gln Gly Gln Ala Thr Asn Glu His Glu
465 470 475 480

Ile Val Asn Leu Lys Gly Asn Leu Ile Lys Thr Leu Glu Val Trp Gly
485 490 495

Asn Gly Ala Ile Asp Glu Ala Lys Phe Thr Leu Thr Asn Gly Asp Val
500 505 510

Leu Thr Ile Gly Gln Arg Asn Ser Ser Asn Tyr Arg Lys Phe Ser Leu
515 520 525

Asp Gly His Tyr Ile Cys Gly Val Phe Ile Ala Asn Asp Arg Ser Gly
530 535 540

```
Leu Ala Gly Gln Ala Ala Asn Ile Ala Val Ser Tyr His Gln Leu Val
545                 550                 555                 560

Glu
```

<210> SEQ ID NO 69
<211> LENGTH: 402
<212> TYPE: DNA
<213> ORGANISM: Photorhabdus asymbiotica
<220> FEATURE:
<221> NAME/KEY: misc_feature
<222> LOCATION: (1)..(402)
<223> OTHER INFORMATION: A nucleic acid sequence obtained from Photorhabdus asymbiotica encoding a TIC10360 pesticidal PirA protein sequence.

<400> SEQUENCE: 69

```
atgtctagaa taactatttt tattgattca gatgaacaaa aatcagaatt taattctgat      60

tctcctgttc cggtacgtaa agacttaaat acagttgttc ctttgagtga tctgactata     120

tcccctcgtt ctagtgtgga agtatttaga atagatacac caataattcc agaatccaga     180

agatctctga gagttgtaaa tacagggctg gcaagtagtg ttacggctaa attttactgg     240

tctcatagtt ttacctctga atggtttgag tctggttcta tcgatgtagg attaggagaa     300

gataaggtat taaacgtgcc taacaactct ttttattata gtaaatttgt tatctataat     360

aacacggata aagttgctta tattacggca aatttggttt aa                        402
```

<210> SEQ ID NO 70
<211> LENGTH: 133
<212> TYPE: PRT
<213> ORGANISM: Photorhabdus asymbiotica
<220> FEATURE:
<221> NAME/KEY: MISC_FEATURE
<222> LOCATION: (1)..(133)
<223> OTHER INFORMATION: The amino acid sequence of the TIC10360 PirA protein.

<400> SEQUENCE: 70

```
Met Ser Arg Ile Thr Ile Phe Ile Asp Ser Asp Glu Gln Lys Ser Glu
1               5                   10                  15

Phe Asn Ser Asp Ser Pro Val Pro Val Arg Lys Asp Leu Asn Thr Val
            20                  25                  30

Val Pro Leu Ser Asp Leu Thr Ile Ser Pro Arg Ser Ser Val Glu Val
        35                  40                  45

Phe Arg Ile Asp Thr Pro Ile Ile Pro Glu Ser Arg Arg Ser Leu Arg
    50                  55                  60

Val Val Asn Thr Gly Leu Ala Ser Ser Val Thr Ala Lys Phe Tyr Trp
65                  70                  75                  80

Ser His Ser Phe Thr Ser Glu Trp Phe Glu Ser Gly Ser Ile Asp Val
                85                  90                  95

Gly Leu Gly Glu Asp Lys Val Leu Asn Val Pro Asn Asn Ser Phe Tyr
            100                 105                 110

Tyr Ser Lys Phe Val Ile Tyr Asn Asn Thr Asp Lys Val Ala Tyr Ile
        115                 120                 125

Thr Ala Asn Leu Val
    130
```

<210> SEQ ID NO 71
<211> LENGTH: 1260
<212> TYPE: DNA
<213> ORGANISM: Photorhabdus asymbiotica
<220> FEATURE:
<221> NAME/KEY: misc_feature
<222> LOCATION: (1)..(1260)
<223> OTHER INFORMATION: A nucleic acid sequence obtained from Photorhabdus asymbiotica encoding a TIC10369 pesticidal PirB protein sequence.

<400> SEQUENCE: 71

```
atgcagacag agaatgtttt agacataaga accattgtgg ctaatgaata tgctataaaa      60
acgagtgcat tagagtggga tgttactgat attgtaaaaa atgcaatcat aggaggcata     120
tcttttatac ctacggttgg tcctgctata tcttttttag tcggtttatt ttggcctcaa     180
tcaaaagaaa atatatggga agggattgtc aaacaaattg agaggatgat agaggaatct     240
gcattaaaga cgattaaagg tatccttgct ggtgatattg cctatataca agagcgaatg     300
gcaactgttg ctgatcttct tgagaaacat ccaggatcgg cagaagcgcg gagtgctttt     360
aataacctgg cagaaaatat agatggttat cacaaaaaat ttaataattt ctcggatgat     420
gtaaattatc agatattacc catgttttct actacagtta tgatgcagat aacatattgg     480
gttgctggtt tagagagaaa agatgaaata gggcttagtg atattgatat tgaaaaagtc     540
cgagggttaa ttaaaaagac agtagaacag gctaataatt atattaataa tatatatggt     600
agagaactta atgatgctct taataattcg acggctgaca ctgttgcaaa taatgttatg     660
tctgttcatg gtcattgtcg tttacatgga attgaatata tcagtatttg ggatagatta     720
agtgaaactg agtctgtaaa taatagaatc tatgttgatg ttttaagtta ttctactttc     780
tttgaccgtc aaacagcaaa ggccagaatt caggcattga cgccagagaa agatatggct     840
ccacctctca aaccggctct taatggagga aagagaagaa agataaattc gttaatggga     900
catattgtac gtattggagg ggcgccaagg gtaggagggc tgacagttat atttgatgat     960
ggtagtcgcc atcaattagg gacaatatct ggtgagacgg catctatttc tctggatggt    1020
aatcgaatta ctagtttgga agtatggggc aatggtgctg ttgataaagc tgtctttact    1080
ttgagtgatg gtcgttcgtt gtcatttggc gcacctggaa catccagata taggaagttt    1140
tatgttggtg aaagtcacta catttcaggg atctatttgt ccagtgatta cagcccgtta    1200
gcaggtcagg cagcaaatat agctgtatct tatcagctga taaatgatga tgaaaaataa    1260
```

<210> SEQ ID NO 72
<211> LENGTH: 419
<212> TYPE: PRT
<213> ORGANISM: Photorhabdus asymbiotica
<220> FEATURE:
<221> NAME/KEY: MISC_FEATURE
<222> LOCATION: (1)..(419)
<223> OTHER INFORMATION: The amino acid sequence of the TIC10369 PirB protein.

<400> SEQUENCE: 72

```
Met Gln Thr Glu Asn Val Leu Asp Ile Arg Thr Ile Val Ala Asn Glu
1               5                   10                  15

Tyr Ala Ile Lys Thr Ser Ala Leu Glu Trp Asp Val Thr Asp Ile Val
            20                  25                  30

Lys Asn Ala Ile Ile Gly Gly Ile Ser Phe Ile Pro Thr Val Gly Pro
        35                  40                  45

Ala Ile Ser Phe Leu Val Gly Leu Phe Trp Pro Gln Ser Lys Glu Asn
    50                  55                  60

Ile Trp Glu Gly Ile Val Lys Gln Ile Glu Arg Met Ile Glu Glu Ser
65                  70                  75                  80
```

-continued

```
Ala Leu Lys Thr Ile Lys Gly Ile Leu Ala Gly Asp Ile Ala Tyr Ile
                85                  90                  95

Gln Glu Arg Met Ala Thr Val Ala Asp Leu Leu Glu Lys His Pro Gly
            100                 105                 110

Ser Ala Glu Ala Arg Ser Ala Phe Asn Asn Leu Ala Glu Asn Ile Asp
        115                 120                 125

Gly Tyr His Lys Lys Phe Asn Asn Phe Ser Asp Asp Val Asn Tyr Gln
    130                 135                 140

Ile Leu Pro Met Phe Ser Thr Thr Val Met Met Gln Ile Thr Tyr Trp
145                 150                 155                 160

Val Ala Gly Leu Glu Arg Lys Asp Glu Ile Gly Leu Ser Asp Ile Asp
                165                 170                 175

Ile Glu Lys Val Arg Gly Leu Ile Lys Lys Thr Val Glu Gln Ala Asn
            180                 185                 190

Asn Tyr Ile Asn Asn Ile Tyr Gly Arg Glu Leu Asn Asp Ala Leu Asn
        195                 200                 205

Asn Ser Thr Ala Asp Thr Val Ala Asn Asn Val Met Ser Val His Gly
    210                 215                 220

His Cys Arg Leu His Gly Ile Glu Tyr Ile Ser Ile Trp Asp Arg Leu
225                 230                 235                 240

Ser Glu Thr Glu Ser Val Asn Asn Arg Ile Tyr Val Asp Val Leu Ser
                245                 250                 255

Tyr Ser Thr Phe Phe Asp Arg Gln Thr Ala Lys Ala Arg Ile Gln Ala
            260                 265                 270

Leu Thr Pro Glu Lys Asp Met Ala Pro Pro Leu Lys Pro Ala Leu Asn
        275                 280                 285

Gly Gly Lys Arg Arg Lys Ile Asn Ser Leu Met Gly His Ile Val Arg
    290                 295                 300

Ile Gly Gly Ala Pro Arg Val Gly Gly Leu Thr Val Ile Phe Asp Asp
305                 310                 315                 320

Gly Ser Arg His Gln Leu Gly Thr Ile Ser Gly Glu Thr Ala Ser Ile
                325                 330                 335

Ser Leu Asp Gly Asn Arg Ile Thr Ser Leu Glu Val Trp Gly Asn Gly
            340                 345                 350

Ala Val Asp Lys Ala Val Phe Thr Leu Ser Asp Gly Arg Ser Leu Ser
        355                 360                 365

Phe Gly Ala Pro Gly Thr Ser Arg Tyr Arg Lys Phe Tyr Val Gly Glu
    370                 375                 380

Ser His Tyr Ile Ser Gly Ile Tyr Leu Ser Ser Asp Tyr Ser Pro Leu
385                 390                 395                 400

Ala Gly Gln Ala Ala Asn Ile Ala Val Ser Tyr Gln Leu Ile Asn Asp
                405                 410                 415

Asp Glu Lys


<210> SEQ ID NO 73
<211> LENGTH: 1659
<212> TYPE: DNA
<213> ORGANISM: Artificial
<220> FEATURE:
<223> OTHER INFORMATION: A nucleic acid sequence encoding a PirAB fusion
      protein, TIC10377 comprised of the TIC10360 and TIC10369 coding
      sequences in operable linkage and in frame.

<400> SEQUENCE: 73

atgtctagaa taactatttt tattgattca gatgaacaaa aatcagaatt taattctgat      60
```

-continued

```
tctcctgttc cggtacgtaa agacttaaat acagttgttc ctttgagtga tctgactata    120

tcccctcgtt ctagtgtgga agtatttaga atagatacac caataattcc agaatccaga    180

agatctctga gagttgtaaa tacagggctg gcaagtagtg ttacggctaa attttactgg    240

tctcatagtt ttacctctga atggtttgag tctggttcta tcgatgtagg attaggagaa    300

gataaggtat taaacgtgcc taacaactct ttttattata gtaaatttgt tatctataat    360

aacacggata aagttgctta tattacggca aatttggtta tgcagacaga gaatgtttta    420

gacataagaa ccattgtggc taatgaatat gctataaaaa cgagtgcatt agagtgggat    480

gttactgata ttgtaaaaaa tgcaatcata ggaggcatat cttttatacc tacggttggt    540

cctgctatat ctttttagt cggtttattt tggcctcaat caaaagaaaa tatatgggaa    600

gggattgtca aacaaattga gaggatgata gaggaatctg cattaaagac gattaaaggt    660

atccttgctg gtgatattgc ctatatacaa gagcgaatgg caactgttgc tgatcttctt    720

gagaaacatc caggatcggc agaagcgcgg agtgctttta ataacctggc agaaaatata    780

gatggttatc acaaaaaatt taataatttc tcggatgatg taaattatca gatattaccc    840

atgttttcta ctacagttat gatgcagata acatattggg ttgctggttt agagagaaaa    900

gatgaaatag ggcttagtga tattgatatt gaaaaagtcc gagggttaat taaaaagaca    960

gtagaacagg ctaataatta tattaataat atatatggta gagaacttaa tgatgctctt   1020

aataattcga cggctgacac tgttgcaaat aatgttatgt ctgttcatgg tcattgtcgt   1080

ttacatggaa ttgaatatat cagtatttgg gatagattaa gtgaaactga gtctgtaaat   1140

aatagaatct atgttgatgt tttaagttat tctactttct ttgaccgtca aacagcaaag   1200

gccagaattc aggcattgac gccagagaaa gatatggctc cacctctcaa accggctctt   1260

aatggaggaa agagaagaaa gataaattcg ttaatgggac atattgtacg tattggaggg   1320

gcgccaaggg taggagggct gacagttata tttgatgatg gtagtcgcca tcaattaggg   1380

acaatatctg gtgagacggc atctatttct ctggatggta atcgaattac tagtttggaa   1440

gtatggggca atggtgctgt tgataaagct gtctttactt tgagtgatgg tcgttcgttg   1500

tcatttggcg cacctggaac atccagatat aggaagtttt atgttggtga aagtcactac   1560

atttcaggga tctatttgtc cagtgattac agcccgttag caggtcaggc agcaaatata   1620

gctgtatctt atcagctgat aaatgatgat gaaaaataa                          1659
```

<210> SEQ ID NO 74
<211> LENGTH: 552
<212> TYPE: PRT
<213> ORGANISM: Artificial
<220> FEATURE:
<223> OTHER INFORMATION: The amino acid sequence of the TIC10377 PirAB fusion protein.

<400> SEQUENCE: 74

```
Met Ser Arg Ile Thr Ile Phe Ile Asp Ser Asp Glu Gln Lys Ser Glu
1               5                   10                  15

Phe Asn Ser Asp Ser Pro Val Pro Val Arg Lys Asp Leu Asn Thr Val
            20                  25                  30

Val Pro Leu Ser Asp Leu Thr Ile Ser Pro Arg Ser Ser Val Glu Val
        35                  40                  45

Phe Arg Ile Asp Thr Pro Ile Ile Pro Glu Ser Arg Arg Ser Leu Arg
    50                  55                  60

Val Val Asn Thr Gly Leu Ala Ser Ser Val Thr Ala Lys Phe Tyr Trp
65                  70                  75                  80
```

```
Ser His Ser Phe Thr Ser Glu Trp Phe Glu Ser Gly Ser Ile Asp Val
                85                  90                  95

Gly Leu Gly Glu Asp Lys Val Leu Asn Val Pro Asn Asn Ser Phe Tyr
            100                 105                 110

Tyr Ser Lys Phe Val Ile Tyr Asn Asn Thr Asp Lys Val Ala Tyr Ile
        115                 120                 125

Thr Ala Asn Leu Val Met Gln Thr Glu Asn Val Leu Asp Ile Arg Thr
    130                 135                 140

Ile Val Ala Asn Glu Tyr Ala Ile Lys Thr Ser Ala Leu Glu Trp Asp
145                 150                 155                 160

Val Thr Asp Ile Val Lys Asn Ala Ile Ile Gly Gly Ile Ser Phe Ile
                165                 170                 175

Pro Thr Val Gly Pro Ala Ile Ser Phe Leu Val Gly Leu Phe Trp Pro
            180                 185                 190

Gln Ser Lys Glu Asn Ile Trp Glu Gly Ile Val Lys Gln Ile Glu Arg
        195                 200                 205

Met Ile Glu Glu Ser Ala Leu Lys Thr Ile Lys Gly Ile Leu Ala Gly
    210                 215                 220

Asp Ile Ala Tyr Ile Gln Glu Arg Met Ala Thr Val Ala Asp Leu Leu
225                 230                 235                 240

Glu Lys His Pro Gly Ser Ala Glu Ala Arg Ser Ala Phe Asn Asn Leu
                245                 250                 255

Ala Glu Asn Ile Asp Gly Tyr His Lys Lys Phe Asn Asn Phe Ser Asp
            260                 265                 270

Asp Val Asn Tyr Gln Ile Leu Pro Met Phe Ser Thr Thr Val Met Met
        275                 280                 285

Gln Ile Thr Tyr Trp Val Ala Gly Leu Glu Arg Lys Asp Glu Ile Gly
    290                 295                 300

Leu Ser Asp Ile Asp Ile Glu Lys Val Arg Gly Leu Ile Lys Lys Thr
305                 310                 315                 320

Val Glu Gln Ala Asn Asn Tyr Ile Asn Asn Ile Tyr Gly Arg Glu Leu
                325                 330                 335

Asn Asp Ala Leu Asn Asn Ser Thr Ala Asp Thr Val Ala Asn Asn Val
            340                 345                 350

Met Ser Val His Gly His Cys Arg Leu His Gly Ile Glu Tyr Ile Ser
        355                 360                 365

Ile Trp Asp Arg Leu Ser Glu Thr Glu Ser Val Asn Asn Arg Ile Tyr
    370                 375                 380

Val Asp Val Leu Ser Tyr Ser Thr Phe Phe Asp Arg Gln Thr Ala Lys
385                 390                 395                 400

Ala Arg Ile Gln Ala Leu Thr Pro Glu Lys Asp Met Ala Pro Pro Leu
                405                 410                 415

Lys Pro Ala Leu Asn Gly Gly Lys Arg Arg Lys Ile Asn Ser Leu Met
            420                 425                 430

Gly His Ile Val Arg Ile Gly Gly Ala Pro Arg Val Gly Gly Leu Thr
        435                 440                 445

Val Ile Phe Asp Asp Gly Ser Arg His Gln Leu Gly Thr Ile Ser Gly
    450                 455                 460

Glu Thr Ala Ser Ile Ser Leu Asp Gly Asn Arg Ile Thr Ser Leu Glu
465                 470                 475                 480

Val Trp Gly Asn Gly Ala Val Asp Lys Ala Val Phe Thr Leu Ser Asp
                485                 490                 495
```

```
Gly Arg Ser Leu Ser Phe Gly Ala Pro Gly Thr Ser Arg Tyr Arg Lys
            500                 505                 510

Phe Tyr Val Gly Glu Ser His Tyr Ile Ser Gly Ile Tyr Leu Ser Ser
        515                 520                 525

Asp Tyr Ser Pro Leu Ala Gly Gln Ala Ala Asn Ile Ala Val Ser Tyr
    530                 535                 540

Gln Leu Ile Asn Asp Asp Glu Lys
545                 550
```

```
<210> SEQ ID NO 75
<211> LENGTH: 432
<212> TYPE: DNA
<213> ORGANISM: Xenorhabdus sp
<220> FEATURE:
<221> NAME/KEY: misc_feature
<222> LOCATION: (1)..(432)
<223> OTHER INFORMATION: A nucleic acid sequence obtained from
      Xenorhabdus sp. strain NBAII XenSa04 encoding a TIC10361
      pesticidal PirA protein sequence.

<400> SEQUENCE: 75

atgatcacaa taaatataaa tacaaacggt gttaatggta ttaccattac aaatagtaat      60

aatgaaccta ctccagtatc gacaacttac ggtccaaata caccagcatc agaacccctt     120

acagtcagta attatagtga tatcacaata gaaccacatt cttctgtgca ggcaacaaga     180

attgacacgc ctattattcc tgaaacacgt ccagattact atgtagccaa ctccggccct     240

gcaccaacag ttagggctgt tttttattgg tctcattctt tcacatcaga atggttcgaa     300

tcttcctcta tcacagtgaa agcaggagag gatggaatat taaaagcacc tggtaattct     360

ttatattaca gcaaagtcgt catttataat gacaccgata aacgggcttt tgttactgga     420

tataataaat aa                                                         432
```

```
<210> SEQ ID NO 76
<211> LENGTH: 143
<212> TYPE: PRT
<213> ORGANISM: Xenorhabdus sp
<220> FEATURE:
<221> NAME/KEY: MISC_FEATURE
<222> LOCATION: (1)..(143)
<223> OTHER INFORMATION: The amino acid sequence of the TIC10361 PirA
      protein.

<400> SEQUENCE: 76

Met Ile Thr Ile Asn Ile Asn Thr Asn Gly Val Asn Gly Ile Thr Ile
1               5                   10                  15

Thr Asn Ser Asn Asn Glu Pro Thr Pro Val Ser Thr Thr Tyr Gly Pro
            20                  25                  30

Asn Thr Pro Ala Ser Glu Pro Leu Thr Val Ser Asn Tyr Ser Asp Ile
        35                  40                  45

Thr Ile Glu Pro His Ser Ser Val Gln Ala Thr Arg Ile Asp Thr Pro
    50                  55                  60

Ile Ile Pro Glu Thr Arg Pro Asp Tyr Tyr Val Ala Asn Ser Gly Pro
65                  70                  75                  80

Ala Pro Thr Val Arg Ala Val Phe Tyr Trp Ser His Ser Phe Thr Ser
                85                  90                  95

Glu Trp Phe Glu Ser Ser Ser Ile Thr Val Lys Ala Gly Glu Asp Gly
            100                 105                 110

Ile Leu Lys Ala Pro Gly Asn Ser Leu Tyr Tyr Ser Lys Val Val Ile
        115                 120                 125
```

```
Tyr Asn Asp Thr Asp Lys Arg Ala Phe Val Thr Gly Tyr Asn Lys
    130                 135                 140


<210> SEQ ID NO 77
<211> LENGTH: 1278
<212> TYPE: DNA
<213> ORGANISM: Xenorhabdus sp
<220> FEATURE:
<221> NAME/KEY: misc_feature
<222> LOCATION: (1)..(1278)
<223> OTHER INFORMATION: A nucleic acid sequence obtained from
      Xenorhabdus sp. strain NBAII XenSa04 encoding a TIC10370
      pesticidal PirB protein sequence.

<400> SEQUENCE: 77

atgaatacca cacctattac tgtatctgaa aatgaaacat cgcctttact gactgacgta     60

atgcctatgg atctttatgc agtatccacc cctgattatg aatgggatat gtcgtcaatc    120

ataaaggatg ctattattgg tggcatagga tttattccag gtccgggtcc ggcattatcc    180

ttcctgttag gactattttg gcctcagcag aaagacaata cttgggagca aattctccaa    240

aaagtagagc agatgataga gaatgctgtt ctacaaacca ttaaaggaat acttaatgga    300

gaaatacaag agatcaaagg gaaaatggaa catgtagaat ctatgctgaa aaactcgccg    360

ggtagtcagg aaagtcatga tgcatatatg ttcctggcaa gatatctggt gagtatagat    420

gaaaaattca aatcttttga taatagaaca aattaccaga ttctcccaat gtatactaat    480

actattatgt tacagatccc ttattggaaa atgggaatag agaagaaaaa agatattggg    540

ctgacagata ttgaagtcaa tgaattaaaa gaacttatcg acaaattagt aggtaaggcc    600

aagaactata ttcatacgat gtatactaat gaatataacg atgctataaa cacatcaaca    660

gcagggagtg tcactaataa tttattatct gtaaggggat attgtttatt acacggtttg    720

gagtgtattg agttaattga gcatatacag aataatagcc ttgaaagtgg tttctatcct    780

aaaactatca gttattcgac agtgtttgat cgtccgacta ataaaatgag aattcaggct    840

cttacagaag acgatgcaat gcaggagcct ttcaagccat ctttaattaa tgggaaatac    900

aataaaatac aatccataat tggatatgta caaagaattg ggaatgcacc tagagttggt    960

ggtattaaaa ttacatttac caatggctca tcttatacac ttggtacggt gacctcagaa   1020

acaaattcaa ttgaactaaa tgatagtgtt atcgagagct tggaagtatg gggaaatggt   1080

gctgttgatg aggcattatt taagttgagt gatgggcgtt tattgcgtat tggtgagcgt   1140

tacgcgaaaa aatacagaaa atatgctgtt gatcatcact atattgcggg aatttacttg   1200

gccagcgatg agccttcact tgctggtcaa gccgcaggta ttgccgtttc atatcatatg   1260

atggccgaca aaaaataa                                                 1278


<210> SEQ ID NO 78
<211> LENGTH: 425
<212> TYPE: PRT
<213> ORGANISM: Xenorhabdus sp
<220> FEATURE:
<221> NAME/KEY: MISC_FEATURE
<222> LOCATION: (1)..(425)
<223> OTHER INFORMATION: The amino acid sequence of the TIC10370 PirB
      protein.

<400> SEQUENCE: 78

Met Asn Thr Thr Pro Ile Thr Val Ser Glu Asn Glu Thr Ser Pro Leu
1               5                   10                  15

Leu Thr Asp Val Met Pro Met Asp Leu Tyr Ala Val Ser Thr Pro Asp
            20                  25                  30
```

-continued

```
Tyr Glu Trp Asp Met Ser Ser Ile Ile Lys Asp Ala Ile Ile Gly Gly
        35                  40                  45

Ile Gly Phe Ile Pro Gly Pro Gly Pro Ala Leu Ser Phe Leu Leu Gly
    50                  55                  60

Leu Phe Trp Pro Gln Gln Lys Asp Asn Thr Trp Glu Gln Ile Leu Gln
65                  70                  75                  80

Lys Val Glu Gln Met Ile Glu Asn Ala Val Leu Gln Thr Ile Lys Gly
                85                  90                  95

Ile Leu Asn Gly Glu Ile Gln Glu Ile Lys Gly Lys Met Glu His Val
            100                 105                 110

Glu Ser Met Leu Lys Asn Ser Pro Gly Ser Gln Glu Ser His Asp Ala
        115                 120                 125

Tyr Met Phe Leu Ala Arg Tyr Leu Val Ser Ile Asp Glu Lys Phe Lys
    130                 135                 140

Ser Phe Asp Asn Arg Thr Asn Tyr Gln Ile Leu Pro Met Tyr Thr Asn
145                 150                 155                 160

Thr Ile Met Leu Gln Ile Pro Tyr Trp Lys Met Gly Ile Glu Lys Lys
                165                 170                 175

Lys Asp Ile Gly Leu Thr Asp Ile Glu Val Asn Glu Leu Lys Glu Leu
            180                 185                 190

Ile Asp Lys Leu Val Gly Lys Ala Lys Asn Tyr Ile His Thr Met Tyr
        195                 200                 205

Thr Asn Glu Tyr Asn Asp Ala Ile Asn Thr Ser Thr Ala Gly Ser Val
    210                 215                 220

Thr Asn Asn Leu Leu Ser Val Arg Gly Tyr Cys Leu Leu His Gly Leu
225                 230                 235                 240

Glu Cys Ile Glu Leu Ile Glu His Ile Gln Asn Asn Ser Leu Glu Ser
                245                 250                 255

Gly Phe Tyr Pro Lys Thr Ile Ser Tyr Ser Thr Val Phe Asp Arg Pro
            260                 265                 270

Thr Asn Lys Met Arg Ile Gln Ala Leu Thr Glu Asp Asp Ala Met Gln
        275                 280                 285

Glu Pro Phe Lys Pro Ser Leu Ile Asn Gly Lys Tyr Asn Lys Ile Gln
    290                 295                 300

Ser Ile Ile Gly Tyr Val Gln Arg Ile Gly Asn Ala Pro Arg Val Gly
305                 310                 315                 320

Gly Ile Lys Ile Thr Phe Thr Asn Gly Ser Ser Tyr Thr Leu Gly Thr
                325                 330                 335

Val Thr Ser Glu Thr Asn Ser Ile Glu Leu Asn Asp Ser Val Ile Glu
            340                 345                 350

Ser Leu Glu Val Trp Gly Asn Gly Ala Val Asp Glu Ala Leu Phe Lys
        355                 360                 365

Leu Ser Asp Gly Arg Leu Leu Arg Ile Gly Glu Arg Tyr Ala Lys Lys
    370                 375                 380

Tyr Arg Lys Tyr Ala Val Asp His His Tyr Ile Ala Gly Ile Tyr Leu
385                 390                 395                 400

Ala Ser Asp Glu Pro Ser Leu Ala Gly Gln Ala Ala Gly Ile Ala Val
                405                 410                 415

Ser Tyr His Met Met Ala Asp Lys Lys
            420                 425
```

<210> SEQ ID NO 79
<211> LENGTH: 1707

```
<212> TYPE: DNA
<213> ORGANISM: Artificial
<220> FEATURE:
<223> OTHER INFORMATION: A nucleic acid sequence encoding a PirAB fusion
      protein, TIC10378 comprised of the TIC10361 and TIC10370 coding
      sequences in operable linkage and in frame.

<400> SEQUENCE: 79

atgatcacaa taaatataaa tacaaacggt gttaatggta ttaccattac aaatagtaat     60

aatgaaccta ctccagtatc gacaacttac ggtccaaata caccagcatc agaacccctt    120

acagtcagta attatagtga tatcacaata gaaccacatt cttctgtgca ggcaacaaga    180

attgacacgc ctattattcc tgaaacacgt ccagattact atgtagccaa ctccggccct    240

gcaccaacag ttagggctgt tttttattgg tctcattctt tcacatcaga atggttcgaa    300

tcttcctcta tcacagtgaa agcaggagag gatggaatat taaaagcacc tggtaattct    360

ttatattaca gcaaagtcgt catttataat gacaccgata aacgggcttt tgttactgga    420

tataataaaa tgaataccac acctattact gtatctgaaa atgaaacatc gcctttactg    480

actgacgtaa tgcctatgga tctttatgca gtatccaccc ctgattatga atgggatatg    540

tcgtcaatca taaaggatgc tattattggt ggcataggat ttattccagg tccgggtccg    600

gcattatcct tcctgttagg actattttgg cctcagcaga aagacaatac ttgggagcaa    660

attctccaaa aagtagagca gatgatagag aatgctgttc tacaaaccat taaaggaata    720

cttaatggag aaatacaaga gatcaaaggg aaaatggaac atgtagaatc tatgctgaaa    780

aactcgccgg gtagtcagga aagtcatgat gcatatatgt tcctggcaag atatctggtg    840

agtatagatg aaaaattcaa atcttttgat aatagaacaa attaccagat tctcccaatg    900

tatactaata ctattatgtt acagatccct tattggaaaa tgggaataga gaagaaaaaa    960

gatattgggc tgacagatat tgaagtcaat gaattaaaag aacttatcga caaattagta   1020

ggtaaggcca agaactatat tcatacgatg tatactaatg aatataacga tgctataaac   1080

acatcaacag cagggagtgt cactaataat ttattatctg taaggggata ttgtttatta   1140

cacggtttgg agtgtattga gttaattgag catatacaga ataatagcct tgaaagtggt   1200

ttctatccta aaactatcag ttattcgaca gtgtttgatc gtccgactaa taaaatgaga   1260

attcaggctc ttacagaaga cgatgcaatg caggagcctt tcaagccatc tttaattaat   1320

gggaaataca ataaaataca atccataatt ggatatgtac aaagaattgg gaatgcacct   1380

agagttggtg gtattaaaat tacatttacc aatggctcat cttatacact tggtacggtg   1440

acctcagaaa caaattcaat tgaactaaat gatagtgtta tcgagagctt ggaagtatgg   1500

ggaaatggtg ctgttgatga ggcattattt aagttgagtg atgggcgttt attgcgtatt   1560

ggtgagcgtt acgcgaaaaa atacagaaaa tatgctgttg atcatcacta tattgcggga   1620

atttacttgg ccagcgatga gccttcactt gctggtcaag ccgcaggtat tgccgtttca   1680

tatcatatga tggccgacaa aaaataa                                       1707


<210> SEQ ID NO 80
<211> LENGTH: 568
<212> TYPE: PRT
<213> ORGANISM: Artificial
<220> FEATURE:
<223> OTHER INFORMATION: The amino acid sequence of the TIC10378 PirAB
      fusion protein.

<400> SEQUENCE: 80

Met Ile Thr Ile Asn Ile Asn Thr Asn Gly Val Asn Gly Ile Thr Ile
```

-continued

```
1               5                   10                  15

Thr Asn Ser Asn Asn Glu Pro Thr Pro Val Ser Thr Thr Tyr Gly Pro
            20                  25                  30

Asn Thr Pro Ala Ser Glu Pro Leu Thr Val Ser Asn Tyr Ser Asp Ile
        35                  40                  45

Thr Ile Glu Pro His Ser Ser Val Gln Ala Thr Arg Ile Asp Thr Pro
    50                  55                  60

Ile Ile Pro Glu Thr Arg Pro Asp Tyr Tyr Val Ala Asn Ser Gly Pro
65                  70                  75                  80

Ala Pro Thr Val Arg Ala Val Phe Tyr Trp Ser His Ser Phe Thr Ser
                85                  90                  95

Glu Trp Phe Glu Ser Ser Ser Ile Thr Val Lys Ala Gly Glu Asp Gly
            100                 105                 110

Ile Leu Lys Ala Pro Gly Asn Ser Leu Tyr Tyr Ser Lys Val Val Ile
        115                 120                 125

Tyr Asn Asp Thr Asp Lys Arg Ala Phe Val Thr Gly Tyr Asn Lys Met
    130                 135                 140

Asn Thr Thr Pro Ile Thr Val Ser Glu Asn Glu Thr Ser Pro Leu Leu
145                 150                 155                 160

Thr Asp Val Met Pro Met Asp Leu Tyr Ala Val Ser Thr Pro Asp Tyr
                165                 170                 175

Glu Trp Asp Met Ser Ser Ile Ile Lys Asp Ala Ile Ile Gly Gly Ile
            180                 185                 190

Gly Phe Ile Pro Gly Pro Gly Pro Ala Leu Ser Phe Leu Leu Gly Leu
        195                 200                 205

Phe Trp Pro Gln Gln Lys Asp Asn Thr Trp Glu Gln Ile Leu Gln Lys
    210                 215                 220

Val Glu Gln Met Ile Glu Asn Ala Val Leu Gln Thr Ile Lys Gly Ile
225                 230                 235                 240

Leu Asn Gly Glu Ile Gln Glu Ile Lys Gly Lys Met Glu His Val Glu
                245                 250                 255

Ser Met Leu Lys Asn Ser Pro Gly Ser Gln Glu Ser His Asp Ala Tyr
            260                 265                 270

Met Phe Leu Ala Arg Tyr Leu Val Ser Ile Asp Glu Lys Phe Lys Ser
        275                 280                 285

Phe Asp Asn Arg Thr Asn Tyr Gln Ile Leu Pro Met Tyr Thr Asn Thr
    290                 295                 300

Ile Met Leu Gln Ile Pro Tyr Trp Lys Met Gly Ile Glu Lys Lys Lys
305                 310                 315                 320

Asp Ile Gly Leu Thr Asp Ile Glu Val Asn Glu Leu Lys Glu Leu Ile
                325                 330                 335

Asp Lys Leu Val Gly Lys Ala Lys Asn Tyr Ile His Thr Met Tyr Thr
            340                 345                 350

Asn Glu Tyr Asn Asp Ala Ile Asn Thr Ser Thr Ala Gly Ser Val Thr
        355                 360                 365

Asn Asn Leu Leu Ser Val Arg Gly Tyr Cys Leu Leu His Gly Leu Glu
    370                 375                 380

Cys Ile Glu Leu Ile Glu His Ile Gln Asn Asn Ser Leu Glu Ser Gly
385                 390                 395                 400

Phe Tyr Pro Lys Thr Ile Ser Tyr Ser Thr Val Phe Asp Arg Pro Thr
                405                 410                 415

Asn Lys Met Arg Ile Gln Ala Leu Thr Glu Asp Asp Ala Met Gln Glu
            420                 425                 430
```

```
Pro Phe Lys Pro Ser Leu Ile Asn Gly Lys Tyr Asn Lys Ile Gln Ser
        435                 440                 445

Ile Ile Gly Tyr Val Gln Arg Ile Gly Asn Ala Pro Arg Val Gly Gly
    450                 455                 460

Ile Lys Ile Thr Phe Thr Asn Gly Ser Ser Tyr Thr Leu Gly Thr Val
465                 470                 475                 480

Thr Ser Glu Thr Asn Ser Ile Glu Leu Asn Asp Ser Val Ile Glu Ser
                485                 490                 495

Leu Glu Val Trp Gly Asn Gly Ala Val Asp Glu Ala Leu Phe Lys Leu
            500                 505                 510

Ser Asp Gly Arg Leu Leu Arg Ile Gly Glu Arg Tyr Ala Lys Lys Tyr
        515                 520                 525

Arg Lys Tyr Ala Val Asp His His Tyr Ile Ala Gly Ile Tyr Leu Ala
    530                 535                 540

Ser Asp Glu Pro Ser Leu Ala Gly Gln Ala Ala Gly Ile Ala Val Ser
545                 550                 555                 560

Tyr His Met Met Ala Asp Lys Lys
                565
```

<210> SEQ ID NO 81
<211> LENGTH: 411
<212> TYPE: DNA
<213> ORGANISM: Yersinia aldovae
<220> FEATURE:
<221> NAME/KEY: misc_feature
<222> LOCATION: (1)..(411)
<223> OTHER INFORMATION: A nucleic acid sequence obtained from Yersinia aldovae strain 670-83 encoding a TIC10362 pesticidal PirA protein sequence.

<400> SEQUENCE: 81

```
atgagcaagg taaccatcac tattgatagc tgttcaaatg aagtcgaagt taaaaatcaa     60

actgaggttg ataccgaaag tctagcgttg accactgcac aagttagagc cagggtgcca    120

actgaggtcg cacctaattc aagcaccgaa gttctgtatc ggagtacacc gattattcct    180

gaaagtcgtc gaaatgtaat gatcactaat gatggtgctg caaatgtcat tacagcccaa    240

tactactggt cgcatagttt cacgagtcaa tggttcttat atacgtctat tgacgtcaat    300

gttggtgatt ctaagctatt agtctcaccc tccaactcat tgtattacag taaggttgtt    360

ctgattaata acacaaaccg taaagcatat gttactgccg aggaaaaata g             411
```

<210> SEQ ID NO 82
<211> LENGTH: 136
<212> TYPE: PRT
<213> ORGANISM: Yersinia aldovae
<220> FEATURE:
<221> NAME/KEY: MISC_FEATURE
<222> LOCATION: (1)..(136)
<223> OTHER INFORMATION: The amino acid sequence of the TIC10362 PirA protein.

<400> SEQUENCE: 82

```
Met Ser Lys Val Thr Ile Thr Ile Asp Ser Cys Ser Asn Glu Val Glu
1               5                   10                  15

Val Lys Asn Gln Thr Glu Val Asp Thr Glu Ser Leu Ala Leu Thr Thr
            20                  25                  30

Ala Gln Val Arg Ala Arg Val Pro Thr Glu Val Ala Pro Asn Ser Ser
        35                  40                  45

Thr Glu Val Leu Tyr Arg Ser Thr Pro Ile Ile Pro Glu Ser Arg Arg
```

-continued

```
    50                  55                  60

Asn Val Met Ile Thr Asn Asp Gly Ala Ala Asn Val Ile Thr Ala Gln
65                  70                  75                  80

Tyr Tyr Trp Ser His Ser Phe Thr Ser Gln Trp Phe Leu Tyr Thr Ser
                85                  90                  95

Ile Asp Val Asn Val Gly Asp Ser Lys Leu Leu Val Ser Pro Ser Asn
            100                 105                 110

Ser Leu Tyr Tyr Ser Lys Val Val Leu Ile Asn Asn Thr Asn Arg Lys
        115                 120                 125

Ala Tyr Val Thr Ala Glu Glu Lys
    130                 135
```

<210> SEQ ID NO 83
<211> LENGTH: 1251
<212> TYPE: DNA
<213> ORGANISM: Yersinia aldovae
<220> FEATURE:
<221> NAME/KEY: misc_feature
<222> LOCATION: (1)..(1251)
<223> OTHER INFORMATION: A nucleic acid sequence obtained from Yersinia aldovae strain 670-83 encoding a TIC10371 pesticidal PirB protein sequence.

<400> SEQUENCE: 83

```
atgaataaca ttacagaata taacaataca gagaactttg tcccttataa tgtatacgct     60

acttcagcct ttgaatttga ctgggattct tcagccattc ttaagcaagc agtgcttaaa    120

ggtatatcat tcattcctta tgtcggtgat tatttatcct ctattattgg cttcttttgg    180

aaagaccaag agagagatat ctggcaggaa attttgggcc gggtacagca acttatcgaa    240

gagaatgtgc ttaaagctat taaaggcatt ttattgggcg atattgctga acttaaaggg    300

aaggttgcat ccgttgtcgc ggccttgcag gaccatcctg gtacaccgga agccaaaagt    360

ttatttatga gcgtatcggt acatttggat agcgtacaac gcaagtttac tacttttgat    420

cacaaaacta attaccatat cctgccgatg tattcagcaa ccgcgttgat gcaaataatg    480

tactggacca tgggcattga gcgtaaagac gatatcggat tgaacagtaa tgaagttggg    540

caacttcaac gaaatattaa tctattggtt acacatgtcg aggattatat tcaagagatt    600

tacgatacag aattagagat ccaatacaac gactcggcac ctaatactgt agccaacaat    660

gttatgtatg tacatggcta ctgtcgggtg catggtttgg agtataccga gatcattcaa    720

agtattcaga agaatagaag caatacacag ggactgtatt caaaaatact gagctactcg    780

actttctttg gttggccaac cagtcaggcg cgaattctcg cattaaaaga cgaaataaat    840

atgccggagc catttaagcc aaaattaata aatggccgta taaaccaagt taagtcagtt    900

aaaggctata tacgacgtat cggaggtgct ttacgggtag gtggattaga aatcaccttt    960

gagaatggta gtaagtactc gcaaggaact gttactggtg aatttagttc aattgacctt   1020

aatgggagtg tcattgaaac aatggaaact tggggtagtg gcgcaattga cgaagctaaa   1080

tttaccttaa gcgatggccg tacctttact gtcggtcaac gttattcaac aaattacaga   1140

aagtttgcac ttgagggaca ctatatttct ggcattttta ttgccagcga tcgaagtgaa   1200

cttgccggcc aagctgcaaa tatttgtgtt tcttatcatc agaaacagtg a            1251
```

<210> SEQ ID NO 84
<211> LENGTH: 416
<212> TYPE: PRT
<213> ORGANISM: Yersinia aldovae
<220> FEATURE:

-continued

<221> NAME/KEY: MISC_FEATURE
<222> LOCATION: (1)..(416)
<223> OTHER INFORMATION: The amino acid sequence of the TIC10371 PirB protein.

<400> SEQUENCE: 84

```
Met Asn Asn Ile Thr Glu Tyr Asn Asn Thr Glu Asn Phe Val Pro Tyr
1               5                   10                  15

Asn Val Tyr Ala Thr Ser Ala Phe Glu Phe Asp Trp Asp Ser Ser Ala
            20                  25                  30

Ile Leu Lys Gln Ala Val Leu Lys Gly Ile Ser Phe Ile Pro Tyr Val
        35                  40                  45

Gly Asp Tyr Leu Ser Ser Ile Ile Gly Phe Phe Trp Lys Asp Gln Glu
    50                  55                  60

Arg Asp Ile Trp Gln Glu Ile Leu Gly Arg Val Gln Gln Leu Ile Glu
65                  70                  75                  80

Glu Asn Val Leu Lys Ala Ile Lys Gly Ile Leu Leu Gly Asp Ile Ala
                85                  90                  95

Glu Leu Lys Gly Lys Val Ala Ser Val Val Ala Ala Leu Gln Asp His
            100                 105                 110

Pro Gly Thr Pro Glu Ala Lys Ser Leu Phe Met Ser Val Ser Val His
        115                 120                 125

Leu Asp Ser Val Gln Arg Lys Phe Thr Thr Phe Asp His Lys Thr Asn
    130                 135                 140

Tyr His Ile Leu Pro Met Tyr Ser Ala Thr Ala Leu Met Gln Ile Met
145                 150                 155                 160

Tyr Trp Thr Met Gly Ile Glu Arg Lys Asp Asp Ile Gly Leu Asn Ser
                165                 170                 175

Asn Glu Val Gly Gln Leu Gln Arg Asn Ile Asn Leu Leu Val Thr His
            180                 185                 190

Val Glu Asp Tyr Ile Gln Glu Ile Tyr Asp Thr Glu Leu Glu Ile Gln
        195                 200                 205

Tyr Asn Asp Ser Ala Pro Asn Thr Val Ala Asn Asn Val Met Tyr Val
    210                 215                 220

His Gly Tyr Cys Arg Val His Gly Leu Glu Tyr Thr Glu Ile Ile Gln
225                 230                 235                 240

Ser Ile Gln Lys Asn Arg Ser Asn Thr Gln Gly Leu Tyr Ser Lys Ile
                245                 250                 255

Leu Ser Tyr Ser Thr Phe Phe Gly Trp Pro Thr Ser Gln Ala Arg Ile
            260                 265                 270

Leu Ala Leu Lys Asp Glu Ile Asn Met Pro Glu Pro Phe Lys Pro Lys
        275                 280                 285

Leu Ile Asn Gly Arg Ile Asn Gln Val Lys Ser Val Lys Gly Tyr Ile
    290                 295                 300

Arg Arg Ile Gly Gly Ala Leu Arg Val Gly Gly Leu Glu Ile Thr Phe
305                 310                 315                 320

Glu Asn Gly Ser Lys Tyr Ser Gln Gly Thr Val Thr Gly Glu Phe Ser
                325                 330                 335

Ser Ile Asp Leu Asn Gly Ser Val Ile Glu Thr Met Glu Thr Trp Gly
            340                 345                 350

Ser Gly Ala Ile Asp Glu Ala Lys Phe Thr Leu Ser Asp Gly Arg Thr
        355                 360                 365

Phe Thr Val Gly Gln Arg Tyr Ser Thr Asn Tyr Arg Lys Phe Ala Leu
    370                 375                 380
```

```
Glu Gly His Tyr Ile Ser Gly Ile Phe Ile Ala Ser Asp Arg Ser Glu
385                 390                 395                 400

Leu Ala Gly Gln Ala Ala Asn Ile Cys Val Ser Tyr His Gln Lys Gln
                405                 410                 415


<210> SEQ ID NO 85
<211> LENGTH: 1659
<212> TYPE: DNA
<213> ORGANISM: Artificial
<220> FEATURE:
<223> OTHER INFORMATION: A nucleic acid sequence encoding a PirAB fusion
      protein, TIC10379 comprised of the TIC10362 and TIC10371 coding
      sequences in operable linkage and in frame.

<400> SEQUENCE: 85

atgagcaagg taaccatcac tattgatagc tgttcaaatg aagtcgaagt taaaaatcaa     60

actgaggttg ataccgaaag tctagcgttg accactgcac aagttagagc cagggtgcca    120

actgaggtcg cacctaattc aagcaccgaa gttctgtatc ggagtacacc gattattcct    180

gaaagtcgtc gaaatgtaat gatcactaat gatggtgctg caaatgtcat tacagcccaa    240

tactactggt cgcatagttt cacgagtcaa tggttcttat atacgtctat tgacgtcaat    300

gttggtgatt ctaagctatt agtctcaccc tccaactcat tgtattacag taaggttgtt    360

ctgattaata acacaaaccg taaagcatat gttactgccg aggaaaaaat gaataacatt    420

acagaatata acaatacaga gaactttgtc ccttataatg tatacgctac ttcagccttt    480

gaatttgact gggattcttc agccattctt aagcaagcag tgcttaaagg tatatcattc    540

attccttatg tcggtgatta tttatcctct attattggct tcttttggaa agaccaagag    600

agagatatct ggcaggaaat tttgggccgg gtacagcaac ttatcgaaga gaatgtgctt    660

aaagctatta aaggcatttt attgggcgat attgctgaac ttaaagggaa ggttgcatcc    720

gttgtcgcgg ccttgcagga ccatcctggt acaccggaag ccaaaagttt atttatgagc    780

gtatcggtac atttggatag cgtacaacgc aagtttacta cttttgatca caaaactaat    840

taccatatcc tgccgatgta ttcagcaacc gcgttgatgc aaataatgta ctggaccatg    900

ggcattgagc gtaaagacga tatcggattg aacagtaatg aagttgggca acttcaacga    960

aatattaatc tattggttac acatgtcgag gattatattc aagagattta cgatacagaa   1020

ttagagatcc aatacaacga ctcggcacct aatactgtag ccaacaatgt tatgtatgta   1080

catggctact gtcgggtgca tggtttggag tataccgaga tcattcaaag tattcagaag   1140

aatagaagca atacacaggg actgtattca aaaatactga gctactcgac tttctttggt   1200

tggccaacca gtcaggcgcg aattctcgca ttaaaagacg aaataaatat gccggagcca   1260

tttaagccaa aattaataaa tggccgtata aaccaagtta agtcagttaa aggctatata   1320

cgacgtatcg gaggtgcttt acgggtaggt ggattagaaa tcacctttga gaatggtagt   1380

aagtactcgc aaggaactgt tactggtgaa tttagttcaa ttgaccttaa tgggagtgtc   1440

attgaaacaa tggaaacttg ggtagtggc gcaattgacg aagctaaatt taccttaagc    1500

gatggccgta cctttactgt cggtcaacgt tattcaacaa attacagaaa gtttgcactt   1560

gagggacact atatttctgg catttttatt gccagcgatc gaagtgaact tgccggccaa   1620

gctgcaaata tttgtgtttc ttatcatcag aaacagtga                          1659


<210> SEQ ID NO 86
<211> LENGTH: 552
<212> TYPE: PRT
<213> ORGANISM: Artificial
```

<220> FEATURE:
<223> OTHER INFORMATION: The amino acid sequence of the TIC10379 PirAB fusion protein.

<400> SEQUENCE: 86

```
Met Ser Lys Val Thr Ile Thr Ile Asp Ser Cys Ser Asn Glu Val Glu
1               5                   10                  15

Val Lys Asn Gln Thr Glu Val Asp Thr Glu Ser Leu Ala Leu Thr Thr
            20                  25                  30

Ala Gln Val Arg Ala Arg Val Pro Thr Glu Val Ala Pro Asn Ser Ser
        35                  40                  45

Thr Glu Val Leu Tyr Arg Ser Thr Pro Ile Ile Pro Glu Ser Arg Arg
    50                  55                  60

Asn Val Met Ile Thr Asn Asp Gly Ala Ala Asn Val Ile Thr Ala Gln
65                  70                  75                  80

Tyr Tyr Trp Ser His Ser Phe Thr Ser Gln Trp Phe Leu Tyr Thr Ser
                85                  90                  95

Ile Asp Val Asn Val Gly Asp Ser Lys Leu Leu Val Ser Pro Ser Asn
            100                 105                 110

Ser Leu Tyr Tyr Ser Lys Val Val Leu Ile Asn Asn Thr Asn Arg Lys
        115                 120                 125

Ala Tyr Val Thr Ala Glu Glu Lys Met Asn Asn Ile Thr Glu Tyr Asn
    130                 135                 140

Asn Thr Glu Asn Phe Val Pro Tyr Asn Val Tyr Ala Thr Ser Ala Phe
145                 150                 155                 160

Glu Phe Asp Trp Asp Ser Ser Ala Ile Leu Lys Gln Ala Val Leu Lys
                165                 170                 175

Gly Ile Ser Phe Ile Pro Tyr Val Gly Asp Tyr Leu Ser Ser Ile Ile
            180                 185                 190

Gly Phe Phe Trp Lys Asp Gln Glu Arg Asp Ile Trp Gln Glu Ile Leu
        195                 200                 205

Gly Arg Val Gln Gln Leu Ile Glu Glu Asn Val Leu Lys Ala Ile Lys
    210                 215                 220

Gly Ile Leu Leu Gly Asp Ile Ala Glu Leu Lys Gly Lys Val Ala Ser
225                 230                 235                 240

Val Val Ala Ala Leu Gln Asp His Pro Gly Thr Pro Glu Ala Lys Ser
                245                 250                 255

Leu Phe Met Ser Val Ser Val His Leu Asp Ser Val Gln Arg Lys Phe
            260                 265                 270

Thr Thr Phe Asp His Lys Thr Asn Tyr His Ile Leu Pro Met Tyr Ser
        275                 280                 285

Ala Thr Ala Leu Met Gln Ile Met Tyr Trp Thr Met Gly Ile Glu Arg
    290                 295                 300

Lys Asp Asp Ile Gly Leu Asn Ser Asn Glu Val Gly Gln Leu Gln Arg
305                 310                 315                 320

Asn Ile Asn Leu Leu Val Thr His Val Glu Asp Tyr Ile Gln Glu Ile
                325                 330                 335

Tyr Asp Thr Glu Leu Glu Ile Gln Tyr Asn Asp Ser Ala Pro Asn Thr
            340                 345                 350

Val Ala Asn Asn Val Met Tyr Val His Gly Tyr Cys Arg Val His Gly
        355                 360                 365

Leu Glu Tyr Thr Glu Ile Ile Gln Ser Ile Gln Lys Asn Arg Ser Asn
    370                 375                 380

Thr Gln Gly Leu Tyr Ser Lys Ile Leu Ser Tyr Ser Thr Phe Phe Gly
```

-continued

```
385                 390                 395                 400

Trp Pro Thr Ser Gln Ala Arg Ile Leu Ala Leu Lys Asp Glu Ile Asn
                405                 410                 415

Met Pro Glu Pro Phe Lys Pro Lys Leu Ile Asn Gly Arg Ile Asn Gln
            420                 425                 430

Val Lys Ser Val Lys Gly Tyr Ile Arg Arg Ile Gly Gly Ala Leu Arg
        435                 440                 445

Val Gly Gly Leu Glu Ile Thr Phe Glu Asn Gly Ser Lys Tyr Ser Gln
    450                 455                 460

Gly Thr Val Thr Gly Glu Phe Ser Ser Ile Asp Leu Asn Gly Ser Val
465                 470                 475                 480

Ile Glu Thr Met Glu Thr Trp Gly Ser Gly Ala Ile Asp Glu Ala Lys
                485                 490                 495

Phe Thr Leu Ser Asp Gly Arg Thr Phe Thr Val Gly Gln Arg Tyr Ser
            500                 505                 510

Thr Asn Tyr Arg Lys Phe Ala Leu Glu Gly His Tyr Ile Ser Gly Ile
        515                 520                 525

Phe Ile Ala Ser Asp Arg Ser Glu Leu Ala Gly Gln Ala Ala Asn Ile
    530                 535                 540

Cys Val Ser Tyr His Gln Lys Gln
545                 550


<210> SEQ ID NO 87
<211> LENGTH: 414
<212> TYPE: DNA
<213> ORGANISM: Xenorhabdus doucetiae
<220> FEATURE:
<221> NAME/KEY: misc_feature
<222> LOCATION: (1)..(414)
<223> OTHER INFORMATION: A nucleic acid sequence obtained from
      Xenorhabdus doucetiae strain FRM16 encoding a TIC10363 pesticidal
      PirA protein sequence.

<400> SEQUENCE: 87

atgattacaa ttaatataag tggtggttca gtaacaatta ataacactta caatatcaca      60

tcagaatctg gcattcaaaa taccccctgcc tcagaacctc tcaccgtcat tccttataga    120

gatatgacaa tagaaccaca ctcttctatt gaggcaacaa gaactgatac gcctattatt    180

cctgaaacac gccccaatta ttatatcgcc aattccggcc ctgcatcaga agttagagca    240

gtgttttatt ggtcgcattc tttcacatca caatggttcg aatcttcctc tatcatagtg    300

aaagcagggg aagacggcat attacaatca ccaagcaact cgctatatta cagcaaggtt    360

gtcatttata atgatacaga taaacgcgcc tttgtgactg gatataataa gtaa          414


<210> SEQ ID NO 88
<211> LENGTH: 137
<212> TYPE: PRT
<213> ORGANISM: Xenorhabdus doucetiae
<220> FEATURE:
<221> NAME/KEY: MISC_FEATURE
<222> LOCATION: (1)..(137)
<223> OTHER INFORMATION: The amino acid sequence of the TIC10363 PirA
      protein.

<400> SEQUENCE: 88

Met Ile Thr Ile Asn Ile Ser Gly Gly Ser Val Thr Ile Asn Asn Thr
1               5                   10                  15

Tyr Asn Ile Thr Ser Glu Ser Gly Ile Gln Asn Thr Pro Ala Ser Glu
            20                  25                  30
```

```
Pro Leu Thr Val Ile Pro Tyr Arg Asp Met Thr Ile Glu Pro His Ser
        35                  40                  45

Ser Ile Glu Ala Thr Arg Thr Asp Thr Pro Ile Ile Pro Glu Thr Arg
    50                  55                  60

Pro Asn Tyr Tyr Ile Ala Asn Ser Gly Pro Ala Ser Glu Val Arg Ala
65                  70                  75                  80

Val Phe Tyr Trp Ser His Ser Phe Thr Ser Gln Trp Phe Glu Ser Ser
                85                  90                  95

Ser Ile Ile Val Lys Ala Gly Glu Asp Gly Ile Leu Gln Ser Pro Ser
            100                 105                 110

Asn Ser Leu Tyr Tyr Ser Lys Val Val Ile Tyr Asn Asp Thr Asp Lys
        115                 120                 125

Arg Ala Phe Val Thr Gly Tyr Asn Lys
    130                 135


<210> SEQ ID NO 89
<211> LENGTH: 1293
<212> TYPE: DNA
<213> ORGANISM: Xenorhabdus doucetiae
<220> FEATURE:
<221> NAME/KEY: misc_feature
<222> LOCATION: (1)..(1293)
<223> OTHER INFORMATION: A nucleic acid sequence obtained from
      Xenorhabdus doucetiae strain FRM16 encoding a TIC10372 pesticidal
      PirB protein sequence.

<400> SEQUENCE: 89

atgaataaca catctataaa tatcaatgag aatgaaacat tacctttaga agttatccct     60

tcaatgcctg aacccatgtt aatcgttcct tatgcaactt ctactcctga ttatgaatgg    120

gatgcctccg gaataataaa agatgccatt attggtggta taggatttat tcctggccca    180

ggtccggcaa tatcttttct gttaggactc ttttggcctc aacaggcaga caatacttgg    240

gaacaaattc tgcaaaaagt cgagcagatg atagaggatg ctgttctcaa aaccattcaa    300

ggtatattga atggcgatat acaagaaatt aaaggtaaaa tggaacatgt ccaatacatg    360

ttggaaacct caccgggtag ccaagaaagc cgtgaagctt atatgtttct ggcgagatat    420

ctggtgagta tagatgaaaa attcaagtcc tttgataata aaacaaatta ccaaattctc    480

ccgatgtata ccaacactct catgttacag gttccttatt ggaaaatggg catagagaag    540

caaaaggata ttggtttatc cgatatagaa gttaatgaat taaaacagct tatcgataaa    600

ttatatacca aggctaacag ctatattcat gaaacgtata cgcgtcaata taacgatgcg    660

ataaacacgt caaccgcagc aaatatcacc aataatttat tttctgtcag aggatattgt    720

ttgttacacg gtttagagtg tcttgaaatg attgagcatc tacaaaagaa tagccttgaa    780

agtggtttct atcccaaaac catcagttat tctaccgtat tcgatcgtca gactcccaaa    840

atgagaattc aggctctgac agaagacgat caaatgcagg agccattaaa gccatcttta    900

atcaacggca aatacaatca aataaaatca ttgactggat atgtccgtag aattggcaat    960

gctcccagag tgggggggat gacgatcaca tttgccaacg gtgcatctta cacactgggt   1020

acagtaacat cagaaacgac gtcaattgag ctcaatggca gtgtgatcga aagcttggaa   1080

gtctggggag atggcgcggt tgatgaggca ttatttacgt taagtgataa acgcctattc   1140

cgtatcggtg agcgctacgc cagaaaatac aaaaaaatatg ctgttgatag ccactatatt   1200

gcagggcttt atttagccag tgatgagcct tcacttgcag gtcaagccgc aggtattgcc   1260

gtttcatacc atatgctgga tgacaaaaaa taa                                1293
```

```
<210> SEQ ID NO 90
<211> LENGTH: 430
<212> TYPE: PRT
<213> ORGANISM: Xenorhabdus doucetiae
<220> FEATURE:
<221> NAME/KEY: MISC_FEATURE
<222> LOCATION: (1)..(430)
<223> OTHER INFORMATION: The amino acid sequence of the TIC10372 PirB
      protein.

<400> SEQUENCE: 90

Met Asn Asn Thr Ser Ile Asn Ile Asn Glu Asn Glu Thr Leu Pro Leu
1               5                   10                  15

Glu Val Ile Pro Ser Met Pro Glu Pro Met Leu Ile Val Pro Tyr Ala
            20                  25                  30

Thr Ser Thr Pro Asp Tyr Glu Trp Asp Ala Ser Gly Ile Ile Lys Asp
        35                  40                  45

Ala Ile Ile Gly Gly Ile Gly Phe Ile Pro Gly Pro Gly Pro Ala Ile
    50                  55                  60

Ser Phe Leu Leu Gly Leu Phe Trp Pro Gln Gln Ala Asp Asn Thr Trp
65                  70                  75                  80

Glu Gln Ile Leu Gln Lys Val Glu Gln Met Ile Glu Asp Ala Val Leu
                85                  90                  95

Lys Thr Ile Gln Gly Ile Leu Asn Gly Asp Ile Gln Glu Ile Lys Gly
            100                 105                 110

Lys Met Glu His Val Gln Tyr Met Leu Glu Thr Ser Pro Gly Ser Gln
        115                 120                 125

Glu Ser Arg Glu Ala Tyr Met Phe Leu Ala Arg Tyr Leu Val Ser Ile
    130                 135                 140

Asp Glu Lys Phe Lys Ser Phe Asp Asn Lys Thr Asn Tyr Gln Ile Leu
145                 150                 155                 160

Pro Met Tyr Thr Asn Thr Leu Met Leu Gln Val Pro Tyr Trp Lys Met
                165                 170                 175

Gly Ile Glu Lys Gln Lys Asp Ile Gly Leu Ser Asp Ile Glu Val Asn
            180                 185                 190

Glu Leu Lys Gln Leu Ile Asp Lys Leu Tyr Thr Lys Ala Asn Ser Tyr
        195                 200                 205

Ile His Glu Thr Tyr Thr Arg Gln Tyr Asn Asp Ala Ile Asn Thr Ser
    210                 215                 220

Thr Ala Ala Asn Ile Thr Asn Asn Leu Phe Ser Val Arg Gly Tyr Cys
225                 230                 235                 240

Leu Leu His Gly Leu Glu Cys Leu Glu Met Ile Glu His Leu Gln Lys
                245                 250                 255

Asn Ser Leu Glu Ser Gly Phe Tyr Pro Lys Thr Ile Ser Tyr Ser Thr
            260                 265                 270

Val Phe Asp Arg Gln Thr Pro Lys Met Arg Ile Gln Ala Leu Thr Glu
        275                 280                 285

Asp Asp Gln Met Gln Glu Pro Leu Lys Pro Ser Leu Ile Asn Gly Lys
    290                 295                 300

Tyr Asn Gln Ile Lys Ser Leu Thr Gly Tyr Val Arg Arg Ile Gly Asn
305                 310                 315                 320

Ala Pro Arg Val Gly Gly Met Thr Ile Thr Phe Ala Asn Gly Ala Ser
                325                 330                 335

Tyr Thr Leu Gly Thr Val Thr Ser Glu Thr Thr Ser Ile Glu Leu Asn
            340                 345                 350
```

-continued

```
Gly Ser Val Ile Glu Ser Leu Glu Val Trp Gly Asp Gly Ala Val Asp
        355                 360                 365

Glu Ala Leu Phe Thr Leu Ser Asp Lys Arg Leu Phe Arg Ile Gly Glu
    370                 375                 380

Arg Tyr Ala Arg Lys Tyr Lys Lys Tyr Ala Val Asp Ser His Tyr Ile
385                 390                 395                 400

Ala Gly Leu Tyr Leu Ala Ser Asp Glu Pro Ser Leu Ala Gly Gln Ala
                405                 410                 415

Ala Gly Ile Ala Val Ser Tyr His Met Leu Asp Asp Lys Lys
            420                 425                 430
```

```
<210> SEQ ID NO 91
<211> LENGTH: 1704
<212> TYPE: DNA
<213> ORGANISM: Artificial
<220> FEATURE:
<223> OTHER INFORMATION: A nucleic acid sequence encoding a PirAB fusion
      protein, TIC10380 comprised of the TIC10363 and TIC10372 coding
      sequences in operable linkage and in frame.

<400> SEQUENCE: 91

atgattacaa ttaatataag tggtggttca gtaacaatta ataacactta caatatcaca     60

tcagaatctg gcattcaaaa taccoctgcc tcagaacctc tcaccgtcat tccttataga    120

gatatgacaa tagaaccaca ctcttctatt gaggcaacaa gaactgatac gcctattatt    180

cctgaaacac gccccaatta ttatatcgcc aattccggcc ctgcatcaga agttagagca    240

gtgttttatt ggtcgcattc tttcacatca caatggttcg aatcttcctc tatcatagtg    300

aaagcagggg aagacggcat attacaatca ccaagcaact cgctatatta cagcaaggtt    360

gtcatttata atgatacaga taaacgcgcc tttgtgactg gatataataa gatgaataac    420

acatctataa atatcaatga gaatgaaaca ttacctttag aagttatccc ttcaatgcct    480

gaacccatgt taatcgttcc ttatgcaact tctactcctg attatgaatg ggatgcctcc    540

ggaataataa aagatgccat tattggtggt ataggattta ttcctggccc aggtccggca    600

atatcttttc tgttaggact cttttggcct caacaggcag acaatacttg ggaacaaatt    660

ctgcaaaaag tcgagcagat gatagaggat gctgttctca aaaccattca aggtatattg    720

aatggcgata tacaagaaat taaaggtaaa atggaacatg tccaatacat gttggaaacc    780

tcaccgggta gccaagaaag ccgtgaagct tatatgtttc tggcgagata tctggtgagt    840

atagatgaaa aattcaagtc ctttgataat aaaacaaatt accaaattct cccgatgtat    900

accaacactc tcatgttaca ggttccttat tggaaaatgg gcatagagaa gcaaaaggat    960

attggtttat ccgatataga agttaatgaa ttaaaacagc ttatcgataa attatatacc   1020

aaggctaaca gctatattca tgaaacgtat acgcgtcaat ataacgatgc gataaacacg   1080

tcaaccgcag caaatatcac caataattta ttttctgtca gaggatattg tttgttacac   1140

ggtttagagt gtcttgaaat gattgagcat ctacaaaaga atagccttga aagtggtttc   1200

tatcccaaaa ccatcagtta ttctaccgta ttcgatcgtc agactcccaa aatgagaatt   1260

caggctctga cagaagacga tcaaatgcag gagccattaa agccatcttt aatcaacggc   1320

aaatacaatc aaataaaatc attgactgga tatgtccgta gaattggcaa tgctcccaga   1380

gtggggggga tgacgatcac atttgccaac ggtgcatctt acacactggg tacagtaaca   1440

tcagaaacga cgtcaattga gctcaatggc agtgtgatcg aaagcttgga agtctgggga   1500

gatggcgcgg ttgatgaggc attatttacg ttaagtgata aacgcctatt ccgtatcggt   1560
```

```
gagcgctacg ccagaaaata caaaaaatat gctgttgata gccactatat tgcagggctt   1620

tatttagcca gtgatgagcc ttcacttgca ggtcaagccg caggtattgc cgtttcatac   1680

catatgctgg atgacaaaaa ataa                                          1704


<210> SEQ ID NO 92
<211> LENGTH: 567
<212> TYPE: PRT
<213> ORGANISM: Artificial
<220> FEATURE:
<223> OTHER INFORMATION: The amino acid sequence of the TIC10380 PirAB
      fusion protein.

<400> SEQUENCE: 92

Met Ile Thr Ile Asn Ile Ser Gly Gly Ser Val Thr Ile Asn Asn Thr
1               5                   10                  15

Tyr Asn Ile Thr Ser Glu Ser Gly Ile Gln Asn Thr Pro Ala Ser Glu
            20                  25                  30

Pro Leu Thr Val Ile Pro Tyr Arg Asp Met Thr Ile Glu Pro His Ser
        35                  40                  45

Ser Ile Glu Ala Thr Arg Thr Asp Thr Pro Ile Ile Pro Glu Thr Arg
    50                  55                  60

Pro Asn Tyr Tyr Ile Ala Asn Ser Gly Pro Ala Ser Glu Val Arg Ala
65                  70                  75                  80

Val Phe Tyr Trp Ser His Ser Phe Thr Ser Gln Trp Phe Glu Ser Ser
                85                  90                  95

Ser Ile Ile Val Lys Ala Gly Glu Asp Gly Ile Leu Gln Ser Pro Ser
            100                 105                 110

Asn Ser Leu Tyr Tyr Ser Lys Val Val Ile Tyr Asn Asp Thr Asp Lys
        115                 120                 125

Arg Ala Phe Val Thr Gly Tyr Asn Lys Met Asn Asn Thr Ser Ile Asn
    130                 135                 140

Ile Asn Glu Asn Glu Thr Leu Pro Leu Glu Val Ile Pro Ser Met Pro
145                 150                 155                 160

Glu Pro Met Leu Ile Val Pro Tyr Ala Thr Ser Thr Pro Asp Tyr Glu
                165                 170                 175

Trp Asp Ala Ser Gly Ile Ile Lys Asp Ala Ile Ile Gly Gly Ile Gly
            180                 185                 190

Phe Ile Pro Gly Pro Gly Pro Ala Ile Ser Phe Leu Leu Gly Leu Phe
        195                 200                 205

Trp Pro Gln Gln Ala Asp Asn Thr Trp Glu Gln Ile Leu Gln Lys Val
    210                 215                 220

Glu Gln Met Ile Glu Asp Ala Val Leu Lys Thr Ile Gln Gly Ile Leu
225                 230                 235                 240

Asn Gly Asp Ile Gln Glu Ile Lys Gly Lys Met Glu His Val Gln Tyr
                245                 250                 255

Met Leu Glu Thr Ser Pro Gly Ser Gln Glu Ser Arg Glu Ala Tyr Met
            260                 265                 270

Phe Leu Ala Arg Tyr Leu Val Ser Ile Asp Glu Lys Phe Lys Ser Phe
        275                 280                 285

Asp Asn Lys Thr Asn Tyr Gln Ile Leu Pro Met Tyr Thr Asn Thr Leu
    290                 295                 300

Met Leu Gln Val Pro Tyr Trp Lys Met Gly Ile Glu Lys Gln Lys Asp
305                 310                 315                 320

Ile Gly Leu Ser Asp Ile Glu Val Asn Glu Leu Lys Gln Leu Ile Asp
                325                 330                 335
```

```
Lys Leu Tyr Thr Lys Ala Asn Ser Tyr Ile His Glu Thr Tyr Thr Arg
            340                 345                 350

Gln Tyr Asn Asp Ala Ile Asn Thr Ser Thr Ala Ala Asn Ile Thr Asn
        355                 360                 365

Asn Leu Phe Ser Val Arg Gly Tyr Cys Leu Leu His Gly Leu Glu Cys
    370                 375                 380

Leu Glu Met Ile Glu His Leu Gln Lys Asn Ser Leu Glu Ser Gly Phe
385                 390                 395                 400

Tyr Pro Lys Thr Ile Ser Tyr Ser Thr Val Phe Asp Arg Gln Thr Pro
                405                 410                 415

Lys Met Arg Ile Gln Ala Leu Thr Glu Asp Asp Gln Met Gln Glu Pro
            420                 425                 430

Leu Lys Pro Ser Leu Ile Asn Gly Lys Tyr Asn Gln Ile Lys Ser Leu
        435                 440                 445

Thr Gly Tyr Val Arg Arg Ile Gly Asn Ala Pro Arg Val Gly Gly Met
    450                 455                 460

Thr Ile Thr Phe Ala Asn Gly Ala Ser Tyr Thr Leu Gly Thr Val Thr
465                 470                 475                 480

Ser Glu Thr Thr Ser Ile Glu Leu Asn Gly Ser Val Ile Glu Ser Leu
                485                 490                 495

Glu Val Trp Gly Asp Gly Ala Val Asp Glu Ala Leu Phe Thr Leu Ser
            500                 505                 510

Asp Lys Arg Leu Phe Arg Ile Gly Glu Arg Tyr Ala Arg Lys Tyr Lys
        515                 520                 525

Lys Tyr Ala Val Asp Ser His Tyr Ile Ala Gly Leu Tyr Leu Ala Ser
    530                 535                 540

Asp Glu Pro Ser Leu Ala Gly Gln Ala Ala Gly Ile Ala Val Ser Tyr
545                 550                 555                 560

His Met Leu Asp Asp Lys Lys
                565
```

<210> SEQ ID NO 93
<211> LENGTH: 429
<212> TYPE: DNA
<213> ORGANISM: Xenorhabdus griffiniae
<220> FEATURE:
<221> NAME/KEY: misc_feature
<222> LOCATION: (1)..(429)
<223> OTHER INFORMATION: A nucleic acid sequence obtained from Xenorhabdus griffiniae strain BMMCB encoding a TIC10364 pesticidal PirA protein sequence.

<400> SEQUENCE: 93

```
atgagcataa tcaatataaa tataagtggt agtagtgaca ttacaatcat aaacaatacc      60

ccatctaacc cagaaccact catttacaat acagacacac ccgcatcaga acctcttacc     120

gtcaatcctt atagggatat gacaatagag ccacactctt ctattgaggc aataagaatt     180

gatacgccaa ttattcccga aacccgcccc aattattacg tagccaattc tggccccgca     240

tcatcagtta gagccgtttt ttattggtct cactctttca catcagaatg gttcgaatat     300

tctgctatca cagtgaaagc cggggaagac ggcatattac aatcaccgag caactctgtg     360

tattacagca aggtcgtcat ttataacgaa accgataaac gcgcctttgt tactggatat     420

aataagtaa                                                             429
```

<210> SEQ ID NO 94
<211> LENGTH: 142

<212> TYPE: PRT
<213> ORGANISM: Xenorhabdus griffiniae
<220> FEATURE:
<221> NAME/KEY: MISC_FEATURE
<222> LOCATION: (1)..(142)
<223> OTHER INFORMATION: The amino acid sequence of the TIC10364 PirA protein.

<400> SEQUENCE: 94

```
Met Ser Ile Ile Asn Ile Asn Ile Ser Gly Ser Ser Asp Ile Thr Ile
1               5                   10                  15

Ile Asn Asn Thr Pro Ser Asn Pro Glu Pro Leu Ile Tyr Asn Thr Asp
            20                  25                  30

Thr Pro Ala Ser Glu Pro Leu Thr Val Asn Pro Tyr Arg Asp Met Thr
        35                  40                  45

Ile Glu Pro His Ser Ser Ile Glu Ala Ile Arg Ile Asp Thr Pro Ile
    50                  55                  60

Ile Pro Glu Thr Arg Pro Asn Tyr Tyr Val Ala Asn Ser Gly Pro Ala
65                  70                  75                  80

Ser Ser Val Arg Ala Val Phe Tyr Trp Ser His Ser Phe Thr Ser Glu
                85                  90                  95

Trp Phe Glu Tyr Ser Ala Ile Thr Val Lys Ala Gly Glu Asp Gly Ile
            100                 105                 110

Leu Gln Ser Pro Ser Asn Ser Val Tyr Tyr Ser Lys Val Val Ile Tyr
        115                 120                 125

Asn Glu Thr Asp Lys Arg Ala Phe Val Thr Gly Tyr Asn Lys
    130                 135                 140
```

<210> SEQ ID NO 95
<211> LENGTH: 1278
<212> TYPE: DNA
<213> ORGANISM: Xenorhabdus griffiniae
<220> FEATURE:
<221> NAME/KEY: misc_feature
<222> LOCATION: (1)..(1278)
<223> OTHER INFORMATION: A nucleic acid sequence obtained from Xenorhabdus griffiniae strain BMMCB encoding a TIC10373 pesticidal PirB protein sequence.

<400> SEQUENCE: 95

```
atgaatacca caccgattaa tgtatctgaa aatgacacat tgcctgtact cactgacgtc      60

atgcttatcg tgccttatac cacctctacc cccgattatg aatgggatat gtcatcaata     120

ataaaggatg ccattattgg cggcgtaggg tttattccag gagtaggttc cgcaatgtct     180

ttcctgttag ggctattttg gccgcaacag aaagataata cctgggagca aatcctccaa     240

aaagtagagc aaatgataga gaatgctgct ctacaaacga ttaaaggaat acttaatgga     300

gatatacaag aaatcaaagg aaaaatggaa catgtgcaat acatgctgga aacctcgcct     360

ggcagccagg aaagccatga cgcctatatg ttcctggcta gatatctggt gagtatcgat     420

gaaagattca agtcttttga taataaaaca aactaccaga tcctgccgat gtacactaac     480

acggttatgt tacagatccc ttattggaaa atggggatag aaaagaaaaa tgatattggg     540

ctgaccgata ttgaagtcaa tgagttaaaa caacttatcg acacattggt tgacagagcc     600

agaaactata ttcatacgat gtatactaat gaatataata atgccataaa tacatcaaca     660

gcagagagtg tcactaataa tttattgtct gtaagagggt attgtttatt acacggttta     720

gagtgtattg agttaattga acatctacaa aataatagcc tggaaagtgg ttttaatcct     780

aaaactatca gttattcaac cgtatttgat cgtcctacta acaaaacgag aattcaggct     840
```

-continued

```
ctgacagaag acgatcaaat gcaggaaccc ttcaagccct ctttaatcga cggtaaatac    900

aataaaataa aatcattgct tggctatgta cgaagaatcg gcaatgcccc cagagtgggt    960

ggtattcaaa tcacatttgc caacgattca tcctatacac tcggcaccgt aacatcagaa   1020

acgagttcta ttgaactcaa tgatagtgtt atcgaaaggt tggaagtatg gggcaatggc   1080

gcggttgatg aggcgttatt tacgttaagt gatgggcgtc aactcagagt cggtgaacgc   1140

tacgcgacaa aatacagaaa atacgctgtt gatggccact atattgcagg gctgtactta   1200

gccagcgatg aaccttcact tgctggtcag gccgcaggta ttgccgtttc ataccatatg   1260

ttagctgata aaaaataa                                                 1278


<210> SEQ ID NO 96
<211> LENGTH: 425
<212> TYPE: PRT
<213> ORGANISM: Xenorhabdus griffiniae
<220> FEATURE:
<221> NAME/KEY: MISC_FEATURE
<222> LOCATION: (1)..(425)
<223> OTHER INFORMATION: The amino acid sequence of the TIC10373 PirB
      protein.

<400> SEQUENCE: 96

Met Asn Thr Thr Pro Ile Asn Val Ser Glu Asn Asp Thr Leu Pro Val
1               5                   10                  15

Leu Thr Asp Val Met Leu Ile Val Pro Tyr Thr Thr Ser Thr Pro Asp
            20                  25                  30

Tyr Glu Trp Asp Met Ser Ser Ile Ile Lys Asp Ala Ile Ile Gly Gly
        35                  40                  45

Val Gly Phe Ile Pro Gly Val Gly Ser Ala Met Ser Phe Leu Leu Gly
    50                  55                  60

Leu Phe Trp Pro Gln Gln Lys Asp Asn Thr Trp Glu Gln Ile Leu Gln
65                  70                  75                  80

Lys Val Glu Gln Met Ile Glu Asn Ala Ala Leu Gln Thr Ile Lys Gly
                85                  90                  95

Ile Leu Asn Gly Asp Ile Gln Glu Ile Lys Gly Lys Met Glu His Val
            100                 105                 110

Gln Tyr Met Leu Glu Thr Ser Pro Gly Ser Gln Glu Ser His Asp Ala
        115                 120                 125

Tyr Met Phe Leu Ala Arg Tyr Leu Val Ser Ile Asp Glu Arg Phe Lys
    130                 135                 140

Ser Phe Asp Asn Lys Thr Asn Tyr Gln Ile Leu Pro Met Tyr Thr Asn
145                 150                 155                 160

Thr Val Met Leu Gln Ile Pro Tyr Trp Lys Met Gly Ile Glu Lys Lys
                165                 170                 175

Asn Asp Ile Gly Leu Thr Asp Ile Glu Val Asn Glu Leu Lys Gln Leu
            180                 185                 190

Ile Asp Thr Leu Val Asp Arg Ala Arg Asn Tyr Ile His Thr Met Tyr
        195                 200                 205

Thr Asn Glu Tyr Asn Asn Ala Ile Asn Thr Ser Thr Ala Glu Ser Val
    210                 215                 220

Thr Asn Asn Leu Leu Ser Val Arg Gly Tyr Cys Leu Leu His Gly Leu
225                 230                 235                 240

Glu Cys Ile Glu Leu Ile Glu His Leu Gln Asn Asn Ser Leu Glu Ser
                245                 250                 255

Gly Phe Asn Pro Lys Thr Ile Ser Tyr Ser Thr Val Phe Asp Arg Pro
            260                 265                 270
```

-continued

```
Thr Asn Lys Thr Arg Ile Gln Ala Leu Thr Glu Asp Asp Gln Met Gln
        275                 280                 285

Glu Pro Phe Lys Pro Ser Leu Ile Asp Gly Lys Tyr Asn Lys Ile Lys
    290                 295                 300

Ser Leu Leu Gly Tyr Val Arg Arg Ile Gly Asn Ala Pro Arg Val Gly
305                 310                 315                 320

Gly Ile Gln Ile Thr Phe Ala Asn Asp Ser Ser Tyr Thr Leu Gly Thr
                325                 330                 335

Val Thr Ser Glu Thr Ser Ser Ile Glu Leu Asn Asp Ser Val Ile Glu
            340                 345                 350

Arg Leu Glu Val Trp Gly Asn Gly Ala Val Asp Glu Ala Leu Phe Thr
        355                 360                 365

Leu Ser Asp Gly Arg Gln Leu Arg Val Gly Glu Arg Tyr Ala Thr Lys
    370                 375                 380

Tyr Arg Lys Tyr Ala Val Asp Gly His Tyr Ile Ala Gly Leu Tyr Leu
385                 390                 395                 400

Ala Ser Asp Glu Pro Ser Leu Ala Gly Gln Ala Ala Gly Ile Ala Val
                405                 410                 415

Ser Tyr His Met Leu Ala Asp Lys Lys
            420                 425
```

<210> SEQ ID NO 97
<211> LENGTH: 1704
<212> TYPE: DNA
<213> ORGANISM: Artificial
<220> FEATURE:
<223> OTHER INFORMATION: A nucleic acid sequence encoding a PirAB fusion protein, TIC10381 comprised of the TIC10364 and TIC10364 coding sequences in operable linkage and in frame.

<400> SEQUENCE: 97

```
atgagcataa tcaatataaa tataagtggt agtagtgaca ttacaatcat aaacaatacc     60

ccatctaacc cagaaccact catttacaat acagacacac ccgcatcaga acctcttacc    120

gtcaatcctt atagggatat gacaatagag ccacactctt ctattgaggc aataagaatt    180

gatacgccaa ttattcccga aacccgcccc aattattacg tagccaattc tggccccgca    240

tcatcagtta gagccgtttt ttattggtct cactctttca catcagaatg gttcgaatat    300

tctgctatca cagtgaaagc cggggaagac ggcatattac aatcaccgag caactctgtg    360

tattacagca aggtcgtcat ttataacgaa accgataaac gcgcctttgt tactggatat    420

aataagatga ataccacacc gattaatgta tctgaaaatg acacattgcc tgtactcact    480

gacgtcatgc ttatcgtgcc ttataccacc tctacccccg attatgaatg ggatatgtca    540

tcaataataa aggatgccat tattggcggc gtagggttta ttccaggagt aggttccgca    600

atgtctttcc tgttagggct attttggccg caacagaaag ataatacctg ggagcaaatc    660

ctccaaaaag tagagcaaat gatagagaat gctgctctac aaacgattaa aggaatactt    720

aatggagata tacaagaaat caaaggaaaa atggaacatg tgcaatacat gctggaaacc    780

tcgcctggca gccaggaaag ccatgacgcc tatatgttcc tggctagata tctggtgagt    840

atcgatgaaa gattcaagtc ttttgataat aaaacaaact accagatcct gccgatgtac    900

actaacacgg ttatgttaca gatcccttat tggaaaatgg ggatagaaaa gaaaaatgat    960

attgggctga ccgatattga agtcaatgag ttaaaacaac ttatcgacac attggttgac   1020

agagccagaa actatattca tacgatgtat actaatgaat ataataatgc cataaataca   1080
```

```
tcaacagcag agagtgtcac taataattta ttgtctgtaa gagggtattg tttattacac   1140

ggtttagagt gtattgagtt aattgaacat ctacaaaata atagcctgga aagtggtttt   1200

aatcctaaaa ctatcagtta ttcaaccgta tttgatcgtc ctactaacaa aacgagaatt   1260

caggctctga cagaagacga tcaaatgcag gaacccttca agccctcttt aatcgacggt   1320

aaatacaata aaataaaatc attgcttggc tatgtacgaa gaatcggcaa tgcccccaga   1380

gtgggtggta ttcaaatcac atttgccaac gattcatcct atacactcgg caccgtaaca   1440

tcagaaacga gttctattga actcaatgat agtgttatcg aaaggttgga agtatggggc   1500

aatggcgcgg ttgatgaggc gttatttacg ttaagtgatg ggcgtcaact cagagtcggt   1560

gaacgctacg cgacaaaata cagaaaatac gctgttgatg gccactatat tgcagggctg   1620

tacttagcca gcgatgaacc ttcacttgct ggtcaggccg caggtattgc cgtttcatac   1680

catatgttag ctgataaaaa ataa                                          1704
```

<210> SEQ ID NO 98
<211> LENGTH: 567
<212> TYPE: PRT
<213> ORGANISM: Artificial
<220> FEATURE:
<223> OTHER INFORMATION: The amino acid sequence of the TIC10381 PirAB fusion protein.

<400> SEQUENCE: 98

```
Met Ser Ile Ile Asn Ile Asn Ile Ser Gly Ser Ser Asp Ile Thr Ile
1               5                   10                  15

Ile Asn Asn Thr Pro Ser Asn Pro Glu Pro Leu Ile Tyr Asn Thr Asp
            20                  25                  30

Thr Pro Ala Ser Glu Pro Leu Thr Val Asn Pro Tyr Arg Asp Met Thr
        35                  40                  45

Ile Glu Pro His Ser Ser Ile Glu Ala Ile Arg Ile Asp Thr Pro Ile
    50                  55                  60

Ile Pro Glu Thr Arg Pro Asn Tyr Tyr Val Ala Asn Ser Gly Pro Ala
65                  70                  75                  80

Ser Ser Val Arg Ala Val Phe Tyr Trp Ser His Ser Phe Thr Ser Glu
                85                  90                  95

Trp Phe Glu Tyr Ser Ala Ile Thr Val Lys Ala Gly Glu Asp Gly Ile
            100                 105                 110

Leu Gln Ser Pro Ser Asn Ser Val Tyr Tyr Ser Lys Val Val Ile Tyr
        115                 120                 125

Asn Glu Thr Asp Lys Arg Ala Phe Val Thr Gly Tyr Asn Lys Met Asn
    130                 135                 140

Thr Thr Pro Ile Asn Val Ser Glu Asn Asp Thr Leu Pro Val Leu Thr
145                 150                 155                 160

Asp Val Met Leu Ile Val Pro Tyr Thr Thr Ser Thr Pro Asp Tyr Glu
                165                 170                 175

Trp Asp Met Ser Ser Ile Ile Lys Asp Ala Ile Ile Gly Gly Val Gly
            180                 185                 190

Phe Ile Pro Gly Val Gly Ser Ala Met Ser Phe Leu Leu Gly Leu Phe
        195                 200                 205

Trp Pro Gln Gln Lys Asp Asn Thr Trp Glu Gln Ile Leu Gln Lys Val
    210                 215                 220

Glu Gln Met Ile Glu Asn Ala Ala Leu Gln Thr Ile Lys Gly Ile Leu
225                 230                 235                 240

Asn Gly Asp Ile Gln Glu Ile Lys Gly Lys Met Glu His Val Gln Tyr
```

```
                245                 250                 255

Met Leu Glu Thr Ser Pro Gly Ser Gln Glu Ser His Asp Ala Tyr Met
            260                 265                 270

Phe Leu Ala Arg Tyr Leu Val Ser Ile Asp Glu Arg Phe Lys Ser Phe
        275                 280                 285

Asp Asn Lys Thr Asn Tyr Gln Ile Leu Pro Met Tyr Thr Asn Thr Val
    290                 295                 300

Met Leu Gln Ile Pro Tyr Trp Lys Met Gly Ile Glu Lys Lys Asn Asp
305                 310                 315                 320

Ile Gly Leu Thr Asp Ile Glu Val Asn Glu Leu Lys Gln Leu Ile Asp
                325                 330                 335

Thr Leu Val Asp Arg Ala Arg Asn Tyr Ile His Thr Met Tyr Thr Asn
            340                 345                 350

Glu Tyr Asn Asn Ala Ile Asn Thr Ser Thr Ala Glu Ser Val Thr Asn
        355                 360                 365

Asn Leu Leu Ser Val Arg Gly Tyr Cys Leu Leu His Gly Leu Glu Cys
    370                 375                 380

Ile Glu Leu Ile Glu His Leu Gln Asn Asn Ser Leu Glu Ser Gly Phe
385                 390                 395                 400

Asn Pro Lys Thr Ile Ser Tyr Ser Thr Val Phe Asp Arg Pro Thr Asn
                405                 410                 415

Lys Thr Arg Ile Gln Ala Leu Thr Glu Asp Asp Gln Met Gln Glu Pro
            420                 425                 430

Phe Lys Pro Ser Leu Ile Asp Gly Lys Tyr Asn Lys Ile Lys Ser Leu
        435                 440                 445

Leu Gly Tyr Val Arg Arg Ile Gly Asn Ala Pro Arg Val Gly Gly Ile
    450                 455                 460

Gln Ile Thr Phe Ala Asn Asp Ser Ser Tyr Thr Leu Gly Thr Val Thr
465                 470                 475                 480

Ser Glu Thr Ser Ser Ile Glu Leu Asn Asp Ser Val Ile Glu Arg Leu
                485                 490                 495

Glu Val Trp Gly Asn Gly Ala Val Asp Glu Ala Leu Phe Thr Leu Ser
            500                 505                 510

Asp Gly Arg Gln Leu Arg Val Gly Glu Arg Tyr Ala Thr Lys Tyr Arg
        515                 520                 525

Lys Tyr Ala Val Asp Gly His Tyr Ile Ala Gly Leu Tyr Leu Ala Ser
    530                 535                 540

Asp Glu Pro Ser Leu Ala Gly Gln Ala Ala Gly Ile Ala Val Ser Tyr
545                 550                 555                 560

His Met Leu Ala Asp Lys Lys
                565


<210> SEQ ID NO 99
<211> LENGTH: 408
<212> TYPE: DNA
<213> ORGANISM: Xenorhabdus nematophila
<220> FEATURE:
<221> NAME/KEY: misc_feature
<222> LOCATION: (1)..(408)
<223> OTHER INFORMATION: A nucleic acid sequence obtained from
      Xenorhabdus nematophila encoding a TIC10359 pesticidal PirA
      protein sequence.

<400> SEQUENCE: 99

atgattacaa tcaatatcac tggtgataat gtaagagtta ataacaatat agcaacagaa      60

accgacctcc aaaatacacc tgcttcagca cccttatcaa ttattaattt tagggatatg     120
```

acaatagaac ctcattcatc tgttgaggcg ataagaaccg atacaccgat tattcctgaa 180
tcacgaccaa attactatgt tgctaattct ggcccggcct catcagtcag agctgttttc 240
tattggtccc actcttttac atcagaatgg tttgaatctt cctctattat tgtaaaagca 300
ggcgaagacg gagtcttaca ttcaccgggt aattctttat attacagcaa ggttgtaatt 360
tataacgata cagacaaacg tgcttttgtt accggctaca atctataa 408

<210> SEQ ID NO 100
<211> LENGTH: 135
<212> TYPE: PRT
<213> ORGANISM: Xenorhabdus nematophila
<220> FEATURE:
<221> NAME/KEY: MISC_FEATURE
<222> LOCATION: (1)..(135)
<223> OTHER INFORMATION: The amino acid sequence of the TIC10359 PirA
protein.

<400> SEQUENCE: 100

Met Ile Thr Ile Asn Ile Thr Gly Asp Asn Val Arg Val Asn Asn Asn
1 5 10 15

Ile Ala Thr Glu Thr Asp Leu Gln Asn Thr Pro Ala Ser Ala Pro Leu
20 25 30

Ser Ile Ile Asn Phe Arg Asp Met Thr Ile Glu Pro His Ser Ser Val
35 40 45

Glu Ala Ile Arg Thr Asp Thr Pro Ile Ile Pro Glu Ser Arg Pro Asn
50 55 60

Tyr Tyr Val Ala Asn Ser Gly Pro Ala Ser Ser Val Arg Ala Val Phe
65 70 75 80

Tyr Trp Ser His Ser Phe Thr Ser Glu Trp Phe Glu Ser Ser Ser Ile
85 90 95

Ile Val Lys Ala Gly Glu Asp Gly Val Leu His Ser Pro Gly Asn Ser
100 105 110

Leu Tyr Tyr Ser Lys Val Val Ile Tyr Asn Asp Thr Asp Lys Arg Ala
115 120 125

Phe Val Thr Gly Tyr Asn Leu
130 135

<210> SEQ ID NO 101
<211> LENGTH: 1290
<212> TYPE: DNA
<213> ORGANISM: Xenorhabdus nematophila
<220> FEATURE:
<221> NAME/KEY: misc_feature
<222> LOCATION: (1)..(1290)
<223> OTHER INFORMATION: A nucleic acid sequence obtained from
Xenorhabdus nematophila encoding a TIC10368 pesticidal PirB
protein sequence.

<400> SEQUENCE: 101
atgaataatg aaccgatgaa tactaatgaa tcacaagctt cagagatagt accctcaatg 60
aatgaatcta tattagcagc accttattca atttctacac ctaattatga atgggatatg 120
tcatcaataa taaaagatgc cattattggt ggtataggct ttattcctgg tccgggctca 180
gcaatatcat ttttgttagg gttattttgg ccacaacaaa ccgacaatac ttgggagcaa 240
attctccaaa aagtagaaca aatgatcgag caagccaatc tcaaaactat tcaaggaata 300
ttgaacggcg atatacaaga aattaaaggc aaaatggaac atgtgcaatt catgctagaa 360
tcctcacctg gcactcaaga aagccatgac gcatacatgt ttctggcgag atatctggtc 420

-continued

```
agtatagacg aaaaattcaa gtcttttgat aacaaaacaa attatcaaat tcttcccatg    480

tataccaata cgattatgtt acaagcccct tattggaaaa tgggtataga gagaaaagat    540

gagataaaac taacagatat agaagttaat gaattaaaag agctgatagg aaaattatct    600

accagcgccg ataaatatat tcatgatgtc tatactcgtg aatatgataa tgcgatgaac    660

acttcaacag cagcaaatat caccaataat ttattatctg taagaggcta ttgtttatta    720

catggtttag aatgtctcga agtcattaac catatacaaa ataatagcct tgagcaaagt    780

ttttatccta aaactatcag ctactccacc gtattcgatc gccagacaaa taaaacaagg    840

gttcaagccc tgacagaaga cgatcaaatg caagagccat tcaagcctgc tttaattaat    900

gggaagtaca acaaaataaa atcattgatt gggtatgtac aaagaatcgg aaacgcaccc    960

agagttggag gcattaaagt cacatttgca aacgatgcat cttataccct cggtacagta   1020

acttcagaag taaactcaat tgaactgaat gacagcgtta taaccagcct ggaagtatgg   1080

ggaaatggcg ctgttgatga ggcattcttt acattaagtg acggacgtca atttaggctt   1140

ggccaacgct atgccagtaa ctatagaaaa tatgctgtcg ataaccacta tatttcagga   1200

ttgtacttag ccagtgatga accttcattg gcaggccaag cagcaggcat tgcagtttca   1260

taccatatga tagctgataa aaaatcatag                                    1290
```

```
<210> SEQ ID NO 102
<211> LENGTH: 429
<212> TYPE: PRT
<213> ORGANISM: Xenorhabdus nematophila
<220> FEATURE:
<221> NAME/KEY: MISC_FEATURE
<222> LOCATION: (1)..(429)
<223> OTHER INFORMATION: The amino acid sequence of the TIC10368 PirB
      protein.

<400> SEQUENCE: 102

Met Asn Asn Glu Pro Met Asn Thr Asn Glu Ser Gln Ala Ser Glu Ile
1               5                   10                  15

Val Pro Ser Met Asn Glu Ser Ile Leu Ala Ala Pro Tyr Ser Ile Ser
            20                  25                  30

Thr Pro Asn Tyr Glu Trp Asp Met Ser Ser Ile Ile Lys Asp Ala Ile
        35                  40                  45

Ile Gly Gly Ile Gly Phe Ile Pro Gly Pro Gly Ser Ala Ile Ser Phe
    50                  55                  60

Leu Leu Gly Leu Phe Trp Pro Gln Gln Thr Asp Asn Thr Trp Glu Gln
65                  70                  75                  80

Ile Leu Gln Lys Val Glu Gln Met Ile Glu Gln Ala Asn Leu Lys Thr
                85                  90                  95

Ile Gln Gly Ile Leu Asn Gly Asp Ile Gln Glu Ile Lys Gly Lys Met
            100                 105                 110

Glu His Val Gln Phe Met Leu Glu Ser Ser Pro Gly Thr Gln Glu Ser
        115                 120                 125

His Asp Ala Tyr Met Phe Leu Ala Arg Tyr Leu Val Ser Ile Asp Glu
    130                 135                 140

Lys Phe Lys Ser Phe Asp Asn Lys Thr Asn Tyr Gln Ile Leu Pro Met
145                 150                 155                 160

Tyr Thr Asn Thr Ile Met Leu Gln Ala Pro Tyr Trp Lys Met Gly Ile
                165                 170                 175

Glu Arg Lys Asp Glu Ile Lys Leu Thr Asp Ile Glu Val Asn Glu Leu
            180                 185                 190
```

-continued

```
Lys Glu Leu Ile Gly Lys Leu Ser Thr Ser Ala Asp Lys Tyr Ile His
        195                 200                 205

Asp Val Tyr Thr Arg Glu Tyr Asp Asn Ala Met Asn Thr Ser Thr Ala
    210                 215                 220

Ala Asn Ile Thr Asn Asn Leu Leu Ser Val Arg Gly Tyr Cys Leu Leu
225                 230                 235                 240

His Gly Leu Glu Cys Leu Glu Val Ile Asn His Ile Gln Asn Asn Ser
                245                 250                 255

Leu Glu Gln Ser Phe Tyr Pro Lys Thr Ile Ser Tyr Ser Thr Val Phe
            260                 265                 270

Asp Arg Gln Thr Asn Lys Thr Arg Val Gln Ala Leu Thr Glu Asp Asp
        275                 280                 285

Gln Met Gln Glu Pro Phe Lys Pro Ala Leu Ile Asn Gly Lys Tyr Asn
    290                 295                 300

Lys Ile Lys Ser Leu Ile Gly Tyr Val Gln Arg Ile Gly Asn Ala Pro
305                 310                 315                 320

Arg Val Gly Gly Ile Lys Val Thr Phe Ala Asn Asp Ala Ser Tyr Thr
                325                 330                 335

Leu Gly Thr Val Thr Ser Glu Val Asn Ser Ile Glu Leu Asn Asp Ser
            340                 345                 350

Val Ile Thr Ser Leu Glu Val Trp Gly Asn Gly Ala Val Asp Glu Ala
        355                 360                 365

Phe Phe Thr Leu Ser Asp Gly Arg Gln Phe Arg Leu Gly Gln Arg Tyr
    370                 375                 380

Ala Ser Asn Tyr Arg Lys Tyr Ala Val Asp Asn His Tyr Ile Ser Gly
385                 390                 395                 400

Leu Tyr Leu Ala Ser Asp Glu Pro Ser Leu Ala Gly Gln Ala Ala Gly
                405                 410                 415

Ile Ala Val Ser Tyr His Met Ile Ala Asp Lys Lys Ser
            420                 425
```

<210> SEQ ID NO 103
<211> LENGTH: 1766
<212> TYPE: DNA
<213> ORGANISM: Artificial
<220> FEATURE:
<223> OTHER INFORMATION: A nucleic acid sequence encoding an operon comprised of the coding sequences TIC10359 and TIC10368.

<400> SEQUENCE: 103

```
atgattacaa tcaatatcac tggtgataat gtaagagtta ataacaatat agcaacagaa     60

accgacctcc aaaatacacc tgcttcagca cccttatcaa ttattaattt tagggatatg    120

acaatagaac ctcattcatc tgttgaggcg ataagaaccg atacaccgat tattcctgaa    180

tcacgaccaa attactatgt tgctaattct ggcccggcct catcagtcag agctgttttc    240

tattggtccc actcttttac atcagaatgg tttgaatctt cctctattat tgtaaaagca    300

ggcgaagacg gagtcttaca ttcaccgggt aattctttat attacagcaa ggttgtaatt    360

tataacgata cagacaaacg tgcttttgtt accggctaca atctataatg acgcagaaat    420

acaatccata tttccaatga atttcaaata acatccttaa ggcaagaaac aaaatcatga    480

ataatgaacc gatgaatact aatgaatcac aagcttcaga gatagtaccc tcaatgaatg    540

aatctatatt agcagcacct tattcaattt ctacacctaa ttatgaatgg gatatgtcat    600

caataataaa agatgccatt attggtggta taggctttat tcctggtccg ggctcagcaa    660

tatcattttt gttagggtta ttttggccac aacaaaccga caatacttgg gagcaaattc    720
```

```
tccaaaaagt agaacaaatg atcgagcaag ccaatctcaa aactattcaa ggaatattga    780

acggcgatat acaagaaatt aaaggcaaaa tggaacatgt gcaattcatg ctagaatcct    840

cacctggcac tcaagaaagc catgacgcat acatgtttct ggcgagatat ctggtcagta    900

tagacgaaaa attcaagtct tttgataaca aaacaaatta tcaaattctt cccatgtata    960

ccaatacgat tatgttacaa gccccttatt ggaaaatggg tatagagaga aaagatgaga   1020

taaaactaac agatatagaa gttaatgaat taaaagagct gataggaaaa ttatctacca   1080

gcgccgataa atatattcat gatgtctata ctcgtgaata tgataatgcg atgaacactt   1140

caacagcagc aaatatcacc aataatttat tatctgtaag aggctattgt ttattacatg   1200

gtttagaatg tctcgaagtc attaaccata tacaaaataa tagccttgag caaagttttt   1260

atcctaaaac tatcagctac tccaccgtat tcgatcgcca gacaaataaa acaagggttc   1320

aagccctgac agaagacgat caaatgcaag agccattcaa gcctgcttta attaatggga   1380

agtacaacaa aataaaatca ttgattgggt atgtacaaag aatcggaaac gcacccagag   1440

ttggaggcat taaagtcaca tttgcaaacg atgcatctta taccctcggt acagtaactt   1500

cagaagtaaa ctcaattgaa ctgaatgaca gcgttataac cagcctggaa gtatggggaa   1560

atggcgctgt tgatgaggca ttctttacat taagtgacgg acgtcaattt aggcttggcc   1620

aacgctatgc cagtaactat agaaaatatg ctgtcgataa ccactatatt tcaggattgt   1680

acttagccag tgatgaacct tcattggcag gccaagcagc aggcattgca gtttcatacc   1740

atatgatagc tgataaaaaa tcatag                                        1766
```

<210> SEQ ID NO 104
<211> LENGTH: 417
<212> TYPE: DNA
<213> ORGANISM: Photorhabdus luminescens
<220> FEATURE:
<221> NAME/KEY: misc_feature
<222> LOCATION: (1)..(417)
<223> OTHER INFORMATION: A nucleic acid sequence obtained from Photorhabdus luminescens strain Hm encoding a PirA_ABE68878 pesticidal PirA protein sequence.

<400> SEQUENCE: 104

```
atgaggaaaa taaatatgtc tagaataacc attgttgttg attcagatac acaaaaagca     60

gaagtttatt ctaattctcc tgtgccggta catagagatt taaatgcagt tggtcctttg    120

agtgatgtga ctatatcacc tcatgctagt gtggaagtat ttagaataga caccccaata    180

attccagaat ccagaagctc tctgagagtt gtaaatacag ggttagcaaa tagtgttacg    240

gctaaatttt actggtctca tagttttacc tctgaatggt ttgaagctgg atctatagat    300

gtaggattag gagaagataa ggtattaaac gtgcctagca gctcttttta ttatagtaaa    360

tttgttatct ataataacac ggatagagtg gcttatgtta cggcaaattt ggtttaa       417
```

<210> SEQ ID NO 105
<211> LENGTH: 138
<212> TYPE: PRT
<213> ORGANISM: Photorhabdus luminescens
<220> FEATURE:
<221> NAME/KEY: MISC_FEATURE
<222> LOCATION: (1)..(138)
<223> OTHER INFORMATION: The amino acid sequence of the PirA_ABE68878 PirA protein.

<400> SEQUENCE: 105

Met Arg Lys Ile Asn Met Ser Arg Ile Thr Ile Val Val Asp Ser Asp

```
1               5                   10                  15

Thr Gln Lys Ala Glu Val Tyr Ser Asn Ser Pro Val Pro Val His Arg
            20                  25                  30

Asp Leu Asn Ala Val Gly Pro Leu Ser Asp Val Thr Ile Ser Pro His
        35                  40                  45

Ala Ser Val Glu Val Phe Arg Ile Asp Thr Pro Ile Ile Pro Glu Ser
    50                  55                  60

Arg Ser Ser Leu Arg Val Val Asn Thr Gly Leu Ala Asn Ser Val Thr
65                  70                  75                  80

Ala Lys Phe Tyr Trp Ser His Ser Phe Thr Ser Glu Trp Phe Glu Ala
                85                  90                  95

Gly Ser Ile Asp Val Gly Leu Gly Glu Asp Lys Val Leu Asn Val Pro
            100                 105                 110

Ser Ser Ser Phe Tyr Tyr Ser Lys Phe Val Ile Tyr Asn Asn Thr Asp
        115                 120                 125

Arg Val Ala Tyr Val Thr Ala Asn Leu Val
    130                 135
```

<210> SEQ ID NO 106
<211> LENGTH: 1260
<212> TYPE: DNA
<213> ORGANISM: Photorhabdus luminescens
<220> FEATURE:
<221> NAME/KEY: misc_feature
<222> LOCATION: (1)..(1260)
<223> OTHER INFORMATION: A nucleic acid sequence obtained from Photorhabdus luminescens strain Hm encoding a PirB_ABE68879 pesticidal PirB protein sequence.

<400> SEQUENCE: 106

```
atgcatacag aaaatgtttt agacatcaga accattgtgg ctaatgaata tgtggtaaaa     60

acgagtgcat tagagtggga tgttacggat attgtaaaaa atgcaatcat agggggtatc    120

tcttttatac cttcggttgg tcctgcgata tctttttgg tcggtttatt ctggcctcaa     180

tcgaaagaaa atatatggga aggaattgtc aaacaaattg agaggatgat agaggagtct    240

gcgttaaaga cgattaaagg tatccttgcg ggtgatattg cctatataca agagcgcatg    300

gcaaccgttg ctgatcttct tgataagcat ccaggatctg acgaagcgag gagcgccttt    360

aataacctgg cagaaaatat agatggttat cacaaaaaat ttaataattt ttcggatgat    420

gttaactatc aaatattacc catgttttct actacggtta tgatgcagat aacctattgg    480

gttgctggtt tagagagaag agctgaaatt gggcttagtg atattgatat tgaaaaagtc    540

cgaggattaa tcaaaaagac ggtagaacaa gctaatagtt atattaatag tatctatgat    600

agagagctta atgatgctct taataactcg acggcggaca ctgttgcaaa taatgttatg    660

tctgttcatg gtcactgtcg tttacatggg attgaatata tcagtatttg ggatagatta    720

agtgaatctg agtctgtaaa taatagaatc tatgttgatg ttttaagtta ttctactttc    780

tttgatcgtc aaacagcaaa agccagaatt caggcattga ctccagagca agatatggct    840

ccgcctctca aaccagctct taatggaggg aagagaagaa agatagattc tttaatggga    900

catattgtac gtattggagg agctccgaga gtaggagggc tgacagttgt atttgatgac    960

ggcagtagcc atcgattagg tacaatatct ggtgagacgg catctatttc tctgaatggt   1020

agtcgaatta ccagtttgga agtatggggc aatggtgctg ttgatagagc cgtctttact   1080

ttgagtgatg gtcggttttt gttatttggc gatcctggaa catctcgata taggaaattt   1140

tatgttggtg atagtcacta tatttcaggg atatatttgt ccagtgatta caacccatta   1200
```

gcaggtcagg cagcaaatat tgctgtatct tatcagttga taaatgatga tgaaaaatag 1260

<210> SEQ ID NO 107
<211> LENGTH: 419
<212> TYPE: PRT
<213> ORGANISM: Photorhabdus luminescens
<220> FEATURE:
<221> NAME/KEY: MISC_FEATURE
<222> LOCATION: (1)..(419)
<223> OTHER INFORMATION: The amino acid sequence of the PirB_ABE68879 PirB protein.

<400> SEQUENCE: 107

Met His Thr Glu Asn Val Leu Asp Ile Arg Thr Ile Val Ala Asn Glu
1 5 10 15

Tyr Val Val Lys Thr Ser Ala Leu Glu Trp Asp Val Thr Asp Ile Val
20 25 30

Lys Asn Ala Ile Ile Gly Gly Ile Ser Phe Ile Pro Ser Val Gly Pro
35 40 45

Ala Ile Ser Phe Leu Val Gly Leu Phe Trp Pro Gln Ser Lys Glu Asn
50 55 60

Ile Trp Glu Gly Ile Val Lys Gln Ile Glu Arg Met Ile Glu Glu Ser
65 70 75 80

Ala Leu Lys Thr Ile Lys Gly Ile Leu Ala Gly Asp Ile Ala Tyr Ile
85 90 95

Gln Glu Arg Met Ala Thr Val Ala Asp Leu Leu Asp Lys His Pro Gly
100 105 110

Ser Asp Glu Ala Arg Ser Ala Phe Asn Asn Leu Ala Glu Asn Ile Asp
115 120 125

Gly Tyr His Lys Lys Phe Asn Asn Phe Ser Asp Asp Val Asn Tyr Gln
130 135 140

Ile Leu Pro Met Phe Ser Thr Thr Val Met Met Gln Ile Thr Tyr Trp
145 150 155 160

Val Ala Gly Leu Glu Arg Arg Ala Glu Ile Gly Leu Ser Asp Ile Asp
165 170 175

Ile Glu Lys Val Arg Gly Leu Ile Lys Lys Thr Val Glu Gln Ala Asn
180 185 190

Ser Tyr Ile Asn Ser Ile Tyr Asp Arg Glu Leu Asn Asp Ala Leu Asn
195 200 205

Asn Ser Thr Ala Asp Thr Val Ala Asn Asn Val Met Ser Val His Gly
210 215 220

His Cys Arg Leu His Gly Ile Glu Tyr Ile Ser Ile Trp Asp Arg Leu
225 230 235 240

Ser Glu Ser Glu Ser Val Asn Asn Arg Ile Tyr Val Asp Val Leu Ser
245 250 255

Tyr Ser Thr Phe Phe Asp Arg Gln Thr Ala Lys Ala Arg Ile Gln Ala
260 265 270

Leu Thr Pro Glu Gln Asp Met Ala Pro Pro Leu Lys Pro Ala Leu Asn
275 280 285

Gly Gly Lys Arg Arg Lys Ile Asp Ser Leu Met Gly His Ile Val Arg
290 295 300

Ile Gly Gly Ala Pro Arg Val Gly Gly Leu Thr Val Val Phe Asp Asp
305 310 315 320

Gly Ser Ser His Arg Leu Gly Thr Ile Ser Gly Glu Thr Ala Ser Ile
325 330 335

-continued

```
Ser Leu Asn Gly Ser Arg Ile Thr Ser Leu Glu Val Trp Gly Asn Gly
            340                 345                 350

Ala Val Asp Arg Ala Val Phe Thr Leu Ser Asp Gly Arg Phe Leu Leu
        355                 360                 365

Phe Gly Asp Pro Gly Thr Ser Arg Tyr Arg Lys Phe Tyr Val Gly Asp
    370                 375                 380

Ser His Tyr Ile Ser Gly Ile Tyr Leu Ser Ser Asp Tyr Asn Pro Leu
385                 390                 395                 400

Ala Gly Gln Ala Ala Asn Ile Ala Val Ser Tyr Gln Leu Ile Asn Asp
                405                 410                 415

Asp Glu Lys
```

<210> SEQ ID NO 108
<211> LENGTH: 1674
<212> TYPE: DNA
<213> ORGANISM: Artificial
<220> FEATURE:
<223> OTHER INFORMATION: A nucleic acid sequence encoding a PirAB fusion protein, TIC10434 comprised of the PirA_ABE68878 and PirB_ABE68879 coding sequences in operable linkage and in frame.

<400> SEQUENCE: 108

```
atgaggaaaa taaatatgtc tagaataacc attgttgttg attcagatac acaaaaagca     60

gaagtttatt ctaattctcc tgtgccggta catagagatt taaatgcagt tggtcctttg    120

agtgatgtga ctatatcacc tcatgctagt gtggaagtat ttagaataga caccccaata    180

attccagaat ccagaagctc tctgagagtt gtaaatacag ggttagcaaa tagtgttacg    240

gctaaatttt actggtctca tagttttacc tctgaatggt ttgaagctgg atctatagat    300

gtaggattag gagaagataa ggtattaaac gtgcctagca gctcttttta ttatagtaaa    360

tttgttatct ataataacac ggatagagtg gcttatgtta cggcaaattt ggttatgcat    420

acagaaaatg ttttagacat cagaaccatt gtggctaatg aatatgtggt aaaaacgagt    480

gcattagagt gggatgttac ggatattgta aaaaatgcaa tcataggggg tatctctttt    540

ataccttcgg ttggtcctgc gatatctttt ttggtcggtt tattctggcc tcaatcgaaa    600

gaaaatatat gggaaggaat tgtcaaacaa attgagagga tgatagagga gtctgcgtta    660

aagacgatta aaggtatcct tgcgggtgat attgcctata tacaagagcg catggcaacc    720

gttgctgatc ttcttgataa gcatccagga tctgacgaag cgaggagcgc ctttaataac    780

ctggcagaaa atatagatgg ttatcacaaa aaatttaata atttttcgga tgatgttaac    840

tatcaaatat tacccatgtt ttctactacg gttatgatgc agataaccta ttgggttgct    900

ggtttagaga gaagagctga aattgggctt agtgatattg atattgaaaa agtccgagga    960

ttaatcaaaa agacggtaga acaagctaat agttatatta atagtatcta tgatagagag   1020

cttaatgatg ctcttaataa ctcgacggcg gacactgttg caaataatgt tatgtctgtt   1080

catggtcact gtcgtttaca tggattgaa tatatcagta tttgggatag attaagtgaa    1140

tctgagtctg taaataatag aatctatgtt gatgttttaa gttattctac tttctttgat   1200

cgtcaaacag caaaagccag aattcaggca ttgactccag agcaagatat ggctccgcct   1260

ctcaaaccag ctcttaatgg agggaagaga agaaagatag attctttaat gggacatatt   1320

gtacgtattg gaggagctcc gagagtagga gggctgacag ttgtatttga tgacggcagt   1380

agccatcgat taggtacaat atctggtgag acggcatcta tttctctgaa tggtagtcga   1440

attaccagtt tggaagtatg ggcaatggt gctgttgata gagccgtctt tactttgagt   1500
```

-continued

```
gatggtcggt ttttgttatt tggcgatcct ggaacatctc gatataggaa attttatgtt   1560

ggtgatagtc actatatttc agggatatat ttgtccagtg attacaaccc attagcaggt   1620

caggcagcaa atattgctgt atcttatcag ttgataaatg atgatgaaaa atag         1674


<210> SEQ ID NO 109
<211> LENGTH: 557
<212> TYPE: PRT
<213> ORGANISM: Artificial
<220> FEATURE:
<223> OTHER INFORMATION: The amino acid sequence of the TIC10434 PirAB
      fusion protein.

<400> SEQUENCE: 109

Met Arg Lys Ile Asn Met Ser Arg Ile Thr Ile Val Val Asp Ser Asp
1               5                   10                  15

Thr Gln Lys Ala Glu Val Tyr Ser Asn Ser Pro Val Pro Val His Arg
            20                  25                  30

Asp Leu Asn Ala Val Gly Pro Leu Ser Asp Val Thr Ile Ser Pro His
        35                  40                  45

Ala Ser Val Glu Val Phe Arg Ile Asp Thr Pro Ile Ile Pro Glu Ser
    50                  55                  60

Arg Ser Ser Leu Arg Val Val Asn Thr Gly Leu Ala Asn Ser Val Thr
65                  70                  75                  80

Ala Lys Phe Tyr Trp Ser His Ser Phe Thr Ser Glu Trp Phe Glu Ala
                85                  90                  95

Gly Ser Ile Asp Val Gly Leu Gly Glu Asp Lys Val Leu Asn Val Pro
            100                 105                 110

Ser Ser Ser Phe Tyr Tyr Ser Lys Phe Val Ile Tyr Asn Asn Thr Asp
        115                 120                 125

Arg Val Ala Tyr Val Thr Ala Asn Leu Val Met His Thr Glu Asn Val
    130                 135                 140

Leu Asp Ile Arg Thr Ile Val Ala Asn Glu Tyr Val Val Lys Thr Ser
145                 150                 155                 160

Ala Leu Glu Trp Asp Val Thr Asp Ile Val Lys Asn Ala Ile Ile Gly
                165                 170                 175

Gly Ile Ser Phe Ile Pro Ser Val Gly Pro Ala Ile Ser Phe Leu Val
            180                 185                 190

Gly Leu Phe Trp Pro Gln Ser Lys Glu Asn Ile Trp Glu Gly Ile Val
        195                 200                 205

Lys Gln Ile Glu Arg Met Ile Glu Glu Ser Ala Leu Lys Thr Ile Lys
    210                 215                 220

Gly Ile Leu Ala Gly Asp Ile Ala Tyr Ile Gln Glu Arg Met Ala Thr
225                 230                 235                 240

Val Ala Asp Leu Leu Asp Lys His Pro Gly Ser Asp Glu Ala Arg Ser
                245                 250                 255

Ala Phe Asn Asn Leu Ala Glu Asn Ile Asp Gly Tyr His Lys Lys Phe
            260                 265                 270

Asn Asn Phe Ser Asp Asp Val Asn Tyr Gln Ile Leu Pro Met Phe Ser
        275                 280                 285

Thr Thr Val Met Met Gln Ile Thr Tyr Trp Val Ala Gly Leu Glu Arg
    290                 295                 300

Arg Ala Glu Ile Gly Leu Ser Asp Ile Asp Ile Glu Lys Val Arg Gly
305                 310                 315                 320

Leu Ile Lys Lys Thr Val Glu Gln Ala Asn Ser Tyr Ile Asn Ser Ile
                325                 330                 335
```

```
Tyr Asp Arg Glu Leu Asn Asp Ala Leu Asn Asn Ser Thr Ala Asp Thr
            340                 345                 350

Val Ala Asn Asn Val Met Ser Val His Gly His Cys Arg Leu His Gly
        355                 360                 365

Ile Glu Tyr Ile Ser Ile Trp Asp Arg Leu Ser Glu Ser Glu Ser Val
    370                 375                 380

Asn Asn Arg Ile Tyr Val Asp Val Leu Ser Tyr Ser Thr Phe Phe Asp
385                 390                 395                 400

Arg Gln Thr Ala Lys Ala Arg Ile Gln Ala Leu Thr Pro Glu Gln Asp
                405                 410                 415

Met Ala Pro Pro Leu Lys Pro Ala Leu Asn Gly Gly Lys Arg Arg Lys
            420                 425                 430

Ile Asp Ser Leu Met Gly His Ile Val Arg Ile Gly Gly Ala Pro Arg
        435                 440                 445

Val Gly Gly Leu Thr Val Val Phe Asp Asp Gly Ser Ser His Arg Leu
    450                 455                 460

Gly Thr Ile Ser Gly Glu Thr Ala Ser Ile Ser Leu Asn Gly Ser Arg
465                 470                 475                 480

Ile Thr Ser Leu Glu Val Trp Gly Asn Gly Ala Val Asp Arg Ala Val
                485                 490                 495

Phe Thr Leu Ser Asp Gly Arg Phe Leu Leu Phe Gly Asp Pro Gly Thr
            500                 505                 510

Ser Arg Tyr Arg Lys Phe Tyr Val Gly Asp Ser His Tyr Ile Ser Gly
        515                 520                 525

Ile Tyr Leu Ser Ser Asp Tyr Asn Pro Leu Ala Gly Gln Ala Ala Asn
    530                 535                 540

Ile Ala Val Ser Tyr Gln Leu Ile Asn Asp Asp Glu Lys
545                 550                 555
```

<210> SEQ ID NO 110
<211> LENGTH: 1668
<212> TYPE: DNA
<213> ORGANISM: Artificial
<220> FEATURE:
<223> OTHER INFORMATION: A nucleic acid sequence encoding a PirAB fusion protein, TIC11210 comprised of the TIC7575 and TIC7665 coding sequences in operable linkage and in frame.

<400> SEQUENCE: 110

```
atgaatacaa tcaatataaa tataagtggc agtaccgtta cagtcataag caataacgat     60

tccaatccag aaccattaac ttataataca aacacaccag catcagaccc tcttacagcc    120

agtccttata gggatatgac aatagagcca cactcttcta ttgaagcaac aagaaccgat    180

acaccgatta ttcccgaaac tcgtcccaat tactatgtag ccaattctgg ccccgcatca    240

tcagttaggg ctgtttttta ttggtctcat tctttcacat cagaatggtt cgaatattcc    300

tctatcatag tgaaagccgg gaaagacgga atattacaat caccgaataa cgctttatat    360

tacagtaaag ttgtcattta taacgatacc gataaacgtg cctttgttac cggatataat    420

aagatgaata atagtccaat gaatgatcag ttatcaatag caccttattc aatttcgaca    480

cccaattatg aatgggatat gtcatcaatc ataaaagatg ccattatcgg tggcatagga    540

tttattcccg gaccaggctc tgcaatctct tttttattag ggctgttctg gcctcaacag    600

acagacaata cctgggatca aatcctccaa aaaatcgaac agatgataga agaagcgaat    660

ttaaaaacca ttaaaggtat attaaatgga gatatacaag aaattaaagg aaaaatggac    720
```

-continued catgtgcaat atatgctaga gaattctcct ggcagccagg aaagccatga tgcttatatg 780
tttttagcaa ggtttttggt cagtattgat gaaaaattca aatctttcga tgatagaaca 840
aattatcaaa ttcttcccat gtatacgaac accattatgt tacaagcgcc ttattggaaa 900
atgggcctcg aaaagaaaga ggatatcggt ttaagcgata ttgaagttag cgaattaaaa 960
gaacttatcg ataaattata tactaaatca tatgattata tccataacac gtataatcgt 1020
gaatatgata atgcaatcaa tacgtcaacc gcagagagta tcaccaataa tttattgtct 1080
gtcagaggat attgtttatt acatggttgt gaatgtcttg aagttattgc gcatatacaa 1140
aacaatagcc ttgataaagg cttctaccct aaaacgatca gctattcgag tgttttcgat 1200
cgtcctacaa acaaaatgag gattcaggcg cttacagaag atgaccaaat gcaagaaccg 1260
ttcaaacctt ctttcgtcaa tggtcaatat aataaaataa aatcattgga gggttatgtc 1320
acaaggatcg gcaatgcccc ccgagtcggt ggaattaaaa tcacatttga aaacaacgca 1380
tcttatactc ttggtactgt gacttcagaa acaaccttta ttgaactcaa tgagagtgtt 1440
ataaccagca tagaagtgtg gggaaatggg gccgttgatg aggcattctt tacattgagt 1500
gacggtcgcc aaatgcggct tggtcaacgc tatgccagtc gctacagaaa atatgctgtc 1560
gatggtcatt atatctcagg attgtactta gccagtgatg aaccatccct tgctggtcaa 1620
gccgccggta ttgccgtttc atatcatatg attgttgata aacaatag 1668

<210> SEQ ID NO 111
<211> LENGTH: 555
<212> TYPE: PRT
<213> ORGANISM: Artificial
<220> FEATURE:
<223> OTHER INFORMATION: The amino acid sequence of the TIC11210 PirAB fusion protein.

<400> SEQUENCE: 111

Met Asn Thr Ile Asn Ile Asn Ile Ser Gly Ser Thr Val Thr Val Ile
1 5 10 15

Ser Asn Asn Asp Ser Asn Pro Glu Pro Leu Thr Tyr Asn Thr Asn Thr
20 25 30

Pro Ala Ser Asp Pro Leu Thr Ala Ser Pro Tyr Arg Asp Met Thr Ile
35 40 45

Glu Pro His Ser Ser Ile Glu Ala Thr Arg Thr Asp Thr Pro Ile Ile
50 55 60

Pro Glu Thr Arg Pro Asn Tyr Tyr Val Ala Asn Ser Gly Pro Ala Ser
65 70 75 80

Ser Val Arg Ala Val Phe Tyr Trp Ser His Ser Phe Thr Ser Glu Trp
85 90 95

Phe Glu Tyr Ser Ser Ile Ile Val Lys Ala Gly Lys Asp Gly Ile Leu
100 105 110

Gln Ser Pro Asn Asn Ala Leu Tyr Tyr Ser Lys Val Val Ile Tyr Asn
115 120 125

Asp Thr Asp Lys Arg Ala Phe Val Thr Gly Tyr Asn Lys Met Asn Asn
130 135 140

Ser Pro Met Asn Asp Gln Leu Ser Ile Ala Pro Tyr Ser Ile Ser Thr
145 150 155 160

Pro Asn Tyr Glu Trp Asp Met Ser Ser Ile Ile Lys Asp Ala Ile Ile
165 170 175

Gly Gly Ile Gly Phe Ile Pro Gly Pro Gly Ser Ala Ile Ser Phe Leu
180 185 190

-continued

```
Leu Gly Leu Phe Trp Pro Gln Gln Thr Asp Asn Thr Trp Asp Gln Ile
        195                 200                 205

Leu Gln Lys Ile Glu Gln Met Ile Glu Glu Ala Asn Leu Lys Thr Ile
    210                 215                 220

Lys Gly Ile Leu Asn Gly Asp Ile Gln Glu Ile Lys Gly Lys Met Asp
225                 230                 235                 240

His Val Gln Tyr Met Leu Glu Asn Ser Pro Gly Ser Gln Glu Ser His
                245                 250                 255

Asp Ala Tyr Met Phe Leu Ala Arg Phe Leu Val Ser Ile Asp Glu Lys
            260                 265                 270

Phe Lys Ser Phe Asp Asp Arg Thr Asn Tyr Gln Ile Leu Pro Met Tyr
        275                 280                 285

Thr Asn Thr Ile Met Leu Gln Ala Pro Tyr Trp Lys Met Gly Leu Glu
    290                 295                 300

Lys Lys Glu Asp Ile Gly Leu Ser Asp Ile Glu Val Ser Glu Leu Lys
305                 310                 315                 320

Glu Leu Ile Asp Lys Leu Tyr Thr Lys Ser Tyr Asp Tyr Ile His Asn
                325                 330                 335

Thr Tyr Asn Arg Glu Tyr Asp Asn Ala Ile Asn Thr Ser Thr Ala Glu
            340                 345                 350

Ser Ile Thr Asn Asn Leu Leu Ser Val Arg Gly Tyr Cys Leu Leu His
        355                 360                 365

Gly Cys Glu Cys Leu Glu Val Ile Ala His Ile Gln Asn Asn Ser Leu
    370                 375                 380

Asp Lys Gly Phe Tyr Pro Lys Thr Ile Ser Tyr Ser Ser Val Phe Asp
385                 390                 395                 400

Arg Pro Thr Asn Lys Met Arg Ile Gln Ala Leu Thr Glu Asp Asp Gln
                405                 410                 415

Met Gln Glu Pro Phe Lys Pro Ser Phe Val Asn Gly Gln Tyr Asn Lys
            420                 425                 430

Ile Lys Ser Leu Glu Gly Tyr Val Thr Arg Ile Gly Asn Ala Pro Arg
        435                 440                 445

Val Gly Gly Ile Lys Ile Thr Phe Glu Asn Asn Ala Ser Tyr Thr Leu
    450                 455                 460

Gly Thr Val Thr Ser Glu Thr Thr Phe Ile Glu Leu Asn Glu Ser Val
465                 470                 475                 480

Ile Thr Ser Ile Glu Val Trp Gly Asn Gly Ala Val Asp Glu Ala Phe
                485                 490                 495

Phe Thr Leu Ser Asp Gly Arg Gln Met Arg Leu Gly Gln Arg Tyr Ala
            500                 505                 510

Ser Arg Tyr Arg Lys Tyr Ala Val Asp Gly His Tyr Ile Ser Gly Leu
        515                 520                 525

Tyr Leu Ala Ser Asp Glu Pro Ser Leu Ala Gly Gln Ala Ala Gly Ile
    530                 535                 540

Ala Val Ser Tyr His Met Ile Val Asp Lys Gln
545                 550                 555
```

<210> SEQ ID NO 112
<211> LENGTH: 1683
<212> TYPE: DNA
<213> ORGANISM: Artificial
<220> FEATURE:
<223> OTHER INFORMATION: A nucleic acid sequence encoding a PirAB fusion protein, TIC11211 comprised of the TIC7575 and TIC7667 coding sequences in operable linkage and in frame.

<400> SEQUENCE: 112

```
atgaatacaa tcaatataaa tataagtggc agtaccgtta cagtcataag caataacgat      60
tccaatccag aaccattaac ttataataca aacacaccag catcagaccc tcttacagcc     120
agtccttata gggatatgac aatagagcca cactcttcta ttgaagcaac aagaaccgat     180
acaccgatta ttcccgaaac tcgtcccaat tactatgtag ccaattctgg ccccgcatca     240
tcagttaggg ctgtttttta ttggtctcat tctttcacat cagaatggtt cgaatattcc     300
tctatcatag tgaaagccgg gaaagacgga atattacaat caccgaataa cgctttatat     360
tacagtaaag ttgtcattta taacgatacc gataaacgtg cctttgttac cggatataat     420
aagatgcata cagaaaatgt tttagacata agaaccattg tggctaatga atatgctgta     480
aaaacgagtg cattagagtg ggatgttact gatattgtaa aaaatgcaat catagggggga     540
atatccttta tcccttcggt tggtcccgct atatcttttt tagtcggttt attctggcct     600
caatcgaaag aaaatatatg ggaagggatt gtcaaacaaa ttgaaaggat gatagaggag     660
tctgcgttaa agacgattaa aggtatcctt gctggtgata ttgcatatat acaagaacga     720
atggcaaccg ttgctgatct tcttgataag catccaggat cagaagaagc gaggagtgct     780
tttaataacc tggcagaaaa tatagatggc tatcacaaaa agtttagtaa tttttcggat     840
gatgttaatt atcagatatt acccatgttt tctactacgg ttatgatgca gataacatat     900
tgggttgctg gtttagagag aaaagatgaa attgggctta gtaatattga tgttgaaaaa     960
gtccgaggat taattaaaaa gacggtagaa caggctaata gttatattaa caatatatat    1020
gatagagagc ttaatgatgc tcttaataac tcgacggctg acactgttgc aaataatgtt    1080
atgtctgttc atggtcactg tcgtttacat gggattgaat atatcagtat ttgggataaa    1140
ttaagtgaag ctgagtcggt aaataataaa atctatgttg atgttttaag ttattctact    1200
ttctttgacc gtcaaacagc aaaagccaga attcaggcat tgactccaga gaaagatatg    1260
actccacctc tcaaaccggc tcttaatgga ggaaaaagaa gaaagataga ttcgttaacg    1320
ggacatattg tgcgtattgg aggggctgcg agggtaggag ggctgacagt tgtatttgat    1380
gatggtaatc gccatcaatt aggtacaata tctggtgaga cgtcatctat ttctctgaat    1440
ggtagtcgaa ttaccagttt ggaagtatgg ggaaatggtg ctgttgatca agcggtcttt    1500
actttaaatg atggtcgttc attgtcattg ggctcgcctg gaacatctcg atataggaag    1560
ttttatgttg gtgaaagcca ctatattgca gggatatatt tgtccagtga ttacaaccca    1620
ttagctggtc aggcagcaaa tattgctgta tcttatcagt tgataaatga tgatgaaaaa    1680
tag                                                                  1683
```

<210> SEQ ID NO 113
<211> LENGTH: 560
<212> TYPE: PRT
<213> ORGANISM: Artificial
<220> FEATURE:
<223> OTHER INFORMATION: The amino acid sequence of the TIC11211 PirAB fusion protein.

<400> SEQUENCE: 113

```
Met Asn Thr Ile Asn Ile Asn Ile Ser Gly Ser Thr Val Thr Val Ile
1               5                   10                  15

Ser Asn Asn Asp Ser Asn Pro Glu Pro Leu Thr Tyr Asn Thr Asn Thr
            20                  25                  30

Pro Ala Ser Asp Pro Leu Thr Ala Ser Pro Tyr Arg Asp Met Thr Ile
        35                  40                  45
```

```
Glu Pro His Ser Ser Ile Glu Ala Thr Arg Thr Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Glu Trp
                85                  90                  95

Phe Glu Tyr Ser Ser Ile Ile Val Lys Ala Gly Lys Asp Gly Ile Leu
            100                 105                 110

Gln Ser Pro Asn Asn Ala Leu Tyr Tyr Ser Lys Val Val Ile Tyr Asn
        115                 120                 125

Asp Thr Asp Lys Arg Ala Phe Val Thr Gly Tyr Asn Lys Met His Thr
    130                 135                 140

Glu Asn Val Leu Asp Ile Arg Thr Ile Val Ala Asn Glu Tyr Ala Val
145                 150                 155                 160

Lys Thr Ser Ala Leu Glu Trp Asp Val Thr Asp Ile Val Lys Asn Ala
                165                 170                 175

Ile Ile Gly Gly Ile Ser Phe Ile Pro Ser Val Gly Pro Ala Ile Ser
            180                 185                 190

Phe Leu Val Gly Leu Phe Trp Pro Gln Ser Lys Glu Asn Ile Trp Glu
        195                 200                 205

Gly Ile Val Lys Gln Ile Glu Arg Met Ile Glu Glu Ser Ala Leu Lys
    210                 215                 220

Thr Ile Lys Gly Ile Leu Ala Gly Asp Ile Ala Tyr Ile Gln Glu Arg
225                 230                 235                 240

Met Ala Thr Val Ala Asp Leu Leu Asp Lys His Pro Gly Ser Glu Glu
                245                 250                 255

Ala Arg Ser Ala Phe Asn Asn Leu Ala Glu Asn Ile Asp Gly Tyr His
            260                 265                 270

Lys Lys Phe Ser Asn Phe Ser Asp Asp Val Asn Tyr Gln Ile Leu Pro
        275                 280                 285

Met Phe Ser Thr Thr Val Met Met Gln Ile Thr Tyr Trp Val Ala Gly
    290                 295                 300

Leu Glu Arg Lys Asp Glu Ile Gly Leu Ser Asn Ile Asp Val Glu Lys
305                 310                 315                 320

Val Arg Gly Leu Ile Lys Lys Thr Val Glu Gln Ala Asn Ser Tyr Ile
                325                 330                 335

Asn Asn Ile Tyr Asp Arg Glu Leu Asn Asp Ala Leu Asn Asn Ser Thr
            340                 345                 350

Ala Asp Thr Val Ala Asn Asn Val Met Ser Val His Gly His Cys Arg
        355                 360                 365

Leu His Gly Ile Glu Tyr Ile Ser Ile Trp Asp Lys Leu Ser Glu Ala
    370                 375                 380

Glu Ser Val Asn Asn Lys Ile Tyr Val Asp Val Leu Ser Tyr Ser Thr
385                 390                 395                 400

Phe Phe Asp Arg Gln Thr Ala Lys Ala Arg Ile Gln Ala Leu Thr Pro
                405                 410                 415

Glu Lys Asp Met Thr Pro Pro Leu Lys Pro Ala Leu Asn Gly Gly Lys
            420                 425                 430

Arg Arg Lys Ile Asp Ser Leu Thr Gly His Ile Val Arg Ile Gly Gly
        435                 440                 445

Ala Ala Arg Val Gly Gly Leu Thr Val Val Phe Asp Asp Gly Asn Arg
    450                 455                 460
```

```
His Gln Leu Gly Thr Ile Ser Gly Glu Thr Ser Ser Ile Ser Leu Asn
465                 470                 475                 480

Gly Ser Arg Ile Thr Ser Leu Glu Val Trp Gly Asn Gly Ala Val Asp
                485                 490                 495

Gln Ala Val Phe Thr Leu Asn Asp Gly Arg Ser Leu Ser Leu Gly Ser
            500                 505                 510

Pro Gly Thr Ser Arg Tyr Arg Lys Phe Tyr Val Gly Glu Ser His Tyr
        515                 520                 525

Ile Ala Gly Ile Tyr Leu Ser Ser Asp Tyr Asn Pro Leu Ala Gly Gln
    530                 535                 540

Ala Ala Asn Ile Ala Val Ser Tyr Gln Leu Ile Asn Asp Asp Glu Lys
545                 550                 555                 560


<210> SEQ ID NO 114
<211> LENGTH: 1668
<212> TYPE: DNA
<213> ORGANISM: Artificial
<220> FEATURE:
<223> OTHER INFORMATION: A nucleic acid sequence encoding a PirAB fusion
      protein, TIC11212 comprised of the TIC7662 and TIC7665 coding
      sequences in operable linkage and in frame.

<400> SEQUENCE: 114

atgagtacaa tcaatatcaa tataagtagc agtaccgtta ccgtcatcac gaataacgga     60

gaaacgccag tcccactcac ttacaataca aatacacctg aatcagaacc tcttaccgtc    120

aatccttata gggatatgac aatagagcca cgctcttcta ttgaagcaac aaggattgat    180

acaccgatta ttcccgaaac acgccctaat tattatgtag ccaattcagg cccggcttca    240

tcagttaggg ccgtttttta ttggtcccat tctttcacat cacaatggtt cgaatattcc    300

tctatcatcg tcaaagccgg ggaagatggc atattagaat caccaagcaa ttctttatat    360

tacagcaaag tcgtcattta taatgatacc gataaacgcg cctttgtgac gggatataat    420

aagatgaata atagtccaat gaatgatcag ttatcaatag caccttattc aatttcgaca    480

cccaattatg aatgggatat gtcatcaatc ataaaagatg ccattatcgg tggcatagga    540

tttattcccg gaccaggctc tgcaatctct tttttattag ggctgttctg gcctcaacag    600

acagacaata cctgggatca aatcctccaa aaaatcgaac agatgataga agaagcgaat    660

ttaaaaacca ttaaaggtat attaaatgga gatatacaag aaattaaagg aaaaatggac    720

catgtgcaat atatgctaga gaattctcct ggcagccagg aaagccatga tgcttatatg    780

tttttagcaa ggtttttggt cagtattgat gaaaaattca aatctttcga tgatagaaca    840

aattatcaaa ttcttcccat gtatacgaac accattatgt tacaagcgcc ttattggaaa    900

atgggcctcg aaaagaaaga ggatatcggt ttaagcgata ttgaagttag cgaattaaaa    960

gaacttatcg ataaattata tactaaatca tatgattata tccataacac gtataatcgt   1020

gaatatgata atgcaatcaa tacgtcaacc gcagagagta tcaccaataa tttattgtct   1080

gtcagaggat attgtttatt acatggttgt gaatgtcttg aagttattgc gcatatacaa   1140

aacaatagcc ttgataaagg cttctaccct aaaacgatca gctattcgag tgttttcgat   1200

cgtcctacaa acaaaatgag gattcaggcg cttacagaag atgaccaaat gcaagaaccg   1260

ttcaaacctt ctttcgtcaa tggtcaatat aataaaaataa aatcattgga gggttatgtc   1320

acaaggatcg gcaatgcccc ccgagtcggt ggaattaaaa tcacatttga aaacaacgca   1380

tcttatactc ttggtactgt gacttcagaa acaaccttta ttgaactcaa tgagagtgtt   1440

ataaccagca tagaagtgtg gggaaatggg gccgttgatg aggcattctt tacattgagt   1500
```

```
gacggtcgcc aaatgcggct tggtcaacgc tatgccagtc gctacagaaa atatgctgtc   1560

gatggtcatt atatctcagg attgtactta gccagtgatg aaccatccct tgctggtcaa   1620

gccgccggta ttgccgtttc atatcatatg attgttgata aacaatag                1668


<210> SEQ ID NO 115
<211> LENGTH: 555
<212> TYPE: PRT
<213> ORGANISM: Artificial
<220> FEATURE:
<223> OTHER INFORMATION: The amino acid sequence of the TIC11212 PirAB
      fusion protein.

<400> SEQUENCE: 115

Met Ser Thr Ile Asn Ile Asn Ile Ser Ser Ser Thr Val Thr Val Ile
1               5                   10                  15

Thr Asn Asn Gly Glu Thr Pro Val Pro Leu Thr Tyr Asn Thr Asn Thr
            20                  25                  30

Pro Glu Ser Glu Pro Leu Thr Val Asn Pro Tyr Arg Asp Met Thr Ile
        35                  40                  45

Glu Pro Arg Ser Ser Ile Glu Ala Thr Arg Ile Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Gln Trp
                85                  90                  95

Phe Glu Tyr Ser Ser Ile Ile Val Lys Ala Gly Glu Asp Gly Ile Leu
            100                 105                 110

Glu Ser Pro Ser Asn Ser Leu Tyr Tyr Ser Lys Val Val Ile Tyr Asn
        115                 120                 125

Asp Thr Asp Lys Arg Ala Phe Val Thr Gly Tyr Asn Lys Met Asn Asn
    130                 135                 140

Ser Pro Met Asn Asp Gln Leu Ser Ile Ala Pro Tyr Ser Ile Ser Thr
145                 150                 155                 160

Pro Asn Tyr Glu Trp Asp Met Ser Ser Ile Ile Lys Asp Ala Ile Ile
                165                 170                 175

Gly Gly Ile Gly Phe Ile Pro Gly Pro Gly Ser Ala Ile Ser Phe Leu
            180                 185                 190

Leu Gly Leu Phe Trp Pro Gln Gln Thr Asp Asn Thr Trp Asp Gln Ile
        195                 200                 205

Leu Gln Lys Ile Glu Gln Met Ile Glu Glu Ala Asn Leu Lys Thr Ile
    210                 215                 220

Lys Gly Ile Leu Asn Gly Asp Ile Gln Glu Ile Lys Gly Lys Met Asp
225                 230                 235                 240

His Val Gln Tyr Met Leu Glu Asn Ser Pro Gly Ser Gln Glu Ser His
                245                 250                 255

Asp Ala Tyr Met Phe Leu Ala Arg Phe Leu Val Ser Ile Asp Glu Lys
            260                 265                 270

Phe Lys Ser Phe Asp Asp Arg Thr Asn Tyr Gln Ile Leu Pro Met Tyr
        275                 280                 285

Thr Asn Thr Ile Met Leu Gln Ala Pro Tyr Trp Lys Met Gly Leu Glu
    290                 295                 300

Lys Lys Glu Asp Ile Gly Leu Ser Asp Ile Glu Val Ser Glu Leu Lys
305                 310                 315                 320

Glu Leu Ile Asp Lys Leu Tyr Thr Lys Ser Tyr Asp Tyr Ile His Asn
```

-continued

```
                325                 330                 335

Thr Tyr Asn Arg Glu Tyr Asp Asn Ala Ile Asn Thr Ser Thr Ala Glu
            340                 345                 350

Ser Ile Thr Asn Asn Leu Leu Ser Val Arg Gly Tyr Cys Leu Leu His
        355                 360                 365

Gly Cys Glu Cys Leu Glu Val Ile Ala His Ile Gln Asn Asn Ser Leu
    370                 375                 380

Asp Lys Gly Phe Tyr Pro Lys Thr Ile Ser Tyr Ser Ser Val Phe Asp
385                 390                 395                 400

Arg Pro Thr Asn Lys Met Arg Ile Gln Ala Leu Thr Glu Asp Asp Gln
                405                 410                 415

Met Gln Glu Pro Phe Lys Pro Ser Phe Val Asn Gly Gln Tyr Asn Lys
            420                 425                 430

Ile Lys Ser Leu Glu Gly Tyr Val Thr Arg Ile Gly Asn Ala Pro Arg
        435                 440                 445

Val Gly Gly Ile Lys Ile Thr Phe Glu Asn Asn Ala Ser Tyr Thr Leu
    450                 455                 460

Gly Thr Val Thr Ser Glu Thr Thr Phe Ile Glu Leu Asn Glu Ser Val
465                 470                 475                 480

Ile Thr Ser Ile Glu Val Trp Gly Asn Gly Ala Val Asp Glu Ala Phe
                485                 490                 495

Phe Thr Leu Ser Asp Gly Arg Gln Met Arg Leu Gly Gln Arg Tyr Ala
            500                 505                 510

Ser Arg Tyr Arg Lys Tyr Ala Val Asp Gly His Tyr Ile Ser Gly Leu
        515                 520                 525

Tyr Leu Ala Ser Asp Glu Pro Ser Leu Ala Gly Gln Ala Ala Gly Ile
    530                 535                 540

Ala Val Ser Tyr His Met Ile Val Asp Lys Gln
545                 550                 555
```

<210> SEQ ID NO 116
<211> LENGTH: 1701
<212> TYPE: DNA
<213> ORGANISM: Artificial
<220> FEATURE:
<223> OTHER INFORMATION: A nucleic acid sequence encoding a PirAB fusion protein, TIC11301 comprised of the TIC7575 and TIC7661 coding sequences in operable linkage and in frame.

<400> SEQUENCE: 116

```
atgaatacaa tcaatataaa tataagtggc agtaccgtta cagtcataag caataacgat     60

tccaatccag aaccattaac ttataataca aacacaccag catcagaccc tcttacagcc    120

agtccttata gggatatgac aatagagcca cactcttcta ttgaagcaac aagaaccgat    180

acaccgatta ttcccgaaac tcgtcccaat tactatgtag ccaattctgg ccccgcatca    240

tcagttaggg ctgtttttta ttggtctcat tctttcacat cagaatggtt cgaatattcc    300

tctatcatag tgaaagccgg gaaagacgga atattacaat caccgaataa cgctttatat    360

tacagtaaag ttgtcattta taacgatacc gataaacgtg cctttgttac cggatataat    420

aagatgaata ctacacctat tactgtatct acaaatgaaa catcgccttt aatgactgac    480

gtaatgccca tggatcttta tgcaatatcc acacctgatt atgaatggga catgtcgtca    540

atcataaagg atgctgttat tggtggcata ggatttattc caggtccggg cccggcaata    600

tccttcctgt tagggctatt ttggcctcag cagaaagaca atacttggga gcaaattctc    660

cagaaagtag agcagatgat agagaatgct gttctacaaa ctattaaagg aatacttaat    720
```

```
ggagaagttc aagagatcaa agggaaaatg gaacatgtag aatccatgct gaaaaactcg    780

cctggcagtc aggaaagtca tgatgcatat atgttcctgg cgagatatct ggttagtata    840

gatgaaaaat tcaaatcttt tgacaataga acaaattacc agcttctccc aatgtatact    900

aacactatta tgttacagat cccttattgg aaaatgggaa tagagaagaa aaaagatatt    960

gggctgacag atattgaagt taatgaatta aaagaactta tcgataaatt ggttgataag   1020

gccaaaaact atattcatac gatgtatact aatgaacata ataatgctgt aaacacatca   1080

acagcagaga gtgtcactaa taatttatta tctgtaagag gatattgttt attacacggt   1140

ttagaatgta ttgagttaat cgagcatata cagaataata gccttgagag tggtttctat   1200

cctaaaatta tcagttattc gactgcgttt gatcgtccta ctaacaaaat gagaattcag   1260

gctcttacag aagatgatgc aatgcaggag cctttcaaac catctttaat caatgggaaa   1320

tataataaaa tccaatcctt gactggatat gtacaaagaa ttgggaatgc acctagagtt   1380

ggtggtatca gaatcacatt taccaacggc tcatcttata cacttggtac agtgacctca   1440

gaaacgcatt caattaagct aaacgatagt gttatcgaaa gcttggaagt atgggggaat   1500

ggtgctgttg atgaggcgtt atttaagtta agtgatgggc gtttattgcg tattggtgag   1560

cgctacgcga aaaaatacag aaaatatgct gttgataatc actatattgc ggggatttac   1620

ttagccagcg atgagccttc acttgctggt caagccgcag gtattgccgt ttcatatcat   1680

atgatggctg acaaaaaata a                                              1701
```

```
<210> SEQ ID NO 117
<211> LENGTH: 566
<212> TYPE: PRT
<213> ORGANISM: Artificial
<220> FEATURE:
<223> OTHER INFORMATION: The amino acid sequence of the TIC11301 PirAB
      fusion protein.

<400> SEQUENCE: 117

Met Asn Thr Ile Asn Ile Asn Ile Ser Gly Ser Thr Val Thr Val Ile
1               5                   10                  15

Ser Asn Asn Asp Ser Asn Pro Glu Pro Leu Thr Tyr Asn Thr Asn Thr
            20                  25                  30

Pro Ala Ser Asp Pro Leu Thr Ala Ser Pro Tyr Arg Asp Met Thr Ile
        35                  40                  45

Glu Pro His Ser Ser Ile Glu Ala Thr Arg Thr Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Glu Trp
                85                  90                  95

Phe Glu Tyr Ser Ser Ile Ile Val Lys Ala Gly Lys Asp Gly Ile Leu
            100                 105                 110

Gln Ser Pro Asn Asn Ala Leu Tyr Tyr Ser Lys Val Val Ile Tyr Asn
        115                 120                 125

Asp Thr Asp Lys Arg Ala Phe Val Thr Gly Tyr Asn Lys Met Asn Thr
    130                 135                 140

Thr Pro Ile Thr Val Ser Thr Asn Glu Thr Ser Pro Leu Met Thr Asp
145                 150                 155                 160

Val Met Pro Met Asp Leu Tyr Ala Ile Ser Thr Pro Asp Tyr Glu Trp
                165                 170                 175
```

-continued

```
Asp Met Ser Ser Ile Ile Lys Asp Ala Val Ile Gly Gly Ile Gly Phe
            180                 185                 190

Ile Pro Gly Pro Gly Pro Ala Ile Ser Phe Leu Leu Gly Leu Phe Trp
        195                 200                 205

Pro Gln Gln Lys Asp Asn Thr Trp Glu Gln Ile Leu Gln Lys Val Glu
    210                 215                 220

Gln Met Ile Glu Asn Ala Val Leu Gln Thr Ile Lys Gly Ile Leu Asn
225                 230                 235                 240

Gly Glu Val Gln Glu Ile Lys Gly Lys Met Glu His Val Glu Ser Met
                245                 250                 255

Leu Lys Asn Ser Pro Gly Ser Gln Glu Ser His Asp Ala Tyr Met Phe
            260                 265                 270

Leu Ala Arg Tyr Leu Val Ser Ile Asp Glu Lys Phe Lys Ser Phe Asp
        275                 280                 285

Asn Arg Thr Asn Tyr Gln Leu Leu Pro Met Tyr Thr Asn Thr Ile Met
    290                 295                 300

Leu Gln Ile Pro Tyr Trp Lys Met Gly Ile Glu Lys Lys Lys Asp Ile
305                 310                 315                 320

Gly Leu Thr Asp Ile Glu Val Asn Glu Leu Lys Glu Leu Ile Asp Lys
                325                 330                 335

Leu Val Asp Lys Ala Lys Asn Tyr Ile His Thr Met Tyr Thr Asn Glu
            340                 345                 350

His Asn Asn Ala Val Asn Thr Ser Thr Ala Glu Ser Val Thr Asn Asn
        355                 360                 365

Leu Leu Ser Val Arg Gly Tyr Cys Leu Leu His Gly Leu Glu Cys Ile
    370                 375                 380

Glu Leu Ile Glu His Ile Gln Asn Asn Ser Leu Glu Ser Gly Phe Tyr
385                 390                 395                 400

Pro Lys Ile Ile Ser Tyr Ser Thr Ala Phe Asp Arg Pro Thr Asn Lys
                405                 410                 415

Met Arg Ile Gln Ala Leu Thr Glu Asp Asp Ala Met Gln Glu Pro Phe
            420                 425                 430

Lys Pro Ser Leu Ile Asn Gly Lys Tyr Asn Lys Ile Gln Ser Leu Thr
        435                 440                 445

Gly Tyr Val Gln Arg Ile Gly Asn Ala Pro Arg Val Gly Gly Ile Arg
    450                 455                 460

Ile Thr Phe Thr Asn Gly Ser Ser Tyr Thr Leu Gly Thr Val Thr Ser
465                 470                 475                 480

Glu Thr His Ser Ile Lys Leu Asn Asp Ser Val Ile Glu Ser Leu Glu
                485                 490                 495

Val Trp Gly Asn Gly Ala Val Asp Glu Ala Leu Phe Lys Leu Ser Asp
            500                 505                 510

Gly Arg Leu Leu Arg Ile Gly Glu Arg Tyr Ala Lys Lys Tyr Arg Lys
        515                 520                 525

Tyr Ala Val Asp Asn His Tyr Ile Ala Gly Ile Tyr Leu Ala Ser Asp
    530                 535                 540

Glu Pro Ser Leu Ala Gly Gln Ala Ala Gly Ile Ala Val Ser Tyr His
545                 550                 555                 560

Met Met Ala Asp Lys Lys
                565
```

<210> SEQ ID NO 118
<211> LENGTH: 1701
<212> TYPE: DNA

<213> ORGANISM: Artificial
<220> FEATURE:
<223> OTHER INFORMATION: A nucleic acid sequence encoding a f PirAB usion protein, TIC11302 comprised of the TIC7660 and TIC7576 coding sequences in operable linkage and in frame.

<400> SEQUENCE: 118

```
atgatcacaa taaatataaa tgtaaacggc aatgatgtta caggtacaaa taataatgaa     60
cctactccag tatcgacaac ttacggtcca aatacaccag catcagaacc ccctgtagtc    120
agtaattata gtgatataac aatagaaccg cattcttctg tgcaggcaac aagaattgat    180
acgcctgtta ttcctgaagc acgccccgat tactatgtag ccaactccgg ccctgcacca    240
tcagttaggg ctgtttttta ttggtctcat tctttcacat cagaatggtt cgaatcttcc    300
tctatcacag tgaaagcagg agaggacgga atattaaaag cacctggtaa ctctttatat    360
tacagcaaag tcgtcattta taatgatacg gataaacgag cctttgttac tggatataat    420
aaaatgaata tctcaccgat taatgtatct gaaaatgaaa cattacctga actcactgat    480
gttatgctta ttgtgcctta tacaacatct accccctgatt atgaatggga tatgtcatca    540
attataaagg atgcgattat tggcggcgta gggtttattc caggagcagg ctctgcaatg    600
tccttcctat tgggactatt ttggcctcaa cagaaagata atacatggga acagatcctc    660
caaaaagtag aacagatgat agagaatgcc gttctgcaaa ctattaaagg aatacttaat    720
ggagatatac aagaaatcaa ggggaaaatg gaacatgtgc aatacatgct ggaaacctcg    780
cctggcagtc aggaaagtca tgacgcatat atgttcctgg ctagatacct ggtgagtata    840
gatgaaaaat tcaagtcttt tgataataaa acaaactacc agatcctgcc gatgtacact    900
aacacggtta tgttacaaat cccttattgg aaaatgggaa tagagaagaa aaatgatatt    960
gggctgacag atattgaagt caatgagtta aaacagctta tcgataaatt ggtcgacaag   1020
gccaagagtt acatccatac gatgtatacg aatgaatata atgatgccat aaatacatca   1080
acagcatcga gtgtcactaa taatttactc tctgtaagag gatattgttt attacacggt   1140
ttagagtgta ttgagttaat tgaacatcta caaaacaata gcctcgaaag tggtttttat   1200
cctaaaacta tcagttattc aactgtattt gatcgtcaga ctaacaaaat gagaattcag   1260
gctcttacag aagacgatca aatgcaggaa ccctttaagc catctttaat caacggcaaa   1320
tacaataaaa tacaatcctt gcttggatat gtacaaagaa ttggaaatgc acctagagtg   1380
gggggtatta aaatcacctt tgccaacggt tcatcctata cacttggcac agtaacatca   1440
gaaacgagtt caattgaact caatgatagt gttatcgaaa gattggaagt atggggcaat   1500
ggcgctgttg atgaggcatt atttacgtta agtgatgggc gtcaactcag agtcggtgag   1560
cgctacgcga caaaatatag aaaatatgct gttgatggac actatattgc aggactgtac   1620
ttagctagcg atgaaccttc acttgctggt caagccgcag gtattgccgt ttcataccat   1680
atgttggatg ataaaaaata a                                             1701
```

<210> SEQ ID NO 119
<211> LENGTH: 566
<212> TYPE: PRT
<213> ORGANISM: Artificial
<220> FEATURE:
<223> OTHER INFORMATION: The amino acid sequence of the TIC11302 f PirAB fusion protein.

<400> SEQUENCE: 119

```
Met Ile Thr Ile Asn Ile Asn Val Asn Gly Asn Asp Val Thr Gly Thr
1               5                   10                  15
```

-continued

```
Asn Asn Asn Glu Pro Thr Pro Val Ser Thr Thr Tyr Gly Pro Asn Thr
            20                  25                  30

Pro Ala Ser Glu Pro Pro Val Val Ser Asn Tyr Ser Asp Ile Thr Ile
        35                  40                  45

Glu Pro His Ser Ser Val Gln Ala Thr Arg Ile Asp Thr Pro Val Ile
    50                  55                  60

Pro Glu Ala Arg Pro Asp Tyr Tyr Val Ala Asn Ser Gly Pro Ala Pro
65                  70                  75                  80

Ser Val Arg Ala Val Phe Tyr Trp Ser His Ser Phe Thr Ser Glu Trp
                85                  90                  95

Phe Glu Ser Ser Ser Ile Thr Val Lys Ala Gly Glu Asp Gly Ile Leu
            100                 105                 110

Lys Ala Pro Gly Asn Ser Leu Tyr Tyr Ser Lys Val Val Ile Tyr Asn
        115                 120                 125

Asp Thr Asp Lys Arg Ala Phe Val Thr Gly Tyr Asn Lys Met Asn Ile
    130                 135                 140

Ser Pro Ile Asn Val Ser Glu Asn Glu Thr Leu Pro Glu Leu Thr Asp
145                 150                 155                 160

Val Met Leu Ile Val Pro Tyr Thr Thr Ser Thr Pro Asp Tyr Glu Trp
                165                 170                 175

Asp Met Ser Ser Ile Ile Lys Asp Ala Ile Ile Gly Gly Val Gly Phe
            180                 185                 190

Ile Pro Gly Ala Gly Ser Ala Met Ser Phe Leu Leu Gly Leu Phe Trp
        195                 200                 205

Pro Gln Gln Lys Asp Asn Thr Trp Glu Gln Ile Leu Gln Lys Val Glu
    210                 215                 220

Gln Met Ile Glu Asn Ala Val Leu Gln Thr Ile Lys Gly Ile Leu Asn
225                 230                 235                 240

Gly Asp Ile Gln Glu Ile Lys Gly Lys Met Glu His Val Gln Tyr Met
                245                 250                 255

Leu Glu Thr Ser Pro Gly Ser Gln Glu Ser His Asp Ala Tyr Met Phe
            260                 265                 270

Leu Ala Arg Tyr Leu Val Ser Ile Asp Glu Lys Phe Lys Ser Phe Asp
        275                 280                 285

Asn Lys Thr Asn Tyr Gln Ile Leu Pro Met Tyr Thr Asn Thr Val Met
    290                 295                 300

Leu Gln Ile Pro Tyr Trp Lys Met Gly Ile Glu Lys Lys Asn Asp Ile
305                 310                 315                 320

Gly Leu Thr Asp Ile Glu Val Asn Glu Leu Lys Gln Leu Ile Asp Lys
                325                 330                 335

Leu Val Asp Lys Ala Lys Ser Tyr Ile His Thr Met Tyr Thr Asn Glu
            340                 345                 350

Tyr Asn Asp Ala Ile Asn Thr Ser Thr Ala Ser Ser Val Thr Asn Asn
        355                 360                 365

Leu Leu Ser Val Arg Gly Tyr Cys Leu Leu His Gly Leu Glu Cys Ile
    370                 375                 380

Glu Leu Ile Glu His Leu Gln Asn Asn Ser Leu Glu Ser Gly Phe Tyr
385                 390                 395                 400

Pro Lys Thr Ile Ser Tyr Ser Thr Val Phe Asp Arg Gln Thr Asn Lys
                405                 410                 415

Met Arg Ile Gln Ala Leu Thr Glu Asp Asp Gln Met Gln Glu Pro Phe
            420                 425                 430
```

```
Lys Pro Ser Leu Ile Asn Gly Lys Tyr Asn Lys Ile Gln Ser Leu Leu
        435                 440                 445

Gly Tyr Val Gln Arg Ile Gly Asn Ala Pro Arg Val Gly Gly Ile Lys
    450                 455                 460

Ile Thr Phe Ala Asn Gly Ser Ser Tyr Thr Leu Gly Thr Val Thr Ser
465                 470                 475                 480

Glu Thr Ser Ser Ile Glu Leu Asn Asp Ser Val Ile Glu Arg Leu Glu
                485                 490                 495

Val Trp Gly Asn Gly Ala Val Asp Glu Ala Leu Phe Thr Leu Ser Asp
            500                 505                 510

Gly Arg Gln Leu Arg Val Gly Glu Arg Tyr Ala Thr Lys Tyr Arg Lys
        515                 520                 525

Tyr Ala Val Asp Gly His Tyr Ile Ala Gly Leu Tyr Leu Ala Ser Asp
    530                 535                 540

Glu Pro Ser Leu Ala Gly Gln Ala Ala Gly Ile Ala Val Ser Tyr His
545                 550                 555                 560

Met Leu Asp Asp Lys Lys
                565
```

<210> SEQ ID NO 120
<211> LENGTH: 2097
<212> TYPE: DNA
<213> ORGANISM: Artificial
<220> FEATURE:
<223> OTHER INFORMATION: A nucleic acid sequence encoding a PirAB fusion protein, TIC11440 comprised of the TIC4771, TIC4771, and TIC4772 coding sequences in operable linkage and in frame.

<400> SEQUENCE: 120

```
atgattacaa taaatataag tggtggtagt ataaaaatta gtaacaacat aggatcagaa      60

actgatatca aaaatacacc tttttcagaa cctctttcaa ttagtaatta taaggatatg     120

acaatagagc cacattcgtc tatccaagca acaagaactg atacaccaat tattcctgaa     180

acacgaccaa attattatgt agctaattcc ggccctgccg catcagtgag agctgttttt     240

tattggtctc attcttttac atcagaatgg ttcgaacatt catctatcat tgtaaaagca     300

ggagaagatg gaatattgaa ctcacctagc aattctgtat attacagtaa ggttgtcatt     360

tacaacgata cggataaacg ggcctttgtc acaggttatg acaaaatgat aaccattaac     420

atctcaggag gtagcataaa gattagtaat aacattggct cggaaactga tatcaagaac     480

acgccgtttt ctgaaccact ttcaattagt aattataaag atatgactat agaaccacac     540

tcgtctattc aggctacaag aacagataca ccaattatac ctgaaacacg acctaattac     600

tatgtagcca attccggacc tgcggcatca gtaagagctg tcttttactg gtcacattct     660

tttacgtcag agtggtttga acattcttca atcatagtaa aagcaggaga ggatggaatt     720

cttaactctc ctagcaactc tgtttattac agtaaagttg tgatatataa tgataccgat     780

aagagagctt tcgtgactgg atacgataag atgaataacg aacttatgaa cacaaatgaa     840

tcacaacctt cagagacatt atctttaatt aatgaatcta tattaacagc accttatgcc     900

gtttctaccc ctaattatga atgggatatg tcatcaataa taaaagatgc cattattgga     960

ggtataggat ttattcccgg gccgggttca gcaatatcgt tttgctaggg gctattttgg    1020

ccgcaacaaa cagacaatac ctgggagcaa attctccaaa aagtagaaca gatgatagag    1080

gaagcgaatt taaaaactat tcaaggaata ctgaacggag atatacaaga aataaaagga    1140

aagatggaac atgtggaata tatgctagaa acctcaccag gcactcaaga aagccatgac    1200
```

-continued

```
gcatatatgt tcttagcgag atatctggta agtatagatg aaaaattcaa atcttttgat   1260

aataaaacaa attatcaaat tcttccaatg tacaccaata cgcttatgtt acaggcacct   1320

tactggaaaa tgggtataga gaagaaaaat gatattttgc taacagatat agaagttaat   1380

gaattaaaac agcttatcga aaatctatat gccaaggcca atagctatat tcatgaagtg   1440

tatacccgtg aatacgataa tgcggtaaat acctcaacag caacaacgat taccaataat   1500

ttattgtctg taagagggta ttgtttatta catggattag agtgccttga agtccttgat   1560

catatacaaa ataataatct tgatcagagc ttctatccga aaactatcag ttattctact   1620

gtatttgatc gctcaacaaa caaaacaaga ctccaggctc ttaccgaaga cgagcaaatg   1680

gaagaaccac tcaaaccctc ttttattaat ggggaatata ataaaataaa atcactgatt   1740

ggatatgtac agagaattgg aaacgcccct agagttggag gtataaaaat tacatttact   1800

aatggatcat ctcatactct gggtacagtg acctcagaat caaactcaat tgaactaaat   1860

gatagtgtta taaccagtgt ggaagtatgg ggaaatggtg ctgttgatga ggcattcttt   1920

acattaagtg acggtcgtca atttaggctt ggtcaacgct atgccagtaa ctacagaaaa   1980

tatgctgttg atggccacta tatttcagga ttgtacttag ccagtgatga gccttcactt   2040

gctggtcaag ccgcaggtat tgcagtttca tatcatatat tggttgataa gaaataa      2097
```

<210> SEQ ID NO 121
<211> LENGTH: 698
<212> TYPE: PRT
<213> ORGANISM: Artificial
<220> FEATURE:
<223> OTHER INFORMATION: The amino acid sequence of the TIC11440 PirAB fusion protein.

<400> SEQUENCE: 121

```
Met Ile Thr Ile Asn Ile Ser Gly Gly Ser Ile Lys Ile Ser Asn Asn
1               5                   10                  15

Ile Gly Ser Glu Thr Asp Ile Lys Asn Thr Pro Phe Ser Glu Pro Leu
            20                  25                  30

Ser Ile Ser Asn Tyr Lys Asp Met Thr Ile Glu Pro His Ser Ser Ile
        35                  40                  45

Gln Ala Thr Arg Thr Asp Thr Pro Ile Ile Pro Glu Thr Arg Pro Asn
    50                  55                  60

Tyr Tyr Val Ala Asn Ser Gly Pro Ala Ala Ser Val Arg Ala Val Phe
65                  70                  75                  80

Tyr Trp Ser His Ser Phe Thr Ser Glu Trp Phe Glu His Ser Ser Ile
                85                  90                  95

Ile Val Lys Ala Gly Glu Asp Gly Ile Leu Asn Ser Pro Ser Asn Ser
            100                 105                 110

Val Tyr Tyr Ser Lys Val Val Ile Tyr Asn Asp Thr Asp Lys Arg Ala
        115                 120                 125

Phe Val Thr Gly Tyr Asp Lys Met Ile Thr Ile Asn Ile Ser Gly Gly
    130                 135                 140

Ser Ile Lys Ile Ser Asn Asn Ile Gly Ser Glu Thr Asp Ile Lys Asn
145                 150                 155                 160

Thr Pro Phe Ser Glu Pro Leu Ser Ile Ser Asn Tyr Lys Asp Met Thr
                165                 170                 175

Ile Glu Pro His Ser Ser Ile Gln Ala Thr Arg Thr Asp Thr Pro Ile
            180                 185                 190

Ile Pro Glu Thr Arg Pro Asn Tyr Tyr Val Ala Asn Ser Gly Pro Ala
        195                 200                 205
```

```
Ala Ser Val Arg Ala Val Phe Tyr Trp Ser His Ser Phe Thr Ser Glu
    210                 215                 220

Trp Phe Glu His Ser Ser Ile Ile Val Lys Ala Gly Glu Asp Gly Ile
225                 230                 235                 240

Leu Asn Ser Pro Ser Asn Ser Val Tyr Tyr Ser Lys Val Val Ile Tyr
                245                 250                 255

Asn Asp Thr Asp Lys Arg Ala Phe Val Thr Gly Tyr Asp Lys Met Asn
            260                 265                 270

Asn Glu Leu Met Asn Thr Asn Glu Ser Gln Pro Ser Glu Thr Leu Ser
        275                 280                 285

Leu Ile Asn Glu Ser Ile Leu Thr Ala Pro Tyr Ala Val Ser Thr Pro
    290                 295                 300

Asn Tyr Glu Trp Asp Met Ser Ser Ile Ile Lys Asp Ala Ile Ile Gly
305                 310                 315                 320

Gly Ile Gly Phe Ile Pro Gly Pro Gly Ser Ala Ile Ser Phe Leu Leu
                325                 330                 335

Gly Leu Phe Trp Pro Gln Gln Thr Asp Asn Thr Trp Glu Gln Ile Leu
            340                 345                 350

Gln Lys Val Glu Gln Met Ile Glu Glu Ala Asn Leu Lys Thr Ile Gln
        355                 360                 365

Gly Ile Leu Asn Gly Asp Ile Gln Glu Ile Lys Gly Lys Met Glu His
    370                 375                 380

Val Glu Tyr Met Leu Glu Thr Ser Pro Gly Thr Gln Glu Ser His Asp
385                 390                 395                 400

Ala Tyr Met Phe Leu Ala Arg Tyr Leu Val Ser Ile Asp Glu Lys Phe
                405                 410                 415

Lys Ser Phe Asp Asn Lys Thr Asn Tyr Gln Ile Leu Pro Met Tyr Thr
            420                 425                 430

Asn Thr Leu Met Leu Gln Ala Pro Tyr Trp Lys Met Gly Ile Glu Lys
        435                 440                 445

Lys Asn Asp Ile Leu Leu Thr Asp Ile Glu Val Asn Glu Leu Lys Gln
    450                 455                 460

Leu Ile Glu Asn Leu Tyr Ala Lys Ala Asn Ser Tyr Ile His Glu Val
465                 470                 475                 480

Tyr Thr Arg Glu Tyr Asp Asn Ala Val Asn Thr Ser Thr Ala Thr Thr
                485                 490                 495

Ile Thr Asn Asn Leu Leu Ser Val Arg Gly Tyr Cys Leu Leu His Gly
            500                 505                 510

Leu Glu Cys Leu Glu Val Leu Asp His Ile Gln Asn Asn Asn Leu Asp
        515                 520                 525

Gln Ser Phe Tyr Pro Lys Thr Ile Ser Tyr Ser Thr Val Phe Asp Arg
    530                 535                 540

Ser Thr Asn Lys Thr Arg Leu Gln Ala Leu Thr Glu Asp Glu Gln Met
545                 550                 555                 560

Glu Glu Pro Leu Lys Pro Ser Phe Ile Asn Gly Glu Tyr Asn Lys Ile
                565                 570                 575

Lys Ser Leu Ile Gly Tyr Val Gln Arg Ile Gly Asn Ala Pro Arg Val
            580                 585                 590

Gly Gly Ile Lys Ile Thr Phe Thr Asn Gly Ser Ser His Thr Leu Gly
        595                 600                 605

Thr Val Thr Ser Glu Ser Asn Ser Ile Glu Leu Asn Asp Ser Val Ile
    610                 615                 620
```

-continued

```
Thr Ser Val Glu Val Trp Gly Asn Gly Ala Val Asp Glu Ala Phe Phe
625                 630                 635                 640

Thr Leu Ser Asp Gly Arg Gln Phe Arg Leu Gly Gln Arg Tyr Ala Ser
                645                 650                 655

Asn Tyr Arg Lys Tyr Ala Val Asp Gly His Tyr Ile Ser Gly Leu Tyr
            660                 665                 670

Leu Ala Ser Asp Glu Pro Ser Leu Ala Gly Gln Ala Ala Gly Ile Ala
        675                 680                 685

Val Ser Tyr His Ile Leu Val Asp Lys Lys
    690                 695
```

<210> SEQ ID NO 122
<211> LENGTH: 2124
<212> TYPE: DNA
<213> ORGANISM: Artificial
<220> FEATURE:
<223> OTHER INFORMATION: A nucleic acid sequence encoding a PirAB fusion protein, TIC11441 comprised of the TIC7575, TIC7575, and TIC7576 coding sequences in operable linkage and in frame.

<400> SEQUENCE: 122

```
atgaatacaa tcaatataaa tataagtggc agtaccgtta cagtcataag caataacgat     60

tccaatccag aaccattaac ttataataca aacacaccag catcagaccc tcttacagcc    120

agtccttata gggatatgac aatagagcca cactcttcta ttgaagcaac aagaaccgat    180

acaccgatta ttcccgaaac tcgtcccaat tactatgtag ccaattctgg ccccgcatca    240

tcagttaggg ctgtttttta ttggtctcat tctttcacat cagaatggtt cgaatattcc    300

tctatcatag tgaaagccgg gaaagacgga atattacaat caccgaataa cgctttatat    360

tacagtaaag ttgtcattta taacgatacc gataaacgtg cctttgttac cggatataat    420

aagatgaaca ctataaacat caacatttcc ggaagcacgg taacggtgat ttctaacaat    480

gattcaaacc ctgagccatt aacatataac actaatacgc ctgcgagtga tccactaaca    540

gccagtccgt atagagatat gactatagag cctcattctt ctattgaggc aacgagaaca    600

gatacaccaa ttattccaga aactcgtccg aattactatg tcgccaattc tggtccagca    660

tcatcagtta gggctgtatt ctattggtct cattcattca catcagagtg gttcgaatat    720

tcatctatca tagtgaaagc aggcaaggac ggtatactac aaagcccaaa taacgcatta    780

tattactcga aggttgtcat ttacaatgat acggataaga gagctttcgt tactggatat    840

aacaaaatga atatctcacc gattaatgta tctgaaaatg aaacattacc tgaactcact    900

gatgttatgc ttattgtgcc ttatacaaca tctacccctg attatgaatg ggatatgtca    960

tcaattataa aggatgcgat tattggcggc gtagggttta ttccaggagc aggctctgca   1020

atgtccttcc tattgggact attttggcct caacagaaag ataatacatg ggaacagatc   1080

ctccaaaaag tagaacagat gatagagaat gccgttctgc aaactattaa aggaatactt   1140

aatggagata tacaagaaat caaggggaaa atggaacatg tgcaatacat gctggaaacc   1200

tcgcctggca gtcaggaaag tcatgacgca tatatgttcc tggctagata cctggtgagt   1260

atagatgaaa aattcaagtc ttttgataat aaaacaaact accagatcct gccgatgtac   1320

actaacacgg ttatgttaca aatcccttat tggaaaatgg gaatagagaa gaaaaatgat   1380

attgggctga cagatattga agtcaatgag ttaaaacagc ttatcgataa attggtcgac   1440

aaggccaaga gttacatcca tacgatgtat acgaatgaat ataatgatgc cataaataca   1500

tcaacagcat cgagtgtcac taataattta ctctctgtaa gaggatattg tttattacac   1560
```

```
ggtttagagt gtattgagtt aattgaacat ctacaaaaca atagcctcga aagtggtttt   1620

tatcctaaaa ctatcagtta ttcaactgta tttgatcgtc agactaacaa aatgagaatt   1680

caggctctta cagaagacga tcaaatgcag gaacccttta agccatcttt aatcaacggc   1740

aaatacaata aaatacaatc cttgcttgga tatgtacaaa gaattggaaa tgcacctaga   1800

gtgggggta ttaaaatcac ctttgccaac ggttcatcct atacacttgg cacagtaaca   1860

tcagaaacga gttcaattga actcaatgat agtgttatcg aaagattgga agtatggggc   1920

aatggcgctg ttgatgaggc attatttacg ttaagtgatg ggcgtcaact cagagtcggt   1980

gagcgctacg cgacaaaata tagaaaatat gctgttgatg gacactatat tgcaggactg   2040

tacttagcta gcgatgaacc ttcacttgct ggtcaagccg caggtattgc cgtttcatac   2100

catatgttgg atgataaaaa ataa                                           2124
```

```
<210> SEQ ID NO 123
<211> LENGTH: 707
<212> TYPE: PRT
<213> ORGANISM: Artificial
<220> FEATURE:
<223> OTHER INFORMATION: The amino acid sequence of the TIC11441 f PirAB
      fusion protein.

<400> SEQUENCE: 123

Met Asn Thr Ile Asn Ile Asn Ile Ser Gly Ser Thr Val Thr Val Ile
1               5                   10                  15

Ser Asn Asn Asp Ser Asn Pro Glu Pro Leu Thr Tyr Asn Thr Asn Thr
            20                  25                  30

Pro Ala Ser Asp Pro Leu Thr Ala Ser Pro Tyr Arg Asp Met Thr Ile
        35                  40                  45

Glu Pro His Ser Ser Ile Glu Ala Thr Arg Thr Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Glu Trp
                85                  90                  95

Phe Glu Tyr Ser Ser Ile Ile Val Lys Ala Gly Lys Asp Gly Ile Leu
            100                 105                 110

Gln Ser Pro Asn Asn Ala Leu Tyr Tyr Ser Lys Val Val Ile Tyr Asn
        115                 120                 125

Asp Thr Asp Lys Arg Ala Phe Val Thr Gly Tyr Asn Lys Met Asn Thr
    130                 135                 140

Ile Asn Ile Asn Ile Ser Gly Ser Thr Val Thr Val Ile Ser Asn Asn
145                 150                 155                 160

Asp Ser Asn Pro Glu Pro Leu Thr Tyr Asn Thr Asn Thr Pro Ala Ser
                165                 170                 175

Asp Pro Leu Thr Ala Ser Pro Tyr Arg Asp Met Thr Ile Glu Pro His
            180                 185                 190

Ser Ser Ile Glu Ala Thr Arg Thr Asp Thr Pro Ile Ile Pro Glu Thr
        195                 200                 205

Arg Pro Asn Tyr Tyr Val Ala Asn Ser Gly Pro Ala Ser Ser Val Arg
    210                 215                 220

Ala Val Phe Tyr Trp Ser His Ser Phe Thr Ser Glu Trp Phe Glu Tyr
225                 230                 235                 240

Ser Ser Ile Ile Val Lys Ala Gly Lys Asp Gly Ile Leu Gln Ser Pro
                245                 250                 255
```

```
Asn Asn Ala Leu Tyr Tyr Ser Lys Val Val Ile Tyr Asn Asp Thr Asp
            260                 265                 270

Lys Arg Ala Phe Val Thr Gly Tyr Asn Lys Met Asn Ile Ser Pro Ile
        275                 280                 285

Asn Val Ser Glu Asn Glu Thr Leu Pro Glu Leu Thr Asp Val Met Leu
    290                 295                 300

Ile Val Pro Tyr Thr Thr Ser Thr Pro Asp Tyr Glu Trp Asp Met Ser
305                 310                 315                 320

Ser Ile Ile Lys Asp Ala Ile Ile Gly Gly Val Gly Phe Ile Pro Gly
                325                 330                 335

Ala Gly Ser Ala Met Ser Phe Leu Leu Gly Leu Phe Trp Pro Gln Gln
            340                 345                 350

Lys Asp Asn Thr Trp Glu Gln Ile Leu Gln Lys Val Glu Gln Met Ile
        355                 360                 365

Glu Asn Ala Val Leu Gln Thr Ile Lys Gly Ile Leu Asn Gly Asp Ile
    370                 375                 380

Gln Glu Ile Lys Gly Lys Met Glu His Val Gln Tyr Met Leu Glu Thr
385                 390                 395                 400

Ser Pro Gly Ser Gln Glu Ser His Asp Ala Tyr Met Phe Leu Ala Arg
                405                 410                 415

Tyr Leu Val Ser Ile Asp Glu Lys Phe Lys Ser Phe Asp Asn Lys Thr
            420                 425                 430

Asn Tyr Gln Ile Leu Pro Met Tyr Thr Asn Thr Val Met Leu Gln Ile
        435                 440                 445

Pro Tyr Trp Lys Met Gly Ile Glu Lys Lys Asn Asp Ile Gly Leu Thr
    450                 455                 460

Asp Ile Glu Val Asn Glu Leu Lys Gln Leu Ile Asp Lys Leu Val Asp
465                 470                 475                 480

Lys Ala Lys Ser Tyr Ile His Thr Met Tyr Thr Asn Glu Tyr Asn Asp
                485                 490                 495

Ala Ile Asn Thr Ser Thr Ala Ser Ser Val Thr Asn Asn Leu Leu Ser
            500                 505                 510

Val Arg Gly Tyr Cys Leu Leu His Gly Leu Glu Cys Ile Glu Leu Ile
        515                 520                 525

Glu His Leu Gln Asn Asn Ser Leu Glu Ser Gly Phe Tyr Pro Lys Thr
    530                 535                 540

Ile Ser Tyr Ser Thr Val Phe Asp Arg Gln Thr Asn Lys Met Arg Ile
545                 550                 555                 560

Gln Ala Leu Thr Glu Asp Asp Gln Met Gln Glu Pro Phe Lys Pro Ser
                565                 570                 575

Leu Ile Asn Gly Lys Tyr Asn Lys Ile Gln Ser Leu Leu Gly Tyr Val
            580                 585                 590

Gln Arg Ile Gly Asn Ala Pro Arg Val Gly Gly Ile Lys Ile Thr Phe
        595                 600                 605

Ala Asn Gly Ser Ser Tyr Thr Leu Gly Thr Val Thr Ser Glu Thr Ser
    610                 615                 620

Ser Ile Glu Leu Asn Asp Ser Val Ile Glu Arg Leu Glu Val Trp Gly
625                 630                 635                 640

Asn Gly Ala Val Asp Glu Ala Leu Phe Thr Leu Ser Asp Gly Arg Gln
                645                 650                 655

Leu Arg Val Gly Glu Arg Tyr Ala Thr Lys Tyr Arg Lys Tyr Ala Val
            660                 665                 670

Asp Gly His Tyr Ile Ala Gly Leu Tyr Leu Ala Ser Asp Glu Pro Ser
```

```
        675                 680                 685

Leu Ala Gly Gln Ala Ala Gly Ile Ala Val Ser Tyr His Met Leu Asp
    690                 695                 700

Asp Lys Lys
705
```

<210> SEQ ID NO 124
<211> LENGTH: 2115
<212> TYPE: DNA
<213> ORGANISM: Artificial
<220> FEATURE:
<223> OTHER INFORMATION: A nucleic acid sequence encoding a PirAB fusion protein, TIC11442 comprised of the TIC7575, TIC4771, and TIC4472 coding sequences in operable linkage and in frame.

<400> SEQUENCE: 124

```
atgaatacaa tcaatataaa tataagtggc agtaccgtta cagtcataag caataacgat     60
tccaatccag aaccattaac ttataataca aacacaccag catcagaccc tcttacagcc    120
agtccttata gggatatgac aatagagcca cactcttcta ttgaagcaac aagaaccgat    180
acaccgatta ttcccgaaac tcgtcccaat tactatgtag ccaattctgg ccccgcatca    240
tcagttaggg ctgtttttta ttggtctcat tctttcacat cagaatggtt cgaatattcc    300
tctatcatag tgaaagccgg gaaagacgga atattacaat caccgaataa cgctttatat    360
tacagtaaag ttgtcattta taacgatacc gataaacgtg cctttgttac cggatataat    420
aagatgatta caataaatat aagtggtggt agtataaaaa ttagtaacaa catagatca     480
gaaactgata tcaaaaatac accttttca gaacctcttt caattagtaa ttataaggat     540
atgacaatag agccacattc gtctatccaa gcaacaagaa ctgatacacc aattattcct    600
gaaacacgac caaattatta tgtagctaat tccggccctg ccgcatcagt gagagctgtt    660
ttttattggt ctcattcttt tacatcagaa tggttcgaac attcatctat cattgtaaaa    720
gcaggagaag atggaatatt gaactcacct agcaattctg tatattacag taaggttgtc    780
atttacaacg atacggataa acgggccttt gtcacaggtt atgacaaaat gaataacgaa    840
cttatgaaca caaatgaatc acaaccttca gagacattat ctttaattaa tgaatctata    900
ttaacagcac cttatgccgt ttctacccct aattatgaat gggatatgtc atcaataata    960
aaagatgcca ttattggagg tataggattt attcccgggc cgggttcagc aatatcgttt   1020
ttgctagggc tattttggcc gcaacaaaca gacaatacct gggagcaaat tctccaaaaa   1080
gtagaacaga tgatagagga agcgaattta aaaactattc aaggaatact gaacggagat   1140
atacaagaaa taaaaggaaa gatggaacat gtggaatata tgctagaaac ctcaccaggc   1200
actcaagaaa gccatgacgc atatatgttc ttagcgagat atctggtaag tatagatgaa   1260
aaattcaaat cttttgataa taaaacaaat tatcaaattc ttccaatgta caccaatacg   1320
cttatgttac aggcacctta ctggaaaatg ggtatagaga agaaaaatga tattttgcta   1380
acagatatag aagttaatga attaaaacag cttatcgaaa atctatatgc caaggccaat   1440
agctatattc atgaagtgta tacccgtgaa tacgataatg cggtaaatac ctcaacagca   1500
acaacgatta ccaataattt attgtctgta agagggtatt gtttattaca tggattagag   1560
tgccttgaag tccttgatca tatacaaaat aataatcttg atcagagctt ctatccgaaa   1620
actatcagtt attctactgt atttgatcgc tcaacaaaca aaacaagact ccaggctctt   1680
accgaagacg agcaaatgga agaaccactc aaaccctctt ttattaatgg ggaatataat   1740
aaaataaaat cactgattgg atatgtacag agaattggaa acgcccctag agttggaggt   1800
```

ataaaaatta catttactaa tggatcatct catactctgg gtacagtgac ctcagaatca 1860
aactcaattg aactaaatga tagtgttata accagtgtgg aagtatgggg aaatggtgct 1920
gttgatgagg cattctttac attaagtgac ggtcgtcaat ttaggcttgg tcaacgctat 1980
gccagtaact acagaaaata tgctgttgat ggccactata tttcaggatt gtacttagcc 2040
agtgatgagc cttcacttgc tggtcaagcc gcaggtattg cagtttcata tcatatattg 2100
gttgataaga aataa 2115

<210> SEQ ID NO 125
<211> LENGTH: 704
<212> TYPE: PRT
<213> ORGANISM: Artificial
<220> FEATURE:
<223> OTHER INFORMATION: The amino acid sequence of the TIC11442 PirAB fusion protein.

<400> SEQUENCE: 125

Met Asn Thr Ile Asn Ile Asn Ile Ser Gly Ser Thr Val Thr Val Ile
1 5 10 15

Ser Asn Asn Asp Ser Asn Pro Glu Pro Leu Thr Tyr Asn Thr Asn Thr
20 25 30

Pro Ala Ser Asp Pro Leu Thr Ala Ser Pro Tyr Arg Asp Met Thr Ile
35 40 45

Glu Pro His Ser Ser Ile Glu Ala Thr Arg Thr Asp Thr Pro Ile Ile
50 55 60

Pro Glu Thr Arg Pro Asn Tyr Tyr Val Ala Asn Ser Gly Pro Ala Ser
65 70 75 80

Ser Val Arg Ala Val Phe Tyr Trp Ser His Ser Phe Thr Ser Glu Trp
85 90 95

Phe Glu Tyr Ser Ser Ile Ile Val Lys Ala Gly Lys Asp Gly Ile Leu
100 105 110

Gln Ser Pro Asn Asn Ala Leu Tyr Tyr Ser Lys Val Val Ile Tyr Asn
115 120 125

Asp Thr Asp Lys Arg Ala Phe Val Thr Gly Tyr Asn Lys Met Ile Thr
130 135 140

Ile Asn Ile Ser Gly Gly Ser Ile Lys Ile Ser Asn Asn Ile Gly Ser
145 150 155 160

Glu Thr Asp Ile Lys Asn Thr Pro Phe Ser Glu Pro Leu Ser Ile Ser
165 170 175

Asn Tyr Lys Asp Met Thr Ile Glu Pro His Ser Ser Ile Gln Ala Thr
180 185 190

Arg Thr Asp Thr Pro Ile Ile Pro Glu Thr Arg Pro Asn Tyr Tyr Val
195 200 205

Ala Asn Ser Gly Pro Ala Ala Ser Val Arg Ala Val Phe Tyr Trp Ser
210 215 220

His Ser Phe Thr Ser Glu Trp Phe Glu His Ser Ser Ile Ile Val Lys
225 230 235 240

Ala Gly Glu Asp Gly Ile Leu Asn Ser Pro Ser Asn Ser Val Tyr Tyr
245 250 255

Ser Lys Val Val Ile Tyr Asn Asp Thr Asp Lys Arg Ala Phe Val Thr
260 265 270

Gly Tyr Asp Lys Met Asn Asn Glu Leu Met Asn Thr Asn Glu Ser Gln
275 280 285

Pro Ser Glu Thr Leu Ser Leu Ile Asn Glu Ser Ile Leu Thr Ala Pro

```
    290                 295                 300

Tyr Ala Val Ser Thr Pro Asn Tyr Glu Trp Asp Met Ser Ser Ile Ile
305                 310                 315                 320

Lys Asp Ala Ile Ile Gly Gly Ile Gly Phe Ile Pro Gly Pro Gly Ser
                325                 330                 335

Ala Ile Ser Phe Leu Leu Gly Leu Phe Trp Pro Gln Gln Thr Asp Asn
            340                 345                 350

Thr Trp Glu Gln Ile Leu Gln Lys Val Glu Gln Met Ile Glu Glu Ala
        355                 360                 365

Asn Leu Lys Thr Ile Gln Gly Ile Leu Asn Gly Asp Ile Gln Glu Ile
    370                 375                 380

Lys Gly Lys Met Glu His Val Glu Tyr Met Leu Glu Thr Ser Pro Gly
385                 390                 395                 400

Thr Gln Glu Ser His Asp Ala Tyr Met Phe Leu Ala Arg Tyr Leu Val
                405                 410                 415

Ser Ile Asp Glu Lys Phe Lys Ser Phe Asp Asn Lys Thr Asn Tyr Gln
            420                 425                 430

Ile Leu Pro Met Tyr Thr Asn Thr Leu Met Leu Gln Ala Pro Tyr Trp
        435                 440                 445

Lys Met Gly Ile Glu Lys Lys Asn Asp Ile Leu Leu Thr Asp Ile Glu
    450                 455                 460

Val Asn Glu Leu Lys Gln Leu Ile Glu Asn Leu Tyr Ala Lys Ala Asn
465                 470                 475                 480

Ser Tyr Ile His Glu Val Tyr Thr Arg Glu Tyr Asp Asn Ala Val Asn
                485                 490                 495

Thr Ser Thr Ala Thr Thr Ile Thr Asn Asn Leu Leu Ser Val Arg Gly
            500                 505                 510

Tyr Cys Leu Leu His Gly Leu Glu Cys Leu Glu Val Leu Asp His Ile
        515                 520                 525

Gln Asn Asn Asn Leu Asp Gln Ser Phe Tyr Pro Lys Thr Ile Ser Tyr
    530                 535                 540

Ser Thr Val Phe Asp Arg Ser Thr Asn Lys Thr Arg Leu Gln Ala Leu
545                 550                 555                 560

Thr Glu Asp Glu Gln Met Glu Glu Pro Leu Lys Pro Ser Phe Ile Asn
                565                 570                 575

Gly Glu Tyr Asn Lys Ile Lys Ser Leu Ile Gly Tyr Val Gln Arg Ile
            580                 585                 590

Gly Asn Ala Pro Arg Val Gly Gly Ile Lys Ile Thr Phe Thr Asn Gly
        595                 600                 605

Ser Ser His Thr Leu Gly Thr Val Thr Ser Glu Ser Asn Ser Ile Glu
    610                 615                 620

Leu Asn Asp Ser Val Ile Thr Ser Val Glu Val Trp Gly Asn Gly Ala
625                 630                 635                 640

Val Asp Glu Ala Phe Phe Thr Leu Ser Asp Gly Arg Gln Phe Arg Leu
                645                 650                 655

Gly Gln Arg Tyr Ala Ser Asn Tyr Arg Lys Tyr Ala Val Asp Gly His
            660                 665                 670

Tyr Ile Ser Gly Leu Tyr Leu Ala Ser Asp Glu Pro Ser Leu Ala Gly
        675                 680                 685

Gln Ala Ala Gly Ile Ala Val Ser Tyr His Ile Leu Val Asp Lys Lys
    690                 695                 700

<210> SEQ ID NO 126
```

```
<211> LENGTH: 2124
<212> TYPE: DNA
<213> ORGANISM: Artificial
<220> FEATURE:
<223> OTHER INFORMATION: A nucleic acid sequence encoding a PirAB fusion
      protein, TIC11443 comprised of the TIC7660, TIC7575, and TIC7576
      coding sequences in operable linkage and in frame.

<400> SEQUENCE: 126

atgatcacaa taaatataaa tgtaaacggc aatgatgtta caggtacaaa taataatgaa     60

cctactccag tatcgacaac ttacggtcca aatacaccag catcagaacc ccctgtagtc    120

agtaattata gtgatataac aatagaaccg cattcttctg tgcaggcaac aagaattgat    180

acgcctgtta ttcctgaagc acgccccgat tactatgtag ccaactccgg ccctgcacca    240

tcagttaggg ctgtttttta ttggtctcat tctttcacat cagaatggtt cgaatcttcc    300

tctatcacag tgaaagcagg agaggacgga atattaaaag cacctggtaa ctctttatat    360

tacagcaaag tcgtcattta taatgatacg gataaacgag cctttgttac tggatataat    420

aaaatgaata caatcaatat aaatataagt ggcagtaccg ttacagtcat aagcaataac    480

gattccaatc cagaaccatt aacttataat acaaacacac cagcatcaga ccctcttaca    540

gccagtcctt atagggatat gacaatagag ccacactctt ctattgaagc aacaagaacc    600

gatacaccga ttattcccga aactcgtccc aattactatg tagccaattc tggccccgca    660

tcatcagtta gggctgtttt ttattggtct cattctttca catcagaatg gttcgaatat    720

tcctctatca tagtgaaagc cgggaaagac ggaatattac aatcaccgaa taacgcttta    780

tattacagta aagttgtcat ttataacgat accgataaac gtgcctttgt taccggatat    840

aataagatga atatctcacc gattaatgta tctgaaaatg aaacattacc tgaactcact    900

gatgttatgc ttattgtgcc ttatacaaca tctacccctg attatgaatg ggatatgtca    960

tcaattataa aggatgcgat tattggcggc gtagggttta ttccaggagc aggctctgca   1020

atgtccttcc tattgggact attttggcct caacagaaag ataatacatg ggaacagatc   1080

ctccaaaaag tagaacagat gatagagaat gccgttctgc aaactattaa aggaatactt   1140

aatggagata tacaagaaat caaggggaaa atggaacatg tgcaatacat gctggaaacc   1200

tcgcctggca gtcaggaaag tcatgacgca tatatgttcc tggctagata cctggtgagt   1260

atagatgaaa aattcaagtc ttttgataat aaaacaaact accagatcct gccgatgtac   1320

actaacacgg ttatgttaca aatcccttat tggaaaatgg gaatagagaa gaaaaatgat   1380

attgggctga cagatattga agtcaatgag ttaaaacagc ttatcgataa attggtcgac   1440

aaggccaaga gttacatcca tacgatgtat acgaatgaat ataatgatgc cataaataca   1500

tcaacagcat cgagtgtcac taataattta ctctctgtaa gaggatattg tttattacac   1560

ggtttagagt gtattgagtt aattgaacat ctacaaaaca atagcctcga aagtggtttt   1620

tatcctaaaa ctatcagtta ttcaactgta tttgatcgtc agactaacaa aatgagaatt   1680

caggctctta cagaagacga tcaaatgcag gaaccccttta agccatcttt aatcaacggc  1740

aaatacaata aaatacaatc cttgcttgga tatgtacaaa gaattggaaa tgcacctaga   1800

gtggggggta ttaaaatcac ctttgccaac ggttcatcct atacacttgg cacagtaaca   1860

tcagaaacga gttcaattga actcaatgat agtgttatcg aaagattgga agtatggggc   1920

aatggcgctg ttgatgaggc attatttacg ttaagtgatg ggcgtcaact cagagtcggt   1980

gagcgctacg cgacaaaata tagaaaatat gctgttgatg gacactatat tgcaggactg   2040

tacttagcta gcgatgaacc ttcacttgct ggtcaagccg caggtattgc cgtttcatac   2100
```

catatgttgg atgataaaaa ataa 2124

<210> SEQ ID NO 127
<211> LENGTH: 707
<212> TYPE: PRT
<213> ORGANISM: Artificial
<220> FEATURE:
<223> OTHER INFORMATION: The amino acid sequence of the TIC11443 PirAB fusion protein.

<400> SEQUENCE: 127

```
Met Ile Thr Ile Asn Ile Asn Val Asn Gly Asn Asp Val Thr Gly Thr
1               5                   10                  15

Asn Asn Asn Glu Pro Thr Pro Val Ser Thr Thr Tyr Gly Pro Asn Thr
            20                  25                  30

Pro Ala Ser Glu Pro Pro Val Val Ser Asn Tyr Ser Asp Ile Thr Ile
        35                  40                  45

Glu Pro His Ser Ser Val Gln Ala Thr Arg Ile Asp Thr Pro Val Ile
    50                  55                  60

Pro Glu Ala Arg Pro Asp Tyr Tyr Val Ala Asn Ser Gly Pro Ala Pro
65                  70                  75                  80

Ser Val Arg Ala Val Phe Tyr Trp Ser His Ser Phe Thr Ser Glu Trp
                85                  90                  95

Phe Glu Ser Ser Ser Ile Thr Val Lys Ala Gly Glu Asp Gly Ile Leu
            100                 105                 110

Lys Ala Pro Gly Asn Ser Leu Tyr Tyr Ser Lys Val Val Ile Tyr Asn
        115                 120                 125

Asp Thr Asp Lys Arg Ala Phe Val Thr Gly Tyr Asn Lys Met Asn Thr
    130                 135                 140

Ile Asn Ile Asn Ile Ser Gly Ser Thr Val Thr Val Ile Ser Asn Asn
145                 150                 155                 160

Asp Ser Asn Pro Glu Pro Leu Thr Tyr Asn Thr Asn Thr Pro Ala Ser
                165                 170                 175

Asp Pro Leu Thr Ala Ser Pro Tyr Arg Asp Met Thr Ile Glu Pro His
            180                 185                 190

Ser Ser Ile Glu Ala Thr Arg Thr Asp Thr Pro Ile Ile Pro Glu Thr
        195                 200                 205

Arg Pro Asn Tyr Tyr Val Ala Asn Ser Gly Pro Ala Ser Ser Val Arg
    210                 215                 220

Ala Val Phe Tyr Trp Ser His Ser Phe Thr Ser Glu Trp Phe Glu Tyr
225                 230                 235                 240

Ser Ser Ile Ile Val Lys Ala Gly Lys Asp Gly Ile Leu Gln Ser Pro
                245                 250                 255

Asn Asn Ala Leu Tyr Tyr Ser Lys Val Val Ile Tyr Asn Asp Thr Asp
            260                 265                 270

Lys Arg Ala Phe Val Thr Gly Tyr Asn Lys Met Asn Ile Ser Pro Ile
        275                 280                 285

Asn Val Ser Glu Asn Glu Thr Leu Pro Glu Leu Thr Asp Val Met Leu
    290                 295                 300

Ile Val Pro Tyr Thr Thr Ser Thr Pro Asp Tyr Glu Trp Asp Met Ser
305                 310                 315                 320

Ser Ile Ile Lys Asp Ala Ile Ile Gly Gly Val Gly Phe Ile Pro Gly
                325                 330                 335

Ala Gly Ser Ala Met Ser Phe Leu Leu Gly Leu Phe Trp Pro Gln Gln
            340                 345                 350
```

```
Lys Asp Asn Thr Trp Glu Gln Ile Leu Gln Lys Val Glu Gln Met Ile
        355                 360                 365

Glu Asn Ala Val Leu Gln Thr Ile Lys Gly Ile Leu Asn Gly Asp Ile
    370                 375                 380

Gln Glu Ile Lys Gly Lys Met Glu His Val Gln Tyr Met Leu Glu Thr
385                 390                 395                 400

Ser Pro Gly Ser Gln Glu Ser His Asp Ala Tyr Met Phe Leu Ala Arg
                405                 410                 415

Tyr Leu Val Ser Ile Asp Glu Lys Phe Lys Ser Phe Asp Asn Lys Thr
            420                 425                 430

Asn Tyr Gln Ile Leu Pro Met Tyr Thr Asn Thr Val Met Leu Gln Ile
        435                 440                 445

Pro Tyr Trp Lys Met Gly Ile Glu Lys Lys Asn Asp Ile Gly Leu Thr
    450                 455                 460

Asp Ile Glu Val Asn Glu Leu Lys Gln Leu Ile Asp Lys Leu Val Asp
465                 470                 475                 480

Lys Ala Lys Ser Tyr Ile His Thr Met Tyr Thr Asn Glu Tyr Asn Asp
                485                 490                 495

Ala Ile Asn Thr Ser Thr Ala Ser Ser Val Thr Asn Asn Leu Leu Ser
            500                 505                 510

Val Arg Gly Tyr Cys Leu Leu His Gly Leu Glu Cys Ile Glu Leu Ile
        515                 520                 525

Glu His Leu Gln Asn Asn Ser Leu Glu Ser Gly Phe Tyr Pro Lys Thr
    530                 535                 540

Ile Ser Tyr Ser Thr Val Phe Asp Arg Gln Thr Asn Lys Met Arg Ile
545                 550                 555                 560

Gln Ala Leu Thr Glu Asp Asp Gln Met Gln Glu Pro Phe Lys Pro Ser
                565                 570                 575

Leu Ile Asn Gly Lys Tyr Asn Lys Ile Gln Ser Leu Leu Gly Tyr Val
            580                 585                 590

Gln Arg Ile Gly Asn Ala Pro Arg Val Gly Gly Ile Lys Ile Thr Phe
        595                 600                 605

Ala Asn Gly Ser Ser Tyr Thr Leu Gly Thr Val Thr Ser Glu Thr Ser
    610                 615                 620

Ser Ile Glu Leu Asn Asp Ser Val Ile Glu Arg Leu Glu Val Trp Gly
625                 630                 635                 640

Asn Gly Ala Val Asp Glu Ala Leu Phe Thr Leu Ser Asp Gly Arg Gln
                645                 650                 655

Leu Arg Val Gly Glu Arg Tyr Ala Thr Lys Tyr Arg Lys Tyr Ala Val
            660                 665                 670

Asp Gly His Tyr Ile Ala Gly Leu Tyr Leu Ala Ser Asp Glu Pro Ser
        675                 680                 685

Leu Ala Gly Gln Ala Ala Gly Ile Ala Val Ser Tyr His Met Leu Asp
    690                 695                 700

Asp Lys Lys
705
```

<210> SEQ ID NO 128
<211> LENGTH: 2124
<212> TYPE: DNA
<213> ORGANISM: Artificial
<220> FEATURE:
<223> OTHER INFORMATION: A nucleic acid sequence encoding a PirAB fusion protein, TIC11444 comprised of the TIC7660 and TIC7576 coding sequences in operable linkage and in frame.

<400> SEQUENCE: 128
atgaatacaa tcaatataaa tataagtggc agtaccgtta cagtcataag caataacgat 60
tccaatccag aaccattaac ttataataca aacacaccag catcagaccc tcttacagcc 120
agtccttata gggatatgac aatagagcca cactcttcta ttgaagcaac aagaaccgat 180
acaccgatta ttcccgaaac tcgtcccaat tactatgtag ccaattctgg ccccgcatca 240
tcagttaggg ctgtttttta ttggtctcat tctttcacat cagaatggtt cgaatattcc 300
tctatcatag tgaaagccgg gaaagacgga atattacaat caccgaataa cgctttatat 360
tacagtaaag ttgtcattta taacgatacc gataaacgtg cctttgttac cggatataat 420
aagatgatca caataaatat aaatgtaaac ggcaatgatg ttacaggtac aaataataat 480
gaacctactc cagtatcgac aacttacggt ccaaatacac cagcatcaga accccctgta 540
gtcagtaatt atagtgatat aacaatagaa ccgcattctt ctgtgcaggc aacaagaatt 600
gatacgcctg ttattcctga agcacgcccc gattactatg tagccaactc cggccctgca 660
ccatcagtta gggctgtttt ttattggtct cattctttca catcagaatg gttcgaatct 720
tcctctatca cagtgaaagc aggagaggac ggaatattaa aagcacctgg taactcttta 780
tattacagca aagtcgtcat ttataatgat acggataaac gagcctttgt tactggatat 840
aataaaatga atactacacc tattactgta tctacaaatg aaacatcgcc tttaatgact 900
gacgtaatgc ccatggatct ttatgcaata tccacacctg attatgaatg ggacatgtcg 960
tcaatcataa aggatgctgt tattggtggc ataggattta ttccaggtcc gggcccggca 1020
atatccttcc tgttagggct attttggcct cagcagaaag acaatacttg ggagcaaatt 1080
ctccagaaag tagagcagat gatagagaat gctgttctac aaactattaa aggaatactt 1140
aatggagaag ttcaagagat caaagggaaa atggaacatg tagaatccat gctgaaaaac 1200
tcgcctggca gtcaggaaag tcatgatgca tatatgttcc tggcgagata tctggttagt 1260
atagatgaaa aattcaaatc ttttgacaat agaacaaatt accagcttct cccaatgtat 1320
actaacacta ttatgttaca gatcccttat tggaaaatgg gaatagagaa gaaaaaagat 1380
attgggctga cagatattga agttaatgaa ttaaaagaac ttatcgataa attggttgat 1440
aaggccaaaa actatattca tacgatgtat actaatgaac ataataatgc tgtaaacaca 1500
tcaacagcag agagtgtcac taataattta ttatctgtaa gaggatattg tttattacac 1560
ggtttagaat gtattgagtt aatcgagcat atacagaata atagccttga gagtggtttc 1620
tatcctaaaa ttatcagtta ttcgactgcg tttgatcgtc ctactaacaa aatgagaatt 1680
caggctctta cagaagatga tgcaatgcag gagcctttca aaccatcttt aatcaatggg 1740
aaatataata aaatccaatc cttgactgga tatgtacaaa gaattgggaa tgcacctaga 1800
gttggtggta tcagaatcac atttaccaac ggctcatctt atacacttgg tacagtgacc 1860
tcagaaacgc attcaattaa gctaaacgat agtgttatcg aaagcttgga agtatggggg 1920
aatggtgctg ttgatgaggc gttatttaag ttaagtgatg ggcgtttatt gcgtattggt 1980
gagcgctacg cgaaaaaata cagaaaatat gctgttgata atcactatat tgcggggatt 2040
tacttagcca gcgatgagcc ttcacttgct ggtcaagccg caggtattgc cgtttcatat 2100
catatgatgg ctgacaaaaa ataa 2124

<210> SEQ ID NO 129
<211> LENGTH: 707
<212> TYPE: PRT

<213> ORGANISM: Artificial
<220> FEATURE:
<223> OTHER INFORMATION: The amino acid sequence of the TIC11444 PirAB fusion protein.

<400> SEQUENCE: 129

```
Met Asn Thr Ile Asn Ile Asn Ile Ser Gly Ser Thr Val Thr Val Ile
1               5                   10                  15

Ser Asn Asn Asp Ser Asn Pro Glu Pro Leu Thr Tyr Asn Thr Asn Thr
            20                  25                  30

Pro Ala Ser Asp Pro Leu Thr Ala Ser Pro Tyr Arg Asp Met Thr Ile
        35                  40                  45

Glu Pro His Ser Ser Ile Glu Ala Thr Arg Thr Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Glu Trp
                85                  90                  95

Phe Glu Tyr Ser Ser Ile Ile Val Lys Ala Gly Lys Asp Gly Ile Leu
            100                 105                 110

Gln Ser Pro Asn Asn Ala Leu Tyr Tyr Ser Lys Val Val Ile Tyr Asn
        115                 120                 125

Asp Thr Asp Lys Arg Ala Phe Val Thr Gly Tyr Asn Lys Met Ile Thr
    130                 135                 140

Ile Asn Ile Asn Val Asn Gly Asn Asp Val Thr Gly Thr Asn Asn Asn
145                 150                 155                 160

Glu Pro Thr Pro Val Ser Thr Thr Tyr Gly Pro Asn Thr Pro Ala Ser
                165                 170                 175

Glu Pro Pro Val Val Ser Asn Tyr Ser Asp Ile Thr Ile Glu Pro His
            180                 185                 190

Ser Ser Val Gln Ala Thr Arg Ile Asp Thr Pro Val Ile Pro Glu Ala
        195                 200                 205

Arg Pro Asp Tyr Tyr Val Ala Asn Ser Gly Pro Ala Pro Ser Val Arg
    210                 215                 220

Ala Val Phe Tyr Trp Ser His Ser Phe Thr Ser Glu Trp Phe Glu Ser
225                 230                 235                 240

Ser Ser Ile Thr Val Lys Ala Gly Glu Asp Gly Ile Leu Lys Ala Pro
                245                 250                 255

Gly Asn Ser Leu Tyr Tyr Ser Lys Val Val Ile Tyr Asn Asp Thr Asp
            260                 265                 270

Lys Arg Ala Phe Val Thr Gly Tyr Asn Lys Met Asn Thr Thr Pro Ile
        275                 280                 285

Thr Val Ser Thr Asn Glu Thr Ser Pro Leu Met Thr Asp Val Met Pro
    290                 295                 300

Met Asp Leu Tyr Ala Ile Ser Thr Pro Asp Tyr Glu Trp Asp Met Ser
305                 310                 315                 320

Ser Ile Ile Lys Asp Ala Val Ile Gly Gly Ile Gly Phe Ile Pro Gly
                325                 330                 335

Pro Gly Pro Ala Ile Ser Phe Leu Leu Gly Leu Phe Trp Pro Gln Gln
            340                 345                 350

Lys Asp Asn Thr Trp Glu Gln Ile Leu Gln Lys Val Glu Gln Met Ile
        355                 360                 365

Glu Asn Ala Val Leu Gln Thr Ile Lys Gly Ile Leu Asn Gly Glu Val
    370                 375                 380
```

-continued

```
Gln Glu Ile Lys Gly Lys Met Glu His Val Glu Ser Met Leu Lys Asn
385                 390                 395                 400

Ser Pro Gly Ser Gln Glu Ser His Asp Ala Tyr Met Phe Leu Ala Arg
                405                 410                 415

Tyr Leu Val Ser Ile Asp Glu Lys Phe Lys Ser Phe Asp Asn Arg Thr
            420                 425                 430

Asn Tyr Gln Leu Leu Pro Met Tyr Thr Asn Thr Ile Met Leu Gln Ile
        435                 440                 445

Pro Tyr Trp Lys Met Gly Ile Glu Lys Lys Lys Asp Ile Gly Leu Thr
    450                 455                 460

Asp Ile Glu Val Asn Glu Leu Lys Glu Leu Ile Asp Lys Leu Val Asp
465                 470                 475                 480

Lys Ala Lys Asn Tyr Ile His Thr Met Tyr Thr Asn Glu His Asn Asn
                485                 490                 495

Ala Val Asn Thr Ser Thr Ala Glu Ser Val Thr Asn Asn Leu Leu Ser
            500                 505                 510

Val Arg Gly Tyr Cys Leu Leu His Gly Leu Glu Cys Ile Glu Leu Ile
        515                 520                 525

Glu His Ile Gln Asn Asn Ser Leu Glu Ser Gly Phe Tyr Pro Lys Ile
    530                 535                 540

Ile Ser Tyr Ser Thr Ala Phe Asp Arg Pro Thr Asn Lys Met Arg Ile
545                 550                 555                 560

Gln Ala Leu Thr Glu Asp Asp Ala Met Gln Glu Pro Phe Lys Pro Ser
                565                 570                 575

Leu Ile Asn Gly Lys Tyr Asn Lys Ile Gln Ser Leu Thr Gly Tyr Val
            580                 585                 590

Gln Arg Ile Gly Asn Ala Pro Arg Val Gly Gly Ile Arg Ile Thr Phe
        595                 600                 605

Thr Asn Gly Ser Ser Tyr Thr Leu Gly Thr Val Thr Ser Glu Thr His
    610                 615                 620

Ser Ile Lys Leu Asn Asp Ser Val Ile Glu Ser Leu Glu Val Trp Gly
625                 630                 635                 640

Asn Gly Ala Val Asp Glu Ala Leu Phe Lys Leu Ser Asp Gly Arg Leu
                645                 650                 655

Leu Arg Ile Gly Glu Arg Tyr Ala Lys Lys Tyr Arg Lys Tyr Ala Val
            660                 665                 670

Asp Asn His Tyr Ile Ala Gly Ile Tyr Leu Ala Ser Asp Glu Pro Ser
        675                 680                 685

Leu Ala Gly Gln Ala Ala Gly Ile Ala Val Ser Tyr His Met Met Ala
    690                 695                 700

Asp Lys Lys
705
```

<210> SEQ ID NO 130
<211> LENGTH: 2124
<212> TYPE: DNA
<213> ORGANISM: Artificial
<220> FEATURE:
<223> OTHER INFORMATION: A nucleic acid sequence encoding a PirAB fusion protein, TIC11445 comprised of the TIC7660, TIC7662, and TIC7663 coding sequences in operable linkage and in frame.

<400> SEQUENCE: 130

```
atgatcacaa taaatataaa tgtaaacggc aatgatgtta caggtacaaa taataatgaa     60

cctactccag tatcgacaac ttacggtcca aatacaccag catcagaacc ccctgtagtc    120
```

-continued

```
agtaattata gtgatataac aatagaaccg cattcttctg tgcaggcaac aagaattgat    180
acgcctgtta ttcctgaagc acgccccgat tactatgtag ccaactccgg ccctgcacca    240
tcagttaggg ctgtttttta ttggtctcat tctttcacat cagaatggtt cgaatcttcc    300
tctatcacag tgaaagcagg agaggacgga atattaaaag cacctggtaa ctctttatat    360
tacagcaaag tcgtcattta taatgatacg gataaacgag cctttgttac tggatataat    420
aaaatgagta caatcaatat caatataagt agcagtaccg ttaccgtcat cacgaataac    480
ggagaaacgc cagtcccact cacttacaat acaaatacac ctgaatcaga acctcttacc    540
gtcaatcctt atagggatat gacaatagag ccacgctctt ctattgaagc aacaaggatt    600
gatacaccga ttattcccga aacacgccct aattattatg tagccaattc aggcccggct    660
tcatcagtta gggccgtttt ttattggtcc cattctttca catcacaatg gttcgaatat    720
tcctctatca tcgtcaaagc cggggaagat ggcatattag aatcaccaag caattcttta    780
tattacagca aagtcgtcat ttataatgat accgataaac gcgcctttgt gacgggatat    840
aataagatga ataccactct gattaatgta tctgaaaaag aaacattgcc tgtacaaact    900
gatatcatgc ttatcgcgcc ttattcagta tcgacccccg attatgaatg ggatatgtcc    960
tcactcatca aggatgccat tattggtggc gtagggttta ttcccgtcgt aggttccgca   1020
atgtccttcc tgctaggatt attttggccc caacagaaag ataatacttg ggagcaaatt   1080
ctccaaaaag tcgagcagat gatcgagaat gcccagctaa atacgattaa aggaatactt   1140
aatggcgata tacaagagat caaaggaaaa atggagcatg tacaatacat gttggaaacc   1200
tcgccgggca gtcaagaaag tcatgatgcc tatatgttcc tggccagata tctggtgagt   1260
atcgatgaga aatttaagtc ttttgataat aaaacaaact atcaaatttt gccgatgtat   1320
acgaacacgg ttatgttgca gatcccttat tggaaaatgg ggatcgagaa gaaaaatgat   1380
attgggctga ccgatattga agtcaatgag ttaaaacagc ttatcgacac attggttgac   1440
agagccagga actatattca tacgatgtat gaaagagaat atgataatgc catcaacacc   1500
tcaaccgcgg cgagcgtcac taataattta ttgtccgtca gaggatattg cctgttacac   1560
ggtttagagt gtattgaaac cattgaacat ctgcaaaata atagccttaa tagtggtttc   1620
tatcctaaaa ccattagtta ttcaacggta tttgatcgtc ccacgaacaa aacgagaatt   1680
caggctctga ccgaagatga ccaaatgcaa gagcctttca agccagcttt aattggcggt   1740
aagtacaata aaataaaatc attgcttggc tatgtacgaa gaattgggaa tgcccccaga   1800
gtggggggaa ttaaggtcac ctttaccaac ggatcatctt atacacttgg cacagtcaca   1860
tcagaaacgg actcaattga gctaaatgag agtgttatcg aaagattaga agtatggggc   1920
aatggtgctg ttgatgaggc attatttacg ttaagcgatg ggcgccaact caggatcggc   1980
gagcgctacg cgaaaaaata cagaaaatat gctgttgatg gacactatat ttcagggctg   2040
tacttagcca gcgatgaacc ttcccttgct ggtcaggccg caggtattgc cgtttcatac   2100
catatgcttg ctgataaaaa ataa                                           2124
```

<210> SEQ ID NO 131
<211> LENGTH: 707
<212> TYPE: PRT
<213> ORGANISM: Artificial
<220> FEATURE:
<223> OTHER INFORMATION: The amino acid sequence of the TIC11445 PirAB fusion protein.

<400> SEQUENCE: 131

-continued

```
Met Ile Thr Ile Asn Ile Asn Val Asn Gly Asn Asp Val Thr Gly Thr
1               5                   10                  15

Asn Asn Asn Glu Pro Thr Pro Val Ser Thr Thr Tyr Gly Pro Asn Thr
            20                  25                  30

Pro Ala Ser Glu Pro Pro Val Val Ser Asn Tyr Ser Asp Ile Thr Ile
        35                  40                  45

Glu Pro His Ser Ser Val Gln Ala Thr Arg Ile Asp Thr Pro Val Ile
    50                  55                  60

Pro Glu Ala Arg Pro Asp Tyr Tyr Val Ala Asn Ser Gly Pro Ala Pro
65                  70                  75                  80

Ser Val Arg Ala Val Phe Tyr Trp Ser His Ser Phe Thr Ser Glu Trp
                85                  90                  95

Phe Glu Ser Ser Ser Ile Thr Val Lys Ala Gly Glu Asp Gly Ile Leu
            100                 105                 110

Lys Ala Pro Gly Asn Ser Leu Tyr Tyr Ser Lys Val Val Ile Tyr Asn
        115                 120                 125

Asp Thr Asp Lys Arg Ala Phe Val Thr Gly Tyr Asn Lys Met Ser Thr
    130                 135                 140

Ile Asn Ile Asn Ile Ser Ser Ser Thr Val Thr Val Ile Thr Asn Asn
145                 150                 155                 160

Gly Glu Thr Pro Val Pro Leu Thr Tyr Asn Thr Asn Thr Pro Glu Ser
                165                 170                 175

Glu Pro Leu Thr Val Asn Pro Tyr Arg Asp Met Thr Ile Glu Pro Arg
            180                 185                 190

Ser Ser Ile Glu Ala Thr Arg Ile Asp Thr Pro Ile Ile Pro Glu Thr
        195                 200                 205

Arg Pro Asn Tyr Tyr Val Ala Asn Ser Gly Pro Ala Ser Ser Val Arg
    210                 215                 220

Ala Val Phe Tyr Trp Ser His Ser Phe Thr Ser Gln Trp Phe Glu Tyr
225                 230                 235                 240

Ser Ser Ile Ile Val Lys Ala Gly Glu Asp Gly Ile Leu Glu Ser Pro
                245                 250                 255

Ser Asn Ser Leu Tyr Tyr Ser Lys Val Val Ile Tyr Asn Asp Thr Asp
            260                 265                 270

Lys Arg Ala Phe Val Thr Gly Tyr Asn Lys Met Asn Thr Thr Leu Ile
        275                 280                 285

Asn Val Ser Glu Lys Glu Thr Leu Pro Val Gln Thr Asp Ile Met Leu
    290                 295                 300

Ile Ala Pro Tyr Ser Val Ser Thr Pro Asp Tyr Glu Trp Asp Met Ser
305                 310                 315                 320

Ser Leu Ile Lys Asp Ala Ile Ile Gly Gly Val Gly Phe Ile Pro Val
                325                 330                 335

Val Gly Ser Ala Met Ser Phe Leu Leu Gly Leu Phe Trp Pro Gln Gln
            340                 345                 350

Lys Asp Asn Thr Trp Glu Gln Ile Leu Gln Lys Val Glu Gln Met Ile
        355                 360                 365

Glu Asn Ala Gln Leu Asn Thr Ile Lys Gly Ile Leu Asn Gly Asp Ile
    370                 375                 380

Gln Glu Ile Lys Gly Lys Met Glu His Val Gln Tyr Met Leu Glu Thr
385                 390                 395                 400

Ser Pro Gly Ser Gln Glu Ser His Asp Ala Tyr Met Phe Leu Ala Arg
                405                 410                 415

Tyr Leu Val Ser Ile Asp Glu Lys Phe Lys Ser Phe Asp Asn Lys Thr
```

```
            420                 425                 430

Asn Tyr Gln Ile Leu Pro Met Tyr Thr Asn Thr Val Met Leu Gln Ile
        435                 440                 445

Pro Tyr Trp Lys Met Gly Ile Glu Lys Lys Asn Asp Ile Gly Leu Thr
    450                 455                 460

Asp Ile Glu Val Asn Glu Leu Lys Gln Leu Ile Asp Thr Leu Val Asp
465                 470                 475                 480

Arg Ala Arg Asn Tyr Ile His Thr Met Tyr Glu Arg Glu Tyr Asp Asn
                485                 490                 495

Ala Ile Asn Thr Ser Thr Ala Ala Ser Val Thr Asn Asn Leu Leu Ser
            500                 505                 510

Val Arg Gly Tyr Cys Leu Leu His Gly Leu Glu Cys Ile Glu Thr Ile
        515                 520                 525

Glu His Leu Gln Asn Asn Ser Leu Asn Ser Gly Phe Tyr Pro Lys Thr
    530                 535                 540

Ile Ser Tyr Ser Thr Val Phe Asp Arg Pro Thr Asn Lys Thr Arg Ile
545                 550                 555                 560

Gln Ala Leu Thr Glu Asp Asp Gln Met Gln Glu Pro Phe Lys Pro Ala
                565                 570                 575

Leu Ile Gly Gly Lys Tyr Asn Lys Ile Lys Ser Leu Leu Gly Tyr Val
            580                 585                 590

Arg Arg Ile Gly Asn Ala Pro Arg Val Gly Gly Ile Lys Val Thr Phe
        595                 600                 605

Thr Asn Gly Ser Ser Tyr Thr Leu Gly Thr Val Thr Ser Glu Thr Asp
    610                 615                 620

Ser Ile Glu Leu Asn Glu Ser Val Ile Glu Arg Leu Glu Val Trp Gly
625                 630                 635                 640

Asn Gly Ala Val Asp Glu Ala Leu Phe Thr Leu Ser Asp Gly Arg Gln
                645                 650                 655

Leu Arg Ile Gly Glu Arg Tyr Ala Lys Lys Tyr Arg Lys Tyr Ala Val
            660                 665                 670

Asp Gly His Tyr Ile Ser Gly Leu Tyr Leu Ala Ser Asp Glu Pro Ser
        675                 680                 685

Leu Ala Gly Gln Ala Ala Gly Ile Ala Val Ser Tyr His Met Leu Ala
    690                 695                 700

Asp Lys Lys
705
```

<210> SEQ ID NO 132
<211> LENGTH: 2124
<212> TYPE: DNA
<213> ORGANISM: Artificial
<220> FEATURE:
<223> OTHER INFORMATION: A nucleic acid sequence encoding a fusion protein, TIC11446 comprised of the TIC7662, TIC7660, and TIC7661 coding sequences in operable linkage and in frame.

<400> SEQUENCE: 132

```
atgagtacaa tcaatatcaa tataagtagc agtaccgtta ccgtcatcac gaataacgga     60

gaaacgccag tcccactcac ttacaataca aatacacctg aatcagaacc tcttaccgtc    120

aatccttata gggatatgac aatagagcca cgctcttcta ttgaagcaac aaggattgat    180

acaccgatta ttcccgaaac acgccctaat tattatgtag ccaattcagg cccggcttca    240

tcagttaggg ccgtttttta ttggtcccat tctttcacat cacaatggtt cgaatattcc    300

tctatcatcg tcaaagccgg ggaagatggc atattagaat caccaagcaa ttctttatat    360
```

```
tacagcaaag tcgtcattta taatgatacc gataaacgcg cctttgtgac gggatataat    420

aagatgatca caataaatat aaatgtaaac ggcaatgatg ttacaggtac aaataataat    480

gaacctactc cagtatcgac aacttacggt ccaaatacac cagcatcaga accccctgta    540

gtcagtaatt atagtgatat aacaatagaa ccgcattctt ctgtgcaggc aacaagaatt    600

gatacgcctg ttattcctga agcacgcccc gattactatg tagccaactc cggccctgca    660

ccatcagtta gggctgtttt ttattggtct cattctttca catcagaatg gttcgaatct    720

tcctctatca cagtgaaagc aggagaggac ggaatattaa aagcacctgg taactcttta    780

tattacagca aagtcgtcat ttataatgat acggataaac gagcctttgt tactggatat    840

aataaaatga atactacacc tattactgta tctacaaatg aaacatcgcc tttaatgact    900

gacgtaatgc ccatggatct ttatgcaata tccacacctg attatgaatg ggacatgtcg    960

tcaatcataa aggatgctgt tattggtggc ataggattta ttccaggtcc gggcccggca   1020

atatccttcc tgttagggct attttggcct cagcagaaag acaatacttg ggagcaaatt   1080

ctccagaaag tagagcagat gatagagaat gctgttctac aaactattaa aggaatactt   1140

aatggagaag ttcaagagat caaagggaaa atggaacatg tagaatccat gctgaaaaac   1200

tcgcctggca gtcaggaaag tcatgatgca tatatgttcc tggcgagata tctggttagt   1260

atagatgaaa aattcaaatc ttttgacaat agaacaaatt accagcttct cccaatgtat   1320

actaacacta ttatgttaca gatcccttat tggaaaatgg gaatagagaa gaaaaaagat   1380

attgggctga cagatattga agttaatgaa ttaaaagaac ttatcgataa attggttgat   1440

aaggccaaaa actatattca tacgatgtat actaatgaac ataataatgc tgtaaacaca   1500

tcaacagcag agagtgtcac taataattta ttatctgtaa gaggatattg tttattacac   1560

ggtttagaat gtattgagtt aatcgagcat atacagaata atagccttga gagtggtttc   1620

tatcctaaaa ttatcagtta ttcgactgcg tttgatcgtc ctactaacaa aatgagaatt   1680

caggctctta cagaagatga tgcaatgcag gagcctttca aaccatcttt aatcaatggg   1740

aaatataata aaatccaatc cttgactgga tatgtacaaa gaattgggaa tgcacctaga   1800

gttggtggta tcagaatcac atttaccaac ggctcatctt atacacttgg tacagtgacc   1860

tcagaaacgc attcaattaa gctaaacgat agtgttatcg aaagcttgga agtatggggg   1920

aatggtgctg ttgatgaggc gttatttaag ttaagtgatg ggcgtttatt gcgtattggt   1980

gagcgctacg cgaaaaaata cagaaaatat gctgttgata atcactatat tgcggggatt   2040

tacttagcca gcgatgagcc ttcacttgct ggtcaagccg caggtattgc cgtttcatat   2100

catatgatgg ctgacaaaaa ataa                                          2124
```

<210> SEQ ID NO 133
<211> LENGTH: 707
<212> TYPE: PRT
<213> ORGANISM: Artificial
<220> FEATURE:
<223> OTHER INFORMATION: The amino acid sequence of the TIC11446 PirAB fusion protein.

<400> SEQUENCE: 133

```
Met Ser Thr Ile Asn Ile Asn Ile Ser Ser Ser Thr Val Thr Val Ile
1               5                   10                  15

Thr Asn Asn Gly Glu Thr Pro Val Pro Leu Thr Tyr Asn Thr Asn Thr
            20                  25                  30

Pro Glu Ser Glu Pro Leu Thr Val Asn Pro Tyr Arg Asp Met Thr Ile
```

```
        35                  40                  45

Glu Pro Arg Ser Ser Ile Glu Ala Thr Arg Ile Asp Thr Pro Ile Ile
    50                  55                  60

Pro Glu Thr Arg Pro Asn Tyr Tyr Val Ala Asn Ser Gly Pro Ala Ser
65                  70                  75                  80

Ser Val Arg Ala Val Phe Tyr Trp Ser His Ser Phe Thr Ser Gln Trp
                85                  90                  95

Phe Glu Tyr Ser Ser Ile Ile Val Lys Ala Gly Glu Asp Gly Ile Leu
            100                 105                 110

Glu Ser Pro Ser Asn Ser Leu Tyr Tyr Ser Lys Val Val Ile Tyr Asn
        115                 120                 125

Asp Thr Asp Lys Arg Ala Phe Val Thr Gly Tyr Asn Lys Met Ile Thr
    130                 135                 140

Ile Asn Ile Asn Val Asn Gly Asn Asp Val Thr Gly Thr Asn Asn Asn
145                 150                 155                 160

Glu Pro Thr Pro Val Ser Thr Thr Tyr Gly Pro Asn Thr Pro Ala Ser
                165                 170                 175

Glu Pro Pro Val Val Ser Asn Tyr Ser Asp Ile Thr Ile Glu Pro His
            180                 185                 190

Ser Ser Val Gln Ala Thr Arg Ile Asp Thr Pro Val Ile Pro Glu Ala
        195                 200                 205

Arg Pro Asp Tyr Tyr Val Ala Asn Ser Gly Pro Ala Pro Ser Val Arg
    210                 215                 220

Ala Val Phe Tyr Trp Ser His Ser Phe Thr Ser Glu Trp Phe Glu Ser
225                 230                 235                 240

Ser Ser Ile Thr Val Lys Ala Gly Glu Asp Gly Ile Leu Lys Ala Pro
                245                 250                 255

Gly Asn Ser Leu Tyr Tyr Ser Lys Val Val Ile Tyr Asn Asp Thr Asp
            260                 265                 270

Lys Arg Ala Phe Val Thr Gly Tyr Asn Lys Met Asn Thr Thr Pro Ile
        275                 280                 285

Thr Val Ser Thr Asn Glu Thr Ser Pro Leu Met Thr Asp Val Met Pro
    290                 295                 300

Met Asp Leu Tyr Ala Ile Ser Thr Pro Asp Tyr Glu Trp Asp Met Ser
305                 310                 315                 320

Ser Ile Ile Lys Asp Ala Val Ile Gly Gly Ile Gly Phe Ile Pro Gly
                325                 330                 335

Pro Gly Pro Ala Ile Ser Phe Leu Leu Gly Leu Phe Trp Pro Gln Gln
            340                 345                 350

Lys Asp Asn Thr Trp Glu Gln Ile Leu Gln Lys Val Glu Gln Met Ile
        355                 360                 365

Glu Asn Ala Val Leu Gln Thr Ile Lys Gly Ile Leu Asn Gly Glu Val
    370                 375                 380

Gln Glu Ile Lys Gly Lys Met Glu His Val Glu Ser Met Leu Lys Asn
385                 390                 395                 400

Ser Pro Gly Ser Gln Glu Ser His Asp Ala Tyr Met Phe Leu Ala Arg
                405                 410                 415

Tyr Leu Val Ser Ile Asp Glu Lys Phe Lys Ser Phe Asp Asn Arg Thr
            420                 425                 430

Asn Tyr Gln Leu Leu Pro Met Tyr Thr Asn Thr Ile Met Leu Gln Ile
        435                 440                 445

Pro Tyr Trp Lys Met Gly Ile Glu Lys Lys Lys Asp Ile Gly Leu Thr
    450                 455                 460
```

Asp Ile Glu Val Asn Glu Leu Lys Glu Leu Ile Asp Lys Leu Val Asp
465 470 475 480

Lys Ala Lys Asn Tyr Ile His Thr Met Tyr Thr Asn Glu His Asn Asn
485 490 495

Ala Val Asn Thr Ser Thr Ala Glu Ser Val Thr Asn Asn Leu Leu Ser
500 505 510

Val Arg Gly Tyr Cys Leu Leu His Gly Leu Glu Cys Ile Glu Leu Ile
515 520 525

Glu His Ile Gln Asn Asn Ser Leu Glu Ser Gly Phe Tyr Pro Lys Ile
530 535 540

Ile Ser Tyr Ser Thr Ala Phe Asp Arg Pro Thr Asn Lys Met Arg Ile
545 550 555 560

Gln Ala Leu Thr Glu Asp Asp Ala Met Gln Glu Pro Phe Lys Pro Ser
565 570 575

Leu Ile Asn Gly Lys Tyr Asn Lys Ile Gln Ser Leu Thr Gly Tyr Val
580 585 590

Gln Arg Ile Gly Asn Ala Pro Arg Val Gly Gly Ile Arg Ile Thr Phe
595 600 605

Thr Asn Gly Ser Ser Tyr Thr Leu Gly Thr Val Thr Ser Glu Thr His
610 615 620

Ser Ile Lys Leu Asn Asp Ser Val Ile Glu Ser Leu Glu Val Trp Gly
625 630 635 640

Asn Gly Ala Val Asp Glu Ala Leu Phe Lys Leu Ser Asp Gly Arg Leu
645 650 655

Leu Arg Ile Gly Glu Arg Tyr Ala Lys Lys Tyr Arg Lys Tyr Ala Val
660 665 670

Asp Asn His Tyr Ile Ala Gly Ile Tyr Leu Ala Ser Asp Glu Pro Ser
675 680 685

Leu Ala Gly Gln Ala Ala Gly Ile Ala Val Ser Tyr His Met Met Ala
690 695 700

Asp Lys Lys
705

<210> SEQ ID NO 134
<211> LENGTH: 1305
<212> TYPE: DNA
<213> ORGANISM: Xenorhabdus nematophila
<220> FEATURE:
<221> NAME/KEY: misc_feature
<222> LOCATION: (1)..(1305)
<223> OTHER INFORMATION: A nucleic acid sequence obtained from Xenorhabdus nematophila strain MDI-0035777 encoding a TIC11505 pesticidal PirB protein sequence.

<400> SEQUENCE: 134
atgaataatg aaccgatgaa tactaatgaa tcacaagctt cagagatagt accctcaatg 60
aatgaatcta tattaaatga atctatatta gcagcacctt attcaatttc tacacctaat 120
tatgaatggg atatgtcatc aataataaaa gatgccatta ttggtggtat aggctttatt 180
cctggtccgg gttcagcaat atcatttttg ttagggttat tttggccaca acaaaccgac 240
aatacttggg agcaaattct ccaaaaagta gaacaaatga tcgagcaagc caatctcaaa 300
actattcaag gaatattgaa cggcgatata caagaaatta aaggcaaaat ggaacatgtg 360
caattcatgc tagaatcctc acctggcact caagaaagcc atgacgcata catgtttctg 420
gcgagatatc tggtcagtat agacgaaaaa ttcaagtctt ttgataacaa aacaaattat 480

-continued

```
caaattcttc ccatgtatac caatacgatt atgttacaag cccccttattg gaaaatgggt    540

atagagagaa aagatgagat aaaactaaca gatatagaag ttaatgaatt aaaagagctg    600

ataggaaaat tatctaccag cgccgataaa tatattcatg atgtctatac tcgtgaatat    660

gataatgcga tgaacacttc aacagcagca aatatcacca ataatttatt atctgtaaga    720

ggctattgtt tattacatgg tttagaatgt ctcgaagtca ttaaccatat acaaaataat    780

agccttgagc aaagttttta tcctaaaact atcagctact ccaccgtatt cgatcgccag    840

acaaataaaa caagggttca agccctgaca gaagacgatc aaatgcaaga gccattcaag    900

cctgctttaa ttaatgggaa gtacaacaaa ataaaatcat tgattgggta tgtacaaaga    960

atcggaaacg cacccagagt tggaggcatt aaagtcacat ttgcaaacga tgcatcttat   1020

accctcggta cagtaacttc agaagtaaac tcaattgaac tgaatgacag cgttataacc   1080

agcctggaag tatggggaaa tggcgctgtt gatgaggcat tctttacatt aagtgacgga   1140

cgtcaattta ggcttggcca acgctatgcc agtaactata gaaaatatgc tgtcgataac   1200

cactatattt caggattgta cttagccagt gatgaacctt cattggcagg ccaagcagca   1260

ggcattgcag tttcatacca tatgatagct gataaaaaat catag                   1305
```

<210> SEQ ID NO 135
<211> LENGTH: 434
<212> TYPE: PRT
<213> ORGANISM: Xenorhabdus nematophila
<220> FEATURE:
<221> NAME/KEY: MISC_FEATURE
<222> LOCATION: (1)..(434)
<223> OTHER INFORMATION: The amino acid sequence of the TIC11505 PirB
      protein.

<400> SEQUENCE: 135

```
Met Asn Asn Glu Pro Met Asn Thr Asn Glu Ser Gln Ala Ser Glu Ile
1               5                   10                  15

Val Pro Ser Met Asn Glu Ser Ile Leu Asn Glu Ser Ile Leu Ala Ala
            20                  25                  30

Pro Tyr Ser Ile Ser Thr Pro Asn Tyr Glu Trp Asp Met Ser Ser Ile
        35                  40                  45

Ile Lys Asp Ala Ile Ile Gly Gly Ile Gly Phe Ile Pro Gly Pro Gly
    50                  55                  60

Ser Ala Ile Ser Phe Leu Leu Gly Leu Phe Trp Pro Gln Gln Thr Asp
65                  70                  75                  80

Asn Thr Trp Glu Gln Ile Leu Gln Lys Val Glu Gln Met Ile Glu Gln
                85                  90                  95

Ala Asn Leu Lys Thr Ile Gln Gly Ile Leu Asn Gly Asp Ile Gln Glu
            100                 105                 110

Ile Lys Gly Lys Met Glu His Val Gln Phe Met Leu Glu Ser Ser Pro
        115                 120                 125

Gly Thr Gln Glu Ser His Asp Ala Tyr Met Phe Leu Ala Arg Tyr Leu
    130                 135                 140

Val Ser Ile Asp Glu Lys Phe Lys Ser Phe Asp Asn Lys Thr Asn Tyr
145                 150                 155                 160

Gln Ile Leu Pro Met Tyr Thr Asn Thr Ile Met Leu Gln Ala Pro Tyr
                165                 170                 175

Trp Lys Met Gly Ile Glu Arg Lys Asp Glu Ile Lys Leu Thr Asp Ile
            180                 185                 190

Glu Val Asn Glu Leu Lys Glu Leu Ile Gly Lys Leu Ser Thr Ser Ala
        195                 200                 205
```

-continued

```
Asp Lys Tyr Ile His Asp Val Tyr Thr Arg Glu Tyr Asp Asn Ala Met
    210                 215                 220

Asn Thr Ser Thr Ala Ala Asn Ile Thr Asn Asn Leu Leu Ser Val Arg
225                 230                 235                 240

Gly Tyr Cys Leu Leu His Gly Leu Glu Cys Leu Glu Val Ile Asn His
                245                 250                 255

Ile Gln Asn Asn Ser Leu Glu Gln Ser Phe Tyr Pro Lys Thr Ile Ser
            260                 265                 270

Tyr Ser Thr Val Phe Asp Arg Gln Thr Asn Lys Thr Arg Val Gln Ala
        275                 280                 285

Leu Thr Glu Asp Asp Gln Met Gln Glu Pro Phe Lys Pro Ala Leu Ile
    290                 295                 300

Asn Gly Lys Tyr Asn Lys Ile Lys Ser Leu Ile Gly Tyr Val Gln Arg
305                 310                 315                 320

Ile Gly Asn Ala Pro Arg Val Gly Gly Ile Lys Val Thr Phe Ala Asn
                325                 330                 335

Asp Ala Ser Tyr Thr Leu Gly Thr Val Thr Ser Glu Val Asn Ser Ile
            340                 345                 350

Glu Leu Asn Asp Ser Val Ile Thr Ser Leu Glu Val Trp Gly Asn Gly
        355                 360                 365

Ala Val Asp Glu Ala Phe Phe Thr Leu Ser Asp Gly Arg Gln Phe Arg
    370                 375                 380

Leu Gly Gln Arg Tyr Ala Ser Asn Tyr Arg Lys Tyr Ala Val Asp Asn
385                 390                 395                 400

His Tyr Ile Ser Gly Leu Tyr Leu Ala Ser Asp Glu Pro Ser Leu Ala
                405                 410                 415

Gly Gln Ala Ala Gly Ile Ala Val Ser Tyr His Met Ile Ala Asp Lys
            420                 425                 430

Lys Ser
```

<210> SEQ ID NO 136
<211> LENGTH: 1731
<212> TYPE: DNA
<213> ORGANISM: Artificial
<220> FEATURE:
<223> OTHER INFORMATION: A nucleic acid sequence encoding a PirAB fusion protein, TIC11506 comprised of the TIC10364 and TIC11505 coding sequences in operable linkage and in frame.

<400> SEQUENCE: 136

```
atgagcataa tcaatataaa tataagtggt agtagtgaca ttacaatcat aaacaatacc      60

ccatctaacc cagaaccact catttacaat acagacacac ccgcatcaga acctcttacc     120

gtcaatcctt atagggatat gacaatagag ccacactctt ctattgaggc aataagaatt     180

gatacgccaa ttattcccga aacccgcccc aattattacg tagccaattc tggccccgca     240

tcatcagtta gagccgtttt ttattggtct cactctttca catcagaatg gttcgaatat     300

tctgctatca cagtgaaagc cggggaagac ggcatattac aatcaccgag caactctgtg     360

tattacagca aggtcgtcat ttataacgaa accgataaac gcgcctttgt tactggatat     420

aataagatga ataatgaacc gatgaatact aatgaatcac aagcttcaga gatagtaccc     480

tcaatgaatg aatctatatt aaatgaatct atattagcag caccttattc aatttctaca     540

cctaattatg aatgggatat gtcatcaata ataaaagatg ccattattgg tggtataggc     600

tttattcctg gtccgggttc agcaatatca tttttgttag ggttattttg gccacaacaa     660
```

```
accgacaata cttgggagca aattctccaa aaagtagaac aaatgatcga gcaagccaat     720

ctcaaaacta ttcaaggaat attgaacggc gatatacaag aaattaaagg caaaatggaa     780

catgtgcaat tcatgctaga atcctcacct ggcactcaag aaagccatga cgcatacatg     840

tttctggcga gatatctggt cagtatagac gaaaaattca agtcttttga taacaaaaca     900

aattatcaaa ttcttcccat gtataccaat acgattatgt tacaagcccc ttattggaaa     960

atgggtatag agagaaaaga tgagataaaa ctaacagata tagaagttaa tgaattaaaa    1020

gagctgatag gaaaattatc taccagcgcc gataaatata ttcatgatgt ctatactcgt    1080

gaatatgata atgcgatgaa cacttcaaca gcagcaaata tcaccaataa tttattatct    1140

gtaagaggct attgtttatt acatggttta gaatgtctcg aagtcattaa ccatatacaa    1200

aataatagcc ttgagcaaag tttttatcct aaaactatca gctactccac cgtattcgat    1260

cgccagacaa ataaaacaag ggttcaagcc ctgacagaag acgatcaaat gcaagagcca    1320

ttcaagcctg ctttaattaa tggaagtac aacaaaataa aatcattgat tgggtatgta    1380

caaagaatcg gaaacgcacc cagagttgga ggcattaaag tcacatttgc aaacgatgca    1440

tcttataccc tcggtacagt aacttcagaa gtaaactcaa ttgaactgaa tgacagcgtt    1500

ataaccagcc tggaagtatg gggaaatggc gctgttgatg aggcattctt tacattaagt    1560

gacggacgtc aatttaggct tggccaacgc tatgccagta actatagaaa atatgctgtc    1620

gataaccact atatttcagg attgtactta gccagtgatg aaccttcatt ggcaggccaa    1680

gcagcaggca ttgcagtttc ataccatatg atagctgata aaaaatcata g             1731
```

<210> SEQ ID NO 137
<211> LENGTH: 576
<212> TYPE: PRT
<213> ORGANISM: Artificial
<220> FEATURE:
<223> OTHER INFORMATION: The amino acid sequence of the TIC11506 PirAB
      fusion protein.

<400> SEQUENCE: 137

```
Met Ser Ile Ile Asn Ile Asn Ile Ser Gly Ser Ser Asp Ile Thr Ile
1               5                   10                  15

Ile Asn Asn Thr Pro Ser Asn Pro Glu Pro Leu Ile Tyr Asn Thr Asp
            20                  25                  30

Thr Pro Ala Ser Glu Pro Leu Thr Val Asn Pro Tyr Arg Asp Met Thr
        35                  40                  45

Ile Glu Pro His Ser Ser Ile Glu Ala Ile Arg Ile Asp Thr Pro Ile
    50                  55                  60

Ile Pro Glu Thr Arg Pro Asn Tyr Tyr Val Ala Asn Ser Gly Pro Ala
65                  70                  75                  80

Ser Ser Val Arg Ala Val Phe Tyr Trp Ser His Ser Phe Thr Ser Glu
                85                  90                  95

Trp Phe Glu Tyr Ser Ala Ile Thr Val Lys Ala Gly Glu Asp Gly Ile
            100                 105                 110

Leu Gln Ser Pro Ser Asn Ser Val Tyr Tyr Ser Lys Val Val Ile Tyr
        115                 120                 125

Asn Glu Thr Asp Lys Arg Ala Phe Val Thr Gly Tyr Asn Lys Met Asn
    130                 135                 140

Asn Glu Pro Met Asn Thr Asn Glu Ser Gln Ala Ser Glu Ile Val Pro
145                 150                 155                 160

Ser Met Asn Glu Ser Ile Leu Asn Glu Ser Ile Leu Ala Ala Pro Tyr
                165                 170                 175
```

```
Ser Ile Ser Thr Pro Asn Tyr Glu Trp Asp Met Ser Ser Ile Ile Lys
            180                 185                 190

Asp Ala Ile Ile Gly Gly Ile Gly Phe Ile Pro Gly Pro Gly Ser Ala
        195                 200                 205

Ile Ser Phe Leu Leu Gly Leu Phe Trp Pro Gln Gln Thr Asp Asn Thr
    210                 215                 220

Trp Glu Gln Ile Leu Gln Lys Val Glu Gln Met Ile Glu Gln Ala Asn
225                 230                 235                 240

Leu Lys Thr Ile Gln Gly Ile Leu Asn Gly Asp Ile Gln Glu Ile Lys
                245                 250                 255

Gly Lys Met Glu His Val Gln Phe Met Leu Glu Ser Ser Pro Gly Thr
            260                 265                 270

Gln Glu Ser His Asp Ala Tyr Met Phe Leu Ala Arg Tyr Leu Val Ser
        275                 280                 285

Ile Asp Glu Lys Phe Lys Ser Phe Asp Asn Lys Thr Asn Tyr Gln Ile
    290                 295                 300

Leu Pro Met Tyr Thr Asn Thr Ile Met Leu Gln Ala Pro Tyr Trp Lys
305                 310                 315                 320

Met Gly Ile Glu Arg Lys Asp Glu Ile Lys Leu Thr Asp Ile Glu Val
                325                 330                 335

Asn Glu Leu Lys Glu Leu Ile Gly Lys Leu Ser Thr Ser Ala Asp Lys
            340                 345                 350

Tyr Ile His Asp Val Tyr Thr Arg Glu Tyr Asp Asn Ala Met Asn Thr
        355                 360                 365

Ser Thr Ala Ala Asn Ile Thr Asn Asn Leu Leu Ser Val Arg Gly Tyr
    370                 375                 380

Cys Leu Leu His Gly Leu Glu Cys Leu Glu Val Ile Asn His Ile Gln
385                 390                 395                 400

Asn Asn Ser Leu Glu Gln Ser Phe Tyr Pro Lys Thr Ile Ser Tyr Ser
                405                 410                 415

Thr Val Phe Asp Arg Gln Thr Asn Lys Thr Arg Val Gln Ala Leu Thr
            420                 425                 430

Glu Asp Asp Gln Met Gln Glu Pro Phe Lys Pro Ala Leu Ile Asn Gly
        435                 440                 445

Lys Tyr Asn Lys Ile Lys Ser Leu Ile Gly Tyr Val Gln Arg Ile Gly
    450                 455                 460

Asn Ala Pro Arg Val Gly Gly Ile Lys Val Thr Phe Ala Asn Asp Ala
465                 470                 475                 480

Ser Tyr Thr Leu Gly Thr Val Thr Ser Glu Val Asn Ser Ile Glu Leu
                485                 490                 495

Asn Asp Ser Val Ile Thr Ser Leu Glu Val Trp Gly Asn Gly Ala Val
            500                 505                 510

Asp Glu Ala Phe Phe Thr Leu Ser Asp Gly Arg Gln Phe Arg Leu Gly
        515                 520                 525

Gln Arg Tyr Ala Ser Asn Tyr Arg Lys Tyr Ala Val Asp Asn His Tyr
    530                 535                 540

Ile Ser Gly Leu Tyr Leu Ala Ser Asp Glu Pro Ser Leu Ala Gly Gln
545                 550                 555                 560

Ala Ala Gly Ile Ala Val Ser Tyr His Met Ile Ala Asp Lys Lys Ser
                565                 570                 575
```

<210> SEQ ID NO 138
<211> LENGTH: 1290

<212> TYPE: DNA
<213> ORGANISM: Xenorhabdus bovienii
<220> FEATURE:
<221> NAME/KEY: misc_feature
<222> LOCATION: (1)..(1290)
<223> OTHER INFORMATION: A nucleic acid sequence obtained from Xenorhabdus bovienii strain MDI-0035808 encoding a TIC11510 pesticidal PirB protein sequence.

<400> SEQUENCE: 138

```
atgaataatg aaccgatgaa tactaatgaa tcacaagctt cagagatagt accctcaatg     60

aatgaatcta tattagcagc accttattca atttctacac ctaattatga atgggatatg    120

tcatcaataa taaaagatgc cattattggt ggtataggct ttattcctgg tccgggctca    180

gcaatatcat ttttgttagg gttattttgg ccacaacaaa ccgacaatac ttgggagcaa    240

attctccaaa aagtagaaca aatgatcgag caagccaatc tcaaaactat tcaaggaata    300

ttgaacggcg atatacaaga aattaaaggc aaaatggaac atgtgcaatt catgctagaa    360

tcctcatctg gcactcaaga aagccatgac gcatacatgt ttctggcgag atatctggtc    420

agtatagacg aaaaattcaa gtcttttgat aacaaaacaa attatcaaat tcttcccatg    480

tataccaata cgattatgtt acaagcccct tattggaaaa tgggtataga gagaaaagat    540

gagatcaaac taacagatat agaagttaat gaattaaaag agctgatagg aaaattatct    600

accagcgccg ataaatatat tcatgatgtc tatactcgtg aatatgataa tgcgatgaac    660

acttcaacag cagcaaatat caccaataat ttattatctg taagaggcta ttgtttatta    720

catggtttag aatgtctcga agtcattaac catatacaaa ataatagcct tgagcaaagt    780

ttttatccta aaactatcag ctactccacc gtattcgatc gccagacaaa taaaacaagg    840

gttcaagccc tgacagaaga cgatcaaatg caagagccat tcaagcctgc tttagttaat    900

gggaagtaca acaaaataaa atcattgatt gggtatgtac aaagaatcgg aaacgcaccc    960

agagttggag gcattaaagt cacatttgca aacgatgcat cttataccct cggtacagta   1020

acttcagaag taaactcaat tgaactgaat gacagcgtta taaccagcct ggaagtatgg   1080

ggaaatggcg ctattgatga ggcattcttt acattaagtg acggacgtca atttaggctt   1140

ggccaacgct atgccagtaa ctatagaaaa tatgctgtcg ataaccacta tatttcagga   1200

ttgtacttag ccagtgatga accttcattg gcaggtcaag cagcaggcat tgcagtttca   1260

taccatatga tagctgataa aaaatcatag                                    1290
```

<210> SEQ ID NO 139
<211> LENGTH: 429
<212> TYPE: PRT
<213> ORGANISM: Xenorhabdus bovienii
<220> FEATURE:
<221> NAME/KEY: MISC_FEATURE
<222> LOCATION: (1)..(429)
<223> OTHER INFORMATION: The amino acid sequence of the TIC11510 PirB protein.

<400> SEQUENCE: 139

```
Met Asn Asn Glu Pro Met Asn Thr Asn Glu Ser Gln Ala Ser Glu Ile
1               5                   10                  15

Val Pro Ser Met Asn Glu Ser Ile Leu Ala Ala Pro Tyr Ser Ile Ser
            20                  25                  30

Thr Pro Asn Tyr Glu Trp Asp Met Ser Ser Ile Ile Lys Asp Ala Ile
        35                  40                  45

Ile Gly Gly Ile Gly Phe Ile Pro Gly Pro Gly Ser Ala Ile Ser Phe
    50                  55                  60
```

```
Leu Leu Gly Leu Phe Trp Pro Gln Gln Thr Asp Asn Thr Trp Glu Gln
65                  70                  75                  80

Ile Leu Gln Lys Val Glu Gln Met Ile Glu Gln Ala Asn Leu Lys Thr
                85                  90                  95

Ile Gln Gly Ile Leu Asn Gly Asp Ile Gln Glu Ile Lys Gly Lys Met
            100                 105                 110

Glu His Val Gln Phe Met Leu Glu Ser Ser Ser Gly Thr Gln Glu Ser
        115                 120                 125

His Asp Ala Tyr Met Phe Leu Ala Arg Tyr Leu Val Ser Ile Asp Glu
    130                 135                 140

Lys Phe Lys Ser Phe Asp Asn Lys Thr Asn Tyr Gln Ile Leu Pro Met
145                 150                 155                 160

Tyr Thr Asn Thr Ile Met Leu Gln Ala Pro Tyr Trp Lys Met Gly Ile
                165                 170                 175

Glu Arg Lys Asp Glu Ile Lys Leu Thr Asp Ile Glu Val Asn Glu Leu
            180                 185                 190

Lys Glu Leu Ile Gly Lys Leu Ser Thr Ser Ala Asp Lys Tyr Ile His
        195                 200                 205

Asp Val Tyr Thr Arg Glu Tyr Asp Asn Ala Met Asn Thr Ser Thr Ala
    210                 215                 220

Ala Asn Ile Thr Asn Asn Leu Leu Ser Val Arg Gly Tyr Cys Leu Leu
225                 230                 235                 240

His Gly Leu Glu Cys Leu Glu Val Ile Asn His Ile Gln Asn Asn Ser
                245                 250                 255

Leu Glu Gln Ser Phe Tyr Pro Lys Thr Ile Ser Tyr Ser Thr Val Phe
            260                 265                 270

Asp Arg Gln Thr Asn Lys Thr Arg Val Gln Ala Leu Thr Glu Asp Asp
        275                 280                 285

Gln Met Gln Glu Pro Phe Lys Pro Ala Leu Val Asn Gly Lys Tyr Asn
    290                 295                 300

Lys Ile Lys Ser Leu Ile Gly Tyr Val Gln Arg Ile Gly Asn Ala Pro
305                 310                 315                 320

Arg Val Gly Gly Ile Lys Val Thr Phe Ala Asn Asp Ala Ser Tyr Thr
                325                 330                 335

Leu Gly Thr Val Thr Ser Glu Val Asn Ser Ile Glu Leu Asn Asp Ser
            340                 345                 350

Val Ile Thr Ser Leu Glu Val Trp Gly Asn Gly Ala Ile Asp Glu Ala
        355                 360                 365

Phe Phe Thr Leu Ser Asp Gly Arg Gln Phe Arg Leu Gly Gln Arg Tyr
    370                 375                 380

Ala Ser Asn Tyr Arg Lys Tyr Ala Val Asp Asn His Tyr Ile Ser Gly
385                 390                 395                 400

Leu Tyr Leu Ala Ser Asp Glu Pro Ser Leu Ala Gly Gln Ala Ala Gly
                405                 410                 415

Ile Ala Val Ser Tyr His Met Ile Ala Asp Lys Lys Ser
            420                 425
```

<210> SEQ ID NO 140
<211> LENGTH: 1716
<212> TYPE: DNA
<213> ORGANISM: Artificial
<220> FEATURE:
<223> OTHER INFORMATION: A nucleic acid sequence encoding a PirAB fusion protein, TIC11512 comprised of the TIC10364 and TIC11510 coding sequences in operable linkage and in frame.

<400> SEQUENCE: 140

```
atgagcataa tcaatataaa tataagtggt agtagtgaca ttacaatcat aaacaatacc     60
ccatctaacc cagaaccact catttacaat acagacacac ccgcatcaga acctcttacc    120
gtcaatcctt atagggatat gacaatagag ccacactctt ctattgaggc aataagaatt    180
gatacgccaa ttattcccga aacccgcccc aattattacg tagccaattc tggccccgca    240
tcatcagtta gagccgtttt ttattggtct cactctttca catcagaatg gttcgaatat    300
tctgctatca cagtgaaagc cggggaagac ggcatattac aatcaccgag caactctgtg    360
tattacagca aggtcgtcat ttataacgaa accgataaac gcgcctttgt tactggatat    420
aataagatga ataatgaacc gatgaatact aatgaatcac aagcttcaga gatagtaccc    480
tcaatgaatg aatctatatt agcagcacct tattcaattt ctacacctaa ttatgaatgg    540
gatatgtcat caataataaa agatgccatt attggtggta taggctttat tcctggtccg    600
ggctcagcaa tatcattttt gttagggtta ttttggccac aacaaaccga caatacttgg    660
gagcaaattc tccaaaaagt agaacaaatg atcgagcaag ccaatctcaa aactattcaa    720
ggaatattga acggcgatat acaagaaatt aaaggcaaaa tggaacatgt gcaattcatg    780
ctagaatcct catctggcac tcaagaaagc catgacgcat acatgtttct ggcgagatat    840
ctggtcagta tagacgaaaa attcaagtct tttgataaca aaacaaatta tcaaattctt    900
cccatgtata ccaatacgat tatgttacaa gccccttatt ggaaaatggg tatagagaga    960
aaagatgaga tcaaactaac agatatagaa gttaatgaat taaaagagct gataggaaaa   1020
ttatctacca gcgccgataa atatattcat gatgtctata ctcgtgaata tgataatgcg   1080
atgaacactt caacagcagc aaatatcacc aataatttat tatctgtaag aggctattgt   1140
ttattacatg gtttagaatg tctcgaagtc attaaccata tacaaaataa tagccttgag   1200
caaagttttt atcctaaaac tatcagctac tccaccgtat tcgatcgcca gacaaataaa   1260
acaagggttc aagccctgac agaagacgat caaatgcaag agccattcaa gcctgcttta   1320
gttaatggga agtacaacaa aataaaatca ttgattgggt atgtacaaag aatcggaaac   1380
gcacccagag ttggaggcat taaagtcaca tttgcaaacg atgcatctta taccctcggt   1440
acagtaactt cagaagtaaa ctcaattgaa ctgaatgaca gcgttataac cagcctggaa   1500
gtatggggaa atggcgctat tgatgaggca ttctttacat taagtgacgg acgtcaattt   1560
aggcttggcc aacgctatgc cagtaactat agaaaatatg ctgtcgataa ccactatatt   1620
tcaggattgt acttagccag tgatgaacct tcattggcag gtcaagcagc aggcattgca   1680
gtttcatacc atatgatagc tgataaaaaa tcatag                             1716
```

<210> SEQ ID NO 141
<211> LENGTH: 571
<212> TYPE: PRT
<213> ORGANISM: Artificial
<220> FEATURE:
<223> OTHER INFORMATION: The amino acid sequence of the TIC11512 PirAB fusion protein.

<400> SEQUENCE: 141

```
Met Ser Ile Ile Asn Ile Asn Ile Ser Gly Ser Ser Asp Ile Thr Ile
1               5                   10                  15

Ile Asn Asn Thr Pro Ser Asn Pro Glu Pro Leu Ile Tyr Asn Thr Asp
            20                  25                  30

Thr Pro Ala Ser Glu Pro Leu Thr Val Asn Pro Tyr Arg Asp Met Thr
```

```
        35                  40                  45

Ile Glu Pro His Ser Ser Ile Glu Ala Ile Arg Ile Asp Thr Pro Ile
    50                  55                  60

Ile Pro Glu Thr Arg Pro Asn Tyr Tyr Val Ala Asn Ser Gly Pro Ala
65                  70                  75                  80

Ser Ser Val Arg Ala Val Phe Tyr Trp Ser His Ser Phe Thr Ser Glu
                85                  90                  95

Trp Phe Glu Tyr Ser Ala Ile Thr Val Lys Ala Gly Glu Asp Gly Ile
            100                 105                 110

Leu Gln Ser Pro Ser Asn Ser Val Tyr Tyr Ser Lys Val Val Ile Tyr
        115                 120                 125

Asn Glu Thr Asp Lys Arg Ala Phe Val Thr Gly Tyr Asn Lys Met Asn
    130                 135                 140

Asn Glu Pro Met Asn Thr Asn Glu Ser Gln Ala Ser Glu Ile Val Pro
145                 150                 155                 160

Ser Met Asn Glu Ser Ile Leu Ala Ala Pro Tyr Ser Ile Ser Thr Pro
                165                 170                 175

Asn Tyr Glu Trp Asp Met Ser Ser Ile Ile Lys Asp Ala Ile Ile Gly
            180                 185                 190

Gly Ile Gly Phe Ile Pro Gly Pro Gly Ser Ala Ile Ser Phe Leu Leu
        195                 200                 205

Gly Leu Phe Trp Pro Gln Gln Thr Asp Asn Thr Trp Glu Gln Ile Leu
    210                 215                 220

Gln Lys Val Glu Gln Met Ile Glu Gln Ala Asn Leu Lys Thr Ile Gln
225                 230                 235                 240

Gly Ile Leu Asn Gly Asp Ile Gln Glu Ile Lys Gly Lys Met Glu His
                245                 250                 255

Val Gln Phe Met Leu Glu Ser Ser Ser Gly Thr Gln Glu Ser His Asp
            260                 265                 270

Ala Tyr Met Phe Leu Ala Arg Tyr Leu Val Ser Ile Asp Glu Lys Phe
        275                 280                 285

Lys Ser Phe Asp Asn Lys Thr Asn Tyr Gln Ile Leu Pro Met Tyr Thr
    290                 295                 300

Asn Thr Ile Met Leu Gln Ala Pro Tyr Trp Lys Met Gly Ile Glu Arg
305                 310                 315                 320

Lys Asp Glu Ile Lys Leu Thr Asp Ile Glu Val Asn Glu Leu Lys Glu
                325                 330                 335

Leu Ile Gly Lys Leu Ser Thr Ser Ala Asp Lys Tyr Ile His Asp Val
            340                 345                 350

Tyr Thr Arg Glu Tyr Asp Asn Ala Met Asn Thr Ser Thr Ala Ala Asn
        355                 360                 365

Ile Thr Asn Asn Leu Leu Ser Val Arg Gly Tyr Cys Leu Leu His Gly
    370                 375                 380

Leu Glu Cys Leu Glu Val Ile Asn His Ile Gln Asn Asn Ser Leu Glu
385                 390                 395                 400

Gln Ser Phe Tyr Pro Lys Thr Ile Ser Tyr Ser Thr Val Phe Asp Arg
                405                 410                 415

Gln Thr Asn Lys Thr Arg Val Gln Ala Leu Thr Glu Asp Asp Gln Met
            420                 425                 430

Gln Glu Pro Phe Lys Pro Ala Leu Val Asn Gly Lys Tyr Asn Lys Ile
        435                 440                 445

Lys Ser Leu Ile Gly Tyr Val Gln Arg Ile Gly Asn Ala Pro Arg Val
    450                 455                 460
```

```
Gly Gly Ile Lys Val Thr Phe Ala Asn Asp Ala Ser Tyr Thr Leu Gly
465                 470                 475                 480

Thr Val Thr Ser Glu Val Asn Ser Ile Glu Leu Asn Asp Ser Val Ile
                485                 490                 495

Thr Ser Leu Glu Val Trp Gly Asn Gly Ala Ile Asp Glu Ala Phe Phe
            500                 505                 510

Thr Leu Ser Asp Gly Arg Gln Phe Arg Leu Gly Gln Arg Tyr Ala Ser
        515                 520                 525

Asn Tyr Arg Lys Tyr Ala Val Asp Asn His Tyr Ile Ser Gly Leu Tyr
    530                 535                 540

Leu Ala Ser Asp Glu Pro Ser Leu Ala Gly Gln Ala Ala Gly Ile Ala
545                 550                 555                 560

Val Ser Tyr His Met Ile Ala Asp Lys Lys Ser
                565                 570


<210> SEQ ID NO 142
<211> LENGTH: 1290
<212> TYPE: DNA
<213> ORGANISM: Xenorhabdus nematophila
<220> FEATURE:
<221> NAME/KEY: misc_feature
<222> LOCATION: (1)..(1290)
<223> OTHER INFORMATION: A nucleic acid sequence obtained from
      Xenorhabdus nematophila strain AN6/1 encoding a TIC11511
      pesticidal PirB protein sequence.

<400> SEQUENCE: 142

atgaataatg aaccgatgaa tactaatgaa tcacaagctt cagagatagt accctcaatg     60

aatgaatcta tattagcagc accttattca atttctacac ctaattatga atgggatatg    120

tcatcaataa taaaagatgc cattattggt ggtataggct ttattcctgg tccgggctca    180

gcaatatcat ttttgttagg gttattttgg ccacaacaaa ccgacaatac ttgggagcaa    240

attctccaaa aagtagaaca aatgatcgag caagccaatc tcaaaactat tcaaggaata    300

ttgaacggcg atatacaaga aattaaaggc aaaatggaac atgtgcaatt catgctagaa    360

tcctcacctg gcactcaaga aagccatgac gcatacatgt ttctggcgag atatctggtc    420

agtatagacg aaaaattcaa gtcttttgat aacaaaacaa attatcaaat tcttcccatg    480

tataccaata cgattatgtt acaagcccct tattggaaaa tgggtataga gagaaaagat    540

gagataaaac taacagatat agaagttaat gaattaaaag agctgatagg aaaattatct    600

accagcgccg ataaatatat tcatgatgtc tatactcgtg aatatgataa tgcgatgaac    660

acttcaacag cagcaaatat caccaataat ttattatctg taagaggcta ttgtttatta    720

catggtttag aatgtctcga agtcattaac catatacaaa ataatagcct tgagcaaagt    780

ttttatccta aaactatcag ctactccacc gtattcgatc gccagacaaa taaaacaagg    840

gttcaagccc tgacagaaga cgatcaaatg caagagccat tcaagcctgc tttaattaat    900

gggaagtaca acaaaataaa atcattgatt gggtatgtac aaagaatcgg aaacgcaccc    960

agagttggag gcattaaagt cacatttgca aacgatgcat cttataccct cggtacagta   1020

acttcagaag taaactcaat tgaactgaat gacagcgtta taaccagcct ggaagtatgg   1080

ggaaatggcg ctattgatga ggcattcttt acattaagtg acggacgtca atttaggctt   1140

ggccaacgct atgccagtaa ctatagaaaa tatgctgtcg ataaccacta tatttcagga   1200

ttgtacttag ccagtgatga accttcattg gcaggccaag cagcaggcat tgcagtttca   1260

taccatatga tagctgataa aaaatcatag                                    1290
```

<210> SEQ ID NO 143
<211> LENGTH: 429
<212> TYPE: PRT
<213> ORGANISM: Xenorhabdus nematophila
<220> FEATURE:
<221> NAME/KEY: MISC_FEATURE
<222> LOCATION: (1)..(429)
<223> OTHER INFORMATION: The amino acid sequence of the TIC11511 PirB protein.

<400> SEQUENCE: 143

```
Met Asn Asn Glu Pro Met Asn Thr Asn Glu Ser Gln Ala Ser Glu Ile
1               5                   10                  15

Val Pro Ser Met Asn Glu Ser Ile Leu Ala Ala Pro Tyr Ser Ile Ser
            20                  25                  30

Thr Pro Asn Tyr Glu Trp Asp Met Ser Ser Ile Ile Lys Asp Ala Ile
        35                  40                  45

Ile Gly Gly Ile Gly Phe Ile Pro Gly Pro Gly Ser Ala Ile Ser Phe
    50                  55                  60

Leu Leu Gly Leu Phe Trp Pro Gln Gln Thr Asp Asn Thr Trp Glu Gln
65                  70                  75                  80

Ile Leu Gln Lys Val Glu Gln Met Ile Glu Gln Ala Asn Leu Lys Thr
                85                  90                  95

Ile Gln Gly Ile Leu Asn Gly Asp Ile Gln Glu Ile Lys Gly Lys Met
            100                 105                 110

Glu His Val Gln Phe Met Leu Glu Ser Ser Pro Gly Thr Gln Glu Ser
        115                 120                 125

His Asp Ala Tyr Met Phe Leu Ala Arg Tyr Leu Val Ser Ile Asp Glu
    130                 135                 140

Lys Phe Lys Ser Phe Asp Asn Lys Thr Asn Tyr Gln Ile Leu Pro Met
145                 150                 155                 160

Tyr Thr Asn Thr Ile Met Leu Gln Ala Pro Tyr Trp Lys Met Gly Ile
                165                 170                 175

Glu Arg Lys Asp Glu Ile Lys Leu Thr Asp Ile Glu Val Asn Glu Leu
            180                 185                 190

Lys Glu Leu Ile Gly Lys Leu Ser Thr Ser Ala Asp Lys Tyr Ile His
        195                 200                 205

Asp Val Tyr Thr Arg Glu Tyr Asp Asn Ala Met Asn Thr Ser Thr Ala
    210                 215                 220

Ala Asn Ile Thr Asn Asn Leu Leu Ser Val Arg Gly Tyr Cys Leu Leu
225                 230                 235                 240

His Gly Leu Glu Cys Leu Glu Val Ile Asn His Ile Gln Asn Asn Ser
                245                 250                 255

Leu Glu Gln Ser Phe Tyr Pro Lys Thr Ile Ser Tyr Ser Thr Val Phe
            260                 265                 270

Asp Arg Gln Thr Asn Lys Thr Arg Val Gln Ala Leu Thr Glu Asp Asp
        275                 280                 285

Gln Met Gln Glu Pro Phe Lys Pro Ala Leu Ile Asn Gly Lys Tyr Asn
    290                 295                 300

Lys Ile Lys Ser Leu Ile Gly Tyr Val Gln Arg Ile Gly Asn Ala Pro
305                 310                 315                 320

Arg Val Gly Gly Ile Lys Val Thr Phe Ala Asn Asp Ala Ser Tyr Thr
                325                 330                 335

Leu Gly Thr Val Thr Ser Glu Val Asn Ser Ile Glu Leu Asn Asp Ser
            340                 345                 350
```

-continued

Val Ile Thr Ser Leu Glu Val Trp Gly Asn Gly Ala Ile Asp Glu Ala
        355                 360                 365

Phe Phe Thr Leu Ser Asp Gly Arg Gln Phe Arg Leu Gly Gln Arg Tyr
    370                 375                 380

Ala Ser Asn Tyr Arg Lys Tyr Ala Val Asp Asn His Tyr Ile Ser Gly
385                 390                 395                 400

Leu Tyr Leu Ala Ser Asp Glu Pro Ser Leu Ala Gly Gln Ala Ala Gly
                405                 410                 415

Ile Ala Val Ser Tyr His Met Ile Ala Asp Lys Lys Ser
            420                 425

<210> SEQ ID NO 144
<211> LENGTH: 1716
<212> TYPE: DNA
<213> ORGANISM: Artificial
<220> FEATURE:
<223> OTHER INFORMATION: A nucleic acid sequence encoding a PirAB fusion protein, TIC11513 comprised of the TIC10364 and TIC11511 coding sequences in operable linkage and in frame.

<400> SEQUENCE: 144
atgagcataa tcaatataaa tataagtggt agtagtgaca ttacaatcat aaacaatacc 60
ccatctaacc cagaaccact catttacaat acagacacac ccgcatcaga acctcttacc 120
gtcaatcctt atagggatat gacaatagag ccacactctt ctattgaggc aataagaatt 180
gatacgccaa ttattcccga aacccgcccc aattattacg tagccaattc tggccccgca 240
tcatcagtta gagccgtttt ttattggtct cactctttca catcagaatg gttcgaatat 300
tctgctatca cagtgaaagc cggggaagac ggcatattac aatcaccgag caactctgtg 360
tattacagca aggtcgtcat ttataacgaa accgataaac gcgcctttgt tactggatat 420
aataagatga ataatgaacc gatgaatact aatgaatcac aagcttcaga gatagtaccc 480
tcaatgaatg aatctatatt agcagcacct tattcaattt ctacacctaa ttatgaatgg 540
gatatgtcat caataataaa agatgccatt attggtggta taggctttat tcctggtccg 600
ggctcagcaa tatcattttt gttagggtta ttttggccac aacaaaccga caatacttgg 660
gagcaaattc tccaaaaagt agaacaaatg atcgagcaag ccaatctcaa aactattcaa 720
ggaatattga acggcgatat acaagaaatt aaaggcaaaa tggaacatgt gcaattcatg 780
ctagaatcct cacctggcac tcaagaaagc catgacgcat acatgtttct ggcgagatat 840
ctggtcagta tagacgaaaa attcaagtct tttgataaca aaacaaatta tcaaattctt 900
cccatgtata ccaatacgat tatgttacaa gccccttatt ggaaaatggg tatagagaga 960
aaagatgaga taaaactaac agatatagaa gttaatgaat taaaagagct gataggaaaa 1020
ttatctacca gcgccgataa atatattcat gatgtctata ctcgtgaata tgataatgcg 1080
atgaacactt caacagcagc aaatatcacc aataatttat tatctgtaag aggctattgt 1140
ttattacatg gtttagaatg tctcgaagtc attaaccata tacaaaataa tagccttgag 1200
caaagttttt atcctaaaac tatcagctac tccaccgtat tcgatcgcca gacaaataaa 1260
acaagggttc aagccctgac agaagacgat caaatgcaag agccattcaa gcctgcttta 1320
attaatggga agtacaacaa aataaaatca ttgattgggt atgtacaaag aatcggaaac 1380
gcacccagag ttggaggcat taaagtcaca tttgcaaacg atgcatctta taccctcggt 1440
acagtaactt cagaagtaaa ctcaattgaa ctgaatgaca gcgttataac cagcctggaa 1500
gtatggggaa atggcgctat tgatgaggca ttctttacat taagtgacgg acgtcaattt 1560
aggcttggcc aacgctatgc cagtaactat agaaaatatg ctgtcgataa ccactatatt 1620
tcaggattgt acttagccag tgatgaacct tcattggcag gccaagcagc aggcattgca 1680
gtttcatacc atatgatagc tgataaaaaa tcatag 1716

<210> SEQ ID NO 145
<211> LENGTH: 571
<212> TYPE: PRT
<213> ORGANISM: Artificial
<220> FEATURE:
<223> OTHER INFORMATION: The amino acid sequence of the TIC11513 PirAB fusion protein.

<400> SEQUENCE: 145

Met Ser Ile Ile Asn Ile Asn Ile Ser Gly Ser Ser Asp Ile Thr Ile
1 5 10 15

Ile Asn Asn Thr Pro Ser Asn Pro Glu Pro Leu Ile Tyr Asn Thr Asp
20 25 30

Thr Pro Ala Ser Glu Pro Leu Thr Val Asn Pro Tyr Arg Asp Met Thr
35 40 45

Ile Glu Pro His Ser Ser Ile Glu Ala Ile Arg Ile Asp Thr Pro Ile
50 55 60

Ile Pro Glu Thr Arg Pro Asn Tyr Tyr Val Ala Asn Ser Gly Pro Ala
65 70 75 80

Ser Ser Val Arg Ala Val Phe Tyr Trp Ser His Ser Phe Thr Ser Glu
85 90 95

Trp Phe Glu Tyr Ser Ala Ile Thr Val Lys Ala Gly Glu Asp Gly Ile
100 105 110

Leu Gln Ser Pro Ser Asn Ser Val Tyr Tyr Ser Lys Val Val Ile Tyr
115 120 125

Asn Glu Thr Asp Lys Arg Ala Phe Val Thr Gly Tyr Asn Lys Met Asn
130 135 140

Asn Glu Pro Met Asn Thr Asn Glu Ser Gln Ala Ser Glu Ile Val Pro
145 150 155 160

Ser Met Asn Glu Ser Ile Leu Ala Ala Pro Tyr Ser Ile Ser Thr Pro
165 170 175

Asn Tyr Glu Trp Asp Met Ser Ser Ile Ile Lys Asp Ala Ile Ile Gly
180 185 190

Gly Ile Gly Phe Ile Pro Gly Pro Gly Ser Ala Ile Ser Phe Leu Leu
195 200 205

Gly Leu Phe Trp Pro Gln Gln Thr Asp Asn Thr Trp Glu Gln Ile Leu
210 215 220

Gln Lys Val Glu Gln Met Ile Glu Gln Ala Asn Leu Lys Thr Ile Gln
225 230 235 240

Gly Ile Leu Asn Gly Asp Ile Gln Glu Ile Lys Gly Lys Met Glu His
245 250 255

Val Gln Phe Met Leu Glu Ser Ser Pro Gly Thr Gln Glu Ser His Asp
260 265 270

Ala Tyr Met Phe Leu Ala Arg Tyr Leu Val Ser Ile Asp Glu Lys Phe
275 280 285

Lys Ser Phe Asp Asn Lys Thr Asn Tyr Gln Ile Leu Pro Met Tyr Thr
290 295 300

Asn Thr Ile Met Leu Gln Ala Pro Tyr Trp Lys Met Gly Ile Glu Arg
305 310 315 320

Lys Asp Glu Ile Lys Leu Thr Asp Ile Glu Val Asn Glu Leu Lys Glu

```
                325                 330                 335

Leu Ile Gly Lys Leu Ser Thr Ser Ala Asp Lys Tyr Ile His Asp Val
            340                 345                 350

Tyr Thr Arg Glu Tyr Asp Asn Ala Met Asn Thr Ser Thr Ala Ala Asn
        355                 360                 365

Ile Thr Asn Asn Leu Leu Ser Val Arg Gly Tyr Cys Leu Leu His Gly
    370                 375                 380

Leu Glu Cys Leu Glu Val Ile Asn His Ile Gln Asn Asn Ser Leu Glu
385                 390                 395                 400

Gln Ser Phe Tyr Pro Lys Thr Ile Ser Tyr Ser Thr Val Phe Asp Arg
                405                 410                 415

Gln Thr Asn Lys Thr Arg Val Gln Ala Leu Thr Glu Asp Asp Gln Met
            420                 425                 430

Gln Glu Pro Phe Lys Pro Ala Leu Ile Asn Gly Lys Tyr Asn Lys Ile
        435                 440                 445

Lys Ser Leu Ile Gly Tyr Val Gln Arg Ile Gly Asn Ala Pro Arg Val
    450                 455                 460

Gly Gly Ile Lys Val Thr Phe Ala Asn Asp Ala Ser Tyr Thr Leu Gly
465                 470                 475                 480

Thr Val Thr Ser Glu Val Asn Ser Ile Glu Leu Asn Asp Ser Val Ile
                485                 490                 495

Thr Ser Leu Glu Val Trp Gly Asn Gly Ala Ile Asp Glu Ala Phe Phe
            500                 505                 510

Thr Leu Ser Asp Gly Arg Gln Phe Arg Leu Gly Gln Arg Tyr Ala Ser
        515                 520                 525

Asn Tyr Arg Lys Tyr Ala Val Asp Asn His Tyr Ile Ser Gly Leu Tyr
    530                 535                 540

Leu Ala Ser Asp Glu Pro Ser Leu Ala Gly Gln Ala Ala Gly Ile Ala
545                 550                 555                 560

Val Ser Tyr His Met Ile Ala Asp Lys Lys Ser
                565                 570
```

<210> SEQ ID NO 146
<211> LENGTH: 1689
<212> TYPE: DNA
<213> ORGANISM: Artificial
<220> FEATURE:
<223> OTHER INFORMATION: a synthetic coding sequence used for expression in plant cells encoding a TIC10376PL PirAB fusion protein with an additional alanine codon inserted after the initiating methionine codon.

<400> SEQUENCE: 146

```
atggctccgg tgaaccagat cgggctccac aacgagaagg tcaagaacat gcggaagatc      60

accgtggaca atgacgtggt gggccacgac accgagatca acagcgtcgt gagcagcacg     120

gccgagaaga tccggcagca gttcggcgtg aaagtcgatc ccaattcgtc ccaggagaag     180

ttctacatcg ccacgcccat catcccggag tcccgcaaga acatcgtggt caccaacgag     240

ggcctggcgg acgtcatcac cgccaagtac tattggagcc acagcttcac cagcgaatac     300

tttgaggaca actcggtgga cgtcaaggtg ggcgagagca aagtgctggt cgctccgagc     360

aaccctctct actacagcaa ggtcgtcatc ttcaacaaca ccaagtcggt ggccttcgtc     420

acggtccgcg agaagatgag cgacatcgtg aagtacaacg acgtcagcgc gcccatcccg     480

tacgcggttt acagtaacgc cgtgtacgcc ttcgagtggg actcgtcggc gatcctcaag     540

caagcagtgg tgaagggctt gtcctacgtg ccgcacgtcg ggaagtacct ctcgtacatc     600
```

-continued gtcggattct tctggaagga caaggagaag gacatctggc aagaggtggt gggcaaggtg 660
cagcagttgg tagaggactc gatcctcaag gcggtgaagg gcatcctgtc cggcaacatc 720
aacgagctaa aggagaagat gaatgaggtg atccgctccc ttgagaagaa tttgggaacc 780
caagaggccc gcgacgacta catgcacctg gcccgcagca tggtgggcaa ggaggcaagc 840
cttatcttcc acgagaacaa gaccaacttc cacatcctgc cgatgtactc tacgctcgcc 900
ctcatgcaga tcatgtactg gacggtgggc atcgaacgcc gcaaggaaat tggtctgagc 960
gacatcgagg tcgagaacct ccggagctac atcaagaagc tcgtcagcga cgcggagcac 1020
cacgtgaacc gggtgtacaa gctggagctg gactccgtgg tcagcgactc ggacgtgaac 1080
cgggtggcgg acaacatcat gtacgtccac ggctactgcc agattcacgg cctggagtac 1140
atggacatca tcaagaacat acagtctcgt ggcaacaaca tcaccggctt ctaccctagg 1200
actatctcgt actctacatt ctttggctcg ccgaccagcg acgcgcggat tctggccctg 1260
cggccggaga aggacatgcc cgagcctttc aagcccaagt tcctgaacga gcggttcaac 1320
aagatcgcgt cggtcaaggg ctacatcgtc cggatcggag gtgccaagag ggtcggcggc 1380
ctggagatca cgttcgagaa cggtcgaag taccagcaag ggcaagcgac caacgagcac 1440
gagatcgtga acctcaaggg caaccttatc aagaccctgg aggtgtgggg aaacggtgcc 1500
atcgacgagg ccaagttcac gctgacgaac ggcgacgtcc tcaccatcgg gcagcgcaac 1560
agcagcaact accggaagtt ctccctggac ggccactaca tctgcggcgt gttcatcgcc 1620
aacgaccgct cgggcctcgc gggacaagcc gcgaacatcg ccgtctccta ccatcagctc 1680
gtcgagtga 1689

<210> SEQ ID NO 147
<211> LENGTH: 562
<212> TYPE: PRT
<213> ORGANISM: Artificial
<220> FEATURE:
<223> OTHER INFORMATION: The amino acid sequence of the TIC10376PL PirAB
fusion protein.

<400> SEQUENCE: 147

Met Ala Pro Val Asn Gln Ile Gly Leu His Asn Glu Lys Val Lys Asn
1 5 10 15

Met Arg Lys Ile Thr Val Asp Asn Asp Val Val Gly His Asp Thr Glu
20 25 30

Ile Asn Ser Val Val Ser Ser Thr Ala Glu Lys Ile Arg Gln Gln Phe
35 40 45

Gly Val Lys Val Asp Pro Asn Ser Ser Gln Glu Lys Phe Tyr Ile Ala
50 55 60

Thr Pro Ile Ile Pro Glu Ser Arg Lys Asn Ile Val Val Thr Asn Glu
65 70 75 80

Gly Leu Ala Asp Val Ile Thr Ala Lys Tyr Tyr Trp Ser His Ser Phe
85 90 95

Thr Ser Glu Tyr Phe Glu Asp Asn Ser Val Asp Val Lys Val Gly Glu
100 105 110

Ser Lys Val Leu Val Ala Pro Ser Asn Pro Leu Tyr Tyr Ser Lys Val
115 120 125

Val Ile Phe Asn Asn Thr Lys Ser Val Ala Phe Val Thr Val Arg Glu
130 135 140

Lys Met Ser Asp Ile Val Lys Tyr Asn Asp Val Ser Ala Pro Ile Pro
145 150 155 160

```
Tyr Ala Val Tyr Ser Asn Ala Val Tyr Ala Phe Glu Trp Asp Ser Ser
                165                 170                 175

Ala Ile Leu Lys Gln Ala Val Val Lys Gly Leu Ser Tyr Val Pro His
            180                 185                 190

Val Gly Lys Tyr Leu Ser Tyr Ile Val Gly Phe Phe Trp Lys Asp Lys
        195                 200                 205

Glu Lys Asp Ile Trp Gln Glu Val Val Gly Lys Val Gln Gln Leu Val
    210                 215                 220

Glu Asp Ser Ile Leu Lys Ala Val Lys Gly Ile Leu Ser Gly Asn Ile
225                 230                 235                 240

Asn Glu Leu Lys Glu Lys Met Asn Glu Val Ile Arg Ser Leu Glu Lys
                245                 250                 255

Asn Leu Gly Thr Gln Glu Ala Arg Asp Asp Tyr Met His Leu Ala Arg
            260                 265                 270

Ser Met Val Gly Lys Glu Ala Ser Leu Ile Phe His Glu Asn Lys Thr
        275                 280                 285

Asn Phe His Ile Leu Pro Met Tyr Ser Thr Leu Ala Leu Met Gln Ile
    290                 295                 300

Met Tyr Trp Thr Val Gly Ile Glu Arg Arg Lys Glu Ile Gly Leu Ser
305                 310                 315                 320

Asp Ile Glu Val Glu Asn Leu Arg Ser Tyr Ile Lys Lys Leu Val Ser
                325                 330                 335

Asp Ala Glu His His Val Asn Arg Val Tyr Lys Leu Glu Leu Asp Ser
            340                 345                 350

Val Val Ser Asp Ser Asp Val Asn Arg Val Ala Asp Asn Ile Met Tyr
        355                 360                 365

Val His Gly Tyr Cys Gln Ile His Gly Leu Glu Tyr Met Asp Ile Ile
    370                 375                 380

Lys Asn Ile Gln Ser Arg Gly Asn Asn Ile Thr Gly Phe Tyr Pro Arg
385                 390                 395                 400

Thr Ile Ser Tyr Ser Thr Phe Phe Gly Ser Pro Thr Ser Asp Ala Arg
                405                 410                 415

Ile Leu Ala Leu Arg Pro Glu Lys Asp Met Pro Glu Pro Phe Lys Pro
            420                 425                 430

Lys Phe Leu Asn Glu Arg Phe Asn Lys Ile Ala Ser Val Lys Gly Tyr
        435                 440                 445

Ile Val Arg Ile Gly Gly Ala Lys Arg Val Gly Gly Leu Glu Ile Thr
    450                 455                 460

Phe Glu Asn Gly Ser Lys Tyr Gln Gln Gly Gln Ala Thr Asn Glu His
465                 470                 475                 480

Glu Ile Val Asn Leu Lys Gly Asn Leu Ile Lys Thr Leu Glu Val Trp
                485                 490                 495

Gly Asn Gly Ala Ile Asp Glu Ala Lys Phe Thr Leu Thr Asn Gly Asp
            500                 505                 510

Val Leu Thr Ile Gly Gln Arg Asn Ser Ser Asn Tyr Arg Lys Phe Ser
        515                 520                 525

Leu Asp Gly His Tyr Ile Cys Gly Val Phe Ile Ala Asn Asp Arg Ser
    530                 535                 540

Gly Leu Ala Gly Gln Ala Ala Asn Ile Ala Val Ser Tyr His Gln Leu
545                 550                 555                 560

Val Glu
```

<210> SEQ ID NO 148
<211> LENGTH: 1710
<212> TYPE: DNA
<213> ORGANISM: Artificial
<220> FEATURE:
<223> OTHER INFORMATION: A synthetic coding sequence used for expression in plant cells encoding a TIC10378PL PirAB fusion protein with an additional alanine codon inserted after the initiating methionine codon.

<400> SEQUENCE: 148
atggctatca cgatcaacat caacaccaac ggcgtgaacg gcatcaccat caccaacagc 60
aacaacgagc cgacgcccgt aagcacgacc tacggtccca acactccggc gagcgagccg 120
ctcaccgtca gcaactactc ggacatcacc atcgagccgc acagctccgt ccaggccacg 180
cgcatcgaca cgccgatcat cccggagacc cggccggact actacgtcgc taactccggg 240
cccgcgccga ccgtccgcgc cgtgttctac tggtcgcaca gcttcacgtc cgagtggttc 300
gagtccagct ccataacggt gaaggcgggc gaggatggta tcctcaaagc gcccggaaac 360
tcgctctact acagcaaggt ggtcatctac aatgacaccg acaagcgcgc cttcgtgacc 420
ggctacaaca agatgaacac gacgccgatc accgtgtcgg agaacgagac gtcgcctctc 480
ctcaccgacg tcatgccgat ggacctgtac gcggtgtcca cacccgacta cgagtgggac 540
atgtcctcca tcatcaagga cgccatcatc ggcggcatcg gcttcattcc cggtcccggc 600
cctgctctgt cgttcttgct cggactgttc tggccgcagc agaaggacaa cacttgggag 660
caaatccttc agaaggtgga gcagatgatc gagaacgcgg tgctccagac gatcaagggc 720
atcctgaacg gcgagatcca ggagatcaag ggcaagatgg agcacgtgga gtccatgctc 780
aagaatagcc ctggtagcca agagtcccac gacgcctaca tgttcctagc ccgttacctc 840
gtttccatcg acgagaaatt caagtccttc gacaaccgca cgaactacca gatcctcccg 900
atgtacacca ataccatcat gctccagatt ccctactgga agatgggcat cgagaagaag 960
aaggacattg gcctgacgga catcgaggtc aacgaactta aagagctgat cgacaagctc 1020
gtcgggaagg ccaagaatta catccacaca atgtacacta atgagtacaa cgacgcgatc 1080
aacacgagca cggctgggtc ggttaccaac aacctgctct ccgtgcgcgg gtactgcttg 1140
ctgcacgggc tagagtgcat tgagctgatc gagcacatcc agaacaatag cctggagagc 1200
gggttctacc ctaagaccat ctcgtactcc acggtgttcg accgccctac gaacaagatg 1260
cggatacagg cgctgaccga ggacgacgcg atgcaagaac cgttcaagcc gagcctgatt 1320
aacggcaagt acaacaagat ccagtcgatt atcgggtacg tccagcggat cgggaacgct 1380
ccgcgcgtcg gcgggattaa gatcaccttc acaaacggta gcagttacac gctcgggact 1440
gtcacgtccg agacaaatag tatcgagttg aacgacagcg tgatcgagtc cctggaggtg 1500
tggggcaacg gcgcggtgga cgaggcgctg tttaagctgt cggatggccg tctgctgcga 1560
ataggcgagc ggtacgccaa gaaataccgc aagtacgccg tggaccacca ttacatcgcc 1620
gggatctacc tcgccagcga tgaaccctcg cttgcgggac aggcggccgg gatcgcggtg 1680
tcgtatcaca tgatggccga caagaaatga 1710

<210> SEQ ID NO 149
<211> LENGTH: 569
<212> TYPE: PRT
<213> ORGANISM: Artificial
<220> FEATURE:
<223> OTHER INFORMATION: The amino acid sequence of the TIC10378PL PirAB fusion protein.

<400> SEQUENCE: 149

```
Met Ala Ile Thr Ile Asn Ile Asn Thr Asn Gly Val Asn Gly Ile Thr
1               5                   10                  15

Ile Thr Asn Ser Asn Asn Glu Pro Thr Pro Val Ser Thr Thr Tyr Gly
            20                  25                  30

Pro Asn Thr Pro Ala Ser Glu Pro Leu Thr Val Ser Asn Tyr Ser Asp
        35                  40                  45

Ile Thr Ile Glu Pro His Ser Ser Val Gln Ala Thr Arg Ile Asp Thr
    50                  55                  60

Pro Ile Ile Pro Glu Thr Arg Pro Asp Tyr Tyr Val Ala Asn Ser Gly
65                  70                  75                  80

Pro Ala Pro Thr Val Arg Ala Val Phe Tyr Trp Ser His Ser Phe Thr
                85                  90                  95

Ser Glu Trp Phe Glu Ser Ser Ser Ile Thr Val Lys Ala Gly Glu Asp
            100                 105                 110

Gly Ile Leu Lys Ala Pro Gly Asn Ser Leu Tyr Tyr Ser Lys Val Val
        115                 120                 125

Ile Tyr Asn Asp Thr Asp Lys Arg Ala Phe Val Thr Gly Tyr Asn Lys
    130                 135                 140

Met Asn Thr Thr Pro Ile Thr Val Ser Glu Asn Glu Thr Ser Pro Leu
145                 150                 155                 160

Leu Thr Asp Val Met Pro Met Asp Leu Tyr Ala Val Ser Thr Pro Asp
                165                 170                 175

Tyr Glu Trp Asp Met Ser Ser Ile Ile Lys Asp Ala Ile Ile Gly Gly
            180                 185                 190

Ile Gly Phe Ile Pro Gly Pro Gly Pro Ala Leu Ser Phe Leu Leu Gly
        195                 200                 205

Leu Phe Trp Pro Gln Gln Lys Asp Asn Thr Trp Glu Gln Ile Leu Gln
    210                 215                 220

Lys Val Glu Gln Met Ile Glu Asn Ala Val Leu Gln Thr Ile Lys Gly
225                 230                 235                 240

Ile Leu Asn Gly Glu Ile Gln Glu Ile Lys Gly Lys Met Glu His Val
                245                 250                 255

Glu Ser Met Leu Lys Asn Ser Pro Gly Ser Gln Glu Ser His Asp Ala
            260                 265                 270

Tyr Met Phe Leu Ala Arg Tyr Leu Val Ser Ile Asp Glu Lys Phe Lys
        275                 280                 285

Ser Phe Asp Asn Arg Thr Asn Tyr Gln Ile Leu Pro Met Tyr Thr Asn
    290                 295                 300

Thr Ile Met Leu Gln Ile Pro Tyr Trp Lys Met Gly Ile Glu Lys Lys
305                 310                 315                 320

Lys Asp Ile Gly Leu Thr Asp Ile Glu Val Asn Glu Leu Lys Glu Leu
                325                 330                 335

Ile Asp Lys Leu Val Gly Lys Ala Lys Asn Tyr Ile His Thr Met Tyr
            340                 345                 350

Thr Asn Glu Tyr Asn Asp Ala Ile Asn Thr Ser Thr Ala Gly Ser Val
        355                 360                 365

Thr Asn Asn Leu Leu Ser Val Arg Gly Tyr Cys Leu Leu His Gly Leu
    370                 375                 380

Glu Cys Ile Glu Leu Ile Glu His Ile Gln Asn Asn Ser Leu Glu Ser
385                 390                 395                 400

Gly Phe Tyr Pro Lys Thr Ile Ser Tyr Ser Thr Val Phe Asp Arg Pro
                405                 410                 415
```

Thr Asn Lys Met Arg Ile Gln Ala Leu Thr Glu Asp Asp Ala Met Gln
420 425 430

Glu Pro Phe Lys Pro Ser Leu Ile Asn Gly Lys Tyr Asn Lys Ile Gln
435 440 445

Ser Ile Ile Gly Tyr Val Gln Arg Ile Gly Asn Ala Pro Arg Val Gly
450 455 460

Gly Ile Lys Ile Thr Phe Thr Asn Gly Ser Ser Tyr Thr Leu Gly Thr
465 470 475 480

Val Thr Ser Glu Thr Asn Ser Ile Glu Leu Asn Asp Ser Val Ile Glu
485 490 495

Ser Leu Glu Val Trp Gly Asn Gly Ala Val Asp Glu Ala Leu Phe Lys
500 505 510

Leu Ser Asp Gly Arg Leu Leu Arg Ile Gly Glu Arg Tyr Ala Lys Lys
515 520 525

Tyr Arg Lys Tyr Ala Val Asp His His Tyr Ile Ala Gly Ile Tyr Leu
530 535 540

Ala Ser Asp Glu Pro Ser Leu Ala Gly Gln Ala Ala Gly Ile Ala Val
545 550 555 560

Ser Tyr His Met Met Ala Asp Lys Lys
565

<210> SEQ ID NO 150
<211> LENGTH: 1707
<212> TYPE: DNA
<213> ORGANISM: Artificial
<220> FEATURE:
<223> OTHER INFORMATION: A synthetic coding sequence used for expression in plant cells encoding a TIC10380PL PirAB fusion protein with an additional alanine codon inserted after the initiating methionine codon.

<400> SEQUENCE: 150
atggctatca ccatcaacat cagcggcggg tccgtgacga tcaacaacac ctacaacatc 60
acttccgaga gcggcatcca gaacacgcca gcgtcggagc ctctcaccgt catcccgtac 120
cgtgacatga ccatcgagcc tcacagcagc attgaggcca cccgcaccga cacgccgatc 180
atcccggaga cgcggcccaa ctactacatc gctaactcgg gcccggcctc cgaggtgcgc 240
gcggtgttct actggtcgca ctcgttcacg tcgcagtggt tcgagtcgtc cagcataatc 300
gtcaaggcgg gcgaggacgg catcctccag tcgccgtcga acagtctgta ctactcgaag 360
gtggtcatct acaatgacac cgacaagcgc gcgttcgtca ccggctacaa caagatgaac 420
aacacctcca tcaacatcaa tgagaacgag acgctgccgc ttgaagtcat cccgtccatg 480
cccgagccca tgctgatcgt cccgtatgcc acgagcacgc cggattacga gtgggacgcc 540
agcgggatca tcaaggatgc catcatcggc gggatcgggt tcataccggg ccctggccca 600
gcgatctcct tcctgctggg cttgttctgg ccgcaacaag ctgacaacac ctgggagcag 660
atcctccaga aggtcgagca gatgatcgag gacgcagtgc taaagaccat ccagggcatc 720
ctgaacggtg acatccagga gatcaagggc aagatggagc acgtgcagta catgctggag 780
acatcgcccg gcagccagga gtcccgtgag gcgtacatgt tcctcgcccg ctacctcgtc 840
agcattgacg agaagttcaa gtccttcgac aacaagacca attaccagat cctgcccatg 900
tacacgaata ctctcatgct ccaagtgcca tactggaaga tgggcatcga gaagcagaag 960
gacatcggcc tctccgacat cgaagtcaac gagcttaaac agctaatcga caagctctac 1020
accaaagcta attcgtacat acacgaaaca tacacacggc agtacaacga cgcgataaac 1080

```
accagcacgg cagccaacat caccaacaac ctgttcagcg tgcgcggcta ctgcttgctg   1140

cacgggctgg agtgcctgga gatgattgag catcttcaga agaatagcct tgaatcgggt   1200

ttctacccta agaccataag ctacagcaca gtctttgacc gtcagacgcc caagatgcgg   1260

atacaagccc tgaccgagga cgatcagatg caagagccgc tcaaaccctc gctgataaac   1320

ggcaagtaca accagatcaa gagcctcacc ggatacgtcc ggcggatcgg caacgctccg   1380

cgcgtcggcg gaatgacgat caccttcgcc aatggcgcgt cctacaccct cgggacggtc   1440

acctccgaga ccaccagtat cgagctgaac ggctccgtga tcgagtccct ggaggtgtgg   1500

ggcgacggcg cggtggacga ggcgctcttc accttaagcg acaagcgcct gttccgtatc   1560

ggcgagcgct atgcgcgcaa gtacaagaag tatgccgtgg acagccacta catcgctggg   1620

ctctacctgg cctcggacga gccatcgttg gccgggcaag ctgcgggcat tgccgtcagc   1680

taccacatgc tcgacgacaa gaaatga                                       1707
```

<210> SEQ ID NO 151
<211> LENGTH: 568
<212> TYPE: PRT
<213> ORGANISM: Artificial
<220> FEATURE:
<223> OTHER INFORMATION: The amino acid sequence of the TIC10380PL PirAB fusion protein.

<400> SEQUENCE: 151

```
Met Ala Ile Thr Ile Asn Ile Ser Gly Gly Ser Val Thr Ile Asn Asn
1               5                   10                  15

Thr Tyr Asn Ile Thr Ser Glu Ser Gly Ile Gln Asn Thr Pro Ala Ser
            20                  25                  30

Glu Pro Leu Thr Val Ile Pro Tyr Arg Asp Met Thr Ile Glu Pro His
        35                  40                  45

Ser Ser Ile Glu Ala Thr Arg Thr Asp Thr Pro Ile Ile Pro Glu Thr
    50                  55                  60

Arg Pro Asn Tyr Tyr Ile Ala Asn Ser Gly Pro Ala Ser Glu Val Arg
65                  70                  75                  80

Ala Val Phe Tyr Trp Ser His Ser Phe Thr Ser Gln Trp Phe Glu Ser
                85                  90                  95

Ser Ser Ile Ile Val Lys Ala Gly Glu Asp Gly Ile Leu Gln Ser Pro
            100                 105                 110

Ser Asn Ser Leu Tyr Tyr Ser Lys Val Val Ile Tyr Asn Asp Thr Asp
        115                 120                 125

Lys Arg Ala Phe Val Thr Gly Tyr Asn Lys Met Asn Asn Thr Ser Ile
    130                 135                 140

Asn Ile Asn Glu Asn Glu Thr Leu Pro Leu Glu Val Ile Pro Ser Met
145                 150                 155                 160

Pro Glu Pro Met Leu Ile Val Pro Tyr Ala Thr Ser Thr Pro Asp Tyr
                165                 170                 175

Glu Trp Asp Ala Ser Gly Ile Ile Lys Asp Ala Ile Ile Gly Gly Ile
            180                 185                 190

Gly Phe Ile Pro Gly Pro Gly Pro Ala Ile Ser Phe Leu Leu Gly Leu
        195                 200                 205

Phe Trp Pro Gln Gln Ala Asp Asn Thr Trp Glu Gln Ile Leu Gln Lys
    210                 215                 220

Val Glu Gln Met Ile Glu Asp Ala Val Leu Lys Thr Ile Gln Gly Ile
225                 230                 235                 240
```

```
Leu Asn Gly Asp Ile Gln Glu Ile Lys Gly Lys Met Glu His Val Gln
                245                 250                 255

Tyr Met Leu Glu Thr Ser Pro Gly Ser Gln Glu Ser Arg Glu Ala Tyr
            260                 265                 270

Met Phe Leu Ala Arg Tyr Leu Val Ser Ile Asp Glu Lys Phe Lys Ser
        275                 280                 285

Phe Asp Asn Lys Thr Asn Tyr Gln Ile Leu Pro Met Tyr Thr Asn Thr
    290                 295                 300

Leu Met Leu Gln Val Pro Tyr Trp Lys Met Gly Ile Glu Lys Gln Lys
305                 310                 315                 320

Asp Ile Gly Leu Ser Asp Ile Glu Val Asn Glu Leu Lys Gln Leu Ile
                325                 330                 335

Asp Lys Leu Tyr Thr Lys Ala Asn Ser Tyr Ile His Glu Thr Tyr Thr
            340                 345                 350

Arg Gln Tyr Asn Asp Ala Ile Asn Thr Ser Thr Ala Ala Asn Ile Thr
        355                 360                 365

Asn Asn Leu Phe Ser Val Arg Gly Tyr Cys Leu Leu His Gly Leu Glu
    370                 375                 380

Cys Leu Glu Met Ile Glu His Leu Gln Lys Asn Ser Leu Glu Ser Gly
385                 390                 395                 400

Phe Tyr Pro Lys Thr Ile Ser Tyr Ser Thr Val Phe Asp Arg Gln Thr
                405                 410                 415

Pro Lys Met Arg Ile Gln Ala Leu Thr Glu Asp Asp Gln Met Gln Glu
            420                 425                 430

Pro Leu Lys Pro Ser Leu Ile Asn Gly Lys Tyr Asn Gln Ile Lys Ser
        435                 440                 445

Leu Thr Gly Tyr Val Arg Arg Ile Gly Asn Ala Pro Arg Val Gly Gly
    450                 455                 460

Met Thr Ile Thr Phe Ala Asn Gly Ala Ser Tyr Thr Leu Gly Thr Val
465                 470                 475                 480

Thr Ser Glu Thr Thr Ser Ile Glu Leu Asn Gly Ser Val Ile Glu Ser
                485                 490                 495

Leu Glu Val Trp Gly Asp Gly Ala Val Asp Glu Ala Leu Phe Thr Leu
            500                 505                 510

Ser Asp Lys Arg Leu Phe Arg Ile Gly Glu Arg Tyr Ala Arg Lys Tyr
        515                 520                 525

Lys Lys Tyr Ala Val Asp Ser His Tyr Ile Ala Gly Leu Tyr Leu Ala
    530                 535                 540

Ser Asp Glu Pro Ser Leu Ala Gly Gln Ala Ala Gly Ile Ala Val Ser
545                 550                 555                 560

Tyr His Met Leu Asp Asp Lys Lys
                565
```

<210> SEQ ID NO 152
<211> LENGTH: 1707
<212> TYPE: DNA
<213> ORGANISM: Artificial
<220> FEATURE:
<223> OTHER INFORMATION: A synthetic coding sequence used for expression in plant cells encoding a TIC10381PL PirAB fusion protein with an additional alanine codon inserted after the initiating methionine codon.

<400> SEQUENCE: 152

```
atggcttcaa tcatcaacat caacattagc gggtcgtcgg acattactat cattaacaac      60

acgccgagca acccggagcc gctgatctac aacactgaca ctccggcctc cgagccgctc     120
```

```
accgtcaacc cttaccggga catgaccatc gagccgcaca gcagcatcga ggccattcga    180

atcgacacac ccatcatccc ggagacgcgg cccaactatt acgtggccaa ctcgggcccg    240

gcctcgtccg tccgggcggt gttctactgg tcgcactcct tcacgtccga gtggttcgag    300

tacagcgcca tcacggtcaa ggcgggcgaa gacggtatcc tccaatcgcc ctcgaacagc    360

gtgtactatt caaaggtcgt catctacaac gagacggata agcgcgcgtt cgtcaccggc    420

tacaacaaga tgaacaccac gccgatcaac gtgagcgaga acgacaccct acccgtgctc    480

accgacgtga tgttgatcgt gccctacaca acctccacgc cggactacga gtgggacatg    540

agtagcatca tcaaggacgc catcatcggc ggcgtgggct tcattcccgg cgtcgggtcg    600

gcgatgtcgt tcctgctggg cttgttctgg ccgcaacaga aggacaacac ctgggagcag    660

atccttcaga aggttgagca gatgatcgag aacgcggcac tccagaccat caagggcatc    720

ctgaacggcg acatccagga gatcaagggc aagatggagc acgtgcagta catgctggaa    780

acgtcgcccg gctctcagga atcccacgac gcctacatgt tcctggccag atacctcgtc    840

tctatcgacg agcgcttcaa gtccttcgac aacaagacga attaccagat cctgccgatg    900

tacacaaata ccgtgatgct acaaattccc tactggaaga tgggcatcga gaagaagaat    960

gacatcgggc tgacggacat cgaggtgaac gagctaaagc agctaatcga caccctggtg   1020

gaccgcgcaa ggaactacat tcacacaatg tacactaacg agtacaacaa cgccatcaac   1080

acttctactg ccgaatccgt gaccaacaac ctcctctccg tacgcggtta ctgcctcctg   1140

cacggcctag agtgcattga gctgatcgag cacctccaga acaattcgtt agagtccggc   1200

tttaacccga agaccatcag ctacagcacc gtcttcgacc ggccgaccaa caagacccgc   1260

atccaggccc tcacggagga cgaccaaatg caagagccgt tcaagccgag cctgatcgac   1320

gggaagtaca acaagatcaa gtcgctgctt ggctacgtcc gcagaatcgg gaacgcaccg   1380

cgcgtcggcg gcatacagat caccttcgcc aacgactcca gctacaccct gggcaccgta   1440

acatccgaga cgtcatccat cgagctgaac gacagcgtta tcgagcggct ggaggtgtgg   1500

ggcaacggcg cggtggatga ggccctgttc acgctgagcg acggccgcca gctccgcgtc   1560

ggcgagcggt acgccacgaa gtatcggaag tacgcggtgg atgggcacta catcgctggc   1620

ttgtacctcg cgtccgacga gcccagcctc gcgggccagg cggctgggat cgccgtatcg   1680

taccacatgc tcgcggacaa gaagtga                                       1707
```

<210> SEQ ID NO 153
<211> LENGTH: 568
<212> TYPE: PRT
<213> ORGANISM: Artificial
<220> FEATURE:
<223> OTHER INFORMATION: The amino acid sequence of the TIC10381PL PirAB fusion protein.

<400> SEQUENCE: 153

```
Met Ala Ser Ile Ile Asn Ile Asn Ile Ser Gly Ser Ser Asp Ile Thr
1               5                   10                  15

Ile Ile Asn Asn Thr Pro Ser Asn Pro Glu Pro Leu Ile Tyr Asn Thr
            20                  25                  30

Asp Thr Pro Ala Ser Glu Pro Leu Thr Val Asn Pro Tyr Arg Asp Met
        35                  40                  45

Thr Ile Glu Pro His Ser Ser Ile Glu Ala Ile Arg Ile Asp Thr Pro
    50                  55                  60

Ile Ile Pro Glu Thr Arg Pro Asn Tyr Tyr Val Ala Asn Ser Gly Pro
```

-continued

```
65                  70                  75                  80

Ala Ser Ser Val Arg Ala Val Phe Tyr Trp Ser His Ser Phe Thr Ser
                85                  90                  95

Glu Trp Phe Glu Tyr Ser Ala Ile Thr Val Lys Ala Gly Glu Asp Gly
            100                 105                 110

Ile Leu Gln Ser Pro Ser Asn Ser Val Tyr Tyr Ser Lys Val Val Ile
        115                 120                 125

Tyr Asn Glu Thr Asp Lys Arg Ala Phe Val Thr Gly Tyr Asn Lys Met
    130                 135                 140

Asn Thr Thr Pro Ile Asn Val Ser Glu Asn Asp Thr Leu Pro Val Leu
145                 150                 155                 160

Thr Asp Val Met Leu Ile Val Pro Tyr Thr Thr Ser Thr Pro Asp Tyr
                165                 170                 175

Glu Trp Asp Met Ser Ser Ile Ile Lys Asp Ala Ile Ile Gly Gly Val
            180                 185                 190

Gly Phe Ile Pro Gly Val Gly Ser Ala Met Ser Phe Leu Leu Gly Leu
        195                 200                 205

Phe Trp Pro Gln Gln Lys Asp Asn Thr Trp Glu Gln Ile Leu Gln Lys
    210                 215                 220

Val Glu Gln Met Ile Glu Asn Ala Ala Leu Gln Thr Ile Lys Gly Ile
225                 230                 235                 240

Leu Asn Gly Asp Ile Gln Glu Ile Lys Gly Lys Met Glu His Val Gln
                245                 250                 255

Tyr Met Leu Glu Thr Ser Pro Gly Ser Gln Glu Ser His Asp Ala Tyr
            260                 265                 270

Met Phe Leu Ala Arg Tyr Leu Val Ser Ile Asp Glu Arg Phe Lys Ser
        275                 280                 285

Phe Asp Asn Lys Thr Asn Tyr Gln Ile Leu Pro Met Tyr Thr Asn Thr
    290                 295                 300

Val Met Leu Gln Ile Pro Tyr Trp Lys Met Gly Ile Glu Lys Lys Asn
305                 310                 315                 320

Asp Ile Gly Leu Thr Asp Ile Glu Val Asn Glu Leu Lys Gln Leu Ile
                325                 330                 335

Asp Thr Leu Val Asp Arg Ala Arg Asn Tyr Ile His Thr Met Tyr Thr
            340                 345                 350

Asn Glu Tyr Asn Asn Ala Ile Asn Thr Ser Thr Ala Glu Ser Val Thr
        355                 360                 365

Asn Asn Leu Leu Ser Val Arg Gly Tyr Cys Leu Leu His Gly Leu Glu
    370                 375                 380

Cys Ile Glu Leu Ile Glu His Leu Gln Asn Asn Ser Leu Glu Ser Gly
385                 390                 395                 400

Phe Asn Pro Lys Thr Ile Ser Tyr Ser Thr Val Phe Asp Arg Pro Thr
                405                 410                 415

Asn Lys Thr Arg Ile Gln Ala Leu Thr Glu Asp Asp Gln Met Gln Glu
            420                 425                 430

Pro Phe Lys Pro Ser Leu Ile Asp Gly Lys Tyr Asn Lys Ile Lys Ser
        435                 440                 445

Leu Leu Gly Tyr Val Arg Arg Ile Gly Asn Ala Pro Arg Val Gly Gly
    450                 455                 460

Ile Gln Ile Thr Phe Ala Asn Asp Ser Ser Tyr Thr Leu Gly Thr Val
465                 470                 475                 480

Thr Ser Glu Thr Ser Ser Ile Glu Leu Asn Asp Ser Val Ile Glu Arg
                485                 490                 495
```

```
Leu Glu Val Trp Gly Asn Gly Ala Val Asp Glu Ala Leu Phe Thr Leu
            500                 505                 510

Ser Asp Gly Arg Gln Leu Arg Val Gly Glu Arg Tyr Ala Thr Lys Tyr
        515                 520                 525

Arg Lys Tyr Ala Val Asp Gly His Tyr Ile Ala Gly Leu Tyr Leu Ala
    530                 535                 540

Ser Asp Glu Pro Ser Leu Ala Gly Gln Ala Ala Gly Ile Ala Val Ser
545                 550                 555                 560

Tyr His Met Leu Ala Asp Lys Lys
                565


<210> SEQ ID NO 154
<211> LENGTH: 1701
<212> TYPE: DNA
<213> ORGANISM: Artificial
<220> FEATURE:
<223> OTHER INFORMATION: A synthetic coding sequence used for expression
      in plant cells encoding a TIC11103 PirAB fusion protein comprised
      of the TIC7661 and TIC7660 coding sequences operably linked.

<400> SEQUENCE: 154

atgaacacca ctccgattac tgtaagcact aacgaaacat cgcctctcat gacggacgtg     60

atgccgatgg acctgtacgc catctcgacg ccagactacg agtgggacat gagttccatc    120

atcaaggacg ccgtaattgg cggcatcggg ttcatccctg ggcccggccc ggccatctcc    180

ttcctgctgg gcctgttctg gccgcagcag aaggacaaca catgggagca gatactccag    240

aaggtcgagc aaatgattga gaatgccgtg ttgcagacga tcaagggaat cctaaacggc    300

gaagtacagg agatcaaggg caagatggag cacgtcgagt ctatgctcaa gaactcgcca    360

ggctctcagg agtcacacga cgcctacatg ttcctggctc gttacctcgt ttcaattgac    420

gagaagttca agagcttcga caaccgcacc aactaccaac tgttgccgat gtacaccaat    480

acgattatgc tccagatacc ttattggaag atgggcatcg agaagaagaa ggacattggc    540

ctgaccgaca ttgaagtcaa cgagcttaag gagctgatcg acaagctggt ggacaaggcc    600

aagaactaca tccacacaat gtacacgaac gagcacaaca acgccgtgaa caccagcact    660

gccgagtccg tcacgaacaa tctcctcagc gtgcgcggct actgcctgtt acacgggctg    720

gagtgcattg agctaatcga gcacatccag aacaactccc tggagagcgg gttctacccg    780

aagatcatca gctacagcac cgctttcgac cgcccgacaa acaagatgcg tatccaagcg    840

ctcacggagg acgacgcgat gcaagagccg tttaaaccgt cgctcattaa cggcaagtac    900

aacaagatcc agagcctcac gggctacgtg cagcggatcg gcaacgcgcc gcgcgtcggc    960

ggcatccgca tcacgttcac caacgggtcg tcctacacgc tcgggacggt gacctccgag   1020

acgcacagca tcaagctgaa cgactccgtg atcgagtcgt tagaggtctg ggaaacggt    1080

gccgtggacg aggccctgtt caagctgtcc gacgggcggc tcctccgcat cggcgagcgg   1140

tacgccaaga agtaccgcaa gtacgcggtg gacaaccact acatcgcggg catctaccta   1200

gcgagcgacg agccgtccct ggcgggtcaa gccgccggga tcgccgtgag ctatcacatg   1260

atggcggaca agaaaatgat tacgatcaac atcaacgtga acggcaacga cgtgacgggc   1320

accaacaaca atgagcccac tccagtcagc acgacgtacg gcccgaacac tccggcctcg   1380

gagccaccgg tcgtctcgaa ctactccgac atcaccattg agccgcacag ctcggtccag   1440

gccacgcgga tcgacacgcc ggtgatcccg gaggcccggc cggactacta cgtggcgaac   1500

tcgggccctg cgccgtccgt gcgggccgtg ttctactggt cgcactcgtt cacctccgag   1560
```

tggttcgagt cgtccagcat caccgtgaag gcgggcgagg acggaatcct caaggctcca 1620
gggaacagcc tgtactacag caaggtcgtc atctacaacg acacagacaa gcgggccttc 1680
gttaccgggt acaacaagtg a 1701

<210> SEQ ID NO 155
<211> LENGTH: 566
<212> TYPE: PRT
<213> ORGANISM: Artificial
<220> FEATURE:
<223> OTHER INFORMATION: The amino acid sequence of the TIC11103 PirAB fusion protein.

<400> SEQUENCE: 155

Met Asn Thr Thr Pro Ile Thr Val Ser Thr Asn Glu Thr Ser Pro Leu
1 5 10 15

Met Thr Asp Val Met Pro Met Asp Leu Tyr Ala Ile Ser Thr Pro Asp
20 25 30

Tyr Glu Trp Asp Met Ser Ser Ile Ile Lys Asp Ala Val Ile Gly Gly
35 40 45

Ile Gly Phe Ile Pro Gly Pro Gly Pro Ala Ile Ser Phe Leu Leu Gly
50 55 60

Leu Phe Trp Pro Gln Gln Lys Asp Asn Thr Trp Glu Gln Ile Leu Gln
65 70 75 80

Lys Val Glu Gln Met Ile Glu Asn Ala Val Leu Gln Thr Ile Lys Gly
85 90 95

Ile Leu Asn Gly Glu Val Gln Glu Ile Lys Gly Lys Met Glu His Val
100 105 110

Glu Ser Met Leu Lys Asn Ser Pro Gly Ser Gln Glu Ser His Asp Ala
115 120 125

Tyr Met Phe Leu Ala Arg Tyr Leu Val Ser Ile Asp Glu Lys Phe Lys
130 135 140

Ser Phe Asp Asn Arg Thr Asn Tyr Gln Leu Leu Pro Met Tyr Thr Asn
145 150 155 160

Thr Ile Met Leu Gln Ile Pro Tyr Trp Lys Met Gly Ile Glu Lys Lys
165 170 175

Lys Asp Ile Gly Leu Thr Asp Ile Glu Val Asn Glu Leu Lys Glu Leu
180 185 190

Ile Asp Lys Leu Val Asp Lys Ala Lys Asn Tyr Ile His Thr Met Tyr
195 200 205

Thr Asn Glu His Asn Asn Ala Val Asn Thr Ser Thr Ala Glu Ser Val
210 215 220

Thr Asn Asn Leu Leu Ser Val Arg Gly Tyr Cys Leu Leu His Gly Leu
225 230 235 240

Glu Cys Ile Glu Leu Ile Glu His Ile Gln Asn Asn Ser Leu Glu Ser
245 250 255

Gly Phe Tyr Pro Lys Ile Ile Ser Tyr Ser Thr Ala Phe Asp Arg Pro
260 265 270

Thr Asn Lys Met Arg Ile Gln Ala Leu Thr Glu Asp Asp Ala Met Gln
275 280 285

Glu Pro Phe Lys Pro Ser Leu Ile Asn Gly Lys Tyr Asn Lys Ile Gln
290 295 300

Ser Leu Thr Gly Tyr Val Gln Arg Ile Gly Asn Ala Pro Arg Val Gly
305 310 315 320

Gly Ile Arg Ile Thr Phe Thr Asn Gly Ser Ser Tyr Thr Leu Gly Thr

-continued

```
                325                 330                 335

Val Thr Ser Glu Thr His Ser Ile Lys Leu Asn Asp Ser Val Ile Glu
            340                 345                 350

Ser Leu Glu Val Trp Gly Asn Gly Ala Val Asp Glu Ala Leu Phe Lys
        355                 360                 365

Leu Ser Asp Gly Arg Leu Leu Arg Ile Gly Glu Arg Tyr Ala Lys Lys
    370                 375                 380

Tyr Arg Lys Tyr Ala Val Asp Asn His Tyr Ile Ala Gly Ile Tyr Leu
385                 390                 395                 400

Ala Ser Asp Glu Pro Ser Leu Ala Gly Gln Ala Ala Gly Ile Ala Val
                405                 410                 415

Ser Tyr His Met Met Ala Asp Lys Lys Met Ile Thr Ile Asn Ile Asn
            420                 425                 430

Val Asn Gly Asn Asp Val Thr Gly Thr Asn Asn Asn Glu Pro Thr Pro
        435                 440                 445

Val Ser Thr Thr Tyr Gly Pro Asn Thr Pro Ala Ser Glu Pro Pro Val
    450                 455                 460

Val Ser Asn Tyr Ser Asp Ile Thr Ile Glu Pro His Ser Ser Val Gln
465                 470                 475                 480

Ala Thr Arg Ile Asp Thr Pro Val Ile Pro Glu Ala Arg Pro Asp Tyr
                485                 490                 495

Tyr Val Ala Asn Ser Gly Pro Ala Pro Ser Val Arg Ala Val Phe Tyr
            500                 505                 510

Trp Ser His Ser Phe Thr Ser Glu Trp Phe Glu Ser Ser Ser Ile Thr
        515                 520                 525

Val Lys Ala Gly Glu Asp Gly Ile Leu Lys Ala Pro Gly Asn Ser Leu
    530                 535                 540

Tyr Tyr Ser Lys Val Val Ile Tyr Asn Asp Thr Asp Lys Arg Ala Phe
545                 550                 555                 560

Val Thr Gly Tyr Asn Lys
                565
```

<210> SEQ ID NO 156
<211> LENGTH: 1701
<212> TYPE: DNA
<213> ORGANISM: Artificial
<220> FEATURE:
<223> OTHER INFORMATION: A synthetic coding sequence used for expression in plant cells encoding a TIC11104 PirAB fusion protein comprised of the TIC7663 and TIC7662 coding sequences operably linked.

<400> SEQUENCE: 156

```
atgaacacca ccctcatcaa cgtaagtgag aaggagacgc tgccggtgca gaccgacatc     60

atgctgatcg cgccgtactc cgtgtccacg ccggactacg agtgggacat gtcatcgctc    120

atcaaggacg cgatcatcgg cggcgtcgga ttcatccctg tcgtcggctc ggccatgtcc    180

ttcctcctcg gcctgttctg gccgcagcag aaggacaaca cttgggaaca aatactgcag    240

aaggtcgagc agatgatcga gaacgcgcag ctcaacacga ttaagggcat tctgaacggc    300

gacatccagg agattaaggg caagatggag cacgtgcagt acatgcttga gacaagtcca    360

gggagtcagg agtcacacga cgcctacatg ttcttagccc gctacctagt gagcatcgac    420

gagaagttca agtcgttcga caacaagaca aactaccaaa tcttgccaat gtacacgaat    480

accgtcatgc tacagatccc atactggaag atgggaattg agaagaagaa cgacattggc    540

ttgacggaca tcgaagtcaa cgagcttaaa cagcttatcg acactctggt ggaccgcgcg    600
```

```
cgcaactaca tccacaccat gtacgagcga gagtacgaca acgccatcaa cacctcaacc    660

gctgcctcgg tgaccaacaa cctgctctcc gtgcgcgggt actgcctcct gcacgggctg    720

gagtgcatcg agactatcga gcaccttcag aacaacagcc tcaacagtgg gttctacccg    780

aagaccatca gctacagcac tgtcttcgac cggcccacga acaagacccg catccaggct    840

ctgacggaag acgaccaaat gcaagagccg ttcaagcccg cgctgatcgg cggcaagtac    900

aacaagatca agtccctgtt gggctacgtg cgaaggatcg gcaacgctcc acgggtcggc    960

ggcatcaagg tgacgttcac caatgggtcg agctacacgc tcgggacggt cacgtcggaa   1020

accgactcca tcgaactgaa cgagtcggtc atcgagcggc tggaggtgtg gggcaacgga   1080

gccgtggacg aggccctctt taccctgagc gatggccgcc agctccgcat cggcgagcgg   1140

tacgccaaga aataccggaa gtacgcggtg gatgggcact acatcagcgg cctctacctc   1200

gcgtcggacg agccctccct cgccggtcaa gcagccggga tcgcggtgtc ctaccacatg   1260

ctcgcagaca agaagatgtc caccatcaac atcaacatct cctccagcac ggtcactgtg   1320

attacaaaca atggcgagac gcccgtcccg ctcacctaca acaccaacac gccggagtcg   1380

gagccgctga cggtcaaccc gtaccgcgac atgaccatcg agccgcgctc ctccattgag   1440

gcgacccgca tcgacacgcc gatcatcccg gagacgagac cgaactacta tgtggcgaac   1500

tccggcccgg ccagcagcgt ccgggcggta ttctactggt cgcacagctt cacctcgcaa   1560

tggttcgagt attcgtcgat catcgtgaag gcgggtgagg acggcatact ggagtcgccg   1620

tcgaacagcc tctactacag caaggtggtg atctacaacg acacggacaa gagggcattc   1680

gtcacgggct acaacaagtg a                                              1701
```

<210> SEQ ID NO 157
<211> LENGTH: 566
<212> TYPE: PRT
<213> ORGANISM: Artificial
<220> FEATURE:
<223> OTHER INFORMATION: The amino acid sequence of the TIC11104 PirAB fusion protein.

<400> SEQUENCE: 157

```
Met Asn Thr Thr Leu Ile Asn Val Ser Glu Lys Glu Thr Leu Pro Val
1               5                   10                  15

Gln Thr Asp Ile Met Leu Ile Ala Pro Tyr Ser Val Ser Thr Pro Asp
            20                  25                  30

Tyr Glu Trp Asp Met Ser Ser Leu Ile Lys Asp Ala Ile Ile Gly Gly
        35                  40                  45

Val Gly Phe Ile Pro Val Val Gly Ser Ala Met Ser Phe Leu Leu Gly
    50                  55                  60

Leu Phe Trp Pro Gln Gln Lys Asp Asn Thr Trp Glu Gln Ile Leu Gln
65                  70                  75                  80

Lys Val Glu Gln Met Ile Glu Asn Ala Gln Leu Asn Thr Ile Lys Gly
                85                  90                  95

Ile Leu Asn Gly Asp Ile Gln Glu Ile Lys Gly Lys Met Glu His Val
            100                 105                 110

Gln Tyr Met Leu Glu Thr Ser Pro Gly Ser Gln Glu Ser His Asp Ala
        115                 120                 125

Tyr Met Phe Leu Ala Arg Tyr Leu Val Ser Ile Asp Glu Lys Phe Lys
    130                 135                 140

Ser Phe Asp Asn Lys Thr Asn Tyr Gln Ile Leu Pro Met Tyr Thr Asn
145                 150                 155                 160
```

-continued

```
Thr Val Met Leu Gln Ile Pro Tyr Trp Lys Met Gly Ile Glu Lys Lys
                165                 170                 175

Asn Asp Ile Gly Leu Thr Asp Ile Glu Val Asn Glu Leu Lys Gln Leu
            180                 185                 190

Ile Asp Thr Leu Val Asp Arg Ala Arg Asn Tyr Ile His Thr Met Tyr
        195                 200                 205

Glu Arg Glu Tyr Asp Asn Ala Ile Asn Thr Ser Thr Ala Ala Ser Val
    210                 215                 220

Thr Asn Asn Leu Leu Ser Val Arg Gly Tyr Cys Leu Leu His Gly Leu
225                 230                 235                 240

Glu Cys Ile Glu Thr Ile Glu His Leu Gln Asn Asn Ser Leu Asn Ser
                245                 250                 255

Gly Phe Tyr Pro Lys Thr Ile Ser Tyr Ser Thr Val Phe Asp Arg Pro
            260                 265                 270

Thr Asn Lys Thr Arg Ile Gln Ala Leu Thr Glu Asp Asp Gln Met Gln
        275                 280                 285

Glu Pro Phe Lys Pro Ala Leu Ile Gly Gly Lys Tyr Asn Lys Ile Lys
    290                 295                 300

Ser Leu Leu Gly Tyr Val Arg Arg Ile Gly Asn Ala Pro Arg Val Gly
305                 310                 315                 320

Gly Ile Lys Val Thr Phe Thr Asn Gly Ser Ser Tyr Thr Leu Gly Thr
                325                 330                 335

Val Thr Ser Glu Thr Asp Ser Ile Glu Leu Asn Glu Ser Val Ile Glu
            340                 345                 350

Arg Leu Glu Val Trp Gly Asn Gly Ala Val Asp Glu Ala Leu Phe Thr
        355                 360                 365

Leu Ser Asp Gly Arg Gln Leu Arg Ile Gly Glu Arg Tyr Ala Lys Lys
    370                 375                 380

Tyr Arg Lys Tyr Ala Val Asp Gly His Tyr Ile Ser Gly Leu Tyr Leu
385                 390                 395                 400

Ala Ser Asp Glu Pro Ser Leu Ala Gly Gln Ala Ala Gly Ile Ala Val
                405                 410                 415

Ser Tyr His Met Leu Ala Asp Lys Lys Met Ser Thr Ile Asn Ile Asn
            420                 425                 430

Ile Ser Ser Ser Thr Val Thr Val Ile Thr Asn Asn Gly Glu Thr Pro
        435                 440                 445

Val Pro Leu Thr Tyr Asn Thr Asn Thr Pro Glu Ser Glu Pro Leu Thr
    450                 455                 460

Val Asn Pro Tyr Arg Asp Met Thr Ile Glu Pro Arg Ser Ser Ile Glu
465                 470                 475                 480

Ala Thr Arg Ile Asp Thr Pro Ile Ile Pro Glu Thr Arg Pro Asn Tyr
                485                 490                 495

Tyr Val Ala Asn Ser Gly Pro Ala Ser Ser Val Arg Ala Val Phe Tyr
            500                 505                 510

Trp Ser His Ser Phe Thr Ser Gln Trp Phe Glu Tyr Ser Ser Ile Ile
        515                 520                 525

Val Lys Ala Gly Glu Asp Gly Ile Leu Glu Ser Pro Ser Asn Ser Leu
    530                 535                 540

Tyr Tyr Ser Lys Val Val Ile Tyr Asn Asp Thr Asp Lys Arg Ala Phe
545                 550                 555                 560

Val Thr Gly Tyr Asn Lys
                565
```

<210> SEQ ID NO 158
<211> LENGTH: 1701
<212> TYPE: DNA
<213> ORGANISM: Artificial
<220> FEATURE:
<223> OTHER INFORMATION: A synthetic coding sequence used for expression in plant cells encoding a TIC11302 PirAB fusion protein.

<400> SEQUENCE: 158

```
atgattacga tcaacatcaa cgtgaacggc aacgacgtga cgggcaccaa caacaatgag     60

cccactccag tcagcacgac gtacggcccg aacactccgg cctcggagcc accggtcgtc    120

tcgaactact ccgacatcac cattgagccg cacagctcgg tccaggccac gcggatcgac    180

acgccggtga tcccggaggc ccggccggac tactacgtgg cgaactcggg ccctgcgccg    240

tccgtgcggg ccgtgttcta ctggtcgcac tcgttcacct ccgagtggtt cgagtcgtcc    300

agcatcaccg tgaaggcggg cgaggacgga atcctcaagg ctccagggaa cagcctgtac    360

tacagcaagg tcgtcatcta caacgacaca gacaagcggg ccttcgttac cgggtacaac    420

aagatgaaca tcagcccgat caacgtctcg gagaacgaga cgctcccgga gctgaccgac    480

gtgatgctga tcgtcccata cacgaccagc acgccggatt acgagtggga catgtcgtcg    540

atcattaagg atgcgatcat cggaggcgtt ggcttcatcc ctggcgcggg ctcggccatg    600

agcttcctgc tcggcctgtt ctggccgcag cagaaggata acacttggga gcagatactt    660

cagaaggtgg aacagatgat cgagaacgcg gtcctccaaa cgatcaaggg catcctcaac    720

ggcgacatcc aggagattaa gggaaagatg gagcacgttc agtacatgct cgaaaccagc    780

cctgggagcc aggagagcca cgacgcctac atgttcttgg cacgttacct cgtctcgatt    840

gacgagaagt tcaagtcctt cgacaacaag acaaactacc agatcttgcc aatgtacacc    900

aatacggtta tgttacagat tccgtactgg aagatgggca tcgagaagaa gaatgacatc    960

ggcttgaccg acatcgaggt caatgagctt aagcaactta tcgacaagct ggtggacaag   1020

gccaagtcct acatccacac aatgtacacc aacgagtaca acgacgcgat caacaccagc   1080

accgcctcaa gcgtcacaaa caacctcctg tccgtgcgcg gttactgcct tctgcacggc   1140

ctggagtgca tcgaacttat tgagcatctc cagaacaaca gcctggagtc cggcttctac   1200

ccgaagacga tcagctactc cacggtcttc gaccggcaga ccaacaagat gcggatacaa   1260

gcgctcactg aggacgacca gatgcaagaa cccttcaagc cctcgctcat caacgggaag   1320

tacaacaaga tccagagcct cctcggctac gtccagcgca tcggcaacgc gccgcgcgtc   1380

ggcgggatca agatcacgtt cgccaacggg tctagttaca cgctgggcac cgtgaccagc   1440

gagacctcca gtattgagct taacgactcg gtgatcgagc ggctggaggt gtggggcaac   1500

ggcgcggtgg acgaggcgct gttcaccctc tcggacgggc ggcagctccg ggtcggcgag   1560

cggtacgcga ccaagtaccg taagtacgcc gtggacggcc actacatcgc cggtctgtac   1620

ctcgccagtg acgagcccag cctagcgggc caggcggctg gcatcgccgt gtcgtaccac   1680

atgctcgacg acaagaagtg a                                             1701
```

<210> SEQ ID NO 159
<211> LENGTH: 24
<212> TYPE: DNA
<213> ORGANISM: Artificial
<220> FEATURE:
<223> OTHER INFORMATION: A synthetic coding sequence encoding a Histidine tag that is operably linked to coding sequences expressed in Escherichia coli and used for protein purification.

<400> SEQUENCE: 159

-continued

```
caccaccatc acgctcacca tcac                                        24


<210> SEQ ID NO 160
<211> LENGTH: 8
<212> TYPE: PRT
<213> ORGANISM: Artificial
<220> FEATURE:
<223> OTHER INFORMATION: The amino acid sequence of the Histidine tag.

<400> SEQUENCE: 160

His His His His Ala His His His
1               5
```

INSECT INHIBITORY PROTEINS

REFERENCE TO RELATED APPLICATION

This application claims the benefit of United States provisional application No. 62/736,236, filed Sep. 25, 2018, which is herein incorporated by reference in its entirety.

INCORPORATION OF SEQUENCE LISTING

The file named "MONS465US-sequence_listing.txt" containing a computer-readable form of the Sequence Listing was created on Sep. 18, 2019. This file is 467,753 bytes (measured in MS-Windows®) is contemporaneously filed by electronic submission (using the United States Patent Office EFS-Web filing system), and is incorporated into this application by reference in its entirety.

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed proteins are insecticidally active against agriculturally-relevant pests of crop plants and seeds, particularly Coleopteran and Lepidopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the Lepidoptera, Coleoptera, and Hemipteran orders, are considered a major cause of damage to field crops, thereby decreasing crop yields over infested areas. Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*), *Paenibacillus popilliae, Photorhabdus* and *Xenorhabdus.*

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors herein disclose a protein toxin family from *Xenorhabdus* and *Photorhabdus* along with similar toxin proteins, variant proteins, and exemplary recombinant proteins that exhibit insecticidal activity against target Lepidopteran, Coleopteran, and Hemipteran pest species.

SUMMARY OF THE INVENTION

Disclosed herein is a group of pesticidal proteins with insect inhibitory activity (toxin proteins), referred to herein as PirAB (*Photorhabdus* insect related) protein toxins, which are shown to exhibit inhibitory activity against one or more pests of crop plants. The proteins in the PirAB protein toxin class can be used alone, or as fusions of a PirA protein and a PirB protein, or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or fragment thereof, wherein: (a) said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143; or (c) said polynucleotide segment hybridizes to a polynucleotide having the nucleotide sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 52, 53, 54, 55, 56, 57, 59, 61, 63, 65, 67, 69, 71, 73, 75, 77, 79, 81, 83, 85, 87, 89, 91, 93, 95, 97, 99, 101, 103, 104, 106, 108, 110, 112, 114, 116, 118, 120, 122, 124, 126, 128, 130, 132, 134, 136, 138, 140, 142, 144, 146, 148, 150, 152, 154, 156, or 158; or (d) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated host cells include *Agrobacterium, Rhizobium, Bacillus, Brevibacillus, Escherichia, Pseudomonas, Klebsiella, Pantoea*, and *Erwinia*. In certain embodiments said *Bacillus* species is *Bacillus cereus* or *Bacillus thuringiensis*, said *Brevibacillus* is *Brevibacillus laterosporus*, or said *Escherichia* is *Escherichia coli*. Contemplated plant host cells include a dicotyledonous cell and a monocotyledonous cell. Further contemplated plant host cells include an alfalfa, banana, barley, bean, broccoli, cabbage, Brassica, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In yet another embodiment, the pesticidal protein exhibits activity against Coleopteran insect, including Western Corn Rootworm, Southern Corn Rootworm, Northern Corn Rootworm, Mexican Corn Rootworm, Brazilian Corn Rootworm, Colorado Potato Beetle, Brazilian Corn Rootworm complex consisting of Diabrotica *viridula* and Diabrotica *speciosa*, Crucifer Flea Beetle, Striped Flea Beetle, and Western Black Flea Beetle.

In another embodiment, the pesticidal protein exhibits activity against a Lepidopteran insect, including Black Cutworm, Corn Earworm, Diamondback Moth, European Corn Borer, Fall Armyworm, Southern Armyworm, Soybean Looper, Southwestern Corn Borer, Tobacco Budworm, Velvetbean Caterpillar, Sugarcane Borer, Lesser Cornstalk Borer, Black Armyworm, Beet Armyworm, Old World Bollworm, Oriental leaf Worm, or Pink Bollworm.

In yet another embodiment, the pesticidal protein exhibits activity against an insect species of the order of Hemiptera, including Southern Green Stinkbug, Neotropical Brown Stinkbug, Southern Green Stink Bug, Neotropical Brown Stink Bug, Redbanded Stink Bug, Black-Spined Green-Belly Stink Bug species, Brown-Winged Stink Bug, Brown Stink Bug, Green Stink Bug, Brown Marmorated Stink Bug, Western Tarnished Plant Bug, or Tarnished Plant Bug.

Also contemplated in this application are plants comprising a recombinant nucleic acid molecule comprising a heterologous promoter operably linked to a polynucleotide segment encoding a pesticidal protein or fragment thereof, wherein: (a said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143; or (c) said polynucleotide segment hybridizes under stringent hybridization conditions to the compliment of the nucleotide sequence of to SEQ ID NOs: 49, 51, 52, 53, 54, 55, 56, 146, 148, 150, 152, 154, 156, or 158; or (d) said plant exhibits a detectable amount of said pesticidal protein. In certain embodiments the pesticidal protein comprises SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157. In one embodiment, the plant is either a monocot or a dicot. In another embodiment, the plant is selected from the group consisting of an alfalfa, banana, barley, bean, broccoli, cabbage, Brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. The at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of: a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 DIG-11, Cry71Aa1, Cry72Aa1, PHI-4 variants, PIP-72 variants, PIP-45 variants, PIP-64 variants, PIP-74 variants, PIP-75 variants, PIP-77 variants, Axmi422, Dig-305, Axmi440, PIP-47 variants, Axmi281, BT-009, BT-0012, BT-0013, BT-0023, BT0067, BT-0044, BT-0051, BT-0068, BT-0128, DIG-17, DIG-90, DIG-79, Cry1JP578V, Cry1JPS1, and Cry1 JPS1P578V.

Commodity products comprising a detectable amount of the recombinant nucleic acid molecules disclosed in this application are contemplated. Such commodity products include commodity corn bagged by a grain handler, corn flakes, corn cakes, corn flour, corn meal, corn syrup, corn oil, corn silage, corn starch, corn cereal, and the like, and corresponding cotton commodity products such as whole or processed cotton seed, cotton oil, lint, seeds and plant parts processed for feed or food, fiber, paper, biomasses, and fuel products such as fuel derived from cotton oil or pellets derived from cotton gin waste, and corresponding soybean commodity products such as whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts, and corresponding rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

Also contemplated in this application is a method of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation is provided, wherein the cells of said plant comprise: (a) a recombinant nucleic acid molecule encoding an insecticidally effective amount of a pesticidal protein as set forth in SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143.

Also disclosed in this application are methods for controlling a Coleopteran or Lepidopteran species pest, and controlling a Coleopteran or Lepidopteran species pest infestation of a plant, particularly a crop plant. The method comprises, in one embodiment, (a) contacting the pest with an insecticidally effective amount of one or more pesticidal proteins as set forth in SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143; or (c) said polynucleotide segment hybridizes to a polynucleotide having the nucleotide sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 52, 53, 54, 55, 56, 57, 59, 61, 63, 65, 67, 69, 71, 73, 75, 77, 79, 81, 83, 85, 87, 89, 91, 93, 95, 97, 99, 101, 103, 104, 106, 108, 110, 112, 114, 116, 118, 120, 122, 124, 126, 128, 130, 132, 134, 136, 138, 140, 142, 144, 146, 148, 150, 152, 154, 156, or 158. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NOs: 49, 51, 52, 53, 54, 55, 56, 146, 148, 150, 152, 154, 156, or 158, or a sequence that encodes a pesticidal protein comprising an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143. In one embodiment, the method comprises: (a) contacting a sample with an immunoreactive antibody; and (b) detecting binding of the antibody with the pesticidal protein or fragment thereof, wherein binding indicates the presence of the protein. In some embodiments, the step of detecting comprises an ELISA, or a Western blot.

BRIEF DESCRIPTION OF THE SEQUENCES

SEQ ID NO:1 is a nucleic acid sequence obtained from *Xenorhabdus nematophila* strain ISB000002 encoding a TIC4771 PirA pesticidal protein sequence.

SEQ ID NO:2 is the amino acid sequence of the TIC4771 PirA protein.

SEQ ID NO:3 is a nucleic acid sequence obtained from *Xenorhabdus nematophila* strain ISB000002 encoding a TIC4772 PirB pesticidal protein sequence.

SEQ ID NO:4 is the amino acid sequence of the TIC4772 PirB protein.

SEQ ID NO:5 is a nucleic acid sequence encoding a PirAB fusion protein, TIC6880 comprised of the TIC4771 and TIC4772 coding sequences in operable linkage and in frame.

SEQ ID NO:6 is the amino acid sequence of the TIC6880 PirAB fusion protein.

SEQ ID NO:7 is a nucleic acid sequence obtained from *Xenorhabdus ehlersii* strain 85823 encoding a TIC7575 PirA pesticidal protein sequence.

SEQ ID NO:8 is the amino acid sequence of the TIC7575 PirA protein.

SEQ ID NO:9 is a nucleic acid sequence obtained from *Xenorhabdus ehlersii* strain 85823 encoding a TIC7576 PirB pesticidal protein sequence.

SEQ ID NO:10 is the amino acid sequence of the TIC7576 PirB protein.

SEQ ID NO:11 is a nucleic acid sequence encoding a PirAB fusion protein, TIC9316 comprised of the TIC7575 and TIC7576 coding sequences in operable linkage and in frame.

SEQ ID NO:12 is the amino acid sequence of the TIC9316 PirAB fusion protein.

SEQ ID NO:13 is a nucleic acid sequence obtained from *Xenorhabdus cabanillasii* strain 85908 encoding a TIC7660 PirA pesticidal protein sequence.

SEQ ID NO:14 is the amino acid sequence of the TIC7660 PirA protein.

SEQ ID NO:15 is a nucleic acid sequence obtained from *Xenorhabdus cabanillasii* strain 85908 encoding a TIC7661 PirB pesticidal protein sequence.

SEQ ID NO:16 is the amino acid sequence of the TIC7661 PirB protein.

SEQ ID NO:17 is a nucleic acid sequence encoding a PirAB fusion protein, TIC9317 comprised of the TIC7660 and TIC7661 coding sequences in operable linkage and in frame.

SEQ ID NO:18 is the amino acid sequence of the TIC9317 PirAB fusion protein.

SEQ ID NO:19 is a nucleic acid sequence obtained from *Xenorhabdus ehlersii* strain 85887 encoding a TIC7662 PirA pesticidal protein sequence.

SEQ ID NO:20 is the amino acid sequence of the TIC7662 PirA protein.

SEQ ID NO:21 is a nucleic acid sequence obtained from *Xenorhabdus ehlersii* strain 85887 encoding a TIC7663 PirB pesticidal protein sequence.

SEQ ID NO:22 is the amino acid sequence of the TIC7663 PirB protein.

SEQ ID NO:23 is a nucleic acid sequence encoding a PirAB fusion protein, TIC9318 comprised of the TIC7662 and TIC7663 coding sequences in operable linkage and in frame.

SEQ ID NO:24 is the amino acid sequence of the TIC9318 PirAB fusion protein.

SEQ ID NO:25 is a nucleic acid sequence obtained from *Xenorhabdus poinarii* strain 86198 encoding a TIC7664 PirA pesticidal protein sequence.

SEQ ID NO:26 is the amino acid sequence of the TIC7664 PirA protein.

SEQ ID NO:27 is a nucleic acid sequence obtained from *Xenorhabdus poinarii* strain 86198 encoding a TIC7665 PirB pesticidal protein sequence.

SEQ ID NO:28 is the amino acid sequence of the TIC7665 PirB protein.

SEQ ID NO:29 is a nucleic acid sequence encoding a PirAB fusion protein, TIC9319 comprised of the TIC7664 and TIC7665 coding sequences in operable linkage and in frame.

SEQ ID NO:30 is the amino acid sequence of the TIC9319 PirAB fusion protein.

SEQ ID NO:31 is a nucleic acid sequence obtained from *Photorhabdus luminescens* strain 86197 encoding a TIC7666 PirA pesticidal protein sequence.

SEQ ID NO:32 is the amino acid sequence of the TIC7666 PirA protein.

SEQ ID NO:33 is a nucleic acid sequence obtained from *Photorhabdus luminescens* strain 86197 encoding a TIC7667 pesticidal PirB protein sequence.

SEQ ID NO:34 is the amino acid sequence of the TIC7667 PirB protein.

SEQ ID NO:35 is a nucleic acid sequence encoding a PirAB fusion protein, TIC9322 comprised of the TIC7666 and TIC7667 coding sequences in operable linkage and in frame.

SEQ ID NO:36 is the amino acid sequence of the TIC9322 PirAB fusion protein.

SEQ ID NO:37 is a nucleic acid sequence obtained from *Photorhabdus luminescens* strain 86194 encoding a TIC7668 PirA pesticidal protein sequence.

SEQ ID NO:38 is the amino acid sequence of the TIC7668 PirA protein.

SEQ ID NO:39 is a nucleic acid sequence obtained from *Photorhabdus luminescens* strain 86194 encoding a TIC7669 PirB pesticidal protein sequence.

SEQ ID NO:40 is the amino acid sequence of the TIC7669 PirB protein.

SEQ ID NO:41 is a nucleic acid sequence encoding a PirAB fusion protein, TIC9320 comprised of the TIC7668 and TIC7669 coding sequences in operable linkage and in frame.

SEQ ID NO:42 is the amino acid sequence of the TIC9320 PirAB fusion protein.

SEQ ID NO:43 is a nucleic acid sequence obtained from an unknown bacterial strain comprised within a microbiome encoding a TIC7939 pesticidal PirA protein sequence.

SEQ ID NO: 44 is the amino acid sequence of the TIC7939 PirA protein.

SEQ ID NO:45 is a nucleic acid sequence obtained from an unknown bacterial strain comprised within a microbiome encoding a TIC7940 PirB pesticidal protein sequence.

SEQ ID NO:46 is the amino acid sequence of the TIC7940 PirB protein.

SEQ ID NO:47 is a nucleic acid sequence encoding a PirAB fusion protein, TIC9321 comprised of the TIC7939 and TIC7940 coding sequences in operable linkage and in frame.

SEQ ID NO:48 is the amino acid sequence of the TIC9321 PirAB fusion protein.

SEQ ID NO:49 is a synthetic coding sequence used for expression in plant cells encoding a TIC6880PL PirAB fusion protein wherein an additional alanine codon is inserted immediately following the initiating methionine codon of the TIC4771 protein encoding fragment.

SEQ ID NO:50 is the amino acid sequence of the TIC6880PL PirAB fusion protein.

SEQ ID NO:51 is a synthetic coding sequence used for expression in plant cells encoding a TIC9316 PirAB fusion protein.

SEQ ID NO:52 is a synthetic coding sequence used for expression in plant cells encoding a TIC9317 PirAB fusion protein.

SEQ ID NO:53 is a synthetic coding sequence used for expression in plant cells encoding a TIC9318 PirAB fusion protein.

SEQ ID NO:54 is a synthetic coding sequence used for expression in plant cells encoding a TIC9319 PirAB fusion protein.

SEQ ID NO:55 is a synthetic coding sequence used for expression in plant cells encoding a TIC9320 PirAB fusion protein.

SEQ ID NO:56 is a synthetic coding sequence used for expression in plant cells encoding a TIC9322 PirAB fusion protein.

SEQ ID NO:57 is a nucleic acid sequence obtained from *Shewanella violacea* strain DSS12 encoding a TIC10357 pesticidal PirA protein sequence.

SEQ ID NO:58 is the amino acid sequence of the TIC10357 PirA protein.

SEQ ID NO:59 is a nucleic acid sequence obtained from *Shewanella violacea* strain DSS12 encoding a TIC10366 pesticidal PirB protein sequence.

SEQ ID NO:60 is the amino acid sequence of the TIC10366 PirB protein.

SEQ ID NO:61 is a nucleic acid sequence encoding a PirAB fusion protein, TIC10375 comprised of the TIC10357 and TIC10366 coding sequences in operable linkage and in frame.

SEQ ID NO:62 is the amino acid sequence of the TIC10375 PirAB fusion protein.

SEQ ID NO:63 is a nucleic acid sequence obtained from *Photorhabdus luminescens* strain laumondii TTO1 encoding a TIC10358 pesticidal PirA protein sequence.

SEQ ID NO:64 is the amino acid sequence of the TIC10358 PirA protein.

SEQ ID NO:65 is a nucleic acid sequence obtained from *Photorhabdus luminescens* strain laumondii TTO1 encoding a TIC10367 pesticidal PirB protein sequence.

SEQ ID NO:66 is the amino acid sequence of the TIC10367 PirB protein.

SEQ ID NO:67 is a nucleic acid sequence encoding a PirAB fusion protein, TIC10376 comprised of the TIC10358 and TIC10367 coding sequences in operable linkage and in frame.

SEQ ID NO:68 is the amino acid sequence of the TIC10376 PirAB fusion protein.

SEQ ID NO:69 is a nucleic acid sequence obtained from *Photorhabdus asymbiotica* encoding a TIC10360 pesticidal PirA protein sequence.

SEQ ID NO:70 is the amino acid sequence of the TIC10360 PirA protein.

SEQ ID NO:71 is a nucleic acid sequence obtained from *Photorhabdus asymbiotica* encoding a TIC10369 pesticidal PirB protein sequence.

SEQ ID NO:72 is the amino acid sequence of the TIC10369 PirB protein.

SEQ ID NO:73 is a nucleic acid sequence encoding a PirAB fusion protein, TIC10377 comprised of the TIC10360 and TIC10369 coding sequences in operable linkage and in frame.

SEQ ID NO:74 is the amino acid sequence of the TIC10377 PirAB fusion protein.

SEQ ID NO:75 is a nucleic acid sequence obtained from *Xenorhabdus* sp. strain NBAII XenSa04 encoding a TIC10361 pesticidal PirA protein sequence.

SEQ ID NO:76 is the amino acid sequence of the TIC10361 PirA protein.

SEQ ID NO:77 is a nucleic acid sequence obtained from *Xenorhabdus* sp. strain NBAII XenSa04 encoding a TIC10370 pesticidal PirB protein sequence.

SEQ ID NO:78 is the amino acid sequence of the TIC10370 PirB protein.

SEQ ID NO:79 is a nucleic acid sequence encoding a PirAB fusion protein, TIC10378 comprised of the TIC10361 and TIC10370 coding sequences in operable linkage and in frame.

SEQ ID NO:80 is the amino acid sequence of the TIC10378 PirAB fusion protein.

SEQ ID NO:81 is a nucleic acid sequence obtained from *Yersinia aldovae* strain 670-83 encoding a TIC10362 pesticidal PirA protein sequence.

SEQ ID NO:82 is the amino acid sequence of the TIC10362 PirA protein.

SEQ ID NO:83 is a nucleic acid sequence obtained from *Yersinia aldovae* strain 670-83 encoding a TIC10371 pesticidal PirB protein sequence.

SEQ ID NO:84 is the amino acid sequence of the TIC10371 PirB protein.

SEQ ID NO:85 is a nucleic acid sequence encoding a PirAB fusion protein, TIC10379 comprised of the TIC10362 and TIC10371 coding sequences in operable linkage and in frame.

SEQ ID NO:86 is the amino acid sequence of the TIC10379 PirAB fusion protein.

SEQ ID NO:87 is a nucleic acid sequence obtained from *Xenorhabdus doucetiae* strain FRM16 encoding a TIC10363 pesticidal PirA protein sequence.

SEQ ID NO:88 is the amino acid sequence of the TIC10363 PirA protein.

SEQ ID NO:89 is a nucleic acid sequence obtained from *Xenorhabdus doucetiae* strain FRM16 encoding a TIC10372 pesticidal PirB protein sequence.

SEQ ID NO:90 is the amino acid sequence of the TIC10372 PirB protein.

SEQ ID NO:91 is a nucleic acid sequence encoding a PirAB fusion protein, TIC10380 comprised of the TIC10363 and TIC10372 coding sequences in operable linkage and in frame.

SEQ ID NO:92 is the amino acid sequence of the TIC10380 PirAB fusion protein.

SEQ ID NO:93 is a nucleic acid sequence obtained from *Xenorhabdus griffiniae* strain BMMCB encoding a TIC10364 pesticidal PirA protein sequence.

SEQ ID NO:94 is the amino acid sequence of the TIC10364 PirA protein.

SEQ ID NO:95 is a nucleic acid sequence obtained from *Xenorhabdus griffiniae* strain BMMCB encoding a TIC10373 pesticidal PirB protein sequence.

SEQ ID NO:96 is the amino acid sequence of the TIC10373 PirB protein.

SEQ ID NO:97 is a nucleic acid sequence encoding a PirAB fusion protein, TIC10381 comprised of the TIC10364 and TIC10364 coding sequences in operable linkage and in frame.

SEQ ID NO:98 is the amino acid sequence of the TIC10381 PirAB fusion protein.

SEQ ID NO:99 is a nucleic acid sequence obtained from *Xenorhabdus nematophila* encoding a TIC10359 pesticidal PirA protein sequence.

SEQ ID NO:100 is the amino acid sequence of the TIC10359 PirA protein.

SEQ ID NO:101 is a nucleic acid sequence obtained from *Xenorhabdus nematophila* encoding a TIC10368 pesticidal PirB protein sequence.

SEQ ID NO:102 is the amino acid sequence of the TIC10368 PirB protein.

SEQ ID NO:103 is a nucleic acid sequence encoding an operon comprised of the coding sequences TIC10359 and TIC10368.

SEQ ID NO:104 is a nucleic acid sequence obtained from *Photorhabdus luminescens* strain Hm encoding a PirA_ABE68878 pesticidal PirA protein sequence.

SEQ ID NO:105 is the amino acid sequence of the PirA_ABE68878 PirA protein.

SEQ ID NO:106 is a nucleic acid sequence obtained from *Photorhabdus luminescens* strain Hm encoding a PirB_ABE68879 pesticidal PirB protein sequence.

SEQ ID NO:107 is the amino acid sequence of the PirB_ABE68879 PirB protein.

SEQ ID NO:108 is a nucleic acid sequence encoding a PirAB fusion protein, TIC10434 comprised of the PirA_ABE68878 and PirB_ABE68879 coding sequences in operable linkage and in frame.

SEQ ID NO:109 is the amino acid sequence of the TIC10434 PirAB fusion protein.

SEQ ID NO:110 is a nucleic acid sequence encoding a PirAB fusion protein, TIC11210 comprised of the TIC7575 and TIC7665 coding sequences in operable linkage and in frame.

SEQ ID NO:111 is the amino acid sequence of the TIC11210 PirAB fusion protein.

SEQ ID NO:112 is a nucleic acid sequence encoding a PirAB fusion protein, TIC11211 comprised of the TIC7575 and TIC7667 coding sequences in operable linkage and in frame.

SEQ ID NO:113 is the amino acid sequence of the TIC11211 PirAB fusion protein.

SEQ ID NO:114 is a nucleic acid sequence encoding a PirAB fusion protein, TIC11212 comprised of the TIC7662 and TIC7665 coding sequences in operable linkage and in frame.

SEQ ID NO:115 is the amino acid sequence of the TIC11212 PirAB fusion protein.

SEQ ID NO:116 is a nucleic acid sequence encoding a PirAB fusion protein, TIC11301 comprised of the TIC7575 and TIC7661 coding sequences in operable linkage and in frame.

SEQ ID NO:117 is the amino acid sequence of the TIC11301 PirAB fusion protein.

SEQ ID NO:118 is a nucleic acid sequence encoding a f PirAB fusion protein, TIC11302 comprised of the TIC7660 and TIC7576 coding sequences in operable linkage and in frame.

SEQ ID NO:119 is the amino acid sequence of the TIC11302 f PirAB fusion protein.

SEQ ID NO:120 is a nucleic acid sequence encoding a PirAB fusion protein, TIC11440 comprised of the TIC4771, TIC4771, and TIC4772 coding sequences in operable linkage and in frame.

SEQ ID NO:121 is the amino acid sequence of the TIC11440 PirAB fusion protein.

SEQ ID NO:122 is a nucleic acid sequence encoding a PirAB fusion protein, TIC11441 comprised of the TIC7575, TIC7575, and TIC7576 coding sequences in operable linkage and in frame.

SEQ ID NO:123 is the amino acid sequence of the TIC11441 f PirAB fusion protein.

SEQ ID NO:124 is a nucleic acid sequence encoding a PirAB fusion protein, TIC11442 comprised of the TIC7575, TIC4771, and TIC4772 coding sequences in operable linkage and in frame.

SEQ ID NO:125 is the amino acid sequence of the TIC11442 PirAB fusion protein.

SEQ ID NO:126 is a nucleic acid sequence encoding a PirAB fusion protein, TIC11443 comprised of the TIC7660, TIC7575, and TIC7576 coding sequences in operable linkage and in frame.

SEQ ID NO:127 is the amino acid sequence of the TIC11443 PirAB fusion protein.

SEQ ID NO:128 is a nucleic acid sequence encoding a PirAB fusion protein, TIC11444 comprised of the TIC7660 and TIC7576 coding sequences in operable linkage and in frame.

SEQ ID NO:129 is the amino acid sequence of the TIC11444 PirAB fusion protein.

SEQ ID NO:130 is a nucleic acid sequence encoding a PirAB fusion protein, TIC11445 comprised of the TIC7660, TIC7662, and TIC7663 coding sequences in operable linkage and in frame.

SEQ ID NO:131 is the amino acid sequence of the TIC11445 PirAB fusion protein.

SEQ ID NO:132 is a nucleic acid sequence encoding a fusion protein, TIC11446 comprised of the TIC7662, TIC7660, and TIC7661 coding sequences in operable linkage and in frame.

SEQ ID NO:133 is the amino acid sequence of the TIC11446 PirAB fusion protein.

SEQ ID NO:134 is a nucleic acid sequence obtained from *Xenorhabdus nematophila* strain MDI-0035777 encoding a TIC11505 pesticidal PirB protein sequence.

SEQ ID NO:135 is the amino acid sequence of the TIC11505 PirB protein.

SEQ ID NO:136 is a nucleic acid sequence encoding a PirAB fusion protein, TIC11506 comprised of the TIC10364 and TIC11505 coding sequences in operable linkage and in frame.

SEQ ID NO:137 is the amino acid sequence of the TIC11506 PirAB fusion protein.

SEQ ID NO:138 is a nucleic acid sequence obtained from *Xenorhabdus bovienii* strain MDI-0035808 encoding a TIC11510 pesticidal PirB protein sequence.

SEQ ID NO:139 is the amino acid sequence of the TIC11510 PirB protein.

SEQ ID NO:140 is a nucleic acid sequence encoding a PirAB fusion protein, TIC11512 comprised of the TIC10364 and TIC11510 coding sequences in operable linkage and in frame.

SEQ ID NO:141 is the amino acid sequence of the TIC11512 PirAB fusion protein.

SEQ ID NO:142 is a nucleic acid sequence obtained from *Xenorhabdus nematophila* strain AN6/1 encoding a TIC11511 pesticidal PirB protein sequence.

SEQ ID NO:143 is the amino acid sequence of the TIC11511 PirB protein.

SEQ ID NO:144 is a nucleic acid sequence encoding a PirAB fusion protein, TIC11513 comprised of the TIC10364 and TIC11511 coding sequences in operable linkage and in frame.

SEQ ID NO:145 is the amino acid sequence of the TIC11513 PirAB fusion protein.

SEQ ID NO:146 is a synthetic coding sequence used for expression in plant cells encoding a TIC10376PL PirAB fusion protein wherein an additional alanine codon is inserted immediately following the initiating methionine codon of the TIC10358 protein encoding fragment.

SEQ ID NO:147 is the amino acid sequence of the TIC10376PL PirAB fusion protein.

SEQ ID NO:148 is a synthetic coding sequence used for expression in plant cells encoding a TIC10378PL PirAB fusion protein wherein an additional alanine codon is inserted immediately following the initiating methionine codon of the TIC10361 protein encoding fragment.

SEQ ID NO:149 is the amino acid sequence of the TIC10378PL PirAB fusion protein.

SEQ ID NO:150 is a synthetic coding sequence used for expression in plant cells encoding a TIC10380PL PirAB fusion protein wherein an additional alanine codon is inserted immediately following the initiating methionine codon of the TIC10363 protein encoding fragment.

SEQ ID NO:151 is the amino acid sequence of the TIC10380PL PirAB fusion protein.

SEQ ID NO:152 is a synthetic coding sequence used for expression in plant cells encoding a TIC10381PL PirAB fusion protein wherein an additional alanine codon is inserted immediately following the initiating methionine codon of the TIC10364 protein encoding fragment.

SEQ ID NO:153 is the amino acid sequence of the TIC10381PL PirAB fusion protein.

SEQ ID NO:154 is a synthetic coding sequence used for expression in plant cells encoding a TIC11103 PirAB fusion protein comprised of the TIC7661 and TIC7660 coding sequences operably linked.

SEQ ID NO:155 is the amino acid sequence of the TIC11103 PirAB fusion protein.

SEQ ID NO:156 is a synthetic coding sequence used for expression in plant cells encoding a TIC11104 PirAB fusion protein comprised of the TIC7663 and TIC7662 coding sequences operably linked.

SEQ ID NO:157 is the amino acid sequence of the TIC11104 PirAB fusion protein.

SEQ ID NO:158 is a synthetic coding sequence used for expression in plant cells encoding a TIC11302 PirAB fusion protein.

SEQ ID NO:159 is a synthetic coding sequence encoding a Histidine tag that is operably linked to coding sequences expressed in *Escherichia coli* and used for protein purification.

SEQ ID NO:160 is the amino acid sequence of the Histidine tag.

DETAILED DESCRIPTION OF THE INVENTION

A problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Disclosed herein are novel PirAB pesticidal protein classes, exemplified by the PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878 (collectively, "The PirA Proteins"); the PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511 (collectively, "The PirB Proteins"); and the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104 (collectively, "The PirAB Fusion Protein") which provide resistance against Coleopteran, Hemipteran, and Lepidopteran insect pests.

Also disclosed are synthetic coding sequences designed for expression in a plant cell that encode the PirAB fusion proteins, TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302. Further disclosed are recombinant nucleic acid molecules comprising a promoter in operable linkage to a coding sequence encoding one or more of The PirA Proteins, The PirB Proteins, or The PirAB Fusion Proteins.

Reference in this application to "PirA proteins", "PirA protein toxin", "PirA toxin protein", "PirA pesticidal protein", "PirA-related toxins", or "PirA-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC4771 (SEQ ID NO:2), TIC7575 (SEQ ID NO:8), TIC7660 (SEQ ID NO:14), TIC7662 (SEQ ID NO:20), TIC7664 (SEQ ID NO:26), TIC7666 (SEQ ID NO:32), TIC7668 (SEQ ID NO:38), TIC7939 (SEQ ID NO:44), TIC10357 (SEQ ID NO:58), TIC10358 (SEQ ID NO:64), TIC10360 (SEQ ID NO:70), TIC10361 (SEQ ID NO:76), TIC10362 (SEQ ID NO:82), TIC10363 (SEQ ID NO:88), TIC10364 (SEQ ID NO:94), TIC10359 (SEQ ID NO:100), and PirA_ABE68878 (SEQ ID NO:105) and pesticidal or insect inhibitory segments thereof, or combinations thereof, that confer activity against Coleopteran pests, Hemipteran pests, and Lepidopteran pests, including any protein exhibiting pesticidal or insect inhibitory activity if alignment of such protein with any of the PirA proteins results in amino acid sequence identity of any fraction percentage from about 20 to about 100 percent.

Reference in this application to "PirB proteins", "PirB protein toxin", "PirB toxin protein", "PirB pesticidal protein", "PirB-related toxins", or "PirB-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC4772 (SEQ ID NO:4), TIC7576 (SEQ ID NO:10), TIC7661 (SEQ ID NO:16), TIC7663 (SEQ ID NO:22), TIC7665 (SEQ ID NO:28), TIC7667 (SEQ ID NO:34), TIC7669 (SEQ ID NO:40), TIC7940 (SEQ ID NO:46), TIC10366 (SEQ ID NO:60), TIC10367 (SEQ ID NO:66), TIC10369 (SEQ ID NO:72), TIC10370 (SEQ ID NO:78), TIC10371 (SEQ ID NO:84), TIC10372 (SEQ ID NO:90), TIC10373 (SEQ ID NO:96), TIC10368 (SEQ ID NO:102), PirB_ABE68879 (SEQ ID NO:107), TIC11505 (SEQ ID NO:135), TIC11510 (SEQ ID NO:139), and TIC11511 (SEQ ID NO:143) and pesticidal or insect inhibitory segments thereof, or combinations thereof, that confer activity against Coleopteran pests, Hemipteran pests, and Lepidopteran pests, including any protein exhibiting pesticidal or insect inhibitory activity if alignment of such protein with and of the PirB proteins results in amino acid sequence identity of any fraction percentage from about 24 to about 100 percent.

The term "PirAB fusion protein" is used in this application to describe a protein that comprises both a PirA protein contiguous with a PirB protein. The DNA sequence encoding the PirAB fusion protein can comprise a coding sequence encoding a PirA protein operably linked and in frame with a coding sequence encoding a PirB protein such that when it is expressed in a cell produces a fusion protein comprising both a PirA protein and PirB protein. The PirA protein can be comprised of a PirA protein and a PirB protein derived from the same bacterial operon, or alternatively, can be comprised of a PirA protein and a PirB protein derived from different bacterial operons. Exemplary PirAB fusion proteins wherein the PirA protein is contiguous with a PirB protein are provided in Table 1.

TABLE 1

Exemplary PirAB fusion proteins comprised of a PirA protein contiguous with a PirB protein and the corresponding PirA and PirB proteins comprised within.

| PirA Protein | | PirB Protein | | PirAB Fusion Protein | |
|---|---|---|---|---|---|
| Toxin | Protein SEQ ID NO: | Toxin | Protein SEQ ID NO: | Toxin | Protein SEQ ID NO: |
| TIC4771 | 2 | TIC4772 | 4 | TIC6880 | 6 |
| TIC7575 | 8 | TIC7576 | 10 | TIC9316 | 12 |
| TIC7660 | 14 | TIC7661 | 16 | TIC9317 | 18 |
| TIC7662 | 20 | TIC7663 | 22 | TIC9318 | 24 |
| TIC7664 | 26 | TIC7665 | 28 | TIC9319 | 30 |
| TIC7666 | 32 | TIC7667 | 34 | TIC9322 | 36 |
| TIC7668 | 38 | TIC7669 | 40 | TIC9320 | 42 |
| TIC7939 | 44 | TIC7940 | 46 | TIC9321 | 48 |
| TIC4771* | 2 | TIC4772 | 4 | TIC6880PL* | 6 |
| TIC10357 | 58 | TIC10366 | 60 | TIC10375 | 62 |
| TIC10358 | 64 | TIC10367 | 66 | TIC10376 | 68 |
| TIC10360 | 70 | TIC10369 | 72 | TIC10377 | 74 |
| TIC10361 | 76 | TIC10370 | 78 | TIC10378 | 80 |
| TIC10362 | 82 | TIC10371 | 84 | TIC10379 | 86 |
| TIC10363 | 88 | TIC10372 | 90 | TIC10380 | 92 |
| TIC10364 | 94 | TIC10373 | 96 | TIC10381 | 98 |
| PirA_ABE68878 | 105 | PirB_ABE68879 | 107 | TIC10434 | 109 |
| TIC10358* | 64 | TIC10367 | 66 | TIC10376PL* | 147 |
| TIC10361* | 76 | TIC10370 | 78 | TIC10378PL* | 149 |
| TIC10363* | 88 | TIC10372 | 90 | TIC10380PL* | 151 |
| TIC10364* | 94 | TIC10373 | 96 | TIC10381PL* | 153 |
| TIC7575 | 8 | TIC7665 | 28 | TIC11210 | 111 |
| TIC7575 | 8 | TIC7667 | 34 | TIC11211 | 113 |
| TIC7662 | 20 | TIC7665 | 28 | TIC11212 | 115 |
| TIC7575 | 8 | TIC7661 | 16 | TIC11301 | 117 |
| TIC7660 | 14 | TIC7576 | 10 | TIC11302 | 119 |
| TIC10364 | 94 | TIC11505 | 135 | TIC11506 | 137 |
| TIC10364 | 94 | TIC11510 | 139 | TIC11512 | 141 |
| TIC10364 | 94 | TIC11511 | 143 | TIC11513 | 145 |

*comprises an additional alanine residue immediately following the initiating methionine residue.

The term "PirAB fusion protein" is also used in this application to describe a protein that comprises a PirB protein contiguous with a PirA protein. The DNA sequence encoding the PirAB fusion protein of this type can comprise a coding sequence encoding a PirB protein operably linked and in frame with a coding sequence encoding a PirA protein such that when it is expressed in a cell it produces a fusion protein comprising both a PirB protein and PirA protein. The PirB protein can be comprised of a PirB protein and a PirA protein derived from the same bacterial operon, or alternatively, can be comprised of a PirB protein and a PirA protein derived from different operons. Exemplary proteins wherein a PirB protein is contiguous with a PirA protein are provided in Table 2.

TABLE 2

Exemplary PirAB fusion proteins comprised of a PirB protein contiguous with a PirA protein and the corresponding PirB and PirA proteins comprised within.

| PirB Protein | | PirA Protein | | PirAB Fusion Protein | |
|---|---|---|---|---|---|
| Toxin | Protein SEQ ID NO: | Toxin | Protein SEQ ID NO: | Toxin | Protein SEQ ID NO: |
| TIC7661 | 16 | TIC7660 | 14 | TIC11103 | 155 |
| TIC7663 | 22 | TIC7662 | 20 | TIC11104 | 157 |

The term "PirAB fusion protein" is also used in this application to describe a protein that comprises two PirA proteins contiguous with a PirB protein. The DNA sequence encoding the PirAB fusion protein of this type can comprise a coding sequence encoding a PirA protein, operably linked to a coding sequence encoding the same PirA protein or a different PirA protein, operably linked to a coding sequence encoding a PirB protein such that when it is expressed in a cell it produces a fusion protein comprising a PirA protein, another PirA protein, and a PirB protein. Exemplary PirAB fusion proteins comprising two PirA proteins contiguous with a PirB protein are provided in Table 3.

TABLE 3

Exemplary PirAB fusion proteins comprised of a PirA protein contiguous with another PirA protein, and contiguous with a PirB protein, and the corresponding PirA and PirB proteins comprised within.

| PirA Protein | | PirA Protein | | PirB Protein | | PirAB Fusion Protein | |
|---|---|---|---|---|---|---|---|
| Toxin | Protein SEQ ID NO: | Toxin | Protein SEQ ID NO: | Toxin | Protein SEQ ID NO: | Toxin | Protein SEQ ID NO: |
| TIC4771 | 2 | TIC4771 | 2 | TIC4772 | 4 | TIC11440 | 121 |
| TIC7575 | 8 | TIC7575 | 8 | TIC7576 | 10 | TIC11441 | 123 |
| TIC7575 | 8 | TIC4771 | 2 | TIC4772 | 4 | TIC11442 | 125 |
| TIC7660 | 14 | TIC7575 | 8 | TIC7576 | 10 | TIC11443 | 127 |
| TIC7575 | 8 | TIC7660 | 14 | TIC7661 | 16 | TIC11444 | 129 |
| TIC7660 | 14 | TIC7662 | 20 | TIC7663 | 22 | TIC11445 | 131 |
| TIC7662 | 20 | TIC7660 | 14 | TIC7661 | 16 | TIC11446 | 133 |

The term "PirAB fusion protein" is also used in this application to describe a protein that comprises multiple PirA and/or multiple PirB proteins contiguous with one another. The multiple PirA and/or PirB proteins can be duplicated PirA or PirB proteins, or can be different PirA or PirB proteins. The combination of multiple PirA and/or PirB proteins as a fusion protein can increase activity against a specific target pest species or may increase the range of pest species in which activity is present.

The term "segment" or "fragment" is used in this application to describe consecutive amino acid or nucleic acid sequences that are shorter than the complete amino acid or nucleic acid sequence describing one of The PirA Proteins, The PirB Proteins, or The PirAB Proteins. A segment or fragment exhibiting insect inhibitory activity is also disclosed in this application if alignment of such segment or fragment, with the corresponding section of the PirA proteins set forth in SEQ ID NOs:2, 8, 14, 20, 26, 32, 38, 44, 58, 64, 70, 76, 82, 88, 94, 100, or 105; the PirB proteins set forth in SEQ ID NOs:4, 10, 16, 22, 28, 34, 40, 46, 60, 66, 72, 78, 84, 90, 96, 102, 107, 135, 139, or 143; or the PirAB fusion proteins set forth in SEQ ID NOs:6, 12, 18, 24, 30, 36, 42, 48, 50, 62, 68, 74, 80, 86, 92, 98, 109, 111, 113, 115, 117, 119, 121, 123, 125, 127, 129, 131, 133, 137, 141, 145, 147, 149, 151, 153, 155, or 157, or related family member insecticidal protein results in an alignment from about 65 to about 100 percent identity between the segment or fragment and the corresponding section of the aligned protein. A segment or fragments of one of The PirA Proteins, The PirB Proteins, or The PirAB Proteins described herein may comprise at least about 50 contiguous amino acids, at least about 75 contiguous amino acids, at least about 100 contiguous amino acids, at least about 125 contiguous amino acids, at least about 150 contiguous amino acids, at least about 200 contiguous amino acids, at least about 250 contiguous amino acids, at least about 300 contiguous amino acids, at least about 350 contiguous amino acids, at least about 400 contiguous amino acids, at least about 450 contiguous amino acids, at least about 500 contiguous amino acids, at least about 550 contiguous amino acids, or at least about 600 contiguous amino acids of one of The PirA Proteins, The PirB Proteins, or The PirAB Proteins. A segment or fragment of one of The PirA Proteins, The PirB Proteins, or The PirAB Proteins described herein may exhibit the activity of the base sequence.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of one or more of The PirA Proteins, The PirB Proteins or The PirAB Fusion Proteins. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera, Coleoptera or Hemiptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include, but are not limited to, dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Coleopteran, Lepidopteran, Hemipteran, Thysanopteran, or Dipteran pest species.

The "*Photorhabdus* insect-related" proteins, or PirAB proteins, are binary toxins with pesticidal activity against some insects. Some PirAB proteins have been shown to have Lepidopteran activity when injected into the insect hemocoel. However, when presented in the insect diet, the oral application of the PirAB proteins have shown little to no activity (see, for example, Yang et al. (2017) PirAB protein from *Xenorhabdus nematophila* HB310 exhibits a binary toxin with insecticidal activity and cytotoxicity in Galleria mellonella. J. Invertebr Pathol, 148: 43-50; Li et al. (2014) *Photorhabdus* luminescens PirAB-fusion protein exhibits both cytotoxicity and insecticidal activity. FEMS Microbial Lett, 356: 23-31; Wu and Yunhong (2016) Scientific Reports 6, Article number: 34996; doi:10.1038/srep34996; and Zhang et al. (2013) XaxAB-like binary toxin from *Photorhabdus* luminescens exhibits both insecticidal activity and cytotoxicity. FEMS Microbiol Lett 350: 48-56). Oral activity of the PirAB proteins against Lepidotera have been reported but those studies have relied on the insect ingesting a diet comprising *E. coli* bacteria expressing the PirAB proteins and not purified toxin provided in the insect diet (see, for example, Waterfield et al. (2005) The *Photorhabdus* Pir toxins are similar to a developmentally regulated insect protein but show no juvenile hormone esterase activity. FEMS Microbiol Lett, 245: 47-52 and Blackburn et al. (2006) Remarkable susceptibility of the diamondback moth (*Plutella xylostella*) to ingestion of Pir toxins from *Photorhabdus luminescens. Entomologia Experimentalis et Applicata,* 121: 31-37). In stark contrast, herein, as described in the Examples, protein preparations of The PirA Proteins, The PirB Proteins, and The PirAB Fusion Proteins were provided in the insect diet bioassays. Oral activity against Lepidopteran, Coleopteran, and Hemipteran insect pests was observed and is presented in the Examples. In addition, leaf discs derived from plants expressing the PirAB fusion proteins, TIC9316, TIC9317, and TIC9318 were used in oral insect feeding studies which demonstrated activity against the Lepidopteran insect pest species European corn borer and Southwestern corn borer (SWCB). Further, leaf discs derived from plants expressing TIC10376, TIC10378, TIC10380, and TIC10381 demonstrated activity against SWCB. Also, as described in the Examples, TIC9315 and TIC11302 demonstrated activity against Western Corn Rootworm pests in stably transformed plants.

It is intended that reference to a pest, particularly a pest of a crop plant, means insect pests of crop plants, particularly those that are controlled by at least one of The PirA Proteins, The PirB Protein, and The PirAB Proteins, a related family member insecticidal protein, or a segment or fragment thereof.

As described in the Examples, one or more of The PirA Proteins, The PirB Proteins, or The PirAB Proteins exhibits insecticidal activity towards insect pests from the Coleopteran, Hemipteran, and Lepidopteran insect pest species, including adults, pupae, larvae, and neonates.

The insects of the order Lepidoptera include, but are not limited to, armyworms, cutworms, loopers, and heliothines in the Family Noctuidae, e.g., fall armyworm (*Spodoptera frugiperda*), Beet armyworm (*Spodoptera exigua*), Black armyworm (*Spodoptera exempta*), Bertha armyworm (*Mamestra configurata*), Southern armyworm (*Spodoptera eridania*), Black cutworm (*Agrotis ipsilon*), Cabbage looper (*Trichoplusia ni*), Soybean looper (Pseudoplusia *includens*), Velvetbean caterpillar (*Anticarsia gemmatalis*), Green cloverworm (*Hypena scabra*), Tobacco budworm (*Heliothis virescens*), Granulate cutworm (*Agrotis subterranea*), Armyworm (*Pseudaletia unipuncta*), Western cutworm (*Agrotis orthogonia*); borers, casebearers, webworms, coneworms, cabbageworms and skeletonizers from the Family Pyralidae, e.g., European corn borer (*Ostrinia nubilalis*), Navel orangeworm (*Amyelois transitella*), Corn root webworm (*Crambus caliginosellus*), Sod webworm (*Herpetogramma licarsisalis*), Sunflower moth (*Homoeosoma* electellum), Lesser cornstalk borer (*Elasmopalpus* lignosellus); leafrollers, budworms, seed worms, and fruit worms in the Family Tortricidae, e.g., Codling moth (*Cydia pomonella*), Grape berry moth (Endopiza *viteana*), Oriental fruit moth (*Grapholita molesta*), Sunflower bud moth (*Suleima helianthana*); and many other economically important Lepidoptera, e.g., Diamondback moth (*Plutella xylostella*), Pink bollworm (*Pectinophora gossypiella*) and Gypsy moth (*Lymantria dispar*). Other insect pests of order Lepidoptera include, e.g., Cotton leaf worm (Alabama *argillacea*), Fruit tree leaf roller (*Archips argyrospila*), European leafroller (*Archips rosana*) and other *Archips* species, (*Chilo suppressalis*, Asiatic rice borer, or rice stem borer), Rice leaf roller (*Cnaphalocrocis medinalis*), Corn root webworm (*Crambus caliginosellus*), Bluegrass webworm (*Crambus* teterrellus), Southwestern corn borer (*Diatraea grandiosella*), Surgarcane borer (*Diatraea saccharalis*), Spiny bollworm (*Earias insulana*), Spotted bollworm (*Earias vittella*), Old World bollworm (*Helicoverpa armigera*), Corn earworm (*Helicoverpa zea*, also known as soybean podworm and cotton bollworm), Tobacco budworm (*Heliothis virescens*), Sod webworm (*Herpetogramma licarsisalis*), Western bean cutworm (*Striacosta albicosta*), European grape vine moth (*Lobesia botrana*), Citrus leafminer (*Phyllocnistis citrella*), large white butterfly (*Pieris brassicae*), small white butterfly (*Pieris rapae*, also known as imported cabbageworm), Tobacco cutworm (*Spodoptera litura*, also known as cluster caterpillar), and Tomato leafminer (*Tuta absoluta*).

The insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., Diabrotica spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is Western Corn Rootworm (Diabrotica virgifera, WCR), Northern Corn Rootworm (Diabrotica *barberi*, NCR), Mexican Corn Rootworm (Diabrotica virgifera *zeae*, MCR), Brazilian Corn Rootworm (Diabrotica *balteata*, BZR), Southern Corn Rootworm (Diabrotica *undecimpunctata howardii*, SCR), Colorado potato beetle (*Leptinotarsa decemlineata*, CPB), a Brazilian Corn Rootworm complex (BCR, consisting of Diabrotica *viridula* and Diabrotica *speciosa*), Crucifer Flea Beetle (*Phyllotreta cruciferae*), Striped Flea Beetle (*Phyllotreta striolata*), and Western Black Flea Beetle (*Phyllotreta pusilla*).

The insects of the order Hemiptera include, but are not limited to, Stink Bugs of the family Pentatomidae: Green Stink Bugs from the genus Chinavia (Chinavia *hilaris*, Chinavia *marginata*, and Chinavia *pensylvanica*), Stink bugs of the genus *Chlorochroa* (*Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia*, and *Chlorochroa senilis*), Southern Green Stink Bug (*Nezara viridula*), Stink Bugs from the genus *Edessa* (*Edessa meditabunda, Edessa bifida*, and *Edessa florida*), the Neotropical Brown Stink Bug (*Euschistus heros*), stink bugs from the genus *Euschistus* (*Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata, Thyanta custator, Thyanta pallidovirens, Thyanta perditor, Thyanta maculate*, and *Thyanta pseudocasta*), the Green Belly Stink Bug (*Dichelops melacanthus*) and other stink bugs of the genus *Dichelops* (*Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix*, and *Dichelops saltensis*), the Red Banded Stink Bug (*Piezodorus guildinni*) as well as *Piezodorus lituratus*; and insects of the family of Plataspidae such as Kudzu Bug (*Megacopta cribraria*), Western tarnished plant bug (*Lygus hesperus*), and Tarnished plant bug (*Lygus lineolaris*).

Reference in this application to an “isolated DNA molecule”, or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be “isolated” so long as the element is within the genome of the organism and at the location within the genome in which it is naturally found. However, each of these elements, and subparts of these elements, would be “isolated” within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further herein, an operon containing two open reading frames (ORFs) encoding the PirA protein, TIC4771 (SEQ ID NO:1) and the PirB protein, TIC4772 (SEQ ID NO:3) was discovered in DNA obtained from *Xenorhabdus nematophila* strain ISB000002 which encodes the protein toxins presented as SEQ ID NO:2 and SEQ ID NO:4, respectively. The two ORFs were used to make a PirAB fusion protein encoding DNA sequence, TIC6880 (SEQ ID NO:5) wherein the two coding sequences were operably linked and in frame to produce the TIC6880 PirAB fusion protein presented as SEQ ID NO:6. Bioassay using microbial host cell-derived TIC4771 demonstrated activity against the Lepidopteran species Corn earworm (*Helicoverpa zea*, CEW), Diamondback Moth (*Plutella xylostella*, DEM), European corn borer (*Ostrinia nubilalis*, ECB), Velvet Bean Caterpillar (*Anticarsia gemmatalis*, VBC), and Southern Army Worm (*Spodoptera eridania*, SAW); the Coleopteran species Colorado potato beetle (*Leptinotarsa decemlineata*, CPB); and the Hemipteran species Tarnished plant bug (*Lygus lineolaris*, TPB). Bioassay using microbial host cell-derived TIC4772 demonstrated activity against the Lepidopteran species CEW, DBM, and VBC and the Hemipteran species TPB. Bioassay using microbial host cell-derived PirAB fusion protein, TIC6880 comprised of TIC4771 and TIC4772, demonstrated activity against the Lepidopteran species Fall armyworm (*Spodoptera frugiperda*, FAW), CEW, Southwestern Corn Borer (*Diatraea grandiosella*, SWCB), DBM, ECB, and VBC, the Coleopteran species CPB and Western Corn Rootworm (Diabrotica virgifera, WCR); the Hemipteran species Tarnished plant bug (*Lygus lineolaris*, TPB), Western tarnished plant bug (*Lygus Hesperus*, WTP), Southern Green Stink Bug (*Nezara viridula*, SGB), and Neotropical Brown Stink Bug (*Euschistus heros*, NBSB), and the *Dipteran* species Yellow fever mosquito (*Aedes aegypti*, YFM).

An operon containing two ORFs encoding the PirA protein, TIC7575 (SEQ ID NO:7) and the PirB protein, TIC7576 (SEQ ID NO:9) was discovered in DNA obtained from *Xenorhabdus ehlersii* strain 85823 which encodes the protein toxins presented as SEQ ID NO:8 and SEQ ID NO:10, respectively. The two ORFs were used to make a PirAB fusion protein encoding DNA sequence, TIC9316 (SEQ ID NO:11) wherein the two coding sequences were operably linked and in frame to produce the TIC9316 PirAB fusion protein presented as SEQ ID NO:12. Bioassay using microbial host cell-derived TIC7575 and TIC7576 did not demonstrate activity against the insects tested in assay. However, bioassay using the PirAB fusion protein TIC9316—comprised of TIC7575 and TIC7576—demonstrated activity against the Lepidopteran species SWCB, Black cutworm (*Agrotis ipsilon*, BCW), SAW, Tobacco budworm (*Heliothis virescens*, TBW), ECB, and VBC, the Coleopteran species CPB, and the Hemipteran species TPB, WTP, SGB, and NBSB.

An operon containing two ORFs encoding the PirA protein, TIC7660 (SEQ ID NO:13) and the PirB protein, TIC7661 (SEQ ID NO:15) was discovered in DNA obtained from *Xenorhabdus cabanillasii* strain 85908 which encodes the protein toxins presented as SEQ ID NO:14 and SEQ ID NO:16, respectively. The two ORFs were used to make a PirAB fusion protein encoding DNA sequence, TIC9317 (SEQ ID NO:17) wherein the two coding sequences were operably linked and in frame to produce the TIC9317 PirAB fusion protein presented as SEQ ID NO:18. Bioassay using microbial host cell-derived TIC7660 and TIC7661 did not demonstrate activity against the insects used in assay. However, bioassay using the PirAB fusion protein TIC9317—comprised of TIC7660 and TIC7661—demonstrated activity against the Lepidopteran species SWCB, ECB, and VBC, the Coleopteran species CPB and WCR, and the Hemipteran species TPB, WTP, and SGB.

An operon containing two ORFs encoding the PirA protein, TIC7662 (SEQ ID NO:19) and the PirB protein, TIC7663 (SEQ ID NO:21) was discovered in DNA obtained from *Xenorhabdus ehlersii* strain 85887 which encodes the protein toxins presented as SEQ ID NO:20 and SEQ ID NO:22, respectively. The two ORFs were used to make a PirAB fusion protein encoding DNA sequence, TIC9318 (SEQ ID NO:23) wherein the two coding sequences were operably linked and in frame to produce the TIC9318 PirAB fusion protein presented as SEQ ID NO:24. Bioassay using microbial host cell-derived TIC7662 and TIC7663 did not demonstrate activity against the insects used in assay. However, bioassay using the PirAB fusion protein TIC9318—comprised of TIC7662 and TIC7663—demonstrated activity against the Lepidopteran species SWCB, BCW, TBW, ECB, and VBC, the Coleopteran species CPB and WCR, and the Hemipteran species TPB, WTP, SGB, and NBSB.

An operon containing two ORFs encoding the PirA protein, TIC7664 (SEQ ID NO:25) and the PirB protein, TIC7665 (SEQ ID NO:27) was discovered in DNA obtained from *Xenorhabdus poinarii* strain 86198 which encodes the protein toxins presented as SEQ ID NO:26 and SEQ ID NO:28, respectively. The two ORFs were used to make a PirAB fusion protein encoding DNA sequence, TIC9319 (SEQ ID NO:29) wherein the two coding sequences were operably linked and in frame to produce the TIC9319 PirAB fusion protein presented as SEQ ID NO:30. Bioassay using microbial host cell-derived TIC7664 demonstrated activity against the Coleopteran species CPB. Bioassay using microbial host cell-derived TIC7665 demonstrated activity against the Lepidopteran species TBW. Bioassay using the PirAB fusion protein, TIC9319—comprised of TIC7664 and TIC76653—demonstrated activity against the Lepidopteran species SWCB, BCW, ECB, and VBC, the Coleopteran species CPB, and the Hemipteran species TPB, WTP, and SGB.

An operon containing two ORFs encoding the PirA protein TIC7666 (SEQ ID NO:31) and the PirB protein TIC7667 (SEQ ID NO:33) was discovered in DNA obtained from *Photorhabdus luminescens* strain 86197 which encodes the protein toxins presented as SEQ ID NO:32 and SEQ ID NO:34, respectively. The two ORFs were used to make a PirAB fusion protein encoding DNA sequence, TIC9322 (SEQ ID NO:35) wherein the two coding sequences were operably linked and in frame to produce the TIC9322 PirAB fusion protein presented as SEQ ID NO:36. Bioassay using microbial host cell-derived TIC7666 did not demonstrate activity against the insects used in assay. Bioassay using microbial host cell-derived TIC7667 demonstrated activity against the Lepidopteran species SWCB. Bioassay using the PirAB fusion protein TIC9322—comprised of TIC7666 and TIC7667—demonstrated activity against the Lepidopteran species SWCB and VBC, the Coleopteran species CPB, and the Hemipteran species TPB.

An operon containing two ORFs encoding the PirA protein, TIC7668 (SEQ ID NO:37) and the PirB protein, TIC7669 (SEQ ID NO:39) was discovered in DNA obtained from *Photorhabdus luminescens* strain 86194 which encodes the protein toxins presented as SEQ ID NO:38 and SEQ ID NO:40, respectively. The two ORFs were used to make a PirAB fusion protein encoding DNA sequence, TIC9320 (SEQ ID NO:41) wherein the two coding sequences were operably linked and in frame to produce the TIC9320 PirAB fusion protein presented as SEQ ID NO:42. Bioassay using microbial host cell-derived TIC7668 and TIC7669 did not demonstrate activity against the insects used in assay. However, bioassay using the PirAB fusion protein TIC9320—comprised of TIC7668 and TIC7669—demonstrated activity against the Lepidopteran species SWCB, ECB, and VBC, the Coleopteran species CPB and WCR, and the Hemipteran species TPB, SGB, and NBSB.

An operon containing two ORFs encoding the PirA protein, TIC7939 (SEQ ID NO:43) and the PirB protein, TIC7940 (SEQ ID NO:45) was discovered in DNA obtained from an unknown bacterial species comprised within a microbiome which encodes the protein toxins presented as SEQ ID NO:44 and SEQ ID NO:46, respectively. The two ORFs were used to make a PirAB fusion protein encoding DNA sequence, TIC9321 (SEQ ID NO:47), wherein the two coding sequences were operably linked and in frame to produce the TIC9321 PirAB fusion protein presented as SEQ ID NO:48.

An operon containing two ORFs encoding the PirA protein, TIC10357 (SEQ ID NO:57) and the PirB protein, TIC10366 (SEQ ID NO:59) was discovered in DNA obtained from *Shewanella violacea* which encodes the protein toxins presented as SEQ ID NO:58 and SEQ ID NO:60, respectively. The two open reading frames were used to make a PirAB fusion protein encoding DNA sequence, TIC10375 (SEQ ID NO:61), wherein the two coding sequences were operably linked and in frame to produce the TIC10375 PirAB fusion protein presented as SEQ ID NO:62.

An operon containing two ORFs encoding the PirA protein, TIC10358 (SEQ ID NO:63) and the PirB protein, TIC10367 (SEQ ID NO:65) was discovered in DNA obtained from *Photorhabdus luminescens* strain laumondii TTO1 which encodes the protein toxins presented as SEQ ID NO:64 and SEQ ID NO:66, respectively. The two ORFs were used to make a PirAB fusion protein encoding DNA sequence TIC10376 (SEQ ID NO:67) wherein the two coding sequences were operably linked and in frame to produce the TIC10376 PirAB fusion protein presented as SEQ ID NO:68. Bioassay using microbial host cell-derived TIC10358 and TIC10367 did not demonstrate activity against the insects used in assay. However, bioassay using the PirAB fusion protein TIC10376—comprised of TIC10358 and TIC10367—demonstrated activity against the Lepidopteran species SWCB and the Coleopteran species Northern Corn Rootworm (Diabrotica *barberi*, NCR) and WCR.

An operon containing two ORFs encoding the PirA protein, TIC10360 (SEQ ID NO:69) and the PirB protein, TIC10369 (SEQ ID NO:71) was discovered in DNA obtained from *Photorhabdus asymbiotica* which encodes the protein toxins presented as SEQ ID NO:70 and SEQ ID NO:72, respectively. The two ORFs were used to make a PirAB fusion protein encoding DNA sequence TIC10377 (SEQ ID NO:73) wherein the two coding sequences were operably linked and in frame to produce the TIC10377 PirAB fusion protein presented as SEQ ID NO:74.

An operon containing two ORFs encoding the PirA protein TIC10361 (SEQ ID NO:75) and the PirB protein TIC10370 (SEQ ID NO:77) was discovered in DNA obtained from *Xenorhabdus* sp. strain NBAII XenSa04 which encodes the protein toxins presented as SEQ ID NO:76 and SEQ ID NO:78, respectively. The two ORFs were used to make a PirAB fusion protein encoding DNA sequence TIC10378 (SEQ ID NO:79) wherein the two coding sequences were operably linked and in frame to produce the TIC10378 PirAB fusion protein presented as SEQ ID NO:80.

An operon containing two ORFs encoding the PirA protein TIC10362 (SEQ ID NO:81) and the PirB protein TIC10371 (SEQ ID NO:83) was discovered in DNA obtained from *Yersinia aldovae* strain 670-83 which encodes the protein toxins presented as SEQ ID NO:82 and SEQ ID NO:84, respectively. The two ORFs were used to make a PirAB fusion protein encoding DNA sequence TIC10379 (SEQ ID NO:85) wherein the two coding sequences were operably linked and in frame to produce the TIC10379 PirAB fusion protein presented as SEQ ID NO:86.

An operon containing two ORFs encoding the PirA protein TIC10363 (SEQ ID NO:87) and the PirB protein TIC10372 (SEQ ID NO:89) was discovered in DNA obtained from *Xenorhabdus doucetiae* strain FRM16 which encodes the protein toxins presented as SEQ ID NO:88 and SEQ ID NO:90, respectively. The two ORFs were used to make a PirAB fusion protein encoding DNA sequence TIC10380 (SEQ ID NO:91) wherein the two coding sequences were operably linked and in frame to produce the TIC10380 PirAB fusion protein presented as SEQ ID NO:92. Bioassay using microbial host cell-derived TIC10363 and TIC10372 did not demonstrate activity against the insects used in assay. However, bioassay using the PirAB fusion protein TIC10380—comprised of TIC10363 and TIC10372—demonstrated activity against the Lepidopteran species FAW, the Coleopteran species NCR and WCR and the Hemipteran species NBSB.

An operon containing two ORFs encoding the PirA protein TIC10364 (SEQ ID NO:93) and the PirB protein TIC10373 (SEQ ID NO:95) was discovered in DNA obtained from *Xenorhabdus griffiniae* strain BMMCB which encodes the protein toxins presented as SEQ ID NO:94 and SEQ ID NO:96, respectively. The two ORFs were used to make a PirAB fusion protein encoding DNA sequence TIC10381 (SEQ ID NO:97) wherein the two coding sequences were operably linked and in frame to produce the TIC10381 PirAB fusion protein presented as SEQ ID NO:98. Bioassay using microbial host cell-derived TIC10364 and TIC10373 did not demonstrate activity against the insects used in assay. However, bioassay using the PirAB fusion protein TIC10378—comprised of TIC10364 and TIC10373—demonstrated activity against the Coleopteran species NCR and WCR and the Hemipteran species NBSB.

An operon containing two ORFs encoding the PirA protein TIC10359 (SEQ ID NO:99) and the PirB protein TIC10368 (SEQ ID NO:101) was discovered in DNA obtained from *Xenorhabdus nematophila* which encodes the protein toxins presented as SEQ ID NO:100 and SEQ ID NO:102, respectively. An operon sequence comprising both TIC10359 and TIC10368 is presented as SEQ ID NO:103.

An operon containing two ORFs encoding the PirA protein PirA_ABE68878 (SEQ ID NO:104) and the PirB protein, PirB_ABE68879 (SEQ ID NO:106) was discovered in DNA obtained from *Photorhabdus luminescens* strain Hm which encodes the protein toxins presented as SEQ ID NO:105 and SEQ ID NO:107, respectively. The two ORFs were used to make a PirAB fusion protein encoding DNA sequence TIC10434 (SEQ ID NO:108) wherein the two coding sequences were operably linked and in frame to produce the TIC10378 PirAB fusion protein presented as SEQ ID NO:109. Bioassay using microbial host cell-derived PirAB fusion protein TIC10434—comprised of PirA_ABE68878 and PirB_ABE68879—demonstrated activity against the Coleopteran species NCR and WCR.

An operon containing the PirB protein ORF encoding TIC11505 (SEQ ID NO:134) was discovered from *Xenorhabdus nematophila* strain MDI-0035777 which encodes the protein toxin presented as SEQ ID NO:135. The PirAB fusion protein TIC11056 encoding sequence (SEQ ID NO:136) comprised the TIC10364 coding sequence operably linked in frame with the TIC11505 coding sequence to produce the TIC11506 PirAB fusion protein presented as SEQ ID NO:137.

An operon containing the PirB protein ORF encoding TIC11510 (SEQ ID NO:138) was discovered from *Xenorhabdus nematophila* strain MDI-0035777 which encodes the protein toxin presented as SEQ ID NO:139. The PirAB fusion protein TIC11512 encoding sequence (SEQ ID NO:140) comprised the TIC10364 coding sequence operably linked in frame with the TIC11505 coding sequence to produce the TIC11056 PirAB fusion protein presented as SEQ ID NO:141.

An operon containing the PirB protein ORF encoding TIC11511 (SEQ ID NO:142) was discovered from *Xenorhabdus nematophila* strain MDI-0035777 which encodes the protein toxin presented as SEQ ID NO:143. The PirAB fusion protein TIC11513 encoding sequence (SEQ ID NO:144) comprised the TIC10364 coding sequence operably linked in frame with the TIC11513 coding sequence to produce the TIC11056 PirAB fusion protein presented as SEQ ID NO:145.

The PirAB fusion proteins, TIC11210, TIC11211, and TIC11301 comprised the PirA protein TIC7575 and the PirB proteins, TIC7665, TIC7667, and TIC7661, respectively. The PirAB fusion protein, TIC11212 comprises the PirA protein TIC7662 and the PirB protein TIC7665. The PirAB fusion protein, TIC11302 comprises the PirA protein, TIC7660 and the PirB protein, TIC7576. The PirAB fusion proteins TIC11210 and TIC11211 demonstrated activity against the Lepidopteran species SWCB and the Hemipteran species NBSB. The PirAB fusion proteins TIC11301 and TIC11302 demonstrated activity against the Lepidopteran species SWCB, ECB, and VBC, the Coleopteran species WCR, and the Hemipteran species NBSB and WTP.

The PirAB fusion proteins, TIC11103 and TIC11104 comprised a PirB protein congruent with a PirA Protein. The PirAB fusion protein, TIC11103 is comprised of the PirB protein, TIC7661 and the PirA protein, TIC7660. The PirAB fusion protein, TIC11104 is comprised of the PirB protein TIC7663 and the PirA protein TIC7662.

The PirAB fusion protein TIC11440 is comprised of a duplication of the PirA protein TIC4771 and the PirB protein TIC4772. The PirAB fusion protein TIC11441 is comprised of a duplication of the PirA protein TIC7575 and the PirB protein TIC7576. The PirAB fusion protein TIC11442 is comprised of the PirA proteins, TIC7575 and TIC4771, and the PirB protein TIC4772. The PirAB fusion protein TIC11443 is comprised of the PirA proteins TIC7660 and TIC7575 and the PirB protein, TIC7576. The PirAB fusion protein TIC11444 is comprised of the PirA proteins TIC7575 and TIC7660 and the PirB protein TIC7661. The PirAB fusion protein TIC11445 is comprised of the PirA proteins TIC7660 and TIC7662 and the PirB protein TIC7663. The PirAB fusion protein TIC11446 is comprised of the PirA proteins TIC7662 and TIC7660 and the PirB protein TIC7661. Bacterial host cell derived TIC11442 demonstrated activity against the Hemipteran pest species NBSB. Bacterial host cell derived TIC11444 demonstrated activity against the Lepidopteran species SWCB and the Hemipteran species NBSB.

As described in the Examples, synthetic DNA sequences encoding the PirAB fusion proteins TIC6880PL (SEQ ID NO:49), TIC9316 (SEQ ID NO:51), TIC9317 (SEQ ID NO:53), TIC9318 (SEQ ID NO:55), TIC9320 (SEQ ID NO:57), TIC9322 (SEQ ID NO:59), TIC10376PL (SEQ ID NO:146), TIC10378PL (SEQ ID NO:148), TIC10380PL (SEQ ID NO:150), TIC10381PL (SEQ ID NO:152), TIC11103 (SEQ ID NO:154), TIC11104 (SEQ ID NO:156), and TIC11302 (SEQ ID NO:158) were designed for expression in a plant cell. Corn plants transformed with binary transformation plasmid constructs expressing TIC9316, TIC9317, and TIC9318 demonstrated activity against the insect pest species European corn borer and Southwestern corn borer.

For expression in plant cells, The PirAB Fusion Proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633,435; and 5,312,910; and EP 0218571; EP 189707; EP 508909; and EP 924299). For targeting one of The PirAB Fusion Proteins to the chloroplast, a sequence encoding a chloroplast transit peptide is placed 5' in operable linkage and in frame to a synthetic coding sequence encoding one of The PirAB Fusion Proteins that has been designed for optimal expression in plant cells.

It is contemplated that additional toxin protein sequences related to The PirA Proteins, The PirB Proteins, and The PirAB Fusion Proteins can be created by using the naturally occurring amino acid sequence of The PirA Proteins, The PirB Proteins, and The PirAB Fusion Proteins to combine differences at the amino acid sequence level into novel amino acid sequence variants and making appropriate changes to the recombinant nucleic acid sequence encoding the variants.

This disclosure further contemplates that improved variants of The PirA Proteins, The PirB Proteins, and The PirAB Fusion Proteins can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

Proteins that resemble The PirA Proteins, The PirB Proteins, and The PirAB Fusion Proteins can be identified by comparison to each other using various computer-based algorithms known in the art. For example, amino acid sequence identities of proteins related to The PirA Proteins, The PirB Proteins, and The PirAB Fusion Proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran, or Coleopteran, or Hemipteran insect species is related to The PirA Proteins if alignment of such query protein with TIC7939 exhibits at least 65% to about 100% amino acid identity along the length of the query protein that is about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC7664 or TIC7666 exhibits at least 97% to about 100% amino acid identity along the length of the query protein that is about 97%, 98%, 99%, 100% amino acid sequence identity (or any fraction of a percentage in this range) between query and subject protein; or if alignment of such query protein with TIC4771 exhibits at least 98% to about 100% amino acid identity along the length of the query protein that is about 98%, 99%, 100% amino acid sequence identity (or any fraction of a percentage in this range) between query and subject protein; or if alignment of such query protein with TIC7575, TIC7660, TIC7662, TIC7668, TIC10357, TIC10358, TIC10360, TIC10361, TIC10362, TIC10364, TIC10359, or PirA_ABE68878 exhibits 100% identity between query and subject protein.

It is also intended that a protein exhibiting insect inhibitory activity against a Lepidopteran, or Coleopteran, or Hemipteran insect species is related to The PirB Proteins if alignment of such query protein with TIC7940 exhibits at least 65% to about 100% amino acid identity along the length of the query protein that is about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC4772 exhibits at least 97% to about 100% amino acid identity along the length of the query protein that is about 97%, 98%, 99%, 100% amino acid sequence identity (or any fraction of a percentage in this range) between query and subject protein; or if alignment of such query protein with TIC4772 exhibits at least 97% to about 100% amino acid identity along the length of the query protein that is about 97%, 98%, 99%, 100% amino acid sequence identity (or any fraction of a percentage in this range) between query and subject protein; or if alignment of such query protein with TIC7665, TIC7667, or TIC10368 exhibits at least 98% to about 100% amino acid identity along the length of the query protein that is about 98%, 99%, 100% amino acid sequence identity (or any fraction of a percentage in this range) between query and subject protein; or if alignment of such query protein with TIC7576, TIC7661, TIC7663, TIC7669, TIC10366, TIC10367, TIC10369, TIC10370, TIC10371, TIC10372, TIC10373, PirB_ABE68879, TIC11510, or TIC11511 exhibits 100% amino acid sequence identity between query and subject protein.

It is also intended that a protein exhibiting insect inhibitory activity against a Lepidopteran, or Coleopteran, or Hemipteran insect species is related to The PirAB Fusion Proteins if alignment of such query protein with TIC9321, TIC11411, TIC11443, TIC11444, TIC11445, TIC11446, TIC11513 exhibits at least 65% to about 100% amino acid identity along the length of the query protein that is about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC10434, TIC11440, or TIC11442 exhibits at least 70% to about 100% amino acid identity along the length of the query protein that is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC9316, TIC9317, TIC9318, TIC9322, TIC9320, TIC10375, TIC10376, TIC10377, TIC10378, TIC10379, TIC10381, TIC11211, TIC11301, TIC11302, TIC10376PL, TIC10378PL, TIC10381PL, TIC11103, or TIC11104 exhibits at least 80% to about 100% amino acid identity along the length of the query protein that is about 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC9319, TIC10380, TIC11210, TIC11212, or TIC10380PL exhibits at least 82% to about 100% amino acid identity along the length of the query protein that is about 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC6880 or TIC6880PL exhibits at least 86% to about 100% amino acid identity along the length of the query protein that is about 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC11506 or TIC11512 exhibits at least 94% to about 100% amino acid identity along the length of the query protein that is about 94%, 95%, 96%, 97%, 98%, 99%, 100% amino acid sequence identity (or any fraction of a percentage in this range) between query and subject protein.

Exemplary PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878 were aligned with each other using a Clustal W algorithm. A pair-wise matrix of percent amino acid sequence identities for each of the full-length proteins was created, as reported in Tables 4 and 5.

TABLE 4

Pair-wise matrix display of PirA proteins.

| Sequence | TIC7666 | TIC7668 | PirA_ABE68878 | TIC10360 | TIC7660 | TIC10361 | TIC7662 | TIC10364 |
|---|---|---|---|---|---|---|---|---|
| TIC7666 | — | 94.7 | 92.5 | 85.7 | 51.1 | 48.1 | 48.1 | 49.6 |
| TIC7668 | 94.7 | — | 94 | 88.7 | 51.1 | 49.6 | 48.9 | 50.4 |
| PirA_ABE68878 | 89.1 | 90.6 | — | 81.2 | 47.8 | 46.4 | 47.1 | 48.6 |
| TIC10360 | 85.7 | 88.7 | 84.2 | — | 50.4 | 50.4 | 52.6 | 52.6 |
| TIC7660 | 48.2 | 48.2 | 46.8 | 47.5 | — | 93.6 | 75.2 | 71.6 |
| TIC10361 | 44.8 | 46.2 | 44.8 | 46.9 | 92.3 | — | 75.5 | 73.4 |
| TIC7662 | 45.4 | 46.1 | 46.1 | 49.6 | 75.2 | 76.6 | — | 85.1 |
| TIC10364 | 46.5 | 47.2 | 47.2 | 49.3 | 71.1 | 73.9 | 84.5 | — |
| TIC7575 | 43.3 | 45.4 | 44 | 47.5 | 72.3 | 73.8 | 87.2 | 83.7 |
| TIC4771 | 45.2 | 45.9 | 45.9 | 48.1 | 72.6 | 75.6 | 75.6 | 76.3 |
| TIC7664 | 45.2 | 45.9 | 45.9 | 48.9 | 70.4 | 71.9 | 74.1 | 74.1 |
| TIC10363 | 45.3 | 46 | 45.3 | 48.2 | 71.5 | 74.5 | 80.3 | 78.8 |
| TIC10359 | 47.4 | 48.9 | 47.4 | 51.1 | 71.9 | 71.9 | 74.1 | 72.6 |
| TIC7939 | 35.3 | 36.7 | 36 | 36.7 | 41.7 | 42.4 | 41.7 | 41.7 |
| TIC10358 | 40.3 | 41 | 41 | 40.3 | 36.8 | 38.2 | 39.6 | 37.5 |
| TIC10362 | 42.6 | 44.9 | 44.1 | 44.9 | 36.8 | 37.5 | 43.4 | 40.4 |
| TIC10357 | 23.7 | 23.7 | 22.8 | 24.6 | 21.9 | 22.8 | 26.3 | 25.4 |

TABLE 5

| Pair-wise matrix display of PirA proteins. | | | | | | | | |
|---|---|---|---|---|---|---|---|---|
| Sequence | TIC7666 | TIC7668 | PirA ABE68878 | TIC10360 | TIC7660 | TIC10361 | TIC7662 | TIC10364 |
| TIC7575 | 43.3 | 45.4 | 44 | 47.5 | 72.3 | 73.8 | 87.2 | 83.7 |
| TIC4771 | 45.2 | 45.9 | 45.9 | 48.1 | 72.6 | 75.6 | 75.6 | 76.3 |
| TIC7664 | 45.2 | 45.9 | 45.9 | 48.9 | 70.4 | 71.9 | 74.1 | 74.1 |
| TIC10363 | 45.3 | 46 | 45.3 | 48.2 | 71.5 | 74.5 | 80.3 | 78.8 |
| TIC10359 | 47.4 | 48.9 | 47.4 | 51.1 | 71.9 | 71.9 | 74.1 | 72.6 |
| TIC7939 | 35.3 | 36.7 | 36 | 36.7 | 41.7 | 42.4 | 41.7 | 41.7 |
| TIC10358 | 40.3 | 41 | 41 | 40.3 | 36.8 | 38.2 | 39.6 | 37.5 |
| TIC10362 | 42.6 | 44.9 | 44.1 | 44.9 | 36.8 | 37.5 | 43.4 | 40.4 |
| TIC10357 | 23.7 | 23.7 | 22.8 | 24.6 | 21.9 | 22.8 | 26.3 | 25.4 |

Exemplary PirB proteins TIC4772, TIC7576, TIC7661, TIC7663, TIC7665, TIC7667, TIC7669, and TIC7940 were aligned with each other using a Clustal W algorithm. A pair-wise matrix of percent amino acid sequence identities for each of the full-length proteins was created, as reported in Tables 6 and 7.

TABLE 6

| Pair-wise matrix display of PirB proteins. | | | | | | | | | |
|---|---|---|---|---|---|---|---|---|---|
| Sequence | TIC7667 | TIC7669 | PirB_ABE68879 | TIC10369 | TIC7576 | TIC10373 | TIC7663 | TIC7661 | TIC10370 |
| TIC7667 | — | 95.5 | 93.6 | 93.3 | 49.6 | 48.7 | 49.6 | 48.9 | 49.4 |
| TIC7669 | 95.5 | — | 95.7 | 94.5 | 50.4 | 49.6 | 50.4 | 49.4 | 49.9 |
| PirB_ABE68879 | 93.6 | 95.7 | — | 94 | 50.1 | 49.2 | 50.8 | 49.2 | 49.9 |
| TIC10369 | 93.3 | 94.5 | 94 | — | 49.4 | 48.9 | 50.4 | 49.2 | 49.4 |
| TIC7576 | 48.9 | 49.6 | 49.4 | 48.7 | — | 94.8 | 90.6 | 87.5 | 89.9 |
| TIC10373 | 48 | 48.9 | 48.5 | 48.2 | 94.8 | — | 92.7 | 86.4 | 87.8 |
| TIC7663 | 48.9 | 49.6 | 50.1 | 49.6 | 90.6 | 92.7 | — | 84.2 | 86.1 |
| TIC7661 | 48.2 | 48.7 | 48.5 | 48.5 | 87.5 | 86.4 | 84.2 | — | 95.3 |
| TIC10370 | 48.7 | 49.2 | 49.2 | 48.7 | 89.9 | 87.8 | 86.1 | 95.3 | — |
| TIC10372 | 48.4 | 49.1 | 48.6 | 47.9 | 84.4 | 82.1 | 80.9 | 79.5 | 80.9 |
| TIC11510 | 47.1 | 47.1 | 47.6 | 47.6 | 79.5 | 79 | 79.7 | 77.2 | 78.3 |
| TIC11511 | 47.3 | 47.3 | 47.8 | 47.8 | 80 | 79.5 | 80.2 | 77.6 | 78.8 |
| TIC10368 | 47.6 | 47.6 | 48 | 48 | 80.2 | 79.7 | 80.4 | 77.9 | 79 |
| TIC11505 | 47 | 47 | 47.5 | 47.5 | 79.3 | 78.8 | 79.5 | 77 | 78.1 |
| TIC4772 | 47.2 | 47.9 | 47.9 | 47.2 | 79.7 | 78.5 | 79.7 | 76.2 | 78 |
| TIC7665 | 49 | 49.3 | 49.5 | 49.5 | 81.2 | 80.2 | 80.9 | 78.7 | 79.7 |
| TIC10367 | 41.7 | 42.4 | 42 | 42.7 | 43.2 | 42.7 | 43.6 | 42.7 | 43.2 |
| TIC10371 | 45.2 | 44.7 | 44.5 | 45 | 48.8 | 48.6 | 48.1 | 48.3 | 48.3 |
| TIC7940 | 37 | 38.2 | 37.7 | 37 | 41.5 | 42.5 | 43 | 41.8 | 42.2 |
| TIC10366 | 24.8 | 25.1 | 24.8 | 25.8 | 25.1 | 24.8 | 24.4 | 24.6 | 25.1 |

TABLE 7

| Pair-wise matrix display of PirB proteins. | | | | | | | | | | | |
|---|---|---|---|---|---|---|---|---|---|---|---|
| Sequence | TIC10372 | TIC11510 | TIC11511 | TIC10368 | TIC11505 | TIC4772 | TIC7665 | TIC10367 | TIC10371 | TIC7940 | TIC10366 |
| TIC7667 | 49.6 | 48.2 | 48.4 | 48.7 | 48.7 | 48.2 | 48.4 | 41.5 | 44.9 | 37 | 25.3 |
| TIC7669 | 50.4 | 48.2 | 48.4 | 48.7 | 48.7 | 48.9 | 48.7 | 42.2 | 44.4 | 38.2 | 25.5 |
| PirB_ABE68879 | 49.9 | 48.7 | 48.9 | 49.2 | 49.2 | 48.9 | 48.9 | 41.8 | 44.2 | 37.7 | 25.3 |
| TIC10369 | 49.2 | 48.7 | 48.9 | 49.2 | 49.2 | 48.2 | 48.9 | 42.5 | 44.6 | 37 | 26.3 |
| TIC7576 | 85.4 | 80.2 | 80.7 | 80.9 | 80.9 | 80.2 | 79.1 | 42.4 | 47.8 | 40.9 | 25.2 |
| TIC10373 | 83.1 | 79.8 | 80.2 | 80.5 | 80.5 | 79.1 | 78.1 | 41.9 | 47.5 | 41.9 | 24.9 |
| TIC7663 | 81.9 | 80.5 | 80.9 | 81.2 | 81.2 | 80.2 | 78.8 | 42.8 | 47.1 | 42.4 | 24.5 |
| TIC7661 | 80.5 | 77.9 | 78.4 | 78.6 | 78.6 | 76.7 | 76.7 | 41.9 | 47.3 | 41.2 | 24.7 |
| TIC10370 | 81.9 | 79.1 | 79.5 | 79.8 | 79.8 | 78.6 | 77.6 | 42.4 | 47.3 | 41.6 | 25.2 |
| TIC10372 | — | 79.1 | 79.5 | 79.8 | 79.8 | 78.8 | 76.5 | 40.5 | 47.2 | 39.8 | 24.2 |
| TIC11510 | 79.3 | — | 99.5 | 99.3 | 99.3 | 86.5 | 81.6 | 42.2 | 46.4 | 41 | 24.5 |
| TIC11511 | 79.7 | 99.5 | — | 99.8 | 99.8 | 86.9 | 81.6 | 42.2 | 46.9 | 41 | 24.2 |
| TIC10368 | 80 | 99.3 | 99.8 | — | 100 | 87.2 | 81.8 | 42 | 46.6 | 41 | 24 |
| TIC11505 | 79 | 98.2 | 98.6 | 98.8 | — | 86.2 | 80.9 | 41.5 | 46.1 | 40.6 | 24 |
| TIC4772 | 79.2 | 86.7 | 87.1 | 87.4 | 87.4 | — | 80.8 | 42.5 | 47 | 41.8 | 24.5 |
| TIC7665 | 79.5 | 84.5 | 84.5 | 84.8 | 84.8 | 83.6 | — | 43 | 47.3 | 41.5 | 25.8 |
| TIC10367 | 41.7 | 43.4 | 43.4 | 43.2 | 43.2 | 43.6 | 42.7 | — | 57.6 | 35 | 22.1 |
| TIC10371 | 48.8 | 47.8 | 48.3 | 48.1 | 48.1 | 48.3 | 47.1 | 57.7 | — | 38.2 | 25.5 |
| TIC7940 | 40.8 | 42 | 42 | 42 | 42 | 42.7 | 41.1 | 34.8 | 37.9 | — | 24.6 |
| TIC10366 | 24.4 | 24.6 | 24.4 | 24.1 | 24.4 | 24.6 | 25.1 | 21.5 | 24.8 | 24.1 | — |

Exemplary PirAB fusion proteins TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104 were aligned with each other using a Clustal W algorithm. A pair-wise matrix of percent amino acid sequence identities for each of the full-length proteins was created, as reported in Tables 8, 9, 10, and 11.

TABLE 8

Pair-wise matrix display of PirAB fusion proteins.

| Sequence | TIC9322 | TIC9320 | TIC10434 | TIC10377 | TIC11211 | TIC6880 | TIC11440 | TIC6880PL | TIC11442 | TIC11506 |
|---|---|---|---|---|---|---|---|---|---|---|
| TIC9322 | — | 95.3 | 93.3 | 91.5 | 87.3 | 47.8 | 47.8 | 47.8 | 47.8 | 48.7 |
| TIC9320 | 95.3 | — | 95.3 | 93.1 | 84.4 | 48.6 | 48.6 | 48.6 | 48.6 | 48.9 |
| TIC10434 | 92.5 | 94.4 | — | 90.8 | 82 | 48.1 | 48.1 | 48.1 | 48.1 | 48.8 |
| TIC10377 | 91.5 | 93.1 | 91.7 | — | 82.6 | 48 | 48 | 48 | 48 | 49.6 |
| TIC11211 | 86.1 | 83.2 | 81.6 | 81.4 | — | 52.7 | 52.7 | 52.9 | 52.7 | 53.4 |
| TIC6880 | 46.9 | 47.6 | 47.6 | 47.1 | 52.4 | — | 99.6 | 99.8 | 99.6 | 85.3 |
| TIC11440 | 37.8 | 38.4 | 38.4 | 38 | 42.3 | 80.4 | — | 80.2 | 95.6 | 68.8 |
| TIC6880PL | 46.8 | 47.5 | 47.5 | 47 | 52.5 | 99.6 | 99.3 | — | 99.3 | 85.1 |
| TIC11442 | 37.5 | 38.1 | 38.1 | 37.6 | 41.9 | 79.7 | 94.7 | 79.5 | — | 68.2 |
| TIC11506 | 46.7 | 46.9 | 47.2 | 47.6 | 51.9 | 83.3 | 83.3 | 83.3 | 83.3 | — |
| TIC11513 | 46.9 | 47.1 | 47.5 | 47.8 | 52.2 | 83.9 | 83.9 | 83.9 | 83.9 | 99.8 |
| TIC11512 | 46.8 | 46.9 | 47.3 | 47.6 | 52 | 83.5 | 83.5 | 83.5 | 83.5 | 99.5 |
| TIC11210 | 47.2 | 47.7 | 47.6 | 48.3 | 55.5 | 81.1 | 81.1 | 81.1 | 81.1 | 84.7 |
| TIC11212 | 47.2 | 47.6 | 47.7 | 48.5 | 54.2 | 80.9 | 80.9 | 80.9 | 80.9 | 84.7 |
| TIC9319 | 47.7 | 48.1 | 48.3 | 48.8 | 54.3 | 83.2 | 83.2 | 83.1 | 83.2 | 82.5 |
| TIC10380 | 47.8 | 48.5 | 48 | 48.1 | 53.8 | 79.2 | 79.2 | 79 | 79.2 | 79.9 |
| TIC10380PL | 47.7 | 48.4 | 47.9 | 48.1 | 53.9 | 78.9 | 78.9 | 79.2 | 78.9 | 79.8 |
| TIC10381 | 47.4 | 48.3 | 48 | 48.1 | 52.7 | 78 | 78 | 78 | 78 | 84.8 |
| TIC10381PL | 47.4 | 48.2 | 47.9 | 48.1 | 52.6 | 77.8 | 77.8 | 77.8 | 77.8 | 84.5 |
| TIC9318 | 47.5 | 48.2 | 48.6 | 48.9 | 54.4 | 78.4 | 78.4 | 78.4 | 78.4 | 81.8 |
| TIC11445 | 38 | 38.6 | 38.9 | 39.2 | 43.6 | 62.8 | 76.5 | 62.8 | 77.2 | 65.5 |
| TIC9316 | 47.5 | 48.4 | 47.9 | 48.1 | 56 | 79 | 79 | 79 | 79 | 81.3 |
| TIC11441 | 38 | 38.8 | 38.3 | 38.5 | 44.8 | 63.2 | 77.8 | 63.2 | 82.9 | 65.1 |
| TIC11302 | 48.1 | 48.8 | 48.1 | 48.1 | 52.3 | 77.7 | 77.7 | 77.7 | 77.7 | 78.3 |
| TIC11443 | 38.5 | 39 | 38.5 | 38.5 | 41.9 | 62.2 | 62.2 | 62.2 | 62.2 | 62.7 |
| TIC9317 | 47.5 | 48.1 | 47.3 | 47.9 | 51.6 | 75.4 | 75.4 | 75.4 | 75.4 | 76.9 |
| TIC11446 | 38 | 38.5 | 37.9 | 38.3 | 41.3 | 60.4 | 74.8 | 60.4 | 77.5 | 61.5 |
| TIC11444 | 38 | 38.5 | 37.9 | 38.3 | 41.3 | 60.4 | 75 | 60.4 | 80.1 | 61.5 |
| TIC11301 | 46.8 | 47.5 | 47 | 47.7 | 54.9 | 76.5 | 76.5 | 76.5 | 76.5 | 80 |
| TIC10378 | 47.7 | 48.6 | 48.1 | 48.4 | 51.8 | 76.9 | 76.9 | 76.9 | 76.9 | 78 |
| TIC10378PL | 47.6 | 48.5 | 48 | 48.3 | 51.7 | 76.8 | 76.8 | 76.8 | 76.8 | 77.7 |
| TIC11103 | 36.2 | 36.6 | 36.4 | 36.4 | 36.2 | 58.1 | 58.1 | 58.1 | 58.1 | 59 |
| TIC11104 | 36.7 | 37.3 | 37.6 | 37.3 | 36.7 | 60.1 | 60.1 | 60.1 | 60.1 | 60.6 |
| TIC10376 | 41.2 | 41.9 | 41.5 | 41.9 | 40.8 | 41.9 | 41.9 | 41.9 | 41.9 | 41.5 |
| TIC10376PL | 41.1 | 41.8 | 41.5 | 41.8 | 40.7 | 41.8 | 41.8 | 41.8 | 41.8 | 41.5 |
| TIC10379 | 43.7 | 43.7 | 43.7 | 43.5 | 43.1 | 46.2 | 46.2 | 46.2 | 46.2 | 46.6 |
| TIC9321 | 36.4 | 37.5 | 37.3 | 36.2 | 37.6 | 42.1 | 42.1 | 42.1 | 42.1 | 41.2 |
| TIC10375 | 24.4 | 24.6 | 24.2 | 25.3 | 24.2 | 23.7 | 23.7 | 23.7 | 23.7 | 23.3 |

TABLE 9

Pair-wise matrix display of PirAB fusion proteins.

| Sequence | TIC11513 | TIC11512 | TIC11210 | TIC11212 | TIC9319 | TIC10380 | TIC10380PL | TIC10381 | TIC10381PL | TIC9318 |
|---|---|---|---|---|---|---|---|---|---|---|
| TIC9322 | 48.6 | 48.4 | 47.5 | 47.5 | 47.5 | 49.1 | 49.1 | 48.7 | 48.7 | 48.7 |
| TIC9320 | 48.7 | 48.6 | 48 | 47.8 | 47.8 | 49.8 | 49.8 | 49.6 | 49.6 | 49.5 |
| TIC10434 | 48.7 | 48.5 | 47.4 | 47.6 | 47.6 | 48.8 | 48.8 | 48.8 | 48.8 | 49.4 |
| TIC10377 | 49.5 | 49.3 | 48.6 | 48.7 | 48.6 | 49.5 | 49.5 | 49.5 | 49.5 | 50.2 |
| TIC11211 | 53.2 | 53 | 55 | 53.8 | 53.2 | 54.5 | 54.6 | 53.4 | 53.4 | 55 |
| TIC6880 | 85.1 | 84.7 | 79.9 | 79.8 | 81.2 | 79.8 | 79.6 | 78.5 | 78.5 | 78.9 |
| TIC11440 | 68.6 | 68.3 | 64.5 | 64.3 | 65.5 | 64.3 | 64.2 | 63.3 | 63.3 | 63.6 |
| TIC6880PL | 84.9 | 84.6 | 79.8 | 79.6 | 80.9 | 79.4 | 79.8 | 78.4 | 78.4 | 78.7 |
| TIC11442 | 68 | 67.8 | 63.9 | 63.8 | 64.9 | 63.8 | 63.6 | 62.8 | 62.8 | 63.1 |
| TIC11506 | 99 | 98.6 | 81.6 | 81.6 | 78.6 | 78.6 | 78.6 | 83.5 | 83.3 | 80.4 |
| TIC11513 | — | 99.6 | 82.1 | 82.1 | 79.2 | 79.2 | 79.2 | 84.1 | 83.9 | 80.9 |
| TIC11512 | 99.6 | — | 82.1 | 82.1 | 79.2 | 78.8 | 78.8 | 83.7 | 83.5 | 80.6 |
| TIC11210 | 84.5 | 84.5 | — | 96.8 | 93.2 | 79.1 | 79.1 | 80.9 | 80.7 | 82.2 |
| TIC11212 | 84.5 | 84.5 | 96.8 | — | 92.8 | 79.3 | 79.3 | 80.9 | 80.7 | 85.2 |
| TIC9319 | 82.3 | 82.3 | 94.2 | 93.8 | — | 79.4 | 79.2 | 78.7 | 78.7 | 79.2 |
| TIC10380 | 79.7 | 79.4 | 77.4 | 77.6 | 76.9 | — | 99.8 | 81.7 | 81.7 | 81.1 |
| TIC10380PL | 79.6 | 79.2 | 77.3 | 77.5 | 76.6 | 99.6 | — | 81.5 | 81.5 | 81 |
| TIC10381 | 84.7 | 84.3 | 79.2 | 79.2 | 76.2 | 81.7 | 81.7 | — | 99.8 | 90.7 |

TABLE 9-continued

Pair-wise matrix display of PirAB fusion proteins.

| Sequence | TIC11513 | TIC11512 | TIC11210 | TIC11212 | TIC9319 | TIC10380 | TIC10380PL | TIC10381 | TIC10381PL | TIC9318 |
|---|---|---|---|---|---|---|---|---|---|---|
| TIC10381PL | 84.3 | 84 | 78.9 | 78.9 | 76.1 | 81.5 | 81.5 | 99.6 | — | 90.3 |
| TIC9318 | 81.6 | 81.3 | 80.6 | 83.6 | 76.9 | 81.3 | 81.3 | 90.8 | 90.6 | — |
| TIC11445 | 65.3 | 65.1 | 64.5 | 66.9 | 61.5 | 65.1 | 65.1 | 72.7 | 72.6 | 80.1 |
| TIC9316 | 81.1 | 80.7 | 83.4 | 80.4 | 77.2 | 83.7 | 83.7 | 92 | 91.9 | 89.8 |
| TIC11441 | 64.9 | 64.6 | 66.8 | 64.4 | 61.8 | 67 | 67 | 73.7 | 73.6 | 71.9 |
| TIC11302 | 78.1 | 77.7 | 77.2 | 77.7 | 76.1 | 81.6 | 81.6 | 89 | 88.9 | 86.7 |
| TIC11443 | 62.5 | 62.2 | 61.8 | 62.2 | 61 | 65.3 | 65.3 | 71.3 | 71.1 | 69.4 |
| TIC9317 | 76.7 | 76.3 | 75.8 | 76.1 | 74.4 | 77.9 | 77.9 | 82.7 | 82.5 | 82 |
| TIC11446 | 61.4 | 61.1 | 60.7 | 61 | 59.5 | 62.4 | 62.4 | 66.2 | 66.1 | 65.6 |
| TIC11444 | 61.4 | 61.1 | 60.7 | 61 | 59.5 | 62.4 | 62.4 | 66.2 | 66.1 | 65.6 |
| TIC11301 | 79.9 | 79.5 | 82.3 | 79.2 | 75.6 | 79.9 | 79.9 | 85.9 | 85.7 | 84.8 |
| TIC10378 | 77.8 | 77.5 | 76.6 | 76.9 | 75.4 | 79.4 | 79.4 | 84.3 | 84.2 | 83.5 |
| TIC10378PL | 77.5 | 77.2 | 76.3 | 76.6 | 75.2 | 79.3 | 79.3 | 84 | 84.4 | 83.1 |
| TIC11103 | 58.8 | 58.5 | 57.4 | 57.4 | 57.4 | 60.4 | 60.4 | 64.8 | 64.8 | 63.3 |
| TIC11104 | 60.4 | 60.1 | 59 | 59 | 59 | 61.5 | 61.5 | 69.6 | 69.6 | 75.1 |
| TIC10376 | 41.7 | 41.7 | 41.4 | 41.7 | 40.8 | 40.6 | 40.6 | 41.5 | 41.5 | 42.8 |
| TIC10376PL | 41.6 | 41.6 | 41.3 | 41.6 | 40.7 | 40.6 | 40.6 | 41.5 | 41.5 | 42.7 |
| TIC10379 | 46.7 | 46.4 | 45.5 | 46.6 | 45.3 | 47.1 | 47.1 | 46.9 | 46.7 | 47.3 |
| TIC9321 | 41.2 | 41.2 | 40.3 | 40.9 | 40.9 | 41 | 41 | 41.9 | 41.9 | 42.5 |
| TIC10375 | 23.5 | 23.7 | 24.6 | 24.6 | 25 | 24.2 | 24.2 | 24.2 | 24.2 | 24 |

TABLE 10

Pair-wise matrix display of PirAB fusion proteins.

| Sequence | TIC11445 | TIC9316 | TIC11441 | TIC11302 | TIC11443 | TIC9317 | TIC11446 | TIC11444 | TIC11301 |
|---|---|---|---|---|---|---|---|---|---|
| TIC9322 | 48.7 | 48.7 | 48.7 | 49.3 | 49.3 | 48.7 | 48.7 | 48.7 | 48 |
| TIC9320 | 49.5 | 49.6 | 49.6 | 50 | 50 | 49.3 | 49.3 | 49.3 | 48.7 |
| TIC10434 | 49.4 | 48.7 | 48.7 | 48.8 | 48.8 | 48.1 | 48.1 | 48.1 | 47.8 |
| TIC10377 | 50.2 | 49.3 | 49.3 | 49.3 | 49.3 | 49.1 | 49.1 | 49.1 | 48.9 |
| TIC11211 | 55 | 56.6 | 56.6 | 52.9 | 52.9 | 52.1 | 52.1 | 52.1 | 55.5 |
| TIC6880 | 78.9 | 79.4 | 79.4 | 78.2 | 78.2 | 75.8 | 75.8 | 75.8 | 76.9 |
| TIC11440 | 77.5 | 64 | 78.8 | 63 | 63 | 61.2 | 75.8 | 75.9 | 62 |
| TIC6880PL | 78.7 | 79.3 | 79.3 | 78 | 78 | 75.7 | 75.7 | 75.7 | 76.8 |
| TIC11442 | 77.6 | 63.5 | 83.2 | 62.5 | 62.5 | 60.7 | 77.8 | 80.4 | 61.5 |
| TIC11506 | 80.4 | 79.9 | 79.9 | 76.9 | 76.9 | 75.5 | 75.5 | 75.5 | 78.6 |
| TIC11513 | 80.9 | 80.4 | 80.4 | 77.4 | 77.4 | 76 | 76 | 76 | 79.2 |
| TIC11512 | 80.6 | 80 | 80 | 77.1 | 77.1 | 75.7 | 75.7 | 75.7 | 78.8 |
| TIC11210 | 82.2 | 85 | 85 | 78.7 | 78.7 | 77.3 | 77.3 | 77.3 | 84 |
| TIC11212 | 85.2 | 82 | 82 | 79.3 | 79.3 | 77.7 | 77.7 | 77.7 | 80.7 |
| TIC9319 | 79.2 | 79.6 | 79.6 | 78.5 | 78.5 | 76.7 | 76.7 | 76.7 | 78 |
| TIC10380 | 81.1 | 83.6 | 83.6 | 81.5 | 81.5 | 77.8 | 77.8 | 77.8 | 79.7 |
| TIC10380PL | 81 | 83.5 | 83.5 | 81.3 | 81.3 | 77.6 | 77.6 | 77.6 | 79.6 |
| TIC10381 | 90.7 | 91.9 | 91.9 | 88.9 | 88.9 | 82.5 | 82.5 | 82.5 | 85.7 |
| TIC10381PL | 90.3 | 91.5 | 91.5 | 88.6 | 88.6 | 82.2 | 82.2 | 82.2 | 85.4 |
| TIC9318 | 100 | 89.8 | 89.8 | 86.7 | 86.7 | 82 | 82 | 82 | 84.8 |
| TIC11445 | — | 71.9 | 86.6 | 69.4 | 69.4 | 65.6 | 80.6 | 80.3 | 67.9 |
| TIC9316 | 89.8 | — | 100 | 93.5 | 93.5 | 83.9 | 83.9 | 83.9 | 90.1 |
| TIC11441 | 86.6 | 80.1 | — | 74.8 | 74.8 | 67.2 | 84.6 | 87.1 | 72.1 |
| TIC11302 | 86.7 | 93.5 | 93.5 | — | 100 | 90.1 | 90.1 | 90.1 | 83.9 |
| TIC11443 | 69.4 | 74.8 | 74.8 | 80.1 | — | 72.1 | 72.1 | 72.1 | 67.2 |
| TIC9317 | 82 | 83.9 | 83.9 | 90.1 | 90.1 | — | 100 | 100 | 93.5 |
| TIC11446 | 80.6 | 67.2 | 84.6 | 72.1 | 72.1 | 80.1 | — | 97.5 | 74.8 |
| TIC11444 | 80.3 | 67.2 | 87.1 | 72.1 | 72.1 | 80.1 | 97.5 | — | 74.8 |
| TIC11301 | 84.8 | 90.1 | 90.1 | 83.9 | 83.9 | 93.5 | 93.5 | 93.5 | — |
| TIC10378 | 83.5 | 85.7 | 85.7 | 90.3 | 90.3 | 94.4 | 94.4 | 94.4 | 90 |
| TIC10378PL | 83.1 | 85.4 | 85.4 | 90 | 90 | 94 | 94 | 94 | 89.6 |
| TIC11103 | 63.3 | 65.7 | 65.7 | 65.7 | 65.7 | 75.1 | 75.1 | 75.1 | 75.1 |
| TIC11104 | 75.1 | 68 | 68 | 68 | 68 | 63.3 | 63.3 | 63.3 | 63.3 |
| TIC10376 | 42.8 | 42.1 | 42.1 | 41.7 | 41.7 | 41.4 | 41.4 | 41.4 | 41.7 |
| TIC10376PL | 42.7 | 42 | 42 | 41.6 | 41.6 | 41.3 | 41.3 | 41.3 | 41.6 |
| TIC10379 | 47.3 | 46.9 | 46.9 | 46 | 46 | 45.7 | 45.7 | 45.7 | 46.4 |
| TIC9321 | 42.5 | 40.9 | 40.9 | 41.2 | 41.2 | 41.4 | 41.4 | 41.4 | 41 |
| TIC10375 | 24 | 24.6 | 24.6 | 24 | 24 | 23.7 | 23.7 | 23.7 | 24.2 |

TABLE 11

| Pair-wise matrix display of PirAB fusion proteins. | | | | | | | | | |
|---|---|---|---|---|---|---|---|---|---|
| Sequence | TIC10378 | TIC10378PL | TIC11103 | TIC11104 | TIC10376 | TIC10376PL | TIC10379 | TIC9321 | TIC10375 |
| TIC9322 | 49.1 | 49.1 | 37.1 | 37.7 | 41.8 | 41.8 | 43.7 | 36.8 | 23.9 |
| TIC9320 | 50 | 50 | 37.5 | 38.2 | 42.6 | 42.6 | 43.7 | 37.9 | 24.1 |
| TIC10434 | 49 | 49 | 37 | 38.2 | 41.8 | 41.8 | 43.3 | 37.3 | 23.5 |
| TIC10377 | 49.8 | 49.8 | 37.3 | 38.2 | 42.6 | 42.6 | 43.5 | 36.6 | 24.8 |
| TIC11211 | 52.5 | 52.5 | 36.6 | 37.1 | 40.9 | 40.9 | 42.5 | 37.5 | 23.4 |
| TIC6880 | 77.6 | 77.6 | 58.4 | 60.4 | 41.7 | 41.7 | 45.3 | 41.7 | 22.7 |
| TIC11440 | 62.6 | 62.6 | 47.1 | 48.7 | 33.7 | 33.7 | 36.5 | 33.7 | 18.3 |
| TIC6880PL | 77.5 | 77.5 | 58.3 | 60.3 | 41.7 | 41.7 | 45.2 | 41.7 | 22.7 |
| TIC11442 | 62.1 | 62.1 | 46.7 | 48.3 | 33.4 | 33.4 | 36.2 | 33.4 | 18.2 |
| TIC11506 | 76.9 | 76.7 | 58 | 59.5 | 40.5 | 40.5 | 44.6 | 39.9 | 21.9 |
| TIC11513 | 77.4 | 77.2 | 58.3 | 59.9 | 41 | 41 | 45.2 | 40.3 | 22.2 |
| TIC11512 | 77.1 | 76.9 | 58 | 59.5 | 41 | 41 | 44.8 | 40.3 | 22.4 |
| TIC11210 | 78.4 | 78.2 | 58.6 | 60.2 | 41.8 | 41.8 | 45.2 | 40.5 | 24 |
| TIC11212 | 78.7 | 78.6 | 58.6 | 60.2 | 42.2 | 42.2 | 46.3 | 41.1 | 24 |
| TIC9319 | 78 | 78 | 59.2 | 60.8 | 41.7 | 41.7 | 45.5 | 41.5 | 24.6 |
| TIC10380 | 79.5 | 79.5 | 60.3 | 61.4 | 40.2 | 40.2 | 45.9 | 40.4 | 23.1 |
| TIC10380PL | 79.4 | 79.4 | 60.2 | 61.3 | 40.1 | 40.1 | 45.8 | 40.3 | 23.1 |
| TIC10381 | 84.5 | 84.3 | 64.7 | 69.5 | 41.1 | 41.1 | 45.7 | 41.3 | 23.1 |
| TIC10381PL | 84.2 | 84.5 | 64.6 | 69.4 | 41 | 41 | 45.4 | 41.2 | 23.1 |
| TIC9318 | 83.7 | 83.6 | 63.3 | 75.1 | 42.4 | 42.4 | 46.1 | 41.9 | 23 |
| TIC11445 | 67 | 66.9 | 50.6 | 60.1 | 33.9 | 33.9 | 36.9 | 33.5 | 18.4 |
| TIC9316 | 86 | 85.9 | 65.7 | 68 | 41.7 | 41.7 | 45.8 | 40.3 | 23.5 |
| TIC11441 | 68.9 | 68.7 | 52.6 | 54.5 | 33.4 | 33.4 | 36.6 | 32.2 | 18.8 |
| TIC11302 | 90.6 | 90.5 | 65.7 | 68 | 41.3 | 41.3 | 44.9 | 40.6 | 23 |
| TIC11443 | 72.6 | 72.4 | 52.6 | 54.5 | 33.1 | 33.1 | 35.9 | 32.5 | 18.4 |
| TIC9317 | 94.7 | 94.5 | 75.1 | 63.3 | 41 | 41 | 44.5 | 40.8 | 22.6 |
| TIC11446 | 75.8 | 75.7 | 60.1 | 50.6 | 32.8 | 32.8 | 35.6 | 32.7 | 18.1 |
| TIC11444 | 75.8 | 75.7 | 60.1 | 50.6 | 32.8 | 32.8 | 35.6 | 32.7 | 18.1 |
| TIC11301 | 90.3 | 90.1 | 75.1 | 63.3 | 41.3 | 41.3 | 45.2 | 40.5 | 23.1 |
| TIC10378 | — | 99.8 | 71.3 | 64.4 | 41.5 | 41.5 | 44.5 | 41.4 | 23.1 |
| TIC10378PL | 99.6 | — | 71.2 | 64.3 | 41.5 | 41.5 | 44.3 | 41.3 | 23 |
| TIC11103 | 71.6 | 71.6 | — | 82 | 31.6 | 31.6 | 35.7 | 30.9 | 18.4 |
| TIC11104 | 64.7 | 64.7 | 82 | — | 32.3 | 32.3 | 35.5 | 31.8 | 18.2 |
| TIC10376 | 42.1 | 42.1 | 31.9 | 32.6 | — | 99.8 | 54.9 | 34.8 | 21.6 |
| TIC10376PL | 42 | 42 | 31.9 | 32.6 | 99.6 | — | 54.8 | 34.7 | 21.5 |
| TIC10379 | 45.8 | 45.7 | 36.6 | 36.4 | 55.8 | 55.8 | — | 37.1 | 24.5 |
| TIC9321 | 42.1 | 42.1 | 31.4 | 32.3 | 34.9 | 34.9 | 36.7 | — | 22 |
| TIC10375 | 24.2 | 24.2 | 19.2 | 19 | 22.4 | 22.4 | 25 | 22.7 | — |

In addition to percent identity, The PirA Proteins, The PirB Proteins, and the PirAB Fusion Proteins can also be related by primary structure (conserved amino acid motifs), by length (about 133 to about 141 amino acids for PirA; about 414 to about 428 amino acids for PirB; about 549 to about 566 amino acids for the PirAB fusion proteins,) and by other characteristics. Characteristics of The PirA Proteins, The PirB Proteins, and The PirAB Fusion Proteins are reported in Table 12.

TABLE 12

| Selected characteristics of PirA proteins, PirB proteins, and PirAB proteins. | | | | | | | | |
|---|---|---|---|---|---|---|---|---|
| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
| TIC4771 | 14963.57 | 135 | 5.6164 | −1.5 | 14 | 14 | 65 | 70 |
| TIC4772 | 48146.05 | 428 | 4.5643 | −16.0 | 41 | 53 | 216 | 212 |
| TIC6880 | 63092.59 | 563 | 4.6836 | −17.5 | 55 | 67 | 281 | 282 |
| TIC6880PL | 63163.67 | 564 | 4.6836 | −17.5 | 55 | 67 | 282 | 282 |
| TIC7575 | 15655.22 | 141 | 5.0636 | −2.0 | 12 | 13 | 68 | 73 |
| TIC7576 | 47775.12 | 425 | 4.7039 | −12.5 | 44 | 53 | 221 | 204 |
| TIC9316 | 63412.32 | 566 | 4.7572 | −14.5 | 56 | 66 | 289 | 277 |
| TIC7660 | 15352.83 | 141 | 4.5839 | −4.0 | 11 | 14 | 72 | 69 |
| TIC7661 | 47774.39 | 425 | 4.7572 | −5.5 | 50 | 51 | 222 | 203 |
| TIC9317 | 63109.20 | 566 | 5.1542 | −9.5 | 61 | 65 | 294 | 272 |
| TIC7662 | 15761.42 | 141 | 4.6130 | −3.5 | 11 | 14 | 68 | 73 |
| TIC7663 | 47895.35 | 425 | 5.0745 | −7.5 | 48 | 52 | 221 | 204 |
| TIC9318 | 63638.76 | 566 | 4.9378 | −11.0 | 59 | 66 | 289 | 277 |
| TIC7664 | 14950.65 | 135 | 5.0636 | −2.0 | 12 | 13 | 68 | 67 |
| TIC7665 | 46819.71 | 414 | 4.6887 | −12.5 | 43 | 52 | 214 | 200 |
| TIC9319 | 61752.34 | 549 | 4.7452 | −14.5 | 55 | 65 | 282 | 267 |
| TIC7666 | 14751.43 | 133 | 4.6137 | −4.0 | 12 | 15 | 68 | 65 |
| TIC7667 | 46246.08 | 419 | 5.4603 | −5.5 | 50 | 51 | 220 | 199 |

TABLE 12-continued

| Selected characteristics of PirA proteins, PirB proteins, and PirAB proteins. | | | | | | | | |
|---|---|---|---|---|---|---|---|---|
| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
| TIC9322 | 60979.49 | 552 | 5.1485 | −9.5 | 62 | 66 | 288 | 264 |
| TIC7668 | 14785.54 | 133 | 5.1215 | −2.5 | 14 | 15 | 68 | 65 |
| TIC7669 | 46249.04 | 419 | 5.3001 | −6.5 | 50 | 52 | 222 | 197 |
| TIC9320 | 61016.56 | 552 | 5.2518 | −9.0 | 64 | 67 | 290 | 262 |
| TIC7939 | 15470.32 | 139 | 6.2480 | −0.5 | 15 | 14 | 70 | 69 |
| TIC7940 | 47493.26 | 419 | 4.8783 | −11.0 | 53 | 60 | 218 | 201 |
| TIC9321 | 62945.57 | 558 | 5.0432 | −11.5 | 68 | 74 | 288 | 270 |
| TIC10357 | 12838.48 | 114 | 4.7910 | −3.0 | 11 | 13 | 68 | 46 |
| TIC10366 | 47691.61 | 427 | 4.3657 | −22.0 | 43 | 62 | 221 | 206 |
| TIC10375 | 60512.07 | 541 | 4.4263 | −25.0 | 54 | 75 | 289 | 252 |
| TIC10358 | 16198.29 | 144 | 7.7512 | 1.5 | 20 | 17 | 68 | 76 |
| TIC10367 | 47147.69 | 417 | 7.7679 | 5.5 | 60 | 49 | 222 | 195 |
| TIC10376 | 63327.96 | 561 | 7.8092 | 7.0 | 80 | 66 | 290 | 271 |
| TIC10376PL | 63399.04 | 562 | 7.8092 | 7.0 | 80 | 66 | 291 | 271 |
| TIC10360 | 14976.76 | 133 | 4.8490 | −2.5 | 14 | 16 | 64 | 69 |
| TIC10369 | 46322.33 | 419 | 5.6804 | −4.0 | 50 | 50 | 224 | 195 |
| TIC10377 | 61281.07 | 552 | 5.3889 | −6.5 | 64 | 66 | 288 | 264 |
| TIC10361 | 15629.20 | 143 | 4.7632 | −3.0 | 11 | 13 | 71 | 72 |
| TIC10370 | 47710.32 | 425 | 5.0742 | −8.0 | 48 | 52 | 225 | 200 |
| TIC10378 | 63321.51 | 568 | 4.9947 | −11.0 | 59 | 65 | 296 | 272 |
| TIC10378PL | 63392.59 | 569 | 4.9947 | −11.0 | 59 | 65 | 297 | 272 |
| TIC10362 | 15173.94 | 136 | 5.1440 | −1.5 | 13 | 14 | 62 | 74 |
| TIC10371 | 46947.97 | 416 | 5.8572 | −3.5 | 47 | 46 | 218 | 198 |
| TIC10379 | 62103.90 | 552 | 5.6801 | −5.0 | 60 | 60 | 280 | 272 |
| TIC10363 | 15195.80 | 137 | 4.7774 | −3.0 | 11 | 13 | 67 | 70 |
| TIC10372 | 48400.97 | 430 | 4.7717 | −11.0 | 45 | 53 | 229 | 201 |
| TIC10380 | 63578.76 | 567 | 4.7697 | −14.0 | 56 | 66 | 296 | 271 |
| TIC10380PL | 63649.84 | 568 | 4.7697 | −14.0 | 56 | 66 | 297 | 271 |
| TIC10364 | 15833.53 | 142 | 4.4792 | −5.0 | 11 | 15 | 72 | 70 |
| TIC10373 | 47791.02 | 425 | 4.7003 | −12.5 | 44 | 53 | 220 | 205 |
| TIC10381 | 63606.54 | 567 | 4.6406 | −17.5 | 55 | 68 | 292 | 275 |
| TIC10381PL | 63677.62 | 568 | 4.6406 | −17.5 | 55 | 68 | 293 | 275 |
| TIC10359 | 14949.54 | 135 | 4.7873 | −3.5 | 12 | 14 | 68 | 67 |
| TIC10368 | 48194.25 | 429 | 4.7481 | −11.5 | 43 | 51 | 219 | 210 |
| PirA_ABE68878 | 15303.18 | 138 | 6.2470 | −5.0 | 15 | 14 | 71 | 67 |
| PirB_ABE68879 | 46424.34 | 419 | 5.2938 | −6.5 | 50 | 52 | 224 | 195 |
| TIC10434 | 61709.50 | 557 | 5.4906 | −7.0 | 65 | 66 | 295 | 262 |
| TIC11103 | 63109.20 | 566 | 5.1542 | −9.5 | 61 | 65 | 294 | 272 |
| TIC11104 | 63638.76 | 566 | 4.9378 | −11.0 | 59 | 66 | 289 | 277 |
| TIC11210 | 62456.91 | 555 | 4.7452 | −14.5 | 55 | 65 | 282 | 273 |
| TIC11211 | 61883.28 | 560 | 5.3591 | −7.5 | 62 | 64 | 288 | 272 |
| TIC11212 | 62563.12 | 555 | 4.6679 | −16.0 | 54 | 66 | 282 | 273 |
| TIC11301 | 63411.60 | 566 | 5.3685 | −7.5 | 62 | 64 | 290 | 276 |
| TIC11302 | 63109.93 | 566 | 4.6735 | −16.5 | 55 | 67 | 293 | 273 |
| TIC11440 | 78037.15 | 698 | 4.7751 | −19.0 | 69 | 81 | 346 | 352 |
| TIC11441 | 79049.52 | 707 | 4.7960 | −16.5 | 68 | 79 | 357 | 350 |
| TIC11442 | 78728.81 | 704 | 4.7287 | −19.5 | 67 | 80 | 349 | 355 |
| TIC11443 | 78747.13 | 707 | 4.7204 | −18.5 | 67 | 80 | 361 | 346 |
| TIC11444 | 78746.41 | 707 | 5.1362 | −11.5 | 73 | 78 | 362 | 345 |
| TIC11445 | 78973.57 | 707 | 4.8575 | −15.0 | 70 | 80 | 361 | 346 |
| TIC11446 | 78852.61 | 707 | 5.0123 | −13.0 | 72 | 79 | 362 | 345 |
| TIC10364 | 15833.53 | 142 | 4.4792 | −5.0 | 11 | 15 | 72 | 70 |
| TIC11505 | 48750.86 | 434 | 4.6998 | −12.5 | 43 | 52 | 221 | 213 |
| TIC11506 | 64566.38 | 576 | 4.6400 | −17.5 | 54 | 67 | 293 | 283 |
| TIC11510 | 48184.21 | 429 | 4.7481 | −11.5 | 43 | 51 | 218 | 211 |
| TIC11512 | 63999.72 | 571 | 4.6730 | −16.5 | 54 | 66 | 290 | 281 |
| TIC11511 | 48208.27 | 429 | 4.7481 | −11.5 | 43 | 51 | 219 | 210 |
| TIC11513 | 64023.79 | 571 | 4.6730 | −16.5 | 54 | 66 | 291 | 280 |

As described further in the Examples of this application, recombinant nucleic acid molecule sequences encoding The PirAB Fusion Proteins were designed for use in plants. Exemplary plant-optimized recombinant nucleic acid molecule sequences that were designed for use in plants are presented as SEQ ID NOs:49, 51, 52, 53, 54, 55, 56, 146, 148, 150, 152, 154, 156, and 158.

Expression cassettes and vectors containing these recombinant nucleic acid molecule sequences can be constructed and introduced into corn, soybean, cotton or other plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express the PirAB fusion proteins TIC6880PL, TIC9316, TIC9317, TIC9318, TIC9319, TIC9320, or TIC9322. To test pesticidal activity, bioassays are performed in the presence of Lepidoptera pest larvae using plant leaf disks obtained from transformed plants as described in the Examples. To test pesticidal activity against Coleopteran pests, transformed plants of $R_o$ and $F_1$ generation are used in root worm assay as described in the example below. To test pesticidal activity against Hemipteran pests, pods, corn ears or leaves of transformed plants are used in assay, either from tissue removed from the plant or remaining on the plant as described in the Examples.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode The PirA Proteins, The PirB Proteins, or the PirAB Fusion Proteins, or related insecticidal proteins are contemplated. For example, The PirA Proteins, The PirB Proteins, or The PirAB Fusion Proteins, or related insecticidal proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the PirAB fusion proteins, TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 or related family member insecticidal protein encoding sequences for expression of the protein in plants or a Bt-functional promoter operably linked to a PirA proteins such as PirA_ABE68878, or the PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511; or the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104; or related insecticidal protein encoding sequences for expression of the protein in a Bt bacterium or other *Bacillus* species. Other elements can be operably linked to the PirA protein PirA_ABE68878, the PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511, or the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104, or related insecticidal protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:52, SEQ ID NO:53, SEQ ID NO:54, SEQ ID NO:55, SEQ ID NO:56, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, and SEQ ID NO:158 that encodes a polypeptide or protein having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, and SEQ ID NO:157. A heterologous promoter can also be operably linked to synthetic DNA coding sequences encoding a plastid targeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 or untargeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 or related insecticidal proteins. The codons of a recombinant nucleic acid molecule encoding for proteins disclosed herein can be substituted by synonymous codons (known in the art as a silent substitution).

As used herein, the term "recombinant" refers to a non-natural DNA, protein, or organism that would not normally be found in nature and was created by human intervention. A "recombinant DNA molecule" is a DNA molecule comprising a combination of DNA molecules that would not naturally occur together and is the result of human intervention. For example, a DNA molecule that is comprised of a combination of at least two DNA molecules heterologous to each other, such as a DNA molecule that comprises a transgene and the plant genomic DNA adjacent to the transgene, is a recombinant DNA molecule.

As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

A recombinant DNA construct comprising an encoding sequence for The PirA Proteins, The PirB Proteins, or The PirAB Fusion Proteins, or related insecticidal protein can further comprise a region of DNA that encodes for one or more insect inhibitory agents which can be configured to concomitantly express or co-express with a DNA sequence encoding The PirA Protein, The PirB Protein, or The PirAB Fusion Protein, or a related insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The PirA Proteins, The PirB Proteins, or the PirAB Fusion Proteins, and related proteins of this invention can be expressed from a multi-gene expression system in which one or more of The PirA Proteins, The PirB Proteins, or The PirAB Fusion Proteins, or related proteins is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules.

Recombinant nucleic acid molecules or recombinant DNA constructs comprising The PirA Proteins, The PirB Proteins, or the PirAB Fusion Proteins, or related family member protein encoding sequence can be delivered to host cells by vectors, e.g., a plasmid, baculovirus, synthetic chromosome, virion, cosmid, phagemid, phage, or viral vector. Such vectors can be used to achieve stable or transient expression of The PirA Proteins, The PirB Proteins, or the PirAB Fusion Proteins, or related protein encoding sequences in a host cell, or subsequent expression of the encoded polypeptide. An exogenous recombinant polynucleotide or recombinant DNA construct that comprises a protein encoding sequence and that is introduced into a host cell is referred herein as a "transgene."

Transgenic bacteria, transgenic plant cells, transgenic plants, and transgenic plant parts that contain a recombinant polynucleotide that expresses any one or more of The PirA Proteins, The PirB Proteins, or the PirAB Fusion Proteins, or related protein encoding sequences. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In other embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera- or Lepidoptera- or Hemiptera-inhibitory amounts of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302; or related protein are provided. Such plants can be made by introducing a recombinant polynucleotide that encodes any TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein provided in this application into a plant cell, and selecting a plant derived from said plant cell that expresses an insect, Coleoptera-, Lepidoptera-, or Hempitera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302; or related protein.

Plants expressing a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As described further in the Examples, sequences encoding TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 were designed for use in plants. Expression cassettes and vectors containing these synthetic or artificial nucleotide sequences can be constructed and introduced into corn, cotton, and soybean plant cells in accordance with transformation methods and techniques which are known in the art. Transformed cells are regenerated into transformed plants that are observed to be expressing TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302. To test pesticidal activity, bioassays are performed in the presence of Lepidopteran, Coleopteran and Hemipteran pests.

As further described in the Examples, sequences encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein and sequences having a substantial percentage identity to these proteins can be identified using methods known to those of ordinary skill in the art such as polymerase chain reaction (PCR), thermal amplification and hybridization. For example, a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein or related proteins can be used to produce antibodies that bind specifically to related proteins, and can be used to screen for and to find other protein members that are closely related.

Furthermore, nucleotide sequences encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related protein can be used as probes and primers for screening to identify other members of the class using thermal-cycle or isothermal amplification and hybridization methods. For example, oligonucleotides derived from sequences as set forth as SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, and SEQ ID NO:158 can be used to determine the presence or absence of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related protein transgene in a deoxyribonucleic acid sample derived from a commodity product. Given the sensitivity of certain nucleic acid detection methods that employ oligonucleotides, it is anticipated that oligonucleotides derived from the sequences as set forth as SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, and SEQ ID NO:158 can be used to detect a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 transgene in commodity products derived from pooled sources where only a fraction of the commodity product is derived from a transgenic plant containing any of SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, or SEQ ID NO:158. It is further recognized that such oligonucleotides can be used to introduce nucleotide sequence variation in SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, or SEQ ID NO:158. Such "mutagenesis" oligonucleotides are useful for identification of TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes under stringent hybridization conditions to the second nucleotide sequence. In such case, the second nucleotide sequence can be the nucleotide sequence selected from the group consisting of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:52, SEQ ID NO:53, SEQ ID NO:54, SEQ ID NO:55, SEQ ID NO:56, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, and SEQ ID NO:158 under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding proteins related to The PirA Proteins, The PirB Proteins, or the PirAB Fusion Proteins, and those sequences, to the extent that they function to express pesticidal proteins either in *Bacillus* strains or in plant cells, are embodiments of the present invention, recognizing of course that many such redundant coding sequences will not hybridize under these conditions to the native *Xenorhabdus* or *Photorhabdus* sequences encoding The PirA Proteins, The PirB Proteins, or The PirAB Fusion Proteins. This application contemplates the use of these and other identification methods known to those of ordinary skill in the art, to identify The PirA Proteins, The PirB Proteins, or The PirAB Fusion Proteins, or related protein-encoding sequences and sequences having a substantial percentage identity thereto.

Methods of controlling insects, in particular Lepidoptera, Coleoptera, or Hempiteran infestations of crop plants, with the TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related proteins, are also disclosed in this application. Such methods can comprise growing a plant comprising an insect-, Coleoptera-, or Lepidoptera- or Hemiptera-inhibitory amount of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related toxin protein. In certain embodiments, such methods can further comprise any one or more of: (i) applying any composition comprising or encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related toxin protein to a plant or a seed that gives rise to a plant; and (ii) transforming a plant or a plant cell that gives rise to a plant with a polynucleotide encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related toxin protein. In general, it is contemplated that a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related toxin protein can be provided in a composition, provided in a microorganism, or provided in a transgenic plant to confer insect inhibitory activity against Lepidopteran, Coleopteran or Hemipteran insects.

In certain embodiments, a recombinant nucleic acid molecule of a The PirA Proteins, The PirB Proteins, or The PirAB Fusion Proteins, or related toxin protein is the insecticidally active ingredient of an insect inhibitory composition prepared by culturing recombinant *Bacillus* or any other recombinant bacterial cell transformed to express one of The PirA Proteins, The PirB Proteins, or The PirAB Fusion Proteins, or related toxin protein under conditions suitable for expression. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising one of The PirA Proteins, The PirB Proteins, or The PirAB Fusion Proteins, or a related protein can further comprise at least one additional polypeptide known to those of ordinary skill in the art that exhibits insect inhibitory activity against the same Lepidopteran, Coleopteran, or Hemipteran insect species, but which is different from The PirA Proteins, The PirB Proteins, or The PirAB Fusion Proteins, or a related toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1).

Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput 1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1), Cry71Aa1 and Cry72Aa1 (US Patent Publication US2016-0230187 A1), Axmi422 (US Patent Publication US2016-0201082 A1), Axmi440 (US Patent Publication US2016-0185830 A1), Axmi281 (US Patent Publication 2016-0177332 A1), BT-0044, BT-0051, BT-0068, BT-0128 and variants thereof (WO 2016-094159 A1), BT-009, BT-0012, BT-0013, BT-0023, BT0067 and variants thereof (WO 2016-094165 A1), Cry1JP578V, Cry1JPS1, Cry1 JPS1P578V (WO 2016-061208 A1); and the like.

Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), 1P3 and variants thereof (U.S. Patent Publication 2012-0210462 A1), $\overline{\omega}$-Hexatoxin-Hv1a (U.S. Patent Application Publication 2014-0366227 A1), PHI-4 variants (U.S. Patent Application Publication 2016-0281105 A1), PIP-72 variants (WO 2016-144688 A1), PIP-45 variants, PIP-64 variants, PIP-74 variants, PIP-75 variants, and PIP-77 variants (WO 2016-144686 A1), DIG-305 (WO 2016109214 A1), PIP-47 variants (U.S. Patent Publication 2016-0186204 A1), DIG-17, DIG-90, DIG-79 (WO 2016-057123 A1), DIG-303 (WO 2016-070079 A1); and the like.

Such additional polypeptides for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC852 and TIC853 (U.S. Patent Publication 2010-0064394 A1), TIC834 and variants thereof (U.S. Patent Publication 2013-0269060 A1), AXMI-036 (U.S. Patent Publication 2010-0137216 A1), and AXMI-171 (U.S. Patent Publication 2013-0055469 A1), Cry64Ba and Cry64Ca (Liu et al., (2018) *Cry64Ba and Cry64Ca, Two ETX/MTX2-Type Bacillus thuringiensis Insecticidal Protein Active against Hemipteran* Pests. Applied and Environmental Microbiology, 84(3): 1-11).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained, e.g., an additional polypeptide that exhibits insect inhibitory activity to Thysanopterans.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran or Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by one of The PirA Proteins, The PirB Proteins, or The PirAB Fusion Proteins, or related pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery of The PirA Proteins and The PirB Proteins and the Construction of The PirAB Fusion Proteins This Example describes the discovery of the pesticidal PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878 (collectively, “The PirA Proteins”), PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB-_ABE68879, TIC11505, TIC11510, and TIC11511 (collectively “The PirB Proteins”), and the creation of the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104 (collectively, “The PirAB Fusion Proteins”).

Sequences encoding *Photorabdus* and *Xenorabdus* PirAB pesticidal proteins were identified from proprietary collections as well as public sequence information, synthesized, cloned, sequence confirmed, and tested in insect bioassay. Bacterial operons were identified from *Photorabdus* and *Xenorabdus* species, each operon comprising a PirA and a PirB coding sequence. The pesticidal PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878; and PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511, were isolated from the *Photorabdus* and *Xenorabdus* species listed in Table 13. With respect to the proteins TIC7939 and TIC7940, the operon was identified from a microbiome sample and the bacterial species from which it was derived is still unknown.

TABLE 13

Novel PirA and PirB pesticidal toxin proteins and corresponding *Photorabdus* and *Xenorabdus* species.

| Bacterial Species | PirA Protein Toxin | PirA Protein Nucleotide SEQ ID NO: | PirA Protein Protein SEQ ID NO: | PirB Protein Toxin | PirB Protein Nucleotide SEQ ID NO: | PirB Protein Protein SEQ ID NO: |
|---|---|---|---|---|---|---|
| *Xenorhabdus nematophila* ISB000002 | TIC4771 | 1 | 2 | TIC4772 | 3 | 4 |

TABLE 13-continued

Novel PirA and PirB pesticidal toxin proteins and corresponding *Photorabdus* and *Xenorabdus* species.

| | PirA Protein | | | PirB Protein | | |
|---|---|---|---|---|---|---|
| Bacterial Species | Toxin | Nucleotide SEQ ID NO: | Protein SEQ ID NO: | Toxin | Nucleotide SEQ ID NO: | Protein SEQ ID NO: |
| *Xenorhabdus ehlersii* 85823 | TIC7575 | 7 | 8 | TIC7576 | 9 | 10 |
| *Xenorhabdus cabanillasii* 85908 | TIC7660 | 13 | 14 | TIC7661 | 15 | 16 |
| *Xenorhabdus ehlersii* 85887 | TIC7662 | 19 | 20 | TIC7663 | 21 | 22 |
| *Xenorhabdus poinarii* 86198 | TIC7664 | 25 | 26 | TIC7665 | 27 | 28 |
| *Photorhabdus luminescens* 86197 | TIC7666 | 31 | 32 | TIC7667 | 33 | 34 |
| *Photorhabdus luminescens* 86194 | TIC7668 | 37 | 38 | TIC7669 | 39 | 40 |
| Microbiome | TIC7939 | 43 | 44 | TIC7940 | 45 | 46 |
| *Shewanella violacea* DSS12 | TIC10357 | 57 | 58 | TIC10366 | 59 | 60 |
| *Photorhabdus luminescens laumondii* TTO1 | TIC10358 | 63 | 64 | TIC10367 | 65 | 66 |
| *Photorhabdus asymbiotica* | TIC10360 | 69 | 70 | TIC10369 | 71 | 72 |
| *Xenorhabdus* sp. NBAII XenSa04 | TIC10361 | 75 | 76 | TIC10370 | 77 | 78 |
| *Yersinia aldovae* 670-83 | TIC10362 | 81 | 82 | TIC10371 | 83 | 84 |
| *Xenorhabdus doucetiae* FRM16 | TIC10363 | 87 | 88 | TIC10372 | 89 | 90 |
| *Xenorhabdus griffiniae* BMMCB | TIC10364 | 93 | 94 | TIC10373 | 95 | 96 |
| *Xenorhabdus nematophila* | TIC10359 | 99 | 100 | TIC10368 | 101 | 102 |
| *Photorhabdus luminescens* Hm | PirA_ABE68878 | 104 | 105 | PirB_ABE68879 | 106 | 107 |
| *Xenorhabdus nematophila* MDI-0035777 | | | | TIC11505 | 134 | 135 |
| *Xenorhabdus bovienii* MDI-0035808 | | | | TIC11510 | 138 | 139 |
| *Xenorhabdus nematophila* AN6/1 | | | | TIC11511 | 142 | 143 |

Sequences encoding *Photorabdus* and *Xenorabdus* PirA and PirB pesticidal proteins were identified from proprietary collections as well as public sequence information, synthesized, cloned, sequence confirmed, and tested in insect bioassay. Bacterial operons were identified and polymerase chain reaction (PCR) primers were designed based upon contigs derived from sequencing of each *Photorabdus* and *Xenorabdus* species listed in Table 13. Amplicons of the full-length coding sequence for each protein toxin were produced using total DNA isolated from each species listed in Table 13. Each of the amplicons were cloned using methods known in the art into *Bacillus thuringiensis* (Bt) expression vectors in operable linkage with a Bt expressible promoter.

Fusion proteins comprising the PirA and PirB proteins were made using methods known in the art. The coding sequences encoding the PirAB fusion proteins comprised PirA and PirB protein coding sequences operably linked, so when expressed in a cell a protein was produced comprising the PirA and PirB proteins contiguous with each other. PirAB fusion proteins comprised of a PirA protein contiguous with a PirB protein are presented in Table 1. The PirAB fusion proteins presented in Table 1 are comprised of a PirA and PirB protein derived from the same bacterial operon, or a PirA and PirB protein derived from different bacterial operons. PirAB fusion proteins comprised of a PirB protein contiguous with a PirA protein are presented in Table 2. The PirAB fusion proteins in Table 2 are comprised of a PirA and PirB protein derived from the same bacterial operon. PirAB fusion proteins comprised of a PirA protein contiguous with another PirA protein which is in turn contiguous with a PirB protein are presented in Table 3. The PirA protein components of the PirAB fusion proteins presented in Table 3 can be duplicated PirA proteins or different PirA proteins.

Example 2

PirA Proteins, PirB Proteins, and PirAB Fusion Proteins Demonstrate Lepidopteran, Coleopteran, and Hemipteran Activity in Insect Bioassay This Example illustrates inhibitory activity exhibited by The PirA Proteins, The PirB Proteins, and The PirAB Fusion Proteins against various species of Lepidoptera, Coleoptera, and Hemiptera.

The PirA Proteins, The PirB proteins, and The PirAB Fusion Proteins were expressed in Bt and *E. coli* and assayed for toxicity against various species of Lepidoptera, Coleoptera, Hemiptera, and Dipteran. Preparations of each toxin were assayed against the Lepidopteran pest species Fall Armyworm (*Spodoptera frugiperda*, FAW), Corn Earworm (*Helicoverpa zea*, (CEW), also known as Soybean Podworm and Cotton Bollworm), Southwestern Corn Borer (*Diatraea grandiosella*, SWCB), Diamondback Moth (*Plutella xylostella*, DBM), European Corn Borer (*Ostrinia nubilalis*, ECB), Velvetbean Caterpillar (*Anticarsia gemmatalis*, VBC), Black Cutworm (*Agrotis ipsilon*, BCW), Southern Armyworm (*Spodoptera eridania*, SAW), Soybean Looper (*Pseudoplusia includes*, SBL), and Tobacco Budworm (*Heliothis virescens*, TBW); the Coleopteran pest species Colorado potato beetle (*Leptinotarsa decemlineata*, CPB), Northern Corn Rootworm (Diabrotica *barberi*, NCR), Southern Corn Rootworm (Diabrotica *undecimpunctata howardii*, SCR), and Western Corn Rootworm (Diabrotica virgifera, WCR); the Hemipteran species Southern Green Stink Bug (*Nezara viridula*, SG), Neotropical Brown Stink Bug (*Euschistus heros*, NBSB), Tarnished plant bug (*Lygus lineolaris*, TPB), and Western tarnished plant bug (*Lygus Hesperus*, WTP); and the *Dipteran* species Yellow Fever Mosquito (*Aedes aegypti*, YFM).

Transformed Bt and *E. coli* expressing The PirA Proteins, The PirB Proteins, and The PirAB Fusion Proteins were grown and spores or solubilized proteins were added to the insect diet for assay. Mortality and stunting were evaluated by comparing the growth and development of insects on a diet containing one or more of The PirA Proteins, The PirB Proteins, and The PirAB Fusion Proteins, to insects on a diet with an untreated control culture. Activity was observed for Lepidopteran, Coleopteran, Hemipteran, and Dipteran insect pests. The bioassay activity observed for each protein is presented in Tables 14 (Lepidopteran) and 15 (Coleopteran, Hemipteran, and Dipteran), wherein "+" indicates activity, an empty cell indicates no activity observed, and "NT" indicates the toxin was not assayed against that specific insect pest.

TABLE 14

Bioassay activity of PirA Proteins, PirB Proteins, and PirAB Fusion proteins, against Lepidopteran insect pests.

| Type | Toxin | FAW | CEW | SWCB | DBM | ECB | VBC | BCW | SAW | SBL | TBW |
|---|---|---|---|---|---|---|---|---|---|---|---|
| PirA | TIC4771 | | + | | + | + | + | | + | | |
| PirB | TIC4772 | | + | | + | | + | | | | |
| Fusion | TIC6880 | + | + | + | + | + | + | | | | |
| PirA | TIC7575 | NT | NT | | NT | | | | | | |
| PirB | TIC7576 | NT | NT | | NT | | | | | | |
| Fusion | TIC9316 | NT | | + | NT | + | + | + | + | | + |
| PirA | TIC7660 | NT | NT | | NT | | | | | | |
| PirB | TIC7661 | NT | NT | | NT | | | | | | |
| Fusion | TIC9317 | NT | NT | + | NT | + | + | | | | |
| PirA | TIC7662 | NT | NT | | NT | | | | | | |
| PirB | TIC7663 | NT | NT | | NT | | | | | | |
| Fusion | TIC9318 | NT | NT | + | NT | + | + | + | | | + |
| PirA | TIC7664 | NT | NT | | NT | | | | | | |
| PirB | TIC7665 | NT | NT | | NT | | | | | | + |
| Fusion | TIC9319 | NT | NT | + | NT | + | + | + | | | |
| PirA | TIC7666 | NT | NT | | NT | | | | | | |
| PirB | TIC7667 | NT | NT | + | NT | | | | | | |
| Fusion | TIC9322 | + | + | + | NT | | + | | | | |
| PirA | TIC7668 | NT | NT | | NT | | | | | | |
| PirB | TIC7669 | NT | NT | | NT | | | | | | |
| Fusion | TIC9320 | NT | NT | + | NT | + | + | | | | |
| Fusion | TIC9321 | NT | NT | | NT | | | | | | |
| PirA | TIC10357 | NT | NT | | NT | NT | NT | | | | NT |
| PirB | TIC10366 | NT | NT | | NT | NT | NT | | | | NT |
| Fusion | TIC10375 | NT | NT | | NT | NT | NT | | | | NT |
| PirA | TIC10358 | NT | NT | | NT | NT | NT | | | | NT |
| PirB | TIC10367 | NT | NT | | NT | NT | NT | | | | NT |
| Fusion | TIC10376 | NT | NT | + | NT | NT | NT | | | | NT |
| PirA | TIC10360 | NT | NT | | NT | NT | NT | | | | NT |
| PirB | TIC10369 | NT | NT | | NT | NT | NT | | | | NT |
| Fusion | TIC10377 | NT | NT | | NT | NT | NT | | | | NT |
| PirA | TIC10361 | NT | NT | | NT | NT | NT | | | | NT |
| PirB | TIC10370 | NT | NT | | NT | NT | NT | | | | NT |
| Fusion | TIC10378 | NT | NT | + | NT | NT | NT | | | | NT |
| PirA | TIC10362 | NT | NT | | NT | NT | NT | | | | NT |
| PirB | TIC10371 | NT | NT | | NT | NT | NT | | | | NT |
| Fusion | TIC10379 | NT | | + | NT | NT | NT | | | | NT |
| PirA | TIC10363 | NT | NT | | NT | NT | NT | | | | NT |
| PirB | TIC10372 | NT | NT | + | NT | NT | NT | | | | NT |
| Fusion | TIC10380 | + | NT | | NT | NT | NT | | | | NT |
| PirA | TIC10364 | NT | NT | | NT | NT | NT | | | | NT |
| PirB | TIC10373 | NT | NT | | NT | NT | NT | | | | NT |
| Fusion | TIC10381 | | NT | | NT | NT | NT | | | | NT |
| PirB | TIC10368 | NT | NT | | NT | NT | NT | | | | NT |
| Fusion | TIC10434 | | NT | | NT | NT | NT | | | | NT |
| Fusion | TIC11103 | NT | NT | + | NT | NT | NT | NT | NT | NT | NT |
| Fusion | TIC11104 | NT | NT | | NT | NT | NT | NT | NT | NT | NT |
| Fusion | TIC11210 | NT | NT | + | NT | NT | NT | + | | | NT |
| Fusion | TIC11211 | NT | NT | + | NT | NT | NT | NT | NT | NT | NT |
| Fusion | TIC11212 | NT | NT | + | NT | NT | NT | | | | NT |
| Fusion | TIC11301 | | NT | + | NT | + | + | | NT | NT | NT |
| Fusion | TIC11302 | | NT | + | NT | + | + | | NT | NT | NT |

TABLE 15

Bioassay activity of PirA Proteins, PirB Proteins, and PirAB Fusion Proteins against Coleopteran, Hemipteran, and Dipteran insect pests.

| | | Coleopteran | | | | Hemipteran | | | | Dipteran |
|---|---|---|---|---|---|---|---|---|---|---|
| Type | Toxin | CPB | NCR | SCR | WCR | SGB | NBSB | TPB | WTP | YFM |
| PirA | TIC4771 | + | NT | NT | NT | NT | | + | | NT |
| PirB | TIC4772 | | NT | NT | | NT | | + | | NT |
| Fusion | TIC6880 | + | NT | | + | + | + | + | + | + |
| PirA | TIC7575 | | NT | NT | | NT | NT | | | NT |
| PirB | TIC7576 | | NT | NT | NT | NT | NT | | | |
| Fusion | TIC9316 | + | NT | NT | | + | + | + | + | NT |
| PirA | TIC7660 | | NT | NT | NT | NT | NT | | | NT |
| PirB | TIC7661 | | NT | NT | NT | NT | NT | | | NT |
| Fusion | TIC9317 | + | | | + | + | | + | + | NT |
| PirA | TIC7662 | | NT | NT | | NT | NT | | | NT |
| PirB | TIC7663 | | NT | NT | NT | NT | NT | | | NT |
| Fusion | TIC9318 | + | | | + | + | + | + | + | NT |
| PirA | TIC7664 | + | NT | NT | NT | NT | NT | | | NT |
| PirB | TIC7665 | | NT | NT | NT | NT | NT | | | NT |
| Fusion | TIC9319 | + | NT | NT | | + | | + | + | NT |
| PirA | TIC7666 | | NT | NT | | NT | NT | | | NT |
| PirB | TIC7667 | | NT | NT | NT | NT | NT | | | NT |
| Fusion | TIC9322 | + | NT | NT | | | | + | | NT |
| PirA | TIC7668 | | NT | NT | NT | NT | NT | | | NT |
| PirB | TIC7669 | | NT | NT | NT | NT | NT | | | NT |
| Fusion | TIC9320 | + | NT | NT | | + | + | + | | NT |
| Fusion | TIC9321 | + | NT | NT | | NT | NT | | | NT |
| PirA | TIC10357 | NT | NT | NT | NT | NT | NT | NT | | NT |
| PirB | TIC10366 | NT | NT | NT | NT | NT | NT | NT | | NT |
| Fusion | TIC10375 | NT | NT | NT | NT | NT | NT | NT | | NT |
| PirA | TIC10358 | NT | NT | NT | NT | NT | NT | NT | | NT |
| PirB | TIC10367 | NT | NT | NT | NT | NT | NT | NT | | NT |
| Fusion | TIC10376 | NT | + | NT | + | NT | | NT | | NT |
| PirA | TIC10360 | NT | NT | NT | NT | NT | NT | NT | | NT |
| PirB | TIC10369 | NT | NT | NT | NT | NT | NT | NT | | NT |
| Fusion | TIC10377 | NT | NT | NT | NT | NT | NT | NT | | NT |
| PirA | TIC10361 | NT | NT | NT | NT | NT | NT | NT | | NT |
| PirB | TIC10370 | NT | NT | NT | NT | NT | NT | NT | | NT |
| Fusion | TIC10378 | NT | + | NT | + | NT | + | NT | | NT |
| PirA | TIC10362 | NT | NT | NT | NT | NT | NT | NT | | NT |
| PirB | TIC10371 | NT | NT | NT | NT | NT | NT | NT | | NT |
| Fusion | TIC10379 | NT | + | NT | + | NT | NT | NT | | NT |
| PirA | TIC10363 | NT | NT | NT | NT | NT | NT | NT | | NT |
| PirB | TIC10372 | NT | NT | NT | NT | NT | NT | NT | | NT |
| Fusion | TIC10380 | NT | + | NT | + | NT | + | NT | NT | NT |
| PirA | TIC10364 | NT | NT | NT | NT | NT | NT | NT | | NT |
| PirB | TIC10373 | NT | NT | NT | NT | NT | NT | NT | | NT |
| Fusion | TIC10381 | NT | + | NT | + | NT | + | NT | | NT |
| PirB | TIC10368 | NT | NT | NT | NT | NT | NT | NT | | NT |
| Fusion | TIC10434 | NT | + | NT | + | NT | | NT | NT | NT |
| Fusion | TIC11103 | NT | NT | NT | NT | NT | | NT | | NT |
| Fusion | TIC11104 | NT | NT | NT | NT | NT | + | NT | NT | NT |
| Fusion | TIC11210 | NT | NT | NT | NT | NT | + | NT | | NT |
| Fusion | TIC11211 | NT | NT | NT | NT | NT | + | NT | | NT |
| Fusion | TIC11212 | NT | NT | NT | NT | NT | | NT | NT | NT |
| Fusion | TIC11301 | NT | + | NT | + | NT | + | NT | + | NT |
| Fusion | TIC11302 | NT | NT | NT | + | NT | + | NT | + | NT |

As can be seen in Tables 14 and 15, the PirA and PirB toxin proteins alone in most instances did not demonstrate insecticidal activity. However, the fusion proteins comprising the PirA and PirB protein from each operon showed a wide spectrum of activity against Lepidopteran, Coleopteran, Hemipteran, and Dipteran insect pest species. Some of the PirA and PirB proteins did demonstrate oral activity when tested in their individual capacity. For example the PirA protein TIC4771 demonstrated activity against the Lepidopteran species CEW, DBM, ECB, VBC, SAW, the Coleopteran species CPB, and the Hemipteran species TPB. The PirB Protein TIC4772 demonstrated activity against the Lepidopteran species CEW, DBM, VBC, SAW, and the Hemipteran species TPB. When the TIC4771 and TIC4772 proteins were combined into the PirAB fusion protein TIC6880 most of the activity against the Lepidopteran activity was retained (CEW, DBM, ECB, and VBC). Activity against SAW was lost, but activity against two more insect species FAW and SWCB was seen. TIC6880 also demonstrated additional activity relative to the individual TIC4771 and TIC4772 with respect to Coleopteran and Hemipteran insect pest species. With respect to Coleoptera, TIC6880 retained activity against CPB, and added activity against WCR. With respect to Hemiptera, TIC6880 retained activity against TPB and added observed activity against SGB, NBSB, and WTP. TIC6880 also demonstrated activity against the Dipteran species YFM, which was not seen by TIC4771 or TIC4772.

While the PirA and PirB proteins TIC7575 and TIC7576, respectively, did not demonstrate insect inhibitory activity against the insects assayed, the corresponding PirAB fusion protein, TIC9316 demonstrated activity against the Lepidopteran species SWCB, ECB, VBC, BCW, SAW, and TBW. TIC9316 also demonstrated activity against the Coleopteran species CPB and the Hemipteran species SGB, NBSB, TPB, and WTP.

The PirA and PirB proteins TIC7660 and TIC7661, respectively did not demonstrate activity. However, the corresponding PirAB fusion protein TIC9317 demonstrated activity against the Lepidopteran species SWCB, ECB, and VBC, the Coleopteran species CPB and WCR, and the Hemipteran species SGB, TPB, and WTP.

The PirA and PirB proteins TIC7662 and TIC7663, respectively, did not demonstrate activity. However, the corresponding PirAB fusion protein TIC9318 demonstrated activity against the Lepidopteran species SWCB, ECB, VBC, BCW, and TBW, the Coleopteran species CPB and WCR, and the Hemipteran species SGB, NBSB, TPB, and WTP.

The PirA protein TIC7664 demonstrated activity against the Coleopteran species CPB. The PirB protein TIC7665 demonstrated activity against the Lepidopteran species TBW. The corresponding PirAB fusion protein TIC9319 demonstrated activity against the Lepidopteran species SWCB, ECB, VBC, and BCW, the Coleopteran species CPB and WCR, and the Hemipteran species SGB, TPB, and WTP.

The PirA protein TIC7666 did not demonstrate insect inhibitory activity. The PirB protein TIC7667 demonstrated activity against the Lepidopteran species SWCB. The corresponding PirAB fusion protein TIC9322 demonstrated activity against the Lepidopteran species FAW, CEW, SWCB and VBC, the Coleopteran species CPB, and the Hemipteran species TPB.

The PirA and PirB proteins TIC7668 and TIC7669, respectively, did not demonstrate activity. The corresponding PirAB fusion protein TIC9320 demonstrated activity against the Lepidopteran species SWCB, ECB, and VBC, the Coleopteran species CPB, and the Hemipteran species SGB, NBSB, and TPB.

The PirAB fusion protein TIC9321 demonstrated activity against the Coleopteran pest CPB.

The PirA protein TIC10357, PirB protein TIC10366, and the corresponding PirAB fusion protein TIC10375 did not demonstrate activity against the limited number of Lepidopteran assayed.

The PirA protein TIC10358 and PirB protein TIC10367, respectively, did not show activity against the insect species assayed. However, the corresponding PirAB fusion protein TIC10376 demonstrated activity against the Lepidopteran insect pest species, SWCB and the Coleopteran insect pest species, NCR and WCR.

The PirA protein TIC10360 and the PirB protein TIC10369, respectively, did not demonstrate activity against the limited number of Lepidopteran insect pest species assayed.

The PirA protein TIC10361 and PirB protein TIC10370, respectively, did not demonstrate activity against the limited number of Lepidopteran insect pest species assayed. However, the corresponding fusion protein TIC10378 demonstrated activity against the Lepidopteran insect pest species, SWCB, the Coleopteran pest species, NCR and WCR, and the Hemipteran pest species, NBSB.

The PirA protein TIC10362 and the PirB protein TIC10371 did not demonstrate activity against the limited number of Lepidopteran insect pest species assayed.

The PirA protein TIC10363 did not demonstrate activity against the limited number of insect pest species assayed. The PirB protein TIC10372 demonstrated activity against the Lepidopteran insect species SWCB. The corresponding fusion protein TIC10380 retained activity against the Lepidopteran insect pest species, SWCB and added activity against the Coleopteran pest species NCR and WCR and the Hemipteran pest species NBSB.

The PirA protein TIC10364 and PirB protein TIC10373 did not demonstrate activity against the limited number of insect pest species assayed. The corresponding fusion protein TIC10381 demonstrated activity against the Coleopteran pest species, NCR and WCR, and the Hemipteran pest species NBSB.

The PirAB fusion protein TIC10434 demonstrated activity against the Coleopteran pest species NCR and WCR.

The PirAB fusion protein TIC11103 demonstrated activity against the Lepidopteran pest species SWCB.

The PirAB fusion protein TIC1104 demonstrated activity against the Hemipteran species NBSB.

The PirAB fusion protein TIC11210 demonstrated activity against the Lepidopteran pest species SWCB and BCW and the Hemipteran pest species NBSB.

The PirAB fusion protein TIC11211 demonstrated activity against the Lepidopteran pest species SWCB and the Hemipteran species NBSB.

The PirAB fusion protein TIC11212 demonstrated activity against the Lepidopteran insect pest species SWCB.

The PirAB fusion protein TIC11301 demonstrated activity against the Lepidopteran pest species SWCB, ECB, and VBC, the Coleopteran pest species NCR and WCR, and the Hemipteran pest species NBSB and WTP.

The PirAB fusion protein TIC11302 demonstrated activity against the Lepidopteran pest species SWCB, ECB, and VBC, the Coleopteran pest species WCR, and the Hemipteran pest species NBS and WTP.

Example 3

Mixtures of the PirA, PirB, and PirAB Fusion Proteins Demonstrate Lepidopteran, Coleopteran, and Hemipteran Activity in Insect Bioassay This Example illustrates inhibitory activity exhibited by mixing the PirA proteins TIC7575 and TIC7660 with the PirB proteins TIC7576 and TIC7661, as well as by mixing the PirAB fusion proteins TIC9316 and TIC9317; TIC9316 with TIC11301; and TIC9317 and TIC11302 in various concentrations.

Mixtures of the PirA and PirB proteins and mixtures of the PirAB fusion proteins at various concentrations were presented in insect diet and assayed for activity against the Lepidopteran pest species BCW, SWC, and VBC, the Coleopteran pest species WCR and NCR, and the Hemipteran pest species NBSB. The mixtures comprised different concentrations of the toxin proteins. Table 16 below shows the insect species in which activity was observed for each mixture.

TABLE 16

Bioassay activity of mixtures of the PirA and PirB toxin proteins and mixtures of the PirAB fusion proteins.

| Mixture | Activity |
|---|---|
| TIC7575 0.0625 mg/mL; TIC7576 0.1875 mg/mL | BCW; VBC; NBSB |
| TIC7575 0.0625 mg/mL; TIC7576 0.1875 mg/mL; double for .5 mg/mL final | NCR; WCR; NBSB |

TABLE 16-continued

Bioassay activity of mixtures of the PirA and PirB toxin proteins and mixtures of the PirAB fusion proteins.

| Mixture | Activity |
|---|---|
| TIC7575 0.0625 mg/mL; TIC7661 0.1875 mg/mL; double for .5 mg/mL final | NCR; WCR |
| TIC7660 0.0625 mg/mL; TIC7576 0.1875 mg/mL; double for .5 mg/mL final | NCR; WCR |
| TIC7660 0.0625 mg/mL; TIC7661 0.1875 mg/mL; double for .5 mg/mL final | NCR; WCR |
| TIC7575 0.0625 mg/mL; TIC7576 0.125 mg/mL; TIC7660 0.0625 mg/mL | WCR; VBC |
| TIC7575 0.0625 mg/ml; TIC7660 0.0625 mg/mL; TIC7661 0.125 mg/mL | WCR |
| TIC9316 0.04 mg/mL; TIC9317 0.01 mg/mL | VBC |
| TIC9316 0.025 mg/mL; TIC9317 0.025 mg/mL | VBC |
| TIC9316 0.25 mg/ml; TIC9317 0.25 mg/mL | NBS |
| TIC9316 0.4 mg/mL; TIC9317 0.1 mg/mL | NBS |
| TIC9316 0.04 mg/mL; TIC11301 0.01 mg/mL | VBC; SWC |
| TIC9316 0.025 mg/mL; TIC11301 0.025 mg/mL | VBC |
| TIC9316 0.01 mg/mL; TIC11301 0.04 mg/mL | VBC |
| TIC9316 0.1 mg/mL; TIC11301 0.4 mg/mL | NBS |
| TIC9316 0.4 mg/mL; TIC11301 0.1 mg/mL | VBC; NBSB |
| TIC9317 0.01 mg/mL; TIC11302 0.04 mg/mL | VBC |
| TIC9317 0.25 mg/mL; TIC11302 0.25 mg/mL | NBS |

As can be seen in Table 16, mixtures of the PirA proteins TIC7575 and TIC7660 with the PirB proteins TIC7576 and TIC7661 provided activity similar to corresponding the corresponding fusion proteins, TIC9316 and TIC9317. Mixtures of the PirAB fusion proteins TIC9316 and TIC9317; TIC9316 with TIC11301; and TIC9317 and TIC11302 demonstrated activity similar to one or both of the fusion proteins.

Example 4

Design of Synthetic Coding Sequences Encoding the PirAB Fusion Proteins TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 for Expression in Plant Cells Synthetic or artificial coding sequences were constructed for use in expression of the PirAB fusion proteins TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 in plants. These synthetic coding sequences were cloned into a binary plant transformation vectors and used to transform plant cells. The synthetic nucleic acid sequences were synthesized according to methods generally described in U.S. Pat. No. 5,500,365, avoiding certain inimical problem sequences such as ATTTA and A/T rich plant polyadenylation sequences while preserving the amino acid sequence of the PirAB Fusion protein. The synthetic coding sequence for the PirAB fusion proteins TIC6880PL, TIC9316, TIC9317, TIC9318, TIC9319, TIC9320, TIC9322, TIC10376PL, TIC10378PL, TIC10380PL, TIC10381PL, and TIC11302 are presented in Table 17. The coding sequences encoding TIC6880PL, TIC10376PL, TIC10378PL, TIC10380PL, and TIC10381PL contained an additional alanine codon immediately following the initiating methionine residue of the corresponding PirA coding sequences portion within the PirAB fusion protein coding sequence.

TABLE 17

Synthetic coding sequences used for expression in plant cells encoding PirAB fusion proteins TIC6880PL, TIC9316, TIC9317, TIC9318, TIC9319, TIC9320, TIC9322, TIC10376PL, TIC10378PL, TIC10380PL, TIC10381PL, and TIC11302.

| PirAB Fusion Protein | Nucleotide SEQ ID NO: | Protein SEQ ID NO: | PirA Protein | PirB Protein |
|---|---|---|---|---|
| TIC6880PL* | 49 | 50 | TIC4771* | TIC4772 |
| TIC9316 | 51 | 12 | TIC7575 | TIC7576 |
| TIC9317 | 52 | 18 | TIC7660 | TIC7661 |
| TIC9318 | 53 | 24 | TIC7662 | TIC7663 |
| TIC9319 | 54 | 30 | TIC7664 | TIC7665 |
| TIC9320 | 55 | 42 | TIC7668 | TIC7669 |
| TIC9322 | 56 | 36 | TIC7666 | TIC7667 |
| TIC10376PL* | 146 | 147 | TIC10358* | TIC10367 |
| TIC10378PL* | 148 | 149 | TIC10361* | TIC10370 |
| TIC10380PL* | 150 | 151 | TIC10363* | TIC10372 |
| TIC10381PL* | 152 | 153 | TIC10364* | TIC10373 |
| TIC11302 | 158 | 119 | TIC7660 | TIC7576 |

*comprises an additional alanine residue immediately following the initiating methionine residue.

The synthetic coding sequences and corresponding protein sequences for TIC11103 and TIC11104 are presented in Table 18 below.

TABLE 18

Synthetic coding sequences used for expression in plant cells encoding PirAB fusion proteins TIC11103 and TIC11104.

| PirAB Fusion Protein | Nucleotide SEQ ID NO: | Protein SEQ ID NO: | PirB Protein | PirA Protein |
|---|---|---|---|---|
| TIC11103 | 154 | 155 | TIC7661 | TIC7660 |
| TIC11104 | 156 | 157 | TIC7663 | TIC7662 |

Example 5

Expression Cassettes for Expression of PirAB Fusion Proteins in Plant Cells

A variety of plant expression cassettes were designed with the sequences as set forth in Table 17. Such expression cassettes are useful for transient expression in plant protoplasts or transformation of plant cells. Typical expression cassettes are designed with respect to the eventual placement of the protein within the plant cell. For a plastid targeted protein, the synthetic TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 pesticidal protein coding sequences are operably linked in frame with a chloroplast targeting signal peptide coding sequence. The resulting plant transformation vectors comprise a first transgene cassette for expression of the pesticidal protein which comprises a constitutive promoter, operably linked 5' to a leader, operably linked 5' to an intron (or optionally no intron), operably linked 5' to a synthetic coding sequence encoding a plastid targeted or untargeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 protein, which is in turn operably linked 5' to a 3' UTR and, a second transgene cassette for the selection of transformed plant cells using glyphosate or antibiotic selection. All of the elements described above are arranged contiguously often with additional sequence provided for the construction of the expression cassette such as restriction endonuclease sites or ligation independent cloning sites.

Example 6

Transgenic Corn Plants Expressing TIC9316, TIC9317, TIC9318, TIC10376, TIC10378, TIC10380, and TIC10381 Demonstrate Activity Against Lepidopteran Pest Species This Example illustrates the inhibitory activity of the PirAB fusion proteins TIC9316, TIC9317, TIC9318, TIC10378, TIC10380, and TIC10381 when expressed in transgenic corn plants and assayed against Lepidopteran insect pest species.

Binary plant transformation vectors comprising transgene cassettes designed to express TIC9316, TIC9317, TIC9318, TIC10376, TIC10378, TIC10380, or TIC10381 were cloned using methods known in the art. The plant transformation vector comprised a first transgene cassette for expression of the TIC9316, TIC9317, TIC9318, TIC10376, TIC10378, TIC10380, or TIC10381 pesticidal protein which comprised a plant expressible promoter, operably linked 5' to a leader, operably linked 5' to an intron, operably linked 5' to a synthetic coding sequence encoding TIC9316, TIC9317, TIC9318, TIC10376, TIC10378, TIC10380, or TIC10381, operably linked 5' to a 3' UTR and, a second transgene cassette for the selection of transformed plant cells using glyphosate. The resulting vectors were used to stably transform corn plants using an *Agrobacterium*-mediated transformation method. The transformed cells were induced to form plants by methods known in the art. Bioassays using plant leaf disks were performed analogous to those described in U.S. Pat. No. 8,344,207. A non-transformed corn plant was used to obtain tissue to be used as a negative control. Multiple transformation events from each binary vector were assessed against the Lepidopteran pest species FAW, CEW, SWCB, ECB, and BCW.

Several transformed events expressing TIC9316 demonstrated good to moderate inhibitory activity against SWCB and ECB. Likewise, transformed events expressing TIC9317 also demonstrated good to moderate inhibitory activity against SWCB and ECB. Transformed events expressing TIC9318 demonstrated good to excellent inhibitory activity against SWCB and ECB. Transformed events expressing TIC10376, TIC10378, TIC10380, and TIC10381 demonstrated good to moderate activity against SWCB.

Example 7

Assay of Activity of PirAB Fusion Proteins Against Coleopteran Corn Rootworm Pests When Expressed in Stably Transformed Corn Plants This Example illustrates the inhibitory activity of TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 against different Coleopteran species that feed on corn roots.

Binary plant transformation vectors comprising transgene cassettes designed to express both plastid targeted and untargeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 are cloned using methods known in the art and comprise the sequences as shown in Tables 17 and 18. The resulting vectors are used to stably transform corn plants using methods known in the art. Single T-DNA insertion events are selected and grown. Pesticidal activity is assayed against the Coleopteran pests NCR, SCR, and WCR feeding on the roots of the stably transformed corn plants.

$R_0$ stably transformed plants are used to assay for Coleopteran resistance as well as generating $F_1$ progeny. Multiple single copy events are selected from each binary vector transformation. A portion of the events arising from each binary vector transformation are used in the $R_0$ Coleopteran assay, while another portion of events are used to generate $F_1$ progeny for further testing.

The $R_0$ assay plants are transplanted to eight inch pots. The plants are inoculated with eggs from WCR, NCR, or SCR. The eggs are incubated for approximately ten (10) days prior to inoculation to allow hatching to occur four (4) days after inoculation to ensure a sufficient number of larvae survive and are able to attack the corn roots. The transformed plants are inoculated at approximately V2 to V3 stage. The plants are grown after infestation for approximately twenty-eight (28) days. The plants are removed from the pots with the roots being carefully washed to remove all soil. The damage to the roots is assessed using a damage rating scale of 1-5, as presented in Table 19. Comparison is also made to the negative controls to assure the assay has been performed properly. Multiple $R_0$ events for each binary vector transformation are used in the Coleopteran assay. Low root damage scores indicate resistance conferred by the tested PirAB fusion protein to the tested Coleopteran pest.

TABLE 19

$R_0$ root damage rating scores.

| Root Damage Score | Description |
|---|---|
| 1 | No visible feeding |
| 2 | Some feeding; no pruning |
| 3 | Pruning of at least one root |
| 4 | Entire node pruned |
| 5 | More than one node pruned |

A portion of the $R_0$ stably transformed events arising from each binary vector transformation are used to produce $F_1$ progeny. The $R_0$ stably transformed plants are allowed to self-fertilize, producing $F_1$ progeny. The $F_1$ seed is planted. Heterozygous plants are identified through molecular methods known in the art and used for assay against Coleopteran pests, as well as ELISA expression measurements of toxin protein. A portion of the heterozygous $F_1$ progeny from each event are used for insect assay, while another portion is used to measure toxin protein expression.

Eggs from WCR, NCR, or SCR are incubated for approximately ten (10) days to allow hatching within four (4) days after inoculation. For WCR, each pot is inoculated with about two thousand eggs. For NCR, less eggs may be used due to the lower availability of eggs from this species. The plants are inoculated at approximately V2 to V3 stage. The plants are grown after infestation for approximately twenty-eight (28) days. The plants are removed from the pots with the roots being carefully washed to remove all soil. The damage to the roots are assessed using a damage rating scale of 0-3, as presented in Table 20. Comparison is made to the negative control to assure the assay has been performed properly. Low root damage scores indicate resistance conferred by TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 to the Coleopteran pest.

TABLE 20

$F_1$ root damage rating scores.

| Root Damage Score | Description |
|---|---|
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

Example 8

Assay of Activity of The PirAB Fusion Proteins Against Lepidopteran Pests When Expressed in Stably Transformed Corn, Soybean or Cotton Plants This Example illustrates the assay of activity against various Lepidopteran pest species fed tissue from stably transformed corn, soybean or cotton plants expressing one of The PirAB Fusion Proteins.

Binary plant transformation vectors comprising transgene cassettes designed to express both plastid targeted and untargeted versions of The PirAB Fusion Proteins are cloned using methods known in the art and comprise the coding sequences as presented in Tables 17 and 18.

Corn, soybean, or cotton is transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed corn, soybean, or cotton plant is used to obtain tissue to be used as a negative control. Multiple transformation events from each binary vector are assessed against Lepidopteran pests such as, but not limited to, BCW, CEW, DBM, ECB, FAW, SAW, SBL, SWCB, TBW, and VBC. Those insects demonstrating stunting and/or mortality in the insect bioassay are determined to be susceptible to the effects of The PirAB Fusion Proteins tested.

Example 9

Assay of Activity of The PirAB Fusion Proteins Against Flea Beetle Pests When Expressed in Stably Transformed Canola Plants This Example illustrates the assay of activity of against various species of Flea Beetle when allowed to feed on whole transgenic canola plants or tissues derived from transgenic canola plants expressing one of The PirAB Fusion Proteins.

Binary plant transformation vectors comprising transgene cassettes designed to express both plastid targeted and untargeted versions of The PirAB Fusion Proteins are cloned using methods known in the art and comprise the coding sequences as presented in Tables 17 and 18.

The resulting binary transformation vectors are used to stably transform canola plant cells using methods known in the art. The transformed cells are induced to form plants. Bioassays using plant leaf disks are performed analogous to those described in U.S. Pat. No. 8,344,207 using field collected Flea Beetles. A non-transformed canola plant is used to obtain tissue to be used as a negative control. Multiple transformation events from each binary vector are assessed against Coleopteran Flea Beetle pests such as, but not limited to, Crucifer Flea Beetle (Phyllotreta *cruciferae*), Striped Flea Beetle (Phyllotreta *striolata*), and Western Black Flea Beetle (Phyllotreta *pusilla*). Flea Beetle mortality is determined each day as the Beetles continue to feed. Leaf discs are changed every two (2) to three (3) days over a twelve (12) day period to assure fresh material is available to the Flea Beetles for feeding, and to reduce any impact of protein degradation in the sample.

Alternatively, transformed canola plants can be planted in a field where Flea Beetle infestations are present. The plants can be housed in a tent to prevent those Flea Beetles that emerge from the soil from escaping the experimental plots. Damage ratings of the canola leaves can be taken to determine which plants experienced lesser damage and demonstrated resistance to the Flea Beetles.

Example 10

Assay of the Activity of the PirAB Fusion Proteins Against Hemipteran Pests in Stably Transformed Soybean Plants This Example describes the assay of activity against Hemipteran insect pests in soybean plants stably transformed to express one of The PirAB Fusion Proteins.

Binary plant transformation vectors comprising transgene cassettes designed to express both plastid targeted and untargeted versions of one of The PirAB Fusion Proteins are cloned using methods known in the art and comprise the coding sequences as presented in Tables 17 and 18. Soybean plants are transformed using the binary plant transformation vectors. The transformed soybean plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the developing seeds and pods of the soybean plant. To assay for activity against Stink Bugs, R5 stage pods are harvested from the transgenic soybean plants expressing one of The PirAB Fusion Proteins and placed in a covered Petri dish or large multi-well plate containing a layer of either agar or wet paper to provide humidity to the feeding environment. Second instar Stink Bug nymphs are placed in the Petri dish or large multi-well plate. A cover providing for the exchange of oxygen while preventing desiccation is placed over the feeding environment. The Stink Bug nymphs are allowed to feed for several days. Measurements of stunting and mortality are taken and compared to Stink Bugs nymphs feeding on pods from untransformed soybean plants.

Alternatively, assay of activity can also be performed on whole stably transformed plants. Transformed plants expressing one of The PirAB Fusion Proteins are grown in a growth chamber or in the greenhouse. At R5 stage, the plants are enclosed in a cage made from breathable plastic "pollination" sheets (Vilutis and Company Inc, Frankfort, Ill.). The sheet sleeves are secured to the main stem just above the soil surface using a Velcro® tie. Each plant is infested with a specific number of second instar Stink Bug nymphs. The nymphs are released into each individual cage through a small slit on the cage side and then the cage is securely closed ensuring the insects won't escape. The nymphs are allowed to feed on the soybean pods for several days to a week or more. Observations are taken each day to determine measurements of stunting and mortality. At the end of the feeding period, the live and dead nymphs are collected. The plants are cut below the cages and moved to a laboratory where the insects are collected for each plant. Before opening the cage, the plants are vigorously shaken to ensure all of the insects fall off from their feeding sites to the base of the cage. Then the cage base is opened and all plant material is removed and placed on a black sheet. The insects can be collected using an aspirator or some other means. The number of insects and their developmental stage is recorded for each plant. Also, the number and developmental stage of dead nymphs is also recorded. These measurements are compared to the measurements obtained from negative control, un-transformed plants.

Delays in development of the Stink Bug nymphs (stunting) or mortality are interpreted as an indication of toxicity if, when compared to the un-transformed controls, there is a significant difference.

Example 11

Assay of the Activity of the PirAB Fusion Proteins Against Hemipteran Pests in Stably Transformed Corn Plants This Example describes the assay of activity against Hemipteran insect pests in corn plants stably transformed to express one of The PirAB Fusion Proteins.

Binary plant transformation vectors comprising transgene cassettes designed to express both plastid targeted and untargeted versions of one of The PirAB Fusion Proteins are cloned using methods known in the art and comprise the coding sequences as presented in Tables 17 and 18. Corn plants are transformed using the binary plant transformation vectors. The transformed corn plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the young corn plants in late spring or early summer, resulting in holes in the leaf, and if severe, deformed plants. In late summer, Stink Bugs typically feed on the ear itself, directly destroying the kernels.

One method to assay for Stink Bug activity is to expose the Stink Bug nymphs to leaf discs derived from stably transformed corn plants expressing one of The PirAB Fusion Proteins in large multi-well plates. Second stage instar Stink Bug nymphs are placed in large multi-well plates with leaf discs derived from the stably transformed corn plants and allowed to feed for several days. Measurements of stunting and mortality are taken and compared to Stink Bug nymphs who have fed on un-transformed corn leaf discs.

Alternatively, whole transformed plants can be used to assay for Stink Bug activity. Stably transformed corn plants expressing one of The PirAB Fusion Proteins are enclosed in cages in a similar manner as described for soybean plants in Example 4. Second instar nymphs are introduced to V3 stage corn plants and allowed to feed for several days to a week. After the prescribed feeding period, the live and dead nymphs are collected. Measurements of stunting and mortality are compared to un-transformed control plants.

To assay Stink Bug activity using stably transformed corn ears, a similar approach can be taken as that of assaying in V3 stage plants. The developing corn ears of stably transformed corn plants expressing one of The PirAB Fusion Proteins are encapsulated using sheets of material that permit the free exchange of air while preventing escape of the Stink Bug nymphs. The encapsulated ears are infested with second instar stage Stink Bug nymphs and allowed to feed on the developing kernels of the ear for several days to a week. Measurements of stunting and mortality are compared to un-transformed control plant ears.

Example 12

Assay of the Activity of the PirAB Fusion Proteins Against Hemipteran Pests in Stably Transformed Cotton Plants This Example describes the assay of activity against Hemipteran insect pests in cotton plants stably transformed to express one of The PirAB Fusion Proteins.

Binary plant transformation vectors comprising transgene cassettes designed to express both plastid targeted and untargeted versions of one of The PirAB Fusion Proteins are cloned using methods known in the art and comprise the coding sequences as presented in Tables 17 and 18. Cotton plants are transformed using the binary plant transformation vectors. The transformed cotton plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs are typically seed feeders, and thus, injury to cotton bolls is the primary concern. They primarily damage cotton by piercing the bolls and feeding on the seeds. Their feeding activity can result in dark spots about 1/16 of an inch in diameter on the outside of larger bolls where feeding occurred. Seed feeding may result in reduced lint production and stained lint near the feeding site. Because of their size, adults and fourth and fifth instar nymphs have the greatest potential for damaging bolls, and it is therefore important to kill the insect in its earlier nymphal stages. The Hemipteran pest species of *Lygus* primarily feed on the squares and young bolls. The nymphs are more voracious feeders and tend to cause the most severe damage. When feeding on squares, *Lygus* target the developing anthers which often results in the square shriveling and falling from the plant. For those squares that develop into bolls, the bolls may have anthers that are incapable of forming pollen, unfertilized seeds, and empty locules. When feeding on bolls, *Lygus* target the developing seeds, causing small black sunken spots on the outside of the boll.

One method to assay activity of The PirAB Fusion Proteins in stably transformed cotton plants is to use squares in an insect bioassay. The squares are harvested from transformed cotton plants expressing TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302. The squares can be put into a petri dish or each square into a well of a large well plate. Young neonate *Lygus* or Stink Bug nymphs are placed into the petri dish or large well plate and allowed to feed for a prescribed time. Measurements of stunting and mortality are taken over the time course of feeding and compared to controls in which squares derived from untransformed cotton plants are used in assay.

Alternatively, assay of activity can be performed on whole transformed cotton plants. For example, to assay against *Lygus* species, $R_1$ seeds derived from plants expressing one of The PirAB Fusion Proteins are sown in 10 inch pots. An untransformed cotton plant, preferably from the same variety as the transformed plants, is used as a negative control. Plants are maintained in an environment chamber with a photoperiod of sixteen (16) hours of light at thirty-two (32) degrees Celsius and eight (8) hours of dark at twenty three (23) degrees Celsius, and a light intensity between eight hundred (800) and nine hundred (900) micro-Einsteins. At forty (40) to forty-five (45) days after planting, the individual plants are enclosed in a cage made from breathable plastic "pollination" sheets (Vilutis and Company Inc, Frankfort, Ill.). The sheet sleeves are secured to the main stem just above the soil surface using a Velcro® tie. Two pairs of sexually mature male and female *Lygus* lineolaris or *Lygus hesperus* adults (six days old) from a laboratory culture are collected into a fourteen-milliliter round-bottom plastic tube (Bacton Dickson Labware, Franklin Lakes, N.J.) and used for each plant. The adults are released into each individual cage through a small slit on the cage side and then the cage is securely closed ensuring the insects would not escape. The insects are allowed to mate and the plants are kept in the cage for twenty-one (21) days.

After twenty-one (21) days, the plants are then cut below the cages and moved to a laboratory where the insects are collected for each plant and counted. Before opening the cage, the plants are vigorously shaken to ensure all of the insects fall off from their feeding sites to the base of the cage. Then the cage base is opened and all plant material removed and placed on a black sheet. The insects are collected using an aspirator. The plant is then thoroughly inspected to recover any remaining insects. The number of insects collected and their developmental stage are recorded for each plant. The insect counts are divided into several groups based upon maturity of the *Lygus*: nymphs up to $3^{rd}$ instar, $4^{th}$ instar, $5^{th}$ instar and adults.

To assay against Stink Bug species, R1 seeds derived from plants expressing one of The PirAB Fusion Proteins are sown into pots and grown and caged as described above. Untransformed cotton plants are also used as a negative control. Second instar Stink Bug nymphs are used to infest the plants and allowed to feed on the squares and bolls for several days or weeks. The caged plants are collected as described above and the collected stink bugs are examined and scored for mortality, as well as, maturity of the nymphs recorded. These scores are then compared to the negative control plants.

Example 13

TIC9318 and TIC11302 Demonstrates Activity Against Western Corn Rootworm Pests When Expressed in Stably Transformed Corn Plants This Example illustrates the inhibitory activity of TIC9318 and TIC11302 against Western Corn Rootworm (Diabrotica virgifera, WCR) in stably transformed corn plants.

Corn plants were transformed with binary plant transformation constructs comprising an expression cassette for the expression of either TIC9318 or TIC11302. The binary plant transformation vectors comprised transgene cassettes designed to express TIC9318 and TIC11302, and were cloned using methods known in the art. The plant transformation vectors comprised a first transgene cassette for expression of the TIC9318 or TIC11302 pesticidal protein which comprised a plant expressible promoter, operably linked 5' to a leader, operably linked 5' to an intron, operably linked 5' to a synthetic coding sequence encoding TIC9318 or TIC11302, operably linked 5' to a 3' UTR and, a second transgene cassette for the selection of transformed plant cells using glyphosate. The resulting vectors were used to stably transform corn plants using an *Agrobacterium*-mediated transformation method. The transformed cells were induced to form plants by methods known in the art.

$R_0$ stably transformed plants were used to assay TIC11302 for WCR resistance as well as generating $F_1$ progeny. Multiple single copy events were selected from each binary vector transformation. A portion of the events arising from each binary vector transformation were used in the $R_0$ WCR assay.

The $R_0$ assay plants were transplanted to eight inch pots. The plants were inoculated with approximately two thousand eggs each from WCR. The eggs were incubated for approximately ten (10) days prior to inoculation to allow hatching to occur four (4) days after inoculation to ensure a sufficient number of larvae survive and were able to attack the corn roots. Each pot was inoculated with approximately two thousand WCR eggs. The transformed plants were inoculated at approximately V2 to V3 stage. The plants were grown after infestation for approximately twenty-eight (28) days. The plants were removed from the pots with the roots being carefully washed to remove all soil. The damage to the roots was assessed using a damage rating scale of 1-5, as presented in Table 19 of Example 17. Comparison was also made to the negative controls to assure the assay has been performed properly. Multiple $R_0$ events for each TIC11302 binary vector transformation were used in the WCR assay.

A portion of the $R_0$ stably transformed events arising from each binary vector transformation of TIC9318 and TIC11302 were used to produce $F_1$ progeny. The $R_0$ stably transformed plants were allowed to self-fertilize, producing $F_1$ progeny. The $F_1$ seed was planted in eight inch pots. Heterozygous plants were identified through molecular methods known in the art and were used for assay against WCR. Inoculation with the WCR eggs was as described for the $R_0$ stably transformed events as described above. The damage to the roots were assessed using a damage rating scale of 0-3, as presented in Table 20 of Example 7. Comparison was made to the negative control to assure the assay has been performed properly. The average Root Damage Rating (RDR) for each construct is presented in Table 21 below, wherein "NT" indicates not tested.

TABLE 21

Average Root Damage Rating (RDR) for corn plants stably transformed with TIC9318 or TIC11302.

| Construct | PirAB Fusion Protein | Nucleotide SEQ ID NO: | Protein SEQ ID NO: | $R_0$ RDR | $R_0$ Neg. Control RDR | $F_1$ RDR | $F_1$ Neg. Control RDR |
|---|---|---|---|---|---|---|---|
| Construct_1 | TIC9318 | 53 | 24 | NT | NT | 1.4 | 2.8 |
| Construct_2 | TIC9318 | 53 | 24 | NT | NT | 1.5 | 1.8 |

TABLE 21-continued

Average Root Damage Rating (RDR) for corn plants stably transformed with TIC9318 or TIC11302.

| Construct | PirAB Fusion Protein | Nucleotide SEQ ID NO: | Protein SEQ ID NO: | $R_0$ RDR | $R_0$ Neg. Control RDR | $F_1$ RDR | $F_1$ Neg. Control RDR |
|---|---|---|---|---|---|---|---|
| Construct_3 | TIC9318 | 53 | 24 | NT | NT | 1.2 | 1.8 |
| Construct_4 | TIC11302 | 158 | 119 | 2.9 | 4.1 | 1.5 | 1.8 |
| Construct_5 | TIC11302 | 158 | 119 | 2.8 | 4.1 | 1.4 | 1.8 |
| Construct_6 | TIC11302 | 158 | 119 | 2.9 | 4.1 | 1.4 | 1.8 |

As can be seen in Table 21 above, both TIC9318 and TIC11302 demonstrated resistance to Western Corn Rootworm (Diabrotica virgifera virgifera) when compared to the negative controls.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein or pesticidal fragment thereof, wherein:
   a. said pesticidal protein comprises the amino acid sequence of SEQ ID NOs:2, 4, or 6; or
   b. said pesticidal protein comprises an amino acid sequence having at least 98% identity to SEQ ID NO:2, SEQ ID NO:4, SEQ ID NO:6, SEQ ID NO:50, or SEQ ID NO:121, and wherein said pesticidal protein exhibits activity against a Coleopteran insect.

2. A construct comprising the recombinant nucleic acid molecule of claim 1, wherein said construct is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial and a plant cell.

4. The host cell of claim 3, wherein the bacterial host cell is from a genus of bacteria selected from the group consisting of: *Agrobacterium, Rhizobium, Bacillus, Brevibacillus, Escherichia, Pseudomonas, Klebsiella, Pantoea*, and *Erwinia*.

5. The host cell of claim 4, wherein the *Bacillus* species is *Bacillus cereus* or *Bacillus thuringiensis*, said *Brevibacillus* is *Brevibacillus laterosperus*, or said *Escherichia* is *Escherichia coli*.

6. The host cell of claim 3, wherein said plant cell is a dicotyledonous or a monocotyledonous plant cell.

7. The host cell of claim 6, wherein said plant host cell is selected from the group consisting of: alfalfa, banana, barley, bean, broccoli, cabbage, Brassica, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. The recombinant nucleic acid molecule of claim 1, wherein said insect is Western Corn Rootworm, or Colorado Potato Beetle.

9. A plant or part thereof comprising the recombinant nucleic acid molecule of claim 1.

10. The plant or part thereof of claim 9, wherein said plant is a monocot plant or a dicot plant.

11. The plant or part thereof of claim 9, wherein the plant is selected from the group consisting of: alfalfa, banana, barley, bean, broccoli, cabbage, Brassica, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

12. A seed of the plant of claim 9, wherein said seed comprises said recombinant nucleic acid molecule.

13. An insect inhibitory composition comprising the recombinant nucleic acid molecule of claim 1.

14. The insect inhibitory composition of claim 13, further comprising a nucleotide sequence encoding at least one other pesticidal agent that is different from said pesticidal protein.

15. The insect inhibitory composition of claim 14, wherein said at least one other pesticidal agent is selected from the group consisting of an insect inhibitory protein, an insect inhibitory dsRNA molecule, and an ancillary protein.

16. The insect inhibitory composition of claim 14, wherein said at least one other pesticidal agent exhibits activity against one or more pest species of the orders Lepidoptera, Coleoptera, or Hemiptera.

17. The insect inhibitory composition of claim 16, wherein said at least one other pesticidal agent is a protein selected from the group consisting of: Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z, AXMI-225z, AXMI-238, AXMI-270, AXMI-279, AXMI-345, AXMI-335, AXMI-R1, AXMI-R1 variants, IP3, IP3 variants, DIG-3, DIG-5, DIG-10, DIG-657, DIG-11, Cry71Aa1, Cry72Aa1, PHI-4 variants, PIP-72 variants, PIP-45 variants, PIP-64 variants, PIP-74 variants, PIP-75 variants, PIP-77 variants, Axmi422, Dig-305, Axmi440, PIP-47 variants, Axmi281, BT-009, BT-0012, BT-0013, BT-0023, BT0067, BT-0044, BT-0051, BT-0068, BT-0128, DIG-17, DIG-90, DIG-79, Cry1JP578V, Cry1JPS1, and Cry1 JPS1P578V.

18. The insect inhibitory composition of claim 13, further defined as comprising a plant cell that expresses said recombinant nucleic acid molecule.

19. A commodity product produced from the plant or part thereof of claim 9, wherein the commodity product comprises a detectable amount of said recombinant nucleic acid molecule.

20. The commodity product of claim 19, selected from the group consisting of: commodity corn bagged by a grain handler, corn flakes, corn cakes, corn flour, corn meal, corn syrup, corn oil, corn silage, corn starch, corn cereal, whole or processed cotton seed, cotton oil, lint, seeds processed for feed or food, plant parts processed for feed or food, fiber, paper, biomasses, fuel products derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

21. A method of producing seed, said method comprising:

a. planting at least a first seed according to claim 12, b. growing a plant from the seed; and c. harvesting seed from the plant, wherein said harvested seed comprises said recombinant nucleic acid molecule.

22. A plant resistant to insect infestation, wherein the cells of said plant comprise the recombinant nucleic acid molecule of claim 1.

23. A method for controlling a Coleopteran, Lepidopteran, or Hemipteran species pest or pest infestation, said method comprising:

a. contacting the pest with a transgenic plant cell expressing an insecticidally effective amount of a pesticidal protein as set forth in SEQ ID NOs:2, 4, 6, 50, or 121; or b. contacting the pest with a transgenic plant cell expressing an insecticidally effective amount of one or more pesticidal proteins comprising an amino acid sequence having:

i. at least 70% identity to SEQ ID NO: 121; or ii. at least 86% identity to SEQ ID NO:6 or SEQ ID NO:50; or iii. at least 97% identity to SEQ ID NO:4; or iv. at least 98% identity to SEQ ID NO:2.

24. The recombinant nucleic acid molecule of claim 1, wherein said pesticidal protein comprises the amino acid sequence of SEQ ID NO:2.

25. The recombinant nucleic acid molecule of claim 1, wherein said pesticidal protein comprises the amino acid sequence of SEQ ID NO:4.

26. The recombinant nucleic acid molecule of claim 1, wherein said pesticidal protein comprise the amino acid sequence of SEQ ID NO:6.

27. The recombinant nucleic acid molecule of claim 1, wherein said pesticidal protein comprises an amino acid sequence having at least 98% identity to SEQ ID NO:2.

28. The recombinant nucleic acid molecule of claim 1, wherein said pesticidal protein comprises an amino acid sequence having at least 98% identity to SEQ ID NO:4.

29. The recombinant nucleic acid molecule of claim 1, wherein said pesticidal protein comprises an amino acid sequence having at least 98% identity to SEQ ID NO:6.

30. The recombinant nucleic acid molecule of claim 1, wherein said pesticidal protein comprises an amino acid sequence having at least 98% identity to SEQ ID NO:50.

31. The recombinant nucleic acid molecule of claim 1, wherein said pesticidal protein comprises an amino acid sequence having at least 98% identity to SEQ ID NO:121.

32. The method of claim 23, the method comprising contacting the pest with a transgenic plant cell expressing an insecticidally effective amount of a pesticidal protein as set forth in SEQ ID NO:2.

33. The method of claim 23, the method comprising contacting the pest with a transgenic plant cell expressing an insecticidally effective amount of a pesticidal protein as set forth in SEQ ID NO:4.

34. The method of claim 23, the method comprising contacting the pest with a transgenic plant cell expressing an insecticidally effective amount of a pesticidal protein as set forth in SEQ ID NO:6.

35. The method of claim 23, the method comprising contacting the pest with a transgenic plant cell expressing an insecticidally effective amount of a pesticidal protein as set forth in SEQ ID NO:50.

36. The method of claim 23, the method comprising contacting the pest with a transgenic plant cell expressing an insecticidally effective amount of a pesticidal protein as set forth in SEQ ID NO:121.

37. The method of claim 23, the method comprising contacting the pest with a transgenic plant cell expressing an insecticidally effective amount of one or more pesticidal proteins comprising an amino acid sequence having at least 70% identity to SEQ ID NO:121.

38. The method of claim 23, the method comprising contacting the pest with a transgenic plant cell expressing an insecticidally effective amount of one or more pesticidal proteins comprising an amino acid sequence having at least 86% identity to SEQ ID NO:6.

39. The method of claim 23, the method comprising contacting the pest with a transgenic plant cell expressing an insecticidally effective amount of one or more pesticidal proteins comprising an amino acid sequence having at least 86% identity to SEQ ID NO:50.

40. The method of claim 23, the method comprising contacting the pest with a transgenic plant cell expressing an insecticidally effective amount of one or more pesticidal proteins comprising an amino acid sequence having at least 97% identity to SEQ ID NO:4.

41. The method of claim 23, the method comprising contacting the pest with a transgenic plant cell expressing an insecticidally effective amount of one or more pesticidal proteins comprising an amino acid sequence having at least 98% identity to SEQ ID NO:2.

* * * * *